United States Patent
Behnke et al.

(10) Patent No.: US 9,133,489 B2
(45) Date of Patent: Sep. 15, 2015

(54) ACETYL COA CARBOXYLASES

(75) Inventors: Craig A. Behnke, San Diego, CA (US); David Molina, San Diego, CA (US); Soyan Lieberman, Solana Beach, CA (US); Jamie Bacher, Emeryville, CA (US); Shuiqin Wu, San Diego, CA (US)

(73) Assignee: SAPPHIRE ENERGY, INC., San Diego, CA (US)

( * ) Notice: Subject to any disclaimer, the term of this patent is extended or adjusted under 35 U.S.C. 154(b) by 596 days.

(21) Appl. No.: 13/496,173

(22) PCT Filed: Sep. 13, 2010

(86) PCT No.: PCT/US2010/048666
§ 371 (c)(1),
(2), (4) Date: May 18, 2012

(87) PCT Pub. No.: WO2011/034823
PCT Pub. Date: Mar. 24, 2011

(65) Prior Publication Data
US 2012/0231546 A1 Sep. 13, 2012

Related U.S. Application Data

(60) Provisional application No. 61/242,489, filed on Sep. 15, 2009.

(51) Int. Cl.
*A01H 13/00* (2006.01)
*C12P 7/64* (2006.01)
*C12N 9/00* (2006.01)
*C12N 15/82* (2006.01)
*C12P 19/32* (2006.01)

(52) U.S. Cl.
CPC ............... *C12P 7/6409* (2013.01); *C12N 9/93* (2013.01); *C12N 15/8247* (2013.01); *C12P 7/6463* (2013.01); *C12P 19/32* (2013.01); *C12Y 604/01002* (2013.01)

(58) Field of Classification Search
None
See application file for complete search history.

(56) References Cited

U.S. PATENT DOCUMENTS

| | | | |
|---|---|---|---|
| 6,222,099 B1 | 4/2001 | Gengenbach et al. | |
| 8,394,621 B2 * | 3/2013 | Roberts et al. | 435/41 |
| 2009/0082286 A1 | 3/2009 | Huang et al. | |

FOREIGN PATENT DOCUMENTS

WO    WO 2007/087815 A2    8/2007

OTHER PUBLICATIONS

GenBank Accession No. EF121986.1, Published Feb. 7, 2007 (cited in the IDS filed Apr. 2, 2014).*
Hu et al, The Plant Journal, (2008), 54. 621-639, cited in the IDS filed Jul. 20, 2012.*
Dunahay et al., "Manipulation of Microalgal Lipid Production Using Genetic Engineering." Applied Biochemistry and Biotechnology, 1996, vol. 57/58, pp. 223-231.
Ha et al., "Critical Phosphorylation Sites for Acetyle-CoA Carboxylase Activity." The Journal of Biological Chemistry, 1994, vol. 269, No. 35, pp. 22162-22168.
Hu et al., "Microalgal triacylglycerols as feedstocks for biofuel production: perspectives and advances." The Plant Journal, 2008, vol. 54, pp. 621-639.
Lopez-Casillas et al., Structure of the coding sequence and primary amino acid sequence of acetyl-coenzyme A carboxylase. Proc. Natl. Acad. Sci. USA, 1988, vol. 85, pp. 5784-5788.
Roessler et al., Cloning and characterization of the gene that encodes acetylcoenzyme A carboxylase in the alga Cyclotella cryptica. The Journal of Biological Chemistry, 1993, vol. 268, No. 26, pp. 19254-19259.
Sasaki et al., "Plant acetyl-CoA carboxylase: Structure, biosynthesis, regulation and gene manipulation for plant breeding." Biosci. Biotech. Biochem., 2004, vol. 68(6), pp. 1175-1184.
Savage et al., "Phosphorylation of pea chloroplast acetyl-CoA carboxylase." The Plant Journal, 1999, vol. 18(5), pp. 521-527.
GenBank Accession No. EF121986.1. Published date Feb. 7, 2007.
Haystead et al. Analysis of sites phosphorylated on acetyl-CoA carboxylase in response to insulin in isolated adipocytes. (1988) Eur. J. Biochem., 175, 347-354.
Haystead et al. Insulin and phorbol ester stimulate phosphorylation of acetyl-CoA carboxylase at similar sites in isolated adipocytes. (1988) Eur. J. Biochem., 175, 339-345.
Kim et al. Role of reversible phosphorylation of acetyl-CoA carboxylase in a long-chain fatty acid synthesis. FASEB J. (1989) 3, 2250-2256.
Kim. Regulation of Acetyl-CoA Carboxylase. 1983. Curr. Top. Cell. Regul. 22:143-176.
Kim. Regulation of mammalian acetyl-Coenzyme a carboxylase. (1997) Annu. Rev. Nutr., 17, 77-99.
Munday et al. Identification by amino acid sequencing of three major regulatory phosphorylation sites on rat acetyl-CoA carboxylase. (1988) Eur. J. Biochem., 175, 331-338.
Wang et al. Acetyl-CoA Carboxylase in Plants (ACCase). Institute of Virology and Biotechnology, Zhejiang Academy of Agricultural Sciences, Hangzhou 310021, China, Nov. 28, 2005.

* cited by examiner

*Primary Examiner* — Eileen B O Hara
(74) *Attorney, Agent, or Firm* — Sapphire Energy, Inc.

(57) ABSTRACT

Provided herein are novel ACCases and nucleotides encoding the same, that when introduced into a cell or organism results in an increase and/or accumulation of fatty acids, glycerol lipids, and/or oils in the cell or organism, and/or a change in the types of fatty acids, glycerol lipids, and/or oils that are normally present in the cell or organism. Also provided herein are organisms transformed with the novel ACCases.

18 Claims, 26 Drawing Sheets

ATGTCTCTTAAGTCCAGCGTGGGCCCCAGCCTGGCCGGCAAGGCGTGC
CACGGAGCAAATGCGCAGGTGCTGCCGCGCATGGCAGTGCCAGCGCCG
CTTGCAGGAACAGCAGTGCGCCCCAGCCTCGCAGTCAATGCAGTCAAC
CCTGAGAAAAACGGCGCTTATGAGGGCTCCCCATTGTCAGCGGCCCC
ATTTCTGTGGGTGCTATGGACAAGGACTCCAAGGGCTCTTCCAAGCCTG
TTGACCGCAGCAAGGGCCTCTGGACGCGCTGCGACAAGTGCGGCGTGA
TTCTCTACATCAAGCACCTGAAGGAGCACCACCACATCTGCTTCGGCTG
CAACTACCACCTCAAGATGAGCAGCCAGGAGAGGATCGACCACATGAT
CGACCCAGGCTCATGGCGCCCCTTTGACGAGACGCTGTCTCCCTGCGAC
CCGCTGGACTTTGTGGACATGAAGCCATACCCAGACAGGGTGCGCGAC
AGCCAGGACAAGACAGGCATGAACGATGCCATCCGCACAGGCACGGG
CCTGCTGCACGGCATCCCAGTGGCGCTGGCAGTGATGGAGTTTGGCTTC
ATGGGCGGCAGCATGGGCAGCGTGGTGGGGGAGAAGCTGACGCGCCT
GATTGAGTACGCCACGCAGGAGGGGCTCACGCTGCTGGTGGTGTGCAC
CAGCGGAGGCGCGCGCATGCAGGAGGGCATCATGAGCCTGATGCAGAT
GGCCAAGATCAGCGGCGCGCTGCACGTGCACCAGAATGAGGCCAACCT
GCTGTACATCTCCATCCTGACCAGCCCCACCACAGGTGGCGTGACCGCA
AGCTTTGGCATGCTGGGGGATGTCATCATTGCTGAGCCGCAGGCCATCA
TCGGCTTTGCAGGACGGCGTGTGATCGAGCAGACGCTGCGTGAGGAGC
TGCCAGATGACTTCCAGACCGCGGAGTACCTGCTTGACAAGGGCCTGC
TCGACCTGGTGGTGCCGCGCAGCTTCCTGAAGGGCGCGCTGTTTGAGAT
CATCGACTTCTACAAGAACGCACCCTACAAGCGCCGCGGCAAGATTCC
ATTTGGCGTGCAGCGCGGTACGTACGGCCTGACCGCTGAGGAGAAGAT
GCGGCGCAGGTGGAGGGAGTGGAGCTCAGCTGGCAGCAACGGCTCGG
GCACGCCCGCGCTGGCAGCAGCAGCAGCATCAGCAGCAGTTGGGTCAG
CAGCCACTTGCGGCAGCTGCCAGCAGCAGCAGCTGGCGCTGTGGGCGG
TGCTGGCAGGCTGTGGCAGCTGTGGGCAGTGGCTGTGGTTTGCTCAGG
GGGTAGGTGCGCTTGAGCGCACAGCGGCAACAGCAGCAGTACTGAGAG
AGGGCAGCGTGCTGCTAGCAGGCGTCTGTTGTTAA

FIG. 18

```
ATGTCTCTTAAGTCCAGCGTGGGCCCCAGCCTGGCCGGCAAGGCGTGC
CACGGAGCAAATGCGCAGGTGCTGCCGCGCATGGCAGTGCCAGCGCCG
CTTGCAGGAACAGCAGTGCGCCCCAGCCTCGCAGTCAATGCAGTCAAC
CCTGAGAAAAACGGCGCTTATGAGGGCTCCCCCATTGTCAGCGGCCCC
ATTTCTGTGGGTGCTATGGACAAGGACTCCAAGGGCTCTTCCAAGCCTG
TTGACCGCAGCAAGGGCCTCTGGACGCGCTGCGACAAGTGCGGCGTGA
TTCTCTACATCAAGCACCTGAAGGAGCACCACCACATCTGCTTCGGCTG
CAACTACCACCTCAAGATGAGCAGCCAGGAGAGGATCGACCACATGAT
CGACCCAGGCTCATGGCGCCCCTTTGACGAGACGCTGTCTCCCTGCGAC
CCGCTGGACTTTGTGGACATGAAGCCATACCCAGACAGGGTGCGCGAC
AGCCAGGACAAGACAGGCATGAACGATGCCATCCGCACAGGCACGGG
CCTGCTGCACGGCATCCCAGTGGCGCTGGCAGTGATGGAGTTTGGCTTC
ATGGGCGGCAGCATGGGCAGCGTGGTGGGGGAGAAGCTGACGCGCCT
GATTGAGTACGCCACGCAGGAGGGGCTCACGCTGCTGGTGGTGTGCAC
CAGCGGAGGCGCGCGCATGCAGGAGGGCATCATGAGCCTGATGCAGAT
GGCCAAGATCAGCGGCGCGCTGCACGTGCACCAGAATGAGGCCAACCT
GCTGTACATCTCCATCCTGACCAGCCCCACCACAGGTGGCGTGACCGCA
AGCTTTGGCATGCTGGGGGATGTCATCATTGCTGAGCCGCAGGCCATCA
TCGGCTTTGCAGGACGGCGTGTGATCGAGCAGACGCTGCGTGAGGAGC
TGCCAGATGACTTCCAGACCGCGGAGTACCTGCTTGACAAGGGCCTGC
TCGACCTGGTGGTGCCGCGCAGCTTCCTGAAGGGCGCGCTGTTTGAGAT
CATCGACTTCTACAAGAACGCACCCTACAAGCGCCGCGGCAAGATTCC
ATTTGGCGTGCAGCGCGGTACGTACGGCCTGACCGCTGAGGAGAAGAT
GCGGCGCAGGTGGAGGGAGTGGAGCTCAGTTGGCAGCATGTTGCATAG
TGTTCACTATGCAGGCCACTGGCCCTCTGGGTGTGCTGGATGTTGCTG
GGCCAGCGCCCACTTCATATGCATTGGCATGTCAATGAAGGGTCAGGTT
GTAGCAAGACCACGTGCCAGAGCTTTAAGTATTGGTCAGCATGTCTG
CTTGGCATGCAGTGTGCCATCGGCGAGGAACACTTCTTGAACATGAACT
TACCAAGCTGATTTCCTGGCAGTTTGATTCATGCTGTTGGCGTGCTGCC
AAAGGTATTCTGCTTAGATCTTGCAATGCTGTGTATGTATATGTGTAA
```

FIG. 19

ATGTCTCTTAAGTCCAGCGTGGGCCCCAGCCTGGCCGGCAAGGCGTGC
CACGGAGCAAATGCGCAGGTGCTGCCGCGCATGGCAGTGCCAGCGCCG
CTTGCAGGAACAGCAGTGCGCCCCAGCCTCGCAGTCAATGCAGTCAAC
CCTGAGAAAAACGGCGCTTATGAGGGCTCCCCATTGTCAGCGGCCCC
ATTTCTGTGGGTGCTATGGACAAGGACTCCAAGGGCTCTTCCAAGCCTG
TTGACCGCAGCAAGGGCCTCTGGACGCGCTGCGACAAGTGCGGCGTGA
TTCTCTACATCAAGCACCTGAAGGAGCACCACCACATCTGCTTCGGCTG
CAACTACCACCTCAAGATGAGCAGCCAGGAGAGGATCGACCACATGAT
CGACCCAGGCTCATGGCGCCCTTTGACGAGACGCTGTCTCCCTGCGAC
CCGCTGGACTTTGTGGACATGAAGCCATACCCAGACAGGGTGCGCGAC
AGCCAGGACAAGACAGGCATGAACGATGCCATCCGCACAGGCACGGG
CCTGCTGCACGGCATCCCAGTGGCGCTGGCAGTGATGGAGTTTGGCTTC
ATGGGCGGCAGCATGGGCAGCGTGGTGGGGGAGAAGCTGACGCGCCT
GATTGAGTACGCCACGCAGGAGGGCTCACGCTGCTGGTGGTGTGCAC
CAGCGGAGGCGCGCGCATGCAGGAGGGCATCATGAGCCTGATGCAGAT
GGCCAAGATCAGCGGCGCGCTGCACGTGCACCAGAATGAGGCCAACCT
GCTGTACATCTCCATCCTGACCAGCCCCACCACAGGTGGCGTGACCGCA
AGCTTTGGCATGCTGGGGGATGTCATCATTGCTGAGCCGCAGGCCATCA
TCGGCTTTGCAGGACGGCGTGTGATCGAGCAGACGCTGCGTGAGGAGC
TGCCAGATGACTTCCAGACCGCGGAGTACCTGCTTGACAAGGGCCTGC
TCGACCTGGTGGTGCCGCGCAGCTTCCTGAAGGGCGCGCTGTTTGAGAT
CATCGACTTTTACAAGAACGCACCCTACAAGCGCCGCGGCAAGATTCC
ATTTGGCGTGCAGCGCGGTACGTACGGCCTGACCGCTGAGGAGAAGAT
GCGGCGCAGGTGGAGGGAGTGGAGCTCAGCTGGCAGCAACGGCTCGG
GCACGCCCGCGCTGGCAGCAGCAGCAGCAGTGGTGGCGCCGTGCAGCA
GTGGAGGAGTTGCATGCGCACTGAGACGAGCTTGTTCAAGAGTTAGTC
GGATGGGCGGGGTGGGGAGCTTGCTACGCTGCTAG

FIG. 20

ATGTCTCTTAAGTCCAGCGTGGGCCCCAGCCTGGCCGGCAAGGCGTGC
CACGGAGCAAATGCGCAGGTGCTGCCGCGCATGGCAGTGCCAGCGCCG
CTTGCAGGAACAGCAGTGCGCCCAGCCTCGCAGTCAATGCAGTCAAC
CCTGAGAAAAACGGCGCTTATGAGGGCTCCCCCATTGTCAGCGGCCCC
ATTTCTGTGGGTGCTATGGACAAGGACTCCAAGGGCTCTTCCAAGCCTG
TTGACCGCAGCAAGGGCCTCTGGACGCGCTGCGACAAGTGCGGCGTGA
TTCTCTACATCAAGCACCTGAAGGAGCACCACCACATCTGCTTCGGCTG
CAACTACCACCTCAAGATGAGCAGCCAGGAGAGGATCGACCACATGAT
CGACCCAGGCTCATGGCGCCCTTTGACGAGACGCTGTCTCCCTGCGAC
CCGCTGGACTTTGTGGACATGAAGCCATACCCAGACAGGGTGCGCGAC
AGCCAGGACAAGACAGGCATGAACGATGCCATCCGCACAGGCACGGG
CCTGCTGCACGGCATCCCAGTGGCGCTGGCAGTGATGGAGTTTGGCTTC
ATGGGCGGCAGCATGGGCAGCGTGGTGGGGGAGAAGCTGACGCGCCT
GATTGAGTACGCCACGCAGGAGGGGCTCACGCTGCTGGTGGTGTGCAC
CAGCGGAGGCGCGCGCATGCAGGAGGGCATCATGAGCCTGATGCAGAT
GGCCAAGATCAGCGGCGCGCTGCACGTGCACCAGAATGAGGCCAACCT
GCTGTACATCTCCATCCTGACCAGCCCCACCACAGGTGGCGTGACCGCA
AGCTTTGGCATGCTGGGGGATGTCATCATTGCTGAGCCGCAGGCCATCA
TCGGCTTTGCAGGACGGCGTGTGATCGAGCAGACGCTGCGTGAGGAGC
TGCCAGATGACTTCCAGACCGCGGAGTACCTGCTTGACAAGGGCCTGC
TCGACCTGGTGGTGCCGCGCAGCTTCCTGAAGGGCGCGCTGTTTGAGAT
CATCGACTTGTACAAGAAAGCACCCCCAAGCGGCGGGGCAAGATTCC
ATTTGGCGTGCATAGCGGTACGTACGGCCAACCGCCGAGGAGAAGATC
CGGCGCAGGTGGAGGGAGGGGAGTTCAGCTGGCAGCAACGGGTGGGG
CACGCCCGCGCTGGCAGCAGCAGCAGCAGGGGGGCGGTGCGGGTTTTG
GCGCCAAGCCATTCCAGGGGGTTGGTATATGTGACAGCAGCCTGTTTG
GTCACAGTCTGGATGGTGCGGCATAA

*FIG. 21*

ATGTCTCTTAAGTCCAGCGTGGGCCCCAGCCTGGCCGGCAAGGCGTGC
CACGGAGCAAATGCGCAGGTGCTGCCGCGCATGGCAGTGCCAGCGCCG
CTTGCAGGAACAGCAGTGCGCCCAGCCTCGCAGTCAATGCAGTCAAC
CCTGAGAAAAACGGCGCTTATGAGGGCTCCCCATTGTCAGCGGCCCC
ATTTCTGTGGGTGCTATGGACAAGGACTCCAAGGGCTCTTCCAAGCCTG
TTGACCGCAGCAAGGGCCTCTGGACGCGCTGCGACAAGTGCGGCGTGA
TTCTCTACATCAAGCACCTGAAGGAGCACCACCACATCTGCTTCGGCTG
CAACTACCACCTCAAGATGAGCAGCCAGGAGAGGATCGACCACATGAT
CGACCCAGGCTCATGGCGCCCCTTTGACGAGACGCTGTCTCCCTGCGAC
CCGCTGGACTTTGTGGACATGAAGCCATACCCAGACAGGGTGCGCGAC
AGCCAGGACAAGACAGGCATGAACGATGCCATCCGCACAGGCACGGG
CCTGCTGCACGGCATCCCAGTGGCGCTGGCAGTGATGGAGTTTGGCTTC
ATGGGCGGCAGCATGGGCAGCGTGGTGGGGGAGAAGCTGACGCGCCT
GATTGAGTACGCCACGCAGGAGGGCTCACGCTGCTGGTGGTGTGCAC
CAGCGGAGGCGCGCGCATGCAGGAGGGCATCATGAGCCTGATGCAGAT
GGCCAAGATCAGCGGCGCGCTGCACGTGCACCAGAATGAGGCCAACCT
GCTGTACATCTCCATCCTGACCAGCCCCACCACAGGTGGCGTGACCGCA
AGCTTTGGCATGCTGGGGGATGTCATCATTGCTGAGCCGCAGGCCATCA
TCGGCTTTGCAGGACGGCGTGTGATCGAGCAGACGCTGCGTGAGGAGC
TGCCAGATGACTTCCAGACCGCGGAGTACCTGCTTGACAAGGGCCTGC
TCGACCTGGTGGTGCCGCGCAGCTTCCTGAAGGGCGCGCTGTTTGAGAT
CATCGACTTTTACAAGAACGCACCCTGCAAGCGCCGCGGCAAGATTCC
ATTTGGCGTGCAGCGCGGTACGTACGGCCTGACCGCTGAGGAGAAGAT
GCGGCGCAGGTGGAGGGAGTGGAGCTCAGCTGGCAGCAACGGCTCGG
GCACGCCCGCGCTGGCAGCAGCAGCAGCAGAGCTGAGAGAGGGCAGC
GTGCTGCTAGCAGGCGTCTGTTGTTAA

ACETYL COA CARBOXYLASES

CROSS REFERENCE TO RELATED APPLICATION

This application is a national phase under 35 U.S.C. §371 of International Application Number PCT/US2010/048666, filed Sep. 13, 2010, which claims the benefit of U.S. Provisional Application No. 61/242,489, filed Sep. 15, 2009, the entire contents of both applications are incorporated by reference for all purposes.

INCORPORATION OF SEQUENCE LISTING

This application contains a Sequence Listing which has been submitted in ASCII format via EFS-Web and is hereby incorporated by reference in its entirety. Said ASCII copy, created on Jul. 15, 2013, is named 0806WO1_ST25.txt and is 352,564 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Acetyl Coenzyme A carboxylase (ACCase) is the rate-limiting enzyme in the fatty acid biosynthesis pathway in plant, animal, yeast, and bacterial cells. Structurally, ACCases are biotinylated and are large enzymes consisting of two or more subunits. For example, most ACCases of animals, the cytoplasmic version in plants, and yeast are dimers of 420 to 700 kD native MW and contain subunits of 200 to 280 kD. Higher plant and algal plastid, and bacterial ACCases are 700 to 740 kD complexes 20 to 180 kD subunits.

Acetyl CoA Carboxylase (ACCase) catalyzes the formation of malonyl-CoA from acetyl-CoA and bicarbonate in animal, plant, and bacterial cells. Malonyl-CoA is an essential substrate for (i) de novo fatty acid (FA) synthesis, (ii) fatty acid elongation, (iii) synthesis of secondary metabolites such as flavonoids and anthocyanins, and (iv) malonylation of some amino acids and secondary metabolites. Synthesis of malonyl-CoA is the first committed step of flavonoid and fatty acid synthesis and current evidence suggests that ACCase catalyzes the rate-limiting step of fatty acid synthesis. Formation of malonyl-CoA by ACCase occurs via two partial reactions and requires a biotin prosthetic group:

(i) Enzyme-biotin+ATP+HCO$_3$→Enzyme-biotin-CO$_2$+ADP+Pi (ii) Enzyme-biotin-CO$_2$+Acetyl-CoA→Enzyme-biotin+malonyl CoA The net reaction is:

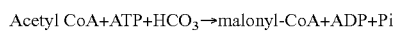

Acetyl CoA+ATP+HCO$_3$→malonyl-CoA+ADP+Pi

In *E. coli*, these reactions are catalyzed by three distinct components; biotin carboxylase, biotin-acetyl CoA transcarboxylase, and biotin carboxyl carrier protein, which can be separated and yet retain partial activity. Plant and animal cytoplasmic ACCases contain all three activities on a single polypeptide.

Two different forms of the ACCase complex exist in plants (as described, for example, in Sasaki, Y. and Nagano, Y. (2004) *Biosci. Biotechnol. Biochem.* 68(6):1175-1184); the cytoplasmic enzyme, consisting of a very large single polypeptide chain, and the plastidic ACCase complex. The plastidic complex is a multi-enzyme complex composed of biotin carboxyl carrier protein (BCCP), biotin carboxylase, and a carboxyltransferase complex made up of two pairs of α and β subunits.

Several pieces of evidence indicate that, at least in higher plants, the chloroplast ACCase complex is subject to control via post-translational modification. Kozaki and Sasaki Biochem J., 339:541 (1999) describe light levels and the addition of reducing agent (dithiothreitol) as being able to increase chloroplast ACCase activity, while the amount of ACCase protein remained roughly unchanged.

Savage and Ohlrogge, Plant J., 18:521 (1999) described purification of pea chloroplast ACCase complex, and showed that the β-subunit of the complex was phosphorylated in vivo. Removal of the phosphates by phosphatase treatment dramatically reduced the ACCase activity in the sample.

Under certain physiological conditions, mammalian ACC activity is rapidly regulated by reversible phosphorylation (for example, as described in Kim, K.-H. (1983) *Curr. Top. Cell Regul.*, 22, 143-176; and Kim, K.-H., et al., *FASEB J.* (1989) 3, 2250-2256) which involves specific protein kinases that phosphorylate and inactivate ACC (for example, as described in Kim, K.-H., et al., FASEB J. (1989) 3, 2250-2256), and phosphatases that dephosphorylate and activate the enzyme.

Ha, J. et al. (The J. of Biol. Chem. (1994) 269 (35) pp. 22162-22168) created and expressed a cDNA of the entire coding region of the rat Acetyl-CoA carboxylase and identified eight different phosphorlyation sites on the carboxylase molecule. The sites were identified by comparing phosphopeptide sequences and the deduced amino acid sequences from rat ACC cDNA (for example, as described in Lopez-Casillas, F., et al. (1988) *Proc. Natl. Acad. Sci. U.S.A.*, 85, 5784-5788; Munday, M. R., et al. (1988) *Eur. J. Biochem.*, 175, 331-338; Haystead, T. A. J. and Hardie, D. G. (1988) *Eur. J. Biochem.*, 175, 339-345; and Haystead, T. A. J. et al. (1988) *Eur. J. Biochem.*, 175, 347-354). The identified sites are Ser 23, 25, 29, 77, 79, 95, 1200, and 1215. The roles of these phosphorylation sites on the activation of ACCase are not well understood.

Increasing the amount of ACCase activity in the cell has been proposed as a mechanism to increase the lipid content (for example, TAG, DAG, and other acyl lipids) in algae, higher plants, yeast, and mammals. Attempts have been made to increase ACCase activity by increasing the amount of protein present via upregulation of a native ACCase gene or by introduction of a transgene under a stronger promoter. These efforts have produced increased levels of ACCase protein in the target organisms, but have not significantly altered lipid level (for example, as described in Hu et al., The Plant J., 54:621 (2008)).

In order to increase fatty acid synthesis in a cell, what is needed is not simply to increase production of an ACCase protein, but rather to increase the level of ACCase activity in the cell, resulting in an increase in lipid production. The present disclosure meets that need.

SUMMARY

Provided herein are novel ACCases, and nucleotides encoding the same, that when introduced into a cell or organism result in an increase and/or accumulation of fatty acids, glycerol lipids, and/or oils. Also, provided herein are novel ACCases, and nucleotides encoding the same, that when introduced into a cell or organism result in a change in the types of fatty acids, glycerol lipids, and/or oils that are normally present in the cell or organism.

1. An isolated polynucleotide capable of transforming a photosynthetic organism comprising a nucleic acid sequence encoding an acetyl CoA carboxylase, wherein the acetyl CoA carboxylase comprises: 1) an amino acid sequence of SEQ ID NO: 157; or 2) an amino acid sequence that has at least 50%, at least 60%, at least 70%, at least 80%, at least 90%, at least 95%, at least 98%, or at least at least 99% sequence identity to the amino acid sequence of SEQ ID NO: 157.

2. An acetyl CoA carboxylase present in a photosynthetic organism comprising: 1) an amino acid sequence of SEQ ID NO: 157; or 2) an amino acid sequence that has at least 50%, at least 60%, at least 70%, at least 80%, at least 90%, at least 95%, at least 98%, or at least at least 99% sequence identity to the amino acid sequence of SEQ ID NO: 157.

3. A nucleotide sequence encoding an acetyl CoA carboxylase wherein the nucleotide sequence comprises: 1) a nucleic acid sequence of SEQ ID NO: 114 or SEQ ID NO: 155; or 2) a nucleic acid sequence that has at least 50%, at least 60%, at least 70%, at least 80%, at least 90%, at least 95%, at least 98%, or at least at least 99% sequence identity to the nucleic acid sequence of SEQ ID NO: 114 or SEQ ID NO: 115, wherein the nucleotide sequence is capable of transforming a photosynthetic organism.

4. A vector comprising a nucleotide sequence encoding an acetyl CoA carboxylase, wherein the acetyl CoA carboxylase comprises: 1) an amino acid sequence of SEQ ID NO: 157; or 2) an amino acid sequence that has at least 50%, at least 60%, at least 70%, at least 80%, at least 90%, at least 95%, at least 98%, or at least at least 99% sequence identity to the amino acid sequence of SEQ ID NO: 157, wherein the vector is used to transform a photosynthetic organism. 5. The vector of claim 4, wherein the vector is an expression vector. 6. The vector of claim 4 or 5, wherein the vector further comprises a 5' regulatory region. 7. The vector of claim 6, wherein the 5' regulatory region further comprises a promoter. 8. The vector of claim 7, wherein the promoter is a constitutive promoter. 9. The vector of claim 7, wherein the promoter is an inducible promoter. 10. The vector of claim 9, wherein the inducible promoter is a light inducible promoter, a nitrate inducible promoter, or a heat responsive promoter. 11. The vector of any one of claims 4 to 10, further comprising a 3' regulatory region.

12. A method for increasing production of malonyl CoA in a photosynthetic organism, comprising transforming the photosynthetic organism with a polynucleotide encoding an ACCase comprising an amino acid sequence of SEQ ID NO: 157, or with a polynucleotide encoding an amino acid sequence that has at least 50%, at least 60%, at least 70%, at least 80%, at least 90%, at least 95%, at least 98%, or at least at least 99% sequence identity to the amino acid sequence of SEQ ID NO: 157. 13. The method of claim 12, wherein the photosynthetic organism is a prokaryote. 14. The method of claim 13, wherein the prokaryote is a *cyanobacterium*. 15. The method of claim 12, wherein the photosynthetic organism is a eukaryote. 16. The method of claim 15, wherein the eukaryote is a vascular plant. 17. The method of claim 15, wherein the eukaryote is a non-vascular photosynthetic organism. 18. The method of claim 17, wherein the non-vascular photosynthetic organism is an alga. 19. The method of claim of any one of claims 12 to 18, further comprising transforming a plastid with the polynucleotide. 20. The method of claim 19, wherein the plastid is a chloroplast.

21. A method for increasing fatty acid synthesis in a photosynthetic organism comprising transforming the photosynthetic organism with a polynucleotide encoding an ACCase comprising an amino acid sequence of SEQ ID NO: 157, or with a polynucleotide encoding an amino acid sequence that has at least 50%, at least 60%, at least 70%, at least 80%, at least 90%, at least 95%, at least 98%, or at least at least 99% sequence identity to the amino acid sequence of SEQ ID NO: 157. 22. The method of claim 21, wherein the photosynthetic organism is a prokaryote. 23. The method of claim 22, wherein the prokaryote is a *cyanobacterium*. 24. The method of claim 21, wherein the organism is a eukaryote. 25. The method of claim 24, wherein the eukaryote is a vascular plant. 26. The method of claim 24, wherein the eukaryote is a non-vascular photosynthetic organism. 27. The method of claim 21, wherein the photosynthetic organism is an alga. 28. The method of claim of any one of claims 21 to 27, further comprising transforming a plastid with the polynucleotide. 29. The method of claim 28, wherein the plastid is a chloroplast.

30. A transgenic host cell comprising a nucleotide sequence encoding an amino acid sequence of SEQ ID NO: 157, or comprising a nucleotide sequence encoding an ACCase comprising an amino acid sequence that has at least 50%, at least 60%, at least 70%, at least 80%, at least 90%, at least 95%, at least 98%, or at least at least 99% sequence identity to the amino acid sequence of SEQ ID NO: 157. 31. The transgenic host cell of claim 30, wherein the host cell is a prokaryote. 32. The transgenic host cell of claim 31, wherein the prokaryote is a *cyanobacterium*. 33. The transgenic host cell of claim 30, wherein the host cell is a plant cell. 34. The transgenic host cell of claim 33, wherein the plant cell is from a vascular plant. 35. The transgenic host cell of claim 33, wherein the plant cell is from an alga. 36. The transgenic host cell of claim 35, wherein the alga is a green alga. 37. The transgenic host cell of claim 36, wherein the green alga is a *Chlorophycean*.

38. A transgenic plastid comprising a polynucleotide encoding an acetyl CoA carboxylase comprising an amino acid sequence of SEQ ID NO: 157, or encoding an acid sequence that has at least 50%, at least 60%, at least 70%, at least 80%, at least 90%, at least 95%, at least 98%, or at least at least 99% sequence identity to the amino acid sequence of SEQ ID NO: 157. 39. The transgenic plastid of claim 38, wherein the plastid is a chloroplast. 40. A host cell comprising the transgenic plastid of claim 38 or claim 39. 41. The host cell of claim 40, wherein the host cell is a prokaryote. 42. The host cell of claim 41, wherein the host cell is a *cyanobacterium*. 43. The host cell of claim 40, wherein the host cell is a plant cell. 44. The host cell of claim 43, wherein the plant cell is from a vascular plant. 45. The host cell of claim 40, wherein the plant cell is an alga. 46. The transgenic host cell of 45, wherein the alga is a green alga. 47. The transgenic host cell of claim 46, wherein the green alga is a *Chlorophycean*.

48. An acetyl CoA carboxylase present in a photosynthetic organism comprising: an amino acid sequence of a mammalian acetyl CoA carboxylase. 49. The acetyl CoA carboxylase of claim 48, wherein the acetyl CoA carboxylase comprises an amino acid sequence of SEQ ID NO: 157, or an amino acid sequence that has at least 50%, at least 60%, at least 70%, at least 80%, at least 90%, at least 95%, at least 98%, or at least at least 99% sequence identity to the amino acid sequence of SEQ ID NO: 157.

50. An isolated polynucleotide comprising a nucleic acid sequence encoding a beta subunit of an acetyl CoA carboxylase, wherein the beta subunit of the acetyl CoA carboxylase comprises an amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24. SEQ ID NO: 163, SEQ ID NO: 164, SEQ ID NO: 165, SEQ ID NO: 166, or SEQ ID NO: 167; or b) an amino acid sequence that has at least 50%, at least 60%, at least 70%, at least 80%, at least 90%, at least 95%, at least 98%, or at least at least 99% sequence identity to the amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167.

51. An acetyl CoA carboxylase comprising an amino acid sequence of: a) SEQ ID NO: 15, SEQ ID NO: 16, SEQ ID NO: 17. SEQ ID NO: 18, SEQ ID NO: 19, SEQ ID NO: 20, SEQ ID NO: 21, SEQ ID NO: 22, SEQ ID. NO: 23, SEQ ID NO: 24, SEQ ID NO: 163, SEQ ID NO: 164, SEQ ID NO: 165, SEQ ID NO: 166, or SEQ ID NO: 167; or b) an amino acid sequence that has at least 50%, at least 60%, at least 70%, at least 80%, at least 90%, at least 95%, at least 98%, or at least at least 99% sequence identity to the amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167.

52. A nucleotide sequence encoding a beta subunit of an acetyl CoA carboxylase wherein the nucleotide sequence comprises: 1) a nucleic acid sequence of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 158, SEQ ID NO: 159, SEQ ID NO:160, SEQ ID NO: 161, SEQ ID NO: 162, SEQ ID NO: 168, or SEQ ID NO: 169; or 2) a nucleic acid sequence that has at least 50%, at least 60%, at least 70%, at least 80%, at least 90%, at least 95%, at least 98%, or at least at least 99% sequence identity to the nucleic acid sequence of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 158, SEQ ID NO: 159, SEQ ID NO:160, SEQ ID NO: 161, SEQ ID NO: 162, SEQ ID NO: 168, or SEQ ID NO: 169.

53. A vector comprising a nucleotide sequence encoding a beta subunit of an acetyl CoA carboxylase, wherein the beta subunit of the acetyl CoA carboxylase comprises an amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167; or b) comprises an amino acid sequence that has at least 50%, at least 60%, at least 70%, at least 80%, at least 90%, at least 95%, at least 98%, or at least at least 99% sequence identity to the amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167. 54. The vector of claim 53, wherein the vector is an expression vector. 55. The vector of claim 53 or claim 54, wherein the vector further comprises a 5' regulatory region. 56. The vector of claim 55, wherein the 5' regulatory region further comprises a promoter. 57. The vector of claim 56, wherein the promoter is a constitutive promoter. 58. The vector of claim 56, wherein the promoter is an inducible promoter. 59. The vector of claim 58, wherein the inducible promoter is a light inducible promoter, a nitrate inducible promoter, Or a heat responsive promoter. 60. The vector of any one of claims 53 to 59, further comprising a 3' regulatory region.

61. A method for increasing production of malonyl CoA in a photosynthetic organism comprising transforming the photosynthetic organism with a polynucleotide encoding a beta subunit of an ACCase, wherein the beta subunit of the ACCase comprises the amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167; or b) comprises an amino acid sequence that has at least 50%, at least 60%, at least 70%, at least 80%, at least 90%, at least 95%, at least 98%, or at least at least 99% sequence identity to the amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167. 62. The method of claim 61, wherein the photosynthetic organism is a prokaryote. 63. The method of claim 62, wherein the prokaryote is a *cyanobacterium*. 64. The method of claim 61, wherein the organism is a eukaryote. 65. The method of claim 64, wherein the eukaryote is a vascular plant. 66. The method of claim 64, wherein the eukaryote is a non-vascular photosynthetic organism. 67. The method of claim 66, wherein the non-vascular photosynthetic organism is an alga. 68. The method of claim of any one of claims 61 to 67, further comprising transforming a plastid with the polynucleotide. 69. The method of claim 68, wherein the plastid is a chloroplast.

70. A method for increasing fatty acid synthesis in a photosynthetic organism comprising transforming the photosynthetic organism with a polynucleotide encoding an ACCase comprising an amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167; or b) encoding an amino acid sequence that has at least 50%, at least 60%, at least 70%, at least 80%, at least 90%, at least 95%, at least 98%, or at least at least 99% sequence identity to the amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167. 71. The method of claim 70, wherein the photosynthetic organism is a prokaryote. 72. The method of claim 71, wherein the prokaryote is a *cyanobacterium*. 73. The method of claim 70, wherein the organism is a eukaryote. 74. The method of claim 73, wherein the eukaryote is a vascular plant. 75. The method of claim 70, wherein the eukaryote is a non-vascular photosynthetic organism. 76. The method of claim 75, wherein the non-vascular photosynthetic organism is an alga. 77. The method of claim of any one of claims 70 to 76, further comprising transforming a plastid with the polynucleotide. 78. The method of claim 77, wherein the plastid is a chloroplast.

79. A transgenic host cell comprising a nucleotide sequence encoding an ACCase comprising an amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167; or b) encoding an amino acid sequence that has at least 50%, at least 60%, at least 70%, at least 80%, at least 90%, at least 95%, at least 98%, or at least at least 99% sequence identity to the amino acids sequence of SEQ ID NO: 15, SEQ ID NO: 16, SEQ ID NO:

17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167. 80. The transgenic host cell of claim 79, wherein the host cell is a prokaryote. 81. The transgenic host cell of claim 80, wherein the prokaryote is a *cyanobacterium*. 82. The transgenic host cell of any one of claims 79 to 81, wherein the host cell is a plant cell. 83. The transgenic host cell of claim 82, wherein the plant cell is from a vascular plant. 84. The transgenic host cell of claim 82, wherein the plant cell is from an alga. 85. The transgenic host cell of claim 84, wherein the alga is a green alga. 86. The transgenic host cell of claim 85, wherein the green alga is a *Chlorophycean*.

87. A transgenic plastid comprising a polynucleotide encoding a beta subunit of an acetyl CoA carboxylase comprising an amino acid sequence of: a) SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167; or b) comprising an amino acid sequence that has at least 50%, at least 60%, at least 70%, at least 80%, at least 90%, at least 95%, at least 98%, or at least at least 99% sequence identity to the amino acids sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, or SEQ ID NO: 167. 88. The transgenic plastid of claim 87, wherein the plastid is a chloroplast. 89. A host cell comprising the transgenic plastid of claim 87 or claim 88. 90. The host cell of claim 89, wherein the host cell is a prokaryote. 91. The host cell of claim 90, wherein the prokaryote is a *cyanobacterium*. 92. The host cell of 89, wherein the host cell is a plant cell. 93. The host cell of claim 92, wherein the plant cell is from a vascular plant. 94. The host cell of claim 92, wherein the plant cell is an alga. 95. The host cell of 94, wherein the alga is a green alga 96. The host cell of claim 95, wherein the green alga is a *Chlorophycean*.

97. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 15; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 15.

98. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 16; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 16.

99. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 17; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 17.

100. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 18; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 18.

101. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 19; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 19.

102. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 20; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 20.

103. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 21; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 21.

104. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 22; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 22.

105. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 23; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 23.

106. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 24; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 24.

107. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 163; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 163.

108. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 164; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 164.

109. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 165; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 165.

110. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 166; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 166.

111. An isolated polynucleotide comprising a nucleic acid sequence encoding a beta subunit of an acetyl CoA carboxylase, wherein the beta subunit of the acetyl CoA carboxylase comprises an amino acid sequence of SEQ ID NO: 167; or comprises an amino acid sequence that has at least 50%, at least 60%, at least 70%, at least 80%, at least 90%, at least 95%, at least 98%, or at least at least 99% sequence identity to the amino acid sequence of SEQ ID NO: 167.

112. An isolated polynucleotide comprising a nucleic acid sequence of SEQ ID NO: 158; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 158.

113. An isolated polynucleotide comprising a nucleic acid sequence of SEQ ID NO: 159; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 159.

114. An isolated polynucleotide comprising a nucleic acid sequence of SEQ ID NO: 160; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 160.

115. An isolated polynucleotide comprising a nucleic acid sequence of SEQ ID NO: 161; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 161.

116. An isolated polynucleotide comprising a nucleic acid sequence of SEQ ID NO: 162; or comprising a nucleic acid sequence that has at least 50%; at least 60%, at least 70%, at least 80%, at least 90%, at least 95%, at least 98%, or at least at least 99% sequence identity to the nucleic acid sequence of SEQ ID NO: 162.

117. An isolated polynucleotide comprising a nucleic acid sequence of SEQ ID NO: 168; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 168.

118. An isolated polynucleotide comprising a nucleic acid sequence of SEQ ID NO: 169; or comprising a nucleic acid sequence that has at least 50%, at least 60%, at least 70%, at least 80%, at least 90%, at least 95%, at least 98%, or at least at least 99% sequence identity to the nucleic acid sequence of SEQ ID NO: 169.

119. An isolated polynucleotide comprising a sequence encoding an acetyl CoA carboxylase comprising an amino acid sequence of: AGEANGSPIVTGPISVNPSMSPALD-PVAAAEAGKSAKAVDRSKGLWTRCD-KCGTILYIKHLKEHHHICFGCNY HLKMSSMERINHLIDAGX$_1$WRPLDEX$_2$LX$_3$PVDPLE FX$_4$DLKX$_5$YTDRIKEAQEKTGLQDGVRTGTGLLHGIPVA LGVMDFTYMGGSMGSVVGEKLTRLIEYATQEG MPVIIVCTSGGARMQEGIFSLMQMAKISAALHVHQ NX$_6$AN LLYIAILTSPTTGGVTASFGMLGDVII-AEPQAIIGFAGRRVIEQTLQEQLPDDFQ-TAEYLLEHGLLDLVVPRSFLK GALX$_7$EIIDFYRAAPYKKRGMIPFGVQHGTFLTTEEKV (SEQ ID NO: 11) wherein X$_1$ is T or D or E or N or H or Q or K; X$_2$ is T or D or E or N or H or Q or K; X$_3$ is S or D or E or N or H or Q or K; X$_4$ is S or D or E or N or H or Q or K; X$_5$ is S or D or E or N or H or Q or K; X$_6$ is C or D or E or N or H or Q or K; X$_7$ is Y or D or E or N or H or Q or K; provided, however, that the combination of X$_1$, X$_2$, X$_3$, X$_4$, X$_5$, X$_6$ and X$_7$ is not T, T, S, S, S, C, Y, respectively. 120. The isolated polynucleotide of claim 119, wherein X$_1$ is T, X$_2$ is T, X$_3$ is S, X$_4$ is D, X$_5$ is 5, X$_6$ is C and X$_7$ is Y. 121. The isolated polynucleotide of claim 119, wherein X$_1$ is T, X$_2$ is T, X$_3$ is S, X$_4$ is 5, X$_5$ is D, X$_6$ is C and X$_7$ is Y. 122. The isolated polynucleotide of claim 119, wherein X$_1$ is T, X$_2$ is T, X$_3$ is 5, X$_4$ is S, X$_5$ is 5, X$_6$ is D and X$_7$ is Y. 123. The isolated polynucleotide of claim 119, wherein X$_1$ is T, X$_2$ is T, X$_3$ is 5, X$_4$ is S, X$_5$ is S, X$_6$ is C and X$_7$ is D. 124. The isolated polynucleotide of claim 119, wherein X$_1$ is T, X$_2$ is T, X$_3$ is S, X$_4$ is D, X$_5$ is D, X$_6$ is C and X$_7$ is Y. 125. The isolated polynucleotide of claim 119, wherein X$_1$ is T, X, is T, X$_3$ is S, X$_4$ is D, X$_5$ is S, X$_6$ is D and X$_7$ is Y. 126. The isolated polynucleotide of claim 119, wherein X$_1$ is T, X$_2$ is T, X$_3$ is S, X$_4$ is D, X$_5$ is D, X$_6$ is C and X$_7$ is D.

127. An acetyl CoA carboxylase comprising an amino acid sequence of: AGEANGSPIVTGPISVNPSMSPALD-PVAAAEAGKSAKAVDRSKGLWIRCD-KCGTILYIKHLKEHHHICFGCNY HLKMSSMER-INHLID AGX$_1$WRPLDEX$_2$LX$_3$PVDPLEFX$_4$DLKX$_5$ YTDRIKEAQEKTGLQDGVRTGTGLLHGIPVA LGV MDFTYMGGSMGSVVGEKLTRLIEYATQEGMPVIIVC TSGGARMQEGIFSLMQMAKISAALHVHQNX$_6$ANLL YIAILTSPTTGGVTASFGMLGDVIIAEPQAIIGFAGRR VIEQTLQEQLPDDFQTAEYLLEHGLLDLVVPRSFLK GALX$_7$EIIDFYRAAPYKKRGMIPFGVQHGTFLTTEEKV (SEQ ID NO: 11) wherein X$_1$ is T or D or E or N or H or Q or K; X$_7$ is T or D or E or N or H or Q or K; X$_3$ is S or D or E or N or H or Q or K; X$_4$ is S or D or E or N or H or Q or K; X$_5$ is S or D or E or N or H or Q or K; X$_6$ is C or D or E or N or H or Q or K; X$_7$ is Y or D or E or N or H or Q or K; provided, however, that the combination of X$_1$, X$_2$, X$_3$, X$_4$, X$_5$, X$_6$ and X$_7$ is not T, T, S, S, S, C, Y, respectively. 128. The acetyl CoA carboxylase of claim 127, wherein X$_1$ is T, X$_2$ is T, X$_3$ is 5, X$_4$ is D, X$_5$ is 5, X$_6$ is C and X$_7$ is Y. 129. The acetyl CoA carboxylase of claim 127 wherein X$_1$ is T, X$_2$ is T, X$_3$ is 5, X$_4$ is S, X$_5$ is D, X$_6$ is C and X$_7$ is Y. 130. The acetyl CoA carboxylase of claim 127, wherein X$_1$ is T, X$_2$ is T, X$_3$ is 5, X$_4$ is S, X$_5$ is 5, X$_6$ is D and X$_7$ is Y. 131. The acetyl CoA carboxylase of claim 127, wherein X$_1$ is T, X$_2$ is T, X$_3$ is S, X$_4$ is 5, X$_5$ is S, X$_6$ is C and X$_7$ is D. 132. The acetyl CoA carboxylase of claim 127, wherein X$_1$ is T, X$_2$ is T, X$_3$ is S, X$_4$ is D, X$_5$ is D, X$_6$ is C and X$_7$ is Y. 133. The acetyl CoA carboxylase of claim 127, wherein X$_1$ is T, X$_2$ is T, X$_3$ is S, X$_4$ is D, X$_5$ is S, X$_6$ is D and X$_7$ is Y. 134. The acetyl CoA carboxylase of claim 127, wherein $X_1$ is T, $X_2$ is T, $X_3$ is S, $X_4$ is D, $X_5$ is D, $X_6$ is C and $X_7$ is D.

135. A vector comprising a nucleotide sequence encoding an acetyl CoA carboxylase comprising an amino acid sequence of: AGEANGSPIVTGPISVNPSMSPALD-PVAAAEAGKSAKAVDRSKGLWIRCDKCGTILYIKHL KEHHHICFGCNY HLKMSSMERINHLIDAGX$_1$WRPL DEX$_2$ LX$_3$PVDPLEFX$_4$DLKX$_5$YTDRIKEAQEKTGLQD GRTGTGLLHGIPVALGVMDFTYMGGSMGSVVGEK LTRLIEYATQEGMPVIIVCTSGGARMQEGIFSLMQMA KISAALHVHQNX$_6$AN LLYIAILTSPITGGVTASFGM-LGDVIIAEPQAIIGFAGR-RVIEQTLQEQLPDDFQTAEYLLEHGLLDLVVPRSFLK GALX$_7$EIIDFYRAAPYKKRGMIPFGVQHGTFLTTEEKV (SEQ ID NO: 11) wherein $X_1$ is T or D or E or N or H or Q or K; $X_2$ is T or D or E or N or H or Q or K; $X_3$ is S or D or E or N or H or Q or K; $X_4$ is S or D or E or N or H or Q or K; $X_5$ is S or D or E or N or H or Q or K; $X_6$ is C or D or E or N or H or Q or K; $X_7$ is Y or D or E or N or H or Q or K; provided, however, that the combination of $X_1$, $X_2$, $X_3$, $X_4$, $X_5$, $X_6$ and $X_7$ is not T, T, S, S, S, C, Y, respectively. 136. The vector of claim 135, wherein $X_1$ is T, $X_2$ is T, $X_3$ is S, $X_4$ is D, $X_5$ is S, $X_6$ is C and $X_7$ is Y. 137. The vector of claim 135, wherein $X_1$ is T, $X_2$ is T, $X_3$ is S, $X_4$ is S, $X_5$ is D, $X_6$ is C and $X_7$ is Y. 138. The vector of claim 135, wherein $X_1$ is T, $X_2$ is T, $X_3$ is 5, $X_4$ is 5, $X_5$ is S, $X_6$ is D and $X_7$ is Y. 139. The vector of claim 135, wherein $X_1$ is T, $X_2$ is T, $X_3$ is S, $X_4$ is S, $X_5$ is S, $X_6$ is C and $X_7$ is D. 140. The vector of claim 135, wherein $X_1$ is T, $X_7$ is T, $X_3$ is 5, $X_4$ is D, $X_5$ is D, $X_6$ is C and $X_7$ is Y. 141. The vector of claim 135, wherein $X_1$ is T, $X_2$ is T, $X_3$ is S, $X_4$ is D, $X_5$ is D, $X_6$ is D and $X_7$ is Y. 142. The vector of claim 135, wherein $X_1$ is T, $X_2$ is T, $X_3$ is 5, $X_4$ is D, $X_5$ is D, $X_6$ is C and $X_7$ is D: 143. The vector of any one of claims 135 to 142, wherein the vector is an expression vector. 144. The vector of any one of claims 135 to 143, wherein the vector further comprises a 5' regulatory region. 145. The vector of claim 144, wherein the 5' regulatory region further comprises a promoter. 146. The vector of claim 145, wherein the promoter is a constitutive promoter. 147. The vector of claim 145, wherein the promoter is an inducible promoter. 148. The vector of claim 147, wherein the inducible promoter is a light inducible promoter, nitrate inducible promoter or a heat responsive promoter. 149. The vector of any one of claims 135 to 148, further comprising a 3' regulatory region.

150. A method for increasing production of malonyl CoA in a photosynthetic organism comprising transforming the photosynthetic organism with a polynucleotide encoding AGEANGSPIVTGPISVNPSMSPALDPVAAAEAGKSA KAVDRSKGLWTRCDKCGTILYIKHLKEHHHICFGCN YHLKMSSMERINHLIDAGX$_1$WRPLDEX$_2$LX$_3$PVDPLE FX$_4$DLKX$_5$YTDRIKEAQEKTGLQDGVRTGTGLLHGIP VALGVMDFTYMGGSMGSVVGEKLTRLIEYATQEGM PVIIVCTSGGARMQEGIFSLMQMAKISAALHVHQN X$_6$ANLLYIAILTSPTTGGVTASFGMLGDVIIAEPQAIIGF AGRRVIEQTLQEQLPDDFQTAEYLLEHGLLDLVVPRS FLK GALX$_7$EIIDFYRAAPYKKRGMIPFGVQHGTFLTT EEKV (SEQ ID NO: 11) wherein $X_1$ is T or D or E or N or H or Q or K; $X_2$ is T or D or E or N or H or Q or K; $X_3$ is S or D or E or N or H or Q or K; $X_4$ is S or D or E or N or H or Q or K; $X_5$ is S or D or E or N or H or Q or K; $X_6$ is C or D or E or N or H or Q or K; $X_7$ is Y or D or E or N or H or Q or K; provided, however, that the combination of $X_1$, $X_2$, $X_3$, $X_4$, $X_5$, $X_6$ and $X_7$ is not T, T, S, S, S, C, Y, respectively. 151. The method of claim 150, wherein $X_1$ is T, $X_2$ is T, $X_3$ is 5, $X_4$ is D, $X_5$ is S, $X_6$ is C and $X_7$ is Y. 152. The method of claim 150, wherein $X_1$ is T, $X_2$ is T, $X_3$ is S, $X_4$ is S, $X_5$ is D, $X_6$ is C and $X_7$ is Y. 153. The method of claim 150, wherein $X_1$ is T, $X_2$ is T, $X_3$ is S, $X_4$ is S, $X_5$ is S, $X_6$ is D and $X_7$ is Y. 154. The method of claim 150, wherein $X_1$ is T, $X_2$ is T, $X_3$ is S, $X_4$ is 5, $X_5$ is S, $X_6$ is C and $X_7$ is D. 155. The method of claim 150, wherein $X_1$ is T, X, is T, $X_3$ is S, $X_4$ is D, $X_5$ is D, $X_6$ is C and $X_7$ is Y. 156. The method of claim 150, wherein $X_1$ is T, $X_2$ is T, $X_3$ is S, $X_4$ is D, $X_5$ is D, $X_6$ is D and $X_7$ is Y. 157. The method of claim 150, wherein $X_1$ is T, $X_2$ is T, $X_3$ is S, $X_4$ is D, $X_5$ is D, $X_6$ is C and $X_7$ is D. 158. The method of any one of claims 150 to 157, wherein the photosynthetic organism is a prokaryote. 159. The method of claim 158, wherein the prokaryote is a *cyanobacterium*. 160. The method of claim 150, wherein the organism is a eukaryote. 161. The method of claim 160, wherein the eukaryote is a vascular plant. 162. The method of claim 160, wherein the eukaryote is a non-vascular photosynthetic organism. 163. The method of claim 162, wherein the non-vascular photosynthetic organism is an alga. 164. The method any one of claims 150 to 163, further comprising transforming a plastid with the polynucleotide. 165. The method of claim 164, wherein the plastid is a chloroplast.

166. A method for increasing fatty acid synthesis in a photosynthetic organism comprising transforming the photosynthetic organism with a polynucleotide encoding AGEANGSPIVTGPISVNPSMSPALDPVAAAEAGKSA KAVDRSKGLWIRCDKCGTILYIKHLKEHHHICFGCNY HLKMSSMERINHLIDAGX$_1$WRPLDEX$_2$LX$_3$PVDPLEF X$_4$DLKX$_5$YTDRIKEAQEKTGLLQDGVRTGTGLLHGIP VALGVMDFTYMGGSMGSVVGEKLTRLIEYATQEG MPVIIVCTSGGARMQEGIFSLMQMAKISAALHVHQN X$_6$ANLLYIAILTSPTTGGVTASFGMLGDVIIAEPQAIIG FAGRRVIEQTLQEQLPDDFQTAEYLLEHGLLDLVVPR SFLK GALX$_7$EIIDFYRAAPYKKRGMIPFGVQHGTFLT TEEKV (SEQ ID NO: 11) wherein $X_1$ is T or D or E or N or H or Q or K; $X_2$ is T or D or E or N or H or Q or K; $X_3$ is S or D or E or N or H or Q or K; $X_4$ is S or D or E or N or H or Q or K; $X_5$ is S or D or E or N or H or Q or K; $X_6$ is C or D or E or N or H or Q or K; $X_7$ is Y or D or E or N or H or Q or K; provided, however, that the combination of $X_1$, $X_2$, $X_3$, $X_4$, $X_5$, $X_6$ and $X_7$ is not T, T, S, S, S, C, Y, respectively. 167. The method of claim 166, wherein $X_1$ is T, $X_2$ is T, $X_3$ is S, $X_4$ is D, $X_5$ is S, $X_6$ is C and $X_7$ is Y. 168. The method of claim 166, wherein $X_1$ is T, $X_2$ is T, $X_3$ is S, $X_4$ is S, $X_5$ is D, $X_6$ is C and $X_7$ is Y. 169. The method of claim 166, wherein $X_1$ is T, $X_2$ is T, $X_3$ is 5, $X_4$ is 5, $X_5$ is 5, $X_6$ is D and $X_7$ is Y. 170. The method of claim 166, wherein $X_1$ is T, $X_2$ is T, $X_3$ is S, $X_4$ is 5, $X_5$ is S, $X_6$ is C and $X_7$ is D. 171. The method of claim 166, wherein $X_1$ is T, $X_2$ is T, $X_3$ is S, $X_4$ is D, $X_5$ is D, $X_6$ is C and $X_7$ is Y. 172. The method of claim 166, wherein $X_1$ is T, $X_2$ is T, $X_3$ is S, $X_4$ is D, $X_5$ is D, $X_6$ is D and $X_7$ is Y. 173. The method of claim 166, wherein $X_1$ is T, $X_2$ is T, $X_3$ is S, $X_4$ is D, $X_5$ is D, $X_6$ is C and $X_7$ is D. 174. The method of any one of claims 166 to 173, wherein the photosynthetic organism is a prokaryote. 175. The method of claim 174, wherein the prokaryote is a *cyanobacterium*. 176. The method of claim 166, wherein the organism is a eukaryote. 177. The method of claim 176, wherein the eukaryote is a vascular plant. 178. The method of claim 176, wherein the eukaryote is a non-vascular photosynthetic organism. 179. The method of claim 178, wherein the non-vascular photosynthetic organism is an alga. 180. The method of any one of claims 166 to 179, further comprising transforming a plastid with the polynucleotide. 181. The method of claim 180, wherein the plastid is a chloroplast.

182. A transgenic host cell comprising a nucleotide sequence encoding AGEANGSPIVTGPISVNPSMSPALD-PVAAAEAGKSAKAVDRSKGLWTRCDKCGTILYIKHL KEHHHICFGCNYHLKMSSMERINHLIDAGX$_1$WRPLD EX$_2$LX$_3$PVDPLEFX$_4$DLKX$_5$YTDRIKEAQEKTGLQDG VRTGTGLLHGIPVALGVMDFTYMGGSMGSVVGEKL TRLIEYATQEGMPVIIVCTSGGARMQEGIFSLMQMA
KISAALHVHQNX$_6$AN LLYIAILTSPTTGGVTASFGM-
LGDVIIAEPQAIIGFAGRRVIEQTLQEQLPDDFQTAEY
LLEHGLLDLVVPRSFLK
GALX$_7$EIIDFYRAAPYKKRGMIPFGVQHGTFLTTEEKV
(SEQ ID NO: 11) wherein X$_1$ is T or D or E or N or H or Q or K; X$_2$ is T or D or E or N or H or Q or K; X$_3$ is S or D or E or N or H or Q or K; X$_4$ is S or D or E or N or H or Q or K; X$_5$ is S or D or E or N or H or Q K; X$_6$ is C or D or E or N or H or Q or K; X$_7$ is Y or D or E or N or H or Q or K; provided, however, that the combination of X$_1$, X$_2$, X$_3$, X$_4$, X$_5$, X$_6$ and X$_7$ is not T, T, S, S, S, C, Y, respectively. 183. The transgenic host cell of claim 182, wherein X$_1$ is T, X$_2$ is T, X$_3$ is S, X$_4$ is D, X$_5$ is S, X$_6$ is C and X$_7$ is Y. 184. The transgenic host cell of claim 182, wherein X$_1$ is T, X$_2$ is T, X$_3$ is 5, X$_4$ is 5, X$_5$ is D, X$_6$ is C and X$_7$ is Y. 185. The transgenic host cell of claim 182, wherein X$_1$ is T, X$_2$ is T, X$_3$ is S, X$_4$ is 5, X$_5$ is 5, X$_6$ is D and X$_7$ is Y. 186. The transgenic host cell of claim 182, wherein X$_1$ is T, X$_2$ is T, X$_3$ is 5, X$_4$ is 5, X$_5$ is S, X$_6$ is C and X$_7$ is D. 187. The transgenic host cell of claim 182, wherein X$_1$ is T, X$_2$ is T, X$_3$ is S, X$_4$ is D, X$_5$ is D, X$_6$ is C and X$_7$ is Y. 188. The transgenic host cell of claim 182, wherein X, is T, X$_2$ is T, X$_3$ is S, X$_4$ is D, X$_5$ is D, X$_6$ is D and X$_7$ is Y. 189. The transgenic host cell of claim 182, wherein X$_1$ is T, X$_2$ is T, X$_3$ is S, X$_4$ is D, X$_5$ is D, X$_6$ is C and X$_7$ is D. 190. The transgenic host cell of any one of claims 182 to 189, wherein the host cell is a prokaryote. 191. The transgenic host cell of claim 190, wherein the host cell is a *cyanobacterium*. 192: The transgenic host cell of claim 182, wherein the host cell is a plant cell. 193. The transgenic host cell of claim 192, wherein the plant cell is from a vascular plant. 194. The transgenic host cell of claim 182, wherein the plant cell is from an alga. 195. The transgenic host cell of claim 194, wherein the alga is a green alga. 196. The transgenic host cell of claim 195, wherein the green alga is a *Chlorophycean*.

197. A transgenic plastid comprising a polynucleotide encoding an acetyl CoA carboxylase comprising an amino acid sequence of: AGEANGSPIVTGPISVNPSMSPALD-
PVAAAEAGKSAKAVDRSKGLWTRCDKCGTILYIKHL
KEHHHICFGCNYHLKMSSMERINHLIDAGX$_1$WRPLD
EX$_2$LX$_3$PVDPLEFX$_4$DLKX$_5$YTDRIKEAQEKTGLQDGV
RTGTGLLHGIPVALGVMDFTYMGGSMGSVVGEKLT
RLIEYATQEGMPVIIVCTSGGARMQEGIFSLMQMAKI
SAALHVHQNX$_6$AN LLYIAILTSPTTGGVTASFGM-
LGDVIIAEPQAIIGFAGR-
RVIEQTLQEQLPDDFQTAEYLLEHGLLDLVVPRSFLK
GALX$_7$EIIDFYRAAPYKKRGMIPFGVQHGTFLTTEEKV
(SEQ ID NO: 11) wherein X$_1$ is T or D or E or N or H or Q or K; X$_2$ is T or D or E or N or H or Q or K; X$_3$ is S or D or E or N or H or Q or K; X$_4$ is S or D or E or N or H or Q or K; X$_5$ is S or D or E or N or H or Q or K; X$_6$ is C or D or E or N or H or Q or K; X$_7$ is Y or D or E or N or H or Q or K; provided, however, that the combination of X$_1$, X$_2$, X$_3$, X$_4$, X$_5$, X$_6$ and X$_7$ is not T, T, S, S, S, C, Y, respectively. 198. The transgenic plastid of claim 197, wherein X$_1$ is T, X$_2$ is T, X$_3$ is 5, X$_4$ is D, X$_5$ is 5, X$_6$ is C and X$_7$ is Y. 199. The transgenic plastid of claim 197, wherein X$_1$ is T, X$_2$ is T, X$_3$ is 5, X$_4$ is S, X$_5$ is D, X$_6$ is C and X$_7$ is Y. 200. The transgenic plastid of claim 197, wherein X$_1$ is T, X$_2$ is T, X$_3$ is S, X$_4$ is 5, X$_5$ is 5, X$_6$ is D and X$_7$ is Y. 201. The transgenic plastid of claim 197, wherein X$_1$ is T, X$_2$ is T, X$_3$ is S, X$_4$ is 5, X$_5$ is S, X$_6$ is C and X$_7$ is D. 202. The transgenic plastid of claim 197, wherein X$_1$ is T, X$_2$ is T, X$_3$ is S, X$_4$ is D, X$_5$ is D, X$_6$ is C and X$_7$ is Y. 203. The transgenic plastid of claim 197, wherein X$_1$ is T, X$_2$ is T, X$_3$ is S, X$_4$ is D, X$_5$ is D, X$_6$ is D and X$_7$ is Y. 204. The transgenic plastid of claim 197, wherein X$_1$ is T, X$_2$ is T, X$_3$ is S, X$_4$ is D, X$_5$ is D, X$_6$ is C and X$_7$ is D. 205. The transgenic plastid of any one of claims 197 to 204, wherein the plastid is a chloroplast. 206. A host cell comprising the transgenic plastid of any one of claims 197 to 205. 207. The host cell of claim 206, wherein the host cell is a prokaryote. 208. The host cell of claim 207, wherein the prokaryote is a *cyanobacterium*. 209. The host cell of claim 206, wherein the host cell is a plant cell. 210. The host cell of claim 209, wherein the plant cell is from a vascular plant. 211. The host cell of claim 209, wherein the plant cell is an alga. 212. The transgenic host cell of 211, wherein the alga is a green alga. 213. The transgenic host cell of claim 212, wherein the green alga is a *Chlorophycean*.

214. The ACCase of claim 48, wherein the mammalian ACCase comprises the amino acid sequence of mouse (*Mus Musculus*: NM__133360.2 Identity: 99%); cattle (*Bos Taurus*: NM__174224.2. Identity: 97%); dog (*Canis Lupus*: XM__862501.1. Identity: 96%); chicken (*Gallus gallus*: NM__205505.1. Identity: 92%); or goat (*Capra hircus*: DQ370054.1. Identity: 98%).

215. The isolated polypeptide of claim 1, wherein the photosynthetic organism is *Chlamydomonas reinhardtii*.

Some of the novel ACCases comprise the following amino acid sequence:
AGEANGSPIVTGPISVNPSMSPALDPVAAAEAGKSA
KAVDRSKGLWTRCDKCGTILYIKHLKEHHHICFGC
NYHLKMSSMERINHLIDAGX1WRPLDEX2LX3PV
DPLEFX4DLKX5YTDRIKEAQEKTGLQDGVRTGTGL
LHGIPVALGVMDFTYMGGSMGSVVGEKLTRLIEYAT
QEGMPVIIVCTSGGARMQEGIFSLMQMAKISAALHV
HQNX6ANLLYIAILTSPTTGGVTASFGMLGDVIIAEPQ
AIIGFAGRRVIEQTLQEQLPDDFQTAEYLLEHGLLDLV
VPRSFLKGALX7EIIDFYRAAPYKKRGMIPFGVQHGT
FLTTEEKVTG (SEQ ID NO: 2) wherein X1 is T or D or E or N or H or Q or K; X2 is T or D or E or N or H or Q or K; X3 is S or D or E or N or H or Q or K; X4 is S or D or E or N or H or Q or K; X5 is S or D or E or N or H or Q or K; X6 is C or D or E or N or H or Q or K; and X7 is Y or D or E or N or H or Q or K. Specifically excluded is the amino acid sequence of the wild type ACCase of SEQ ID NO: 1, that is, that the combination of X1, X2, X3, X4, X5, X6 and X7 is not T, T, S, S, S, C, Y, respectively, is expressly excluded from the scope of the present disclosure.

The present disclosure encompasses any polypeptide which has one of the possible amino acid sequences allowed by SEQ ID NO: 2. For example, and without limitation, in certain embodiments, X1 is T, X2 is T, X3 is S, X4 is D, X5 is S, X6 is C and X7 is Y. In other embodiments, X1 is T, X2 is T, X3 is S, X4 is S, X5 is D, X6 is C and X7 is Y. In further embodiments X1 is T, X2 is T, X3 is S, X4 is S, X5 is S, X6 is D and X7 is Y. In still further embodiments X1 is T, X2 is T, X3 is S, X4 is S, X5 is S, X6 is C and X7 is D. In other embodiments X1 is T, X2 is T, X3 is S, X4 is D, X5 is D, X6 is C and X7 is Y. In additional embodiments X1 is T, X2 is T, X3 is S, X4 is D, X5 is S, X6 is D and X7 is Y. While in yet another exemplary embodiment X1 is T, X2 is T, X3 is S, X4 is D, X5 is D, X6 is C and X7 is D.

Also provided are polypeptides and polynucleotides consisting of or consisting essentially of any of the amino acid sequences described herein. The above polypeptides and polynucleotides may be provided in an isolated, purified or substantially purified form.

Also provided are vectors comprising polynucleotides encoding any of the novel ACCases described by SEQ ID NO: 2, provided that the polynucleotide does not encode for a polypeptide of SEQ ID NO: 2, wherein is the combination of X1, X2, X3, X4, X5, X6 and X7 is T, T, S, S, S, C, Y, respectively. The vector may be a cloning vector or an expression vector. In the case of an expression vector, the vector may further comprise a 5' regulatory region, a 3' regulatory region, or both. In certain embodiments, the 5' regulatory region contains a promoter, which may be a constitutive promoter or an inducible promoter. Also provided are vectors consisting of a polynucleotide encoding a polypeptide of SEQ ID NO: 2 and vectors consisting essentially of a polynucleotide encoding a polypeptide of SEQ ID NO: 2.

One aspect provides a method for increasing the production of malonyl CoA in a photosynthetic cell or organism by transforming said cell or organism with a polynucleotide encoding any of the novel ACCase polypeptides of SEQ ID NO: 2. The cell or organism may be a prokaryote or a eukaryote. In one embodiment, the cell or organism is a *cyanobacterium*. In another embodiment, the photosynthetic organisms is a vascular plant, while in other embodiments the cell or organism is a non-vascular photosynthetic eukaryote such as an alga. In one embodiment, the method further comprises transforming a plastid of the photosynthetic cell or organism with a polynucleotide encoding a polypeptide of SEQ ID NO: 2. Any plastid may be transformed, for example a chloroplast, a chloroplast or a leucoplast.

Another aspect provides a method for increasing fatty acid synthesis in a photosynthetic cell or organism comprising transforming said cell or organism with a polynucleotide encoding any of the novel ACCase polypeptides of SEQ ID NO: 2. The photosynthetic cell or organism may be a prokaryote or a eukaryote. In the case of prokaryote, the photosynthetic cell or organism may be a *cyanobacterium*. In the case of a eukaryote, the photosynthetic cell or organism may be a vascular plant or a non-vascular photosynthetic organism, such as an alga. In certain embodiments, the method further comprises transforming the polynucleotide encoding the novel ACCase into a plastid of the photosynthetic cell or organism. The plastid may be, but is not limited to, a chloroplast, a chloroplast, or a leucoplast.

Yet another aspect provides a transgenic host cell comprising a polynucleotide encoding a polypeptide of SEQ ID NO: 2. The transgenic host cell may be a prokaryote or a eukaryote. The host cell may be a single cell organism or a part of a multicellular organism. In one embodiment, the host cell is a bacterium, for example a *cyanobacterium*. In other embodiments, the cell is a plant cell. The plant cell may be from a vascular plant or from a non-vascular plant, such as an alga.

Still another aspect provides a transgenic plastid comprising a polynucleotide encoding a polypeptide of SEQ ID NO: 2. The plastid may be a chloroplast, a chloroplast or a leucoplast. In a further embodiment, the transgenic plastid is contained in a plant cell. In one embodiment, the plant cell is from or is part of a vascular plant. In other embodiments, the plant cell is an algal cell.

BRIEF DESCRIPTION OF THE DRAWINGS

These and other features, aspects, and advantages of the present disclosure will become better understood with regard to the following description, appended claims and accompanying figures where:

FIG. 18 shows the open reading frame of the first transcript (cSDACC1; SEQ ID NO: 74) of the novel ACCase β-subunit of *Scenedesmus dimorphus*. A putative chloroplast targeting transit peptide is underlined.

FIG. 19 shows the open reading frame of the second transcript (cSDACC2; SEQ ID NO: 80) of the novel ACCase β-subunit of *Scenedesmus dimorphus*. A putative chloroplast targeting transit peptide is underlined.

FIG. 20 shows the open reading frame of the third transcript (cSDACC3; SEQ ID NO: 84) of the novel ACCase β-subunit of *Scenedesmus dimorphus*. A putative chloroplast targeting transit peptide is underlined.

FIG. 21 shows the open reading frame of the fourth transcript (cSDACC4; SEQ ID NO: 88) of the novel ACCase βsubunit of *Scenedesmus dimorphus*. A putative chloroplast targeting transit peptide is underlined.

FIG. 22 shows the open reading frame of the fifth transcript (cSDACC5; SEQ ID NO: 92) of the novel ACCase β-subunit of *Scenedesmus dimorphus*. A putative chloroplast targeting transit peptide is underlined.

FIG. 23 shows an alignment of all five transcripts of the novel *Scenedesmus dimorphus* ACCase β-subunit. From top to bottom: Majority (SEQ ID NO: 171): cSDACC1 (SEQ ID NO: 170); cSDACC2 (SEQ ID NO: 80); cSDACC3 (SEQ ID NO: 84); cSDACC4 (SEQ ID NO: 88); and cSDACC5 (SEQ ID NO: 92). SEQ ID NO: 170 is the same sequence as SEQ ID NO: 74 with an "A" missing at the 3-prime end of the sequence.

FIG. 24 shows an alignment of the coded proteins of the five transcripts of the novel *Scenedesmus dimorphus* ACCase β-subunit. From top to bottom: Majority (SEQ ID NO: 172); cSDACC1-P (SEQ ID NO: 78): cSDACC2-P (SEQ ID NO: 81); cSDACC3-P (SEQ ID NO: 173); cSDACC4-P (SEQ ID NO: 89); and cSDACC5-P (SEQ ID NO: 94). SEQ ID NO: 173 is a portion of SEC ID NO: 85.

DETAILED DESCRIPTION

Figure 1:
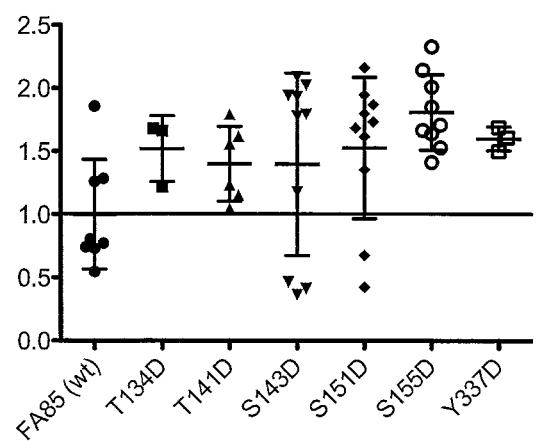
FIG. 1 shows BODIPY staining by Guava of algae transformed with mutated ACCases described herein. The fold change in population median fluorescence as compared to the wild-type organism (FA85) is shown for six mutant ACCase overexpression strains (T134D, T141D, S143D, S151D, S155D, and Y337D).

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present inventive discovery.

As used in this specification and the appended claims, the singular forms "a", "an" and "the" include plural reference unless the context clearly dictates otherwise Endogenous An endogenous nucleic acid, nucleotide, polypeptide, or protein as described herein is defined in relationship to the host organism. An endogenous nucleic acid, nucleotide, polypeptide, or protein is one that naturally occurs in the host organism.

Exogenous

An exogenous nucleic acid, nucleotide, polypeptide, or protein as described herein is defined in relationship to the host organism. An exogenous nucleic acid, nucleotide, polypeptide, or protein is one that does not naturally occur in the host organism or is a different location in the host organism.

The following (SEQ ID NOs: 1 to 55) are amino acid and nucleotide sequences for the β-subunit of acetyl-CoA carboxylase from *Chlamydomonas reinhardtii* (CC-503 cw92 mt+) that are useful in the embodiments disclosed herein.

If a stop codon is not present at the end of a coding sequence, one of skill in the art would know to insert nucleotides encoding for a stop codon (TAA, TAG, or TGA) at the end of the nucleotide sequence. If an initial start codon (Met) is not present from the amino acid sequence, one of skill in the art would be able to include, at the nucleotide level, an initial ATG, so that the translated polypeptide would have the initial Met.

Also listed below are primer sequences and affinity tags useful in the embodiments disclosed herein.

For SEQ ID NOs: 1-10, the last two amino acids, Thr and Gly, are not part of the protein sequence.

SEQ ID NO: 1 is the amino acid sequence for the β-subunit of acetyl-CoA carboxylase. The first 43 amino acids are a probable transit peptide.

SEQ ID NO: 2 is a protein sequence for the β-subunit of acetyl-CoA carboxylase without an initial Met.

SEQ ID NO: 3 is a Strep affinity tag (positions 1 to 13) and the protein sequence for the β-subunit of acetyl-CoA carboxylase.

SEQ ID NO: 4 is a protein sequence for the β-subunit of acetyl-CoA carboxylase without an initial Met and with a Thr to Asp mutation at position 91.

SEQ ID NO: 5 is a protein sequence for the β-subunit of acetyl-CoA carboxylase without an initial Met and with a Thr to Asp mutation at position 98.

SEQ ID NO: 6 is a protein sequence for the β-subunit of acetyl-CoA carboxylase without an initial Met and with a Ser to Asp mutation at position 100.

SEQ ID NO: 7 is a protein sequence for the β-subunit of acetyl-CoA carboxylase without an initial Met and with a Ser to Asp mutation at position 108.

SEQ ID NO: 8 is a protein sequence for the β-subunit of acetyl-CoA carboxylase without an initial Met and with a Ser to Asp mutation at position 112.

SEQ ID NO: 9 is a protein sequence for the β-subunit of acetyl-CoA carboxylase without an initial Met and with a Tyr to Asp mutation at position 294.

SEQ ID NO: 10 is a protein sequence for the β-subunit of acetyl-CoA carboxylase without an initial Met and with a Cys to Ser mutation at position 212.

SEQ ID NO: 11 is a protein sequence for the β-subunit of acetyl-CoA carboxylase with variable amino acids at $X_1$, $X_2$, $X_3$, $X_4$, $X_5$, $X_6$, and $X_7$.

SEQ ID NO: 12 is a protein sequence for the β-subunit of acetyl-CoA carboxylase without variable amino acids at $X_1$, $X_2$, $X_3$, $X_4$, $X_5$, $X_6$, and $X_7$.

SEQ ID NO: 13 is an open reading frame for the O-subunit of acetyl-CoA carboxylase. The first 43 amino acids are a probable transit peptide.

SEQ ID NO: 14 is a Strep affinity tag (positions 1 to 13) and the protein sequence for the β-subunit of acetyl-CoA carboxylase.

SEQ ID NO: 15 is a protein sequence for the β-subunit of acetyl-CoA carboxylase with a Thr to Asp mutation at position 92.

SEQ ID NO: 16 is a protein sequence for the O-subunit of acetyl-CoA carboxylase with a Thr to Asp mutation at position 99.

SEQ ID NO: 17 is a protein sequence for the β-subunit of acetyl-CoA carboxylase with a Ser to Asp mutation at position 101.

SEQ ID NO: 18 is a protein sequence for the β-subunit of acetyl-CoA carboxylase with a Ser to Asp mutation at position 109.

SEQ ID NO: 19 is a protein sequence for the β-subunit of acetyl-CoA carboxylase with a Ser to Asp mutation at position 113.

SEQ ID NO: 20 is a protein sequence for the β-subunit of acetyl-CoA carboxylase with a Cys to Ser mutation at position 213.

SEQ ID NO: 21 is a protein sequence for the β-subunit of acetyl-CoA carboxylase with a Tyr to Asp mutation at position 295.

SEQ ID NO: 22 is a protein sequence for the β-subunit of acetyl-CoA carboxylase with a Ser to Asp mutation at 109 and a Ser to Asp mutation at 113.

SEQ ID NO: 23 is a protein sequence for the β-subunit of acetyl-CoA carboxylase with a Ser to Asp mutation at 109, a Ser to Asp mutation at 113, and a Cys to Ser mutation at 213.

SEQ ID NO: 24 is a protein sequence for the β-subunit of acetyl-CoA carboxylase with a Ser to Asp mutation at 109, a Ser to Asp mutation at 113, and a Tyr to Asp mutation at 295.

SEQ ID NO: 25 is a nucleotide sequence of a Strep affinity tag codon optimized for the chloroplast genome of *C. reinhardtii*.

SEQ ID NO: 26 is a codon optimized (for the chloroplast genome of *C. reinhardtii*) nucleic acid sequence encoding the β-subunit of acetyl-CoA carboxylase.

SEQ ID NO: 27 is a codon optimized (for the chloroplast genome of *C. reinhardtii*) nucleic acid sequence encoding the β-subunit of acetyl-CoA carboxylase with a C213S mutation, according to the numbering of SEQ ID NO: 26.

SEQ ID NO: 28 is a codon optimized (for the chloroplast genome of *C. reinhardtii*) nucleic acid sequence encoding the β-subunit of acetyl-CoA carboxylase with a S101D mutation, according to the numbering of SEQ ID NO: 26.

SEQ ID NO: 29 is a codon optimized (for the chloroplast genome of *C. reinhardtii*) nucleic acid sequence encoding the β-subunit of acetyl-CoA carboxylase with a S109D mutation, according to the numbering of SEQ ID NO: 26.

SEQ ID NO: 30 is a codon optimized (for the chloroplast genome of *C. reinhardtii*) nucleic acid sequence encoding the β-subunit of acetyl-CoA carboxylase with a S113D mutation, according to the numbering of SEQ ID NO: 26.

SEQ ID NO: 31 is a codon optimized (for the chloroplast genome of *C. reinhardtii*) nucleic acid sequence encoding the β-subunit of acetyl-CoA carboxylase with a T92D mutation, according to the numbering of SEQ ID NO: 26.

SEQ ID NO: 32 is a codon optimized (for the chloroplast genome of *C. reinhardtii*) nucleic acid sequence encoding the β-subunit of acetyl-CoA carboxylase with a T99D mutation, according to the numbering of SEQ ID NO: 26.

SEQ ID NO: 33 is a codon optimized (for the chloroplast genome of *C. reinhardtii*) nucleic acid sequence encoding the β-subunit of acetyl-CoA carboxylase with a Y295D mutation, according to the numbering of SEQ ID NO: 26).

SEQ ID NO: 34 is a codon optimized (for the chloroplast genome of *C. reinhardtii*) nucleic acid sequence encoding the β-subunit of acetyl-CoA carboxylase with a S109D and a S113D mutation, according to the numbering of SEQ ID NO: 26).

SEQ ID NO: 35 is a codon optimized (for the chloroplast genome of *C. reinhardtii*) nucleic acid sequence encoding the β-subunit of acetyl-CoA carboxylase with a S109D, a S113D, and a Y295D mutation, according to the numbering of SEQ ID NO: 26).

SEQ ID NO: 36 is a codon optimized (for the chloroplast genome of *C. reinhardtii*) nucleic acid sequence encoding the β-subunit of acetyl-CoA carboxylase with a S109D mutation, a S113D mutation, and a C213S mutation, according to the numbering of SEQ ID NO: 26).

SEQ ID NO: 37 is a non codon optimized nucleic acid sequence encoding the β-subunit of acetyl-CoA carboxylase without a stop codon.

SEQ ID NO: 38 is an amino acid sequence of a Strep affinity tag.

SEQ ID NO: 39 is an amino acid sequence of the probable transit peptide for the β-subunit of acetyl-CoA carboxylase.

SEQ ID NO: 40 is a PCR primer.
SEQ ID NO: 41 is a PCR primer.
SEQ ID NO: 42 is a PCR primer.
SEQ ID NO: 43 is a PCR primer.
SEQ ID NO: 44 is a PCR primer.
SEQ ID NO: 45 is a PCR primer.
SEQ ID NO: 46 is a PCR primer.
SEQ ID NO: 47 is a PCR primer.
SEQ ID NO: 48 is a PCR primer.
SEQ ID NO: 49, is a PCR primer.
SEQ ID NO: 50 is a PCR primer.
SEQ ID NO: 51 is a PCR primer.
SEQ ID NO: 52 is a PCR primer.
SEQ ID NO: 53 is a PCR primer.
SEQ ID NO: 54 is a PCR primer.
SEQ ID NO: 55 is a PCR primer.

The following are amino acid and nucleotide sequences (SEQ ID NOs: 56 to 113) of five transcripts of a newly cloned acetyl-CoA carboxylase β-subunit from *Scenedesmus dimorphus* that are useful in the embodiments disclosed herein. If a stop codon is not present at the end of a coding sequence, one of skill in the art would know to insert nucleotides encoding for a stop codon (TAA, TAG, or TGA) at the end of the nucleotide sequence. If an initial start codon (Met) is not present from the amino acid sequence, one of skill in the art would be able to include, at the nucleotide level, an initial ATG, so that the translated polypeptide would have the initial Met. Also listed below are primer sequences, conserved motifs, and affinity tags useful in the embodiments disclosed herein.

A transcript is an unique mRNA encoding an unique protein sequence that may have been produced by alternative splicing from one gene.

SEQ ID NO: 56 is a conserved amino acid motif found in a diverse range of ACCase protein sequences.

SEQ ID NO: 57 is a conserved amino acid motif found in a diverse range of ACCase protein sequences.

SEQ ID NO: 58 is a conserved amino acid motif found in a diverse range of ACCase protein sequences.

SEQ ID NO: 59 is a conserved amino acid motif found in a diverse range of ACCase protein sequences.

SEQ ID NO: 60 is a conserved amino acid motif found in a diverse range of ACCase protein sequences.

SEQ ID NO: 61 is a conserved amino acid motif found in a diverse range of ACCase protein sequences.

SEQ ID NO: 62 is a PCR primer.
SEQ ID NO: 63 is a PCR primer.
SEQ ID NO: 64 is a PCR primer.
SEQ ID NO: 65 is a PCR primer.
SEQ ID NO: 66 is a PCR primer.
SEQ ID NO: 67 is a PCR primer.
SEQ ID NO: 68 is a PCR primer.
SEQ ID NO: 69 is an oligo (dT) PCR primer.
SEQ ID NO: 70 is a putative ACC fragment.
SEQ ID NO: 71 is a putative ACC fragment.
SEQ ID NO: 72 is a putative ACC fragment.
SEQ ID NO: 73 is a putative ACC fragment.

SEQ ID NO: 74 is a nucleotide sequence of the first transcript of the novel acetyl-CoA carboxylase β-subunit from *Scenedesmus dimorphus* (SDACC1). The open reading frame includes a putative chloroplast targeting transit peptide sequence.

SEQ ID NO: 75 is a nucleotide sequence encoding for the first novel ACCase β-subunit protein. SEQ ID NO: 75 does not include a nucleic acid encoding for a putative chloroplast targeting transit peptide.

SEQ ID NO: 76 is a nucleotide sequence encoding for a putative chloroplast targeting transit peptide. This nucleotide sequence was found at the 5' end of each of the five transcripts encoding for all of the five novel ACCase β-subunit proteins.

SEQ ID NO: 77 is the translated amino acid sequence of SEQ ID NO: 75.

SEQ ID NO: 78 is the translated amino acid sequence of SEQ ID NO: 74.

SEQ ID NO: 79 is the translated amino acid sequence of SEQ ID NO: 76.

SEQ ID NO: 80 is a nucleotide sequence of the second transcript of the novel acetyl-CoA carboxylase β-subunit from *Scenedesmus dimorphus* (SDACC2). The open reading frame includes a putative chloroplast targeting transit peptide sequence.

SEQ ID NO: 81 is the translated amino acid sequence of SEQ ID NO: 80.

SEQ ID NO: 82 is a nucleotide sequence encoding for the second novel ACCase β-subunit protein. SEQ ID NO: 82 does not include a nucleic acid encoding for a putative chloroplast targeting transit peptide.

SEQ ID NO: 83 is the translated amino acid sequence of SEQ ID NO: 82.

SEQ ID NO: 84 is a nucleotide sequence of the third transcript of the newly cloned acetyl-CoA carboxylase β-subunit from *Scenedesmus dimorphus* (SDACC3). The open reading frame includes a putative chloroplast targeting transit peptide sequence.

SEQ ID NO: 85 is the translated amino acid sequence of SEQ ID NO: 84.

SEQ ID NO: 86 is a nucleotide sequence encoding for the third novel ACCase β-subunit protein. SEQ ID NO: 86 does not include a nucleic acid encoding for a putative chloroplast targeting transit peptide.

SEQ ID NO: 87 is the translated amino acid sequence of SEQ ID NO: 86.

SEQ ID NO: 88 is a nucleotide sequence of the fourth transcript of the newly cloned acetyl-CoA carboxylase β-subunit from *Scenedesmus dimorphus* (SDACC4). The open reading frame includes a putative chloroplast targeting transit peptide sequence.

SEQ ID NO: 89 is the translated amino acid sequence of SEQ ID NO: 88.

SEQ ID NO: 90 is a nucleotide sequence encoding for the fourth novel ACCase β-subunit protein. SEQ ID NO: 90 does not include a nucleic acid encoding for a putative chloroplast targeting transit peptide.

SEQ ID NO: 91 is the translated amino acid sequence of SEQ ID NO: 90.

SEQ ID NO: 92 is a nucleotide sequence of the fifth transcript of the newly cloned acetyl-CoA carboxylase β-subunit from *Scenedesmus dimorphus* (SDACC5). The open reading frame includes a putative chloroplast targeting transit peptide sequence.

SEQ ID NO: 93 is a nucleotide sequence encoding for the fifth novel ACCase β-subunit protein. SEQ ID NO: 93 does not include a nucleic acid encoding for a putative chloroplast targeting transit peptide.

SEQ ID NO: 94 is the translated amino acid sequence of SEQ ID NO: 92.

SEQ ID NO: 95 is the translated amino acid sequence of SEQ ID NO: 93.

SEQ ID NO: 96 is the genomic sequence encoding for the second novel ACCase β-subunit protein (SDACC2). The last 81 nucleotides were not resolved because of a lack of sequencing information.

SEQ ID NO: 97 is the nucleotide sequence of SEQ ID NO: 75, codon optimized for expression in the chloroplast of *Scenedesmus dimorphus* based on the *Chlamydomonas reinhardtii* tRNA codon usage table. In addition, a Flag tag has been attached to the 5' prime end of the nucleotide sequence after the initial ATG. The Flag tag was also codon optimized for expression in the chloroplast of *Scenedesmus dimorphus* based on the *Chlamydomonas reinhardtii* tRNA codon usage table.

SEQ ID NO: 98 is the sequence of SEQ ID NO: 97 without the Flag tag.

SEQ ID NO: 99 is the nucleotide sequence of SEQ ID NO: 82, codon optimized for expression in the chloroplast of *Scenedesmus dimorphus* based on the *Chlamydomonas reinhardtii* tRNA codon usage table.

SEQ ID NO: 100 is the amino acid sequence of SEQ ID NO: 77 with Ser 91 mutated to Asp.

SEQ ID NO: 101 is the amino acid sequence of SEQ ID NO: 77 with Thr 98 mutated to Asp.

SEQ ID NO: 102 is the amino acid sequence of SEQ ID NO: 77 with Ser 100 mutated to Asp.

SEQ ID NO: 103 is the amino acid sequence of SEQ ID NO: 77 with Val 108 mutated to Asp.

SEQ ID NO: 104 is the amino acid sequence of SEQ ID NO: 77 with Pro 112 mutated to Asp.

SEQ ID NO: 105 is the amino acid sequence of SEQ ID NO: 77 with Ser 120 mutated to Asp.

SEQ ID NO: 106 is the amino acid sequence of SEQ ID NO: 77 with Thr 259 mutated to Asp.

SEQ ID NO: 107 is the amino acid sequence of SEQ ID NO: 83 with Ser 91 mutated to Asp.

SEQ ID NO: 108 is the amino acid sequence of SEQ ID NO: 83 with Thr 98 mutated to Asp.

SEQ ID NO: 109 is the amino acid sequence of SEQ ID NO: 83 with Ser 100 mutated to Asp.

SEQ ID NO: 110 is the amino acid sequence of SEQ ID NO: 83 with Val 108 mutated to Asp.

SEQ ID NO: 111 is the amino acid sequence of SEQ ID NO: 83 with Pro 112 mutated to Asp.

SEQ ID NO: 112 is the amino acid sequence of SEQ ID NO: 83 with Ser 120 mutated to Asp.

SEQ ID NO: 113 is the amino acid sequence of SEQ ID NO: 83 with Thr 259 mutated to Asp.

The following are additional amino acid and nucleotide sequences that are useful in the embodiments disclosed herein. If a stop codon is not present at the end of a coding sequence, one of skill in the art would know to insert nucleotides encoding for a stop codon (TAA, TAG, or TGA) at the end of the nucleotide sequence. If an initial start codon (Met) is not present from the amino acid sequence, one of skill in the art would be able to include, at the nucleotide level, an initial ATG, so that the translated polypeptide would have the initial Met.

SEQ ID NO: 114 is the nucleotide sequence of the Rat ACCase gene codon optimized for expression in the chloroplast genome of *Chlamydomonas reinhardtii*.

SEQ ID NO: 115 is the nucleotide sequence of the Rat ACCase gene. This gene is not codon optimized.

SEQ ID NO: 116 is the nucleotide sequence of the Flag tag that was attached to the 3' end of the codon-optimized nucleotide sequence of the Rat ACCase gene (SEQ ID NO: 114). The Flag tag was codon optimized for the chloroplast genome of *C. reinhardtii*.

SEQ ID NO: 117 is the nucleotide sequence of the Flag tag that was attached to the 5' end of the sequence of SEQ ID NO: 98 after the initial "ATG", and SEQ ID NO: 99 after the initial "ATG". The Flag tag was codon optimized for the chloroplast genome of *Scenedesmus dimorphus* based on the *Chlamydomonas reinhardtii* tRNA codon usage table.

SEQ ID NO: 118 is the translated amino acid sequence of SEQ ID NO: 116.

SEQ ID NO: 119 is a PCR primer.
SEQ ID NO: 120 is a PCR primer.
SEQ ID NO: 121 is a PCR primer.
SEQ ID NO: 122 is a PCR primer.
SEQ ID NO: 123 is a PCR primer.
SEQ ID NO: 124 is a PCR primer.
SEQ ID NO: 125 is a PCR primer.
SEQ ID NO: 126 is a PCR primer.

SEQ ID NO: 127 is the codon-optimized (for the chloroplast genome of *Scenedesmus dimorphus* based on the *C. reinhardtii* tRNA codon usage table) sequence (SEQ ID NO: 99) of SDACC2 with a Flag tag (SEQ ID NO: 117).

SEQ ID NO: 128 is the codon-optimized (for the chloroplast genome of *Scenedesmus dimorphus* based on the *C. reinhardtii* tRNA codon usage table) sequence (SEQ ID NO: 98) of SDACC1 with a Flag tag (SEQ ID NO: 117), and a mutation changing the nucleotides at positions 295-297 from TCA to GAT.

SEQ ID NO: 129 is the codon-optimized (for the chloroplast genome of *Scenedesmus dimorphus* based on the *C. reinhardtii* tRNA codon usage table) sequence of SDACC1 with a Flag tag, and a mutation changing the nucleotides at positions 316-318 from ACA to GAT.

SEQ ID NO: 130 is the codon-optimized (for the chloroplast genome of *Scenedesmus dimorphus* based on the *C. reinhardtii* tRNA codon usage table) sequence of SDACC1 with a Flag tag, and a mutation changing the nucleotides at positions 322-324 from TCA to GAT.

SEQ ID NO: 131 is the codon-optimized (for the chloroplast genome of *Scenedesmus dimorphus* based on the *C. reinhardtii* tRNA codon usage table) sequence of SDACC1 with a Flag tag, and a mutation changing the nucleotides at positions 346-348 from GTA to GAT.

SEQ ID NO: 132 is the codon-optimized (for the chloroplast genome of *Scenedesmus dimorphus* based on the *C. reinhardtii* tRNA codon usage table) sequence of SDACC1 with a Flag tag, and a mutation changing the nucleotides at positions 358-360 from CCA to GAT.

SEQ ID NO: 133 is the codon-optimized sequence (for the chloroplast genome of *Scenedesmus dimorphus* based on the *C. reinhardtii* tRNA codon usage table) of SDACC1 with a Flag tag, and a mutation changing the nucleotides at positions 382-384 from TCA to GAT.

SEQ ID NO: 134 is the codon-optimized (for the chloroplast genome of *Scenedesmus dimorphus* based on the *C. reinhardtii* tRNA codon usage table) sequence of SDACC1 with a Flag tag, and a mutation changing the nucleotides at positions 799-801 from ACA to GAT.

SEQ ID NO: 135 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 295-297 from TCA to GAT.

SEQ ID NO: 136 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 316-318 from ACA to GAT.

SEQ ID NO: 137 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 322-324 from TCA to GAT.

SEQ ID NO: 138 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 346-348 from GTA to GAT.

SEQ ID NO: 139 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 358-360 from CCA to GAT.

SEQ ID NO: 140 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 382-384 from TCA to GAT.

SEQ ID NO: 141 is the codon-optimized (for the chloroplast genome of *Scenedesmus dimorphus* based on the *C. reinhardtii* tRNA codon usage table) sequence of SDACC2 with a Flag tag, and a mutation changing the nucleotides at positions 799-801 from ACA to GAT.

SEQ ID NO: 142 is a PCR primer.
SEQ ID NO: 143 is a PCR primer.
SEQ ID NO: 144 is a PCR primer.
SEQ ID NO: 145 is a PCR primer.
SEQ ID NO: 146 is a PCR primer.
SEQ ID NO: 147 is a PCR primer.
SEQ ID NO: 148 is a PCR primer.
SEQ ID NO: 149 is a PCR primer.
SEQ ID NO: 150 is a PCR primer.
SEQ ID NO: 151 is a PCR primer.
SEQ ID NO: 152 is a PCR primer.
SEQ ID NO: 153 is a PCR primer.
SEQ ID NO: 154 is a PCR primer.
SEQ ID NO: 155 is a PCR primer.
SEQ ID NO: 156 is the codon-optimized sequence of the rat ACCase gene (SEQ ID NO: 114) with a 3' Flag tag (SEQ ID NO: 116) inserted prior to the stop codon (TAA).

SEQ ID NO: 157 is the protein sequence of the rat ACCase gene.

SEQ ID NO: 158 is the nucleotide sequence of SEQ ID NO: 75, without the initial "ATG".

SEQ ID NO: 159 is the nucleotide sequence of SEQ ID NO: 82, without the initial "ATG".

SEQ ID NO: 160 the nucleotide sequence of SEQ ID NO: 86, without the initial "ATG".

SEQ ID NO: 161 is the nucleotide sequence of SEQ ID NO: 90, without the initial "ATG".

SEQ ID NO: 162 the nucleotide sequence of SEQ ID NO: 93, without the initial "ATG".

SEQ ID NO: 163 is the translated sequence of SEQ ID NO: 158.

SEQ ID NO: 164 is the translated sequence of SEQ ID NO: 159.

SEQ ID NO: 165 is the translated sequence of SEQ ID NO: 160.

SEQ ID NO: 166 is the translated sequence of SEQ ID NO: 161.

SEQ ID NO: 167 is the translated sequence of SEQ ID NO: 162.

SEQ ID NO: 168 is the sequence of SEQ ID NO: 98 without the initial "ATG".

SEQ ID NO: 169 is the sequence of SEQ ID NO: 99 without the initial "ATG".

The present disclosure relates to novel ACCases having an improved activity (for example, being constitutively active) that are useful in increasing the production and/or accumulation of malonyl-CoA, fatty acids, glycerol lipids, and/or oils, in an organism, for example, a photosynthetic organism. Also provided are nucleic acids encoding the novel ACCases disclosed herein.

Provided herein are novel ACCases comprising SEQ ID NO: 2, wherein the amino acids at position X3, X4 and X5 may be serine or aspartic acid or glutamic acid or asparagine or histidine or glutamine or lysine; the amino acids at position X6 may be cysteine or aspartic acid or glutamic acid or asparagine or histidine or glutamine or lysine; and the amino acids at X7 may be tyrosine or aspartic acid or glutamic acid or asparagine or histidine or glutamine or lysine, provided, however, that the combination of X1, X2, X3, X4, X5, X6, and X7 is not threonine, threonine, serine, serine, cysteine, and tyrosine, respectively (wild type, SEQ ID NO: 1). In certain embodiments, the amino acid at X4 is aspartic acid and X1, X2, X3, X5, X6, and X7 are threonine, threonine, serine, serine, cysteine and tyrosine, respectively. In other embodiments, the amino acid at X5 is aspartic acid and X1, X2, X3, X4, X6, and X7 are threonine, threonine, serine, serine, cysteine and tyrosine, respectively. In other embodiments, the amino acid X6 is aspartic acid and X1, X2, X3, X4, X5, and X7 are threonine, threonine, serine, serine, serine and tyrosine, respectively. In still other embodiments, X7 is aspartic acid and X1, X2, X3, X4, X5, and X6 are threonine, threonine, serine, serine, serine and cysteine, respectively. In still other embodiments, X4 and X5 are aspartic acid and X1, X2, X3, X6 and X7 are threonine, threonine, serine, cysteine and tyrosine, respectively. In other embodiments, X4, X5, and X6 are aspartic acid and X1, X2, X3, X7 are threonine, threonine, serine, and tyrosine, respectively; while in still other embodiments, X4, X5 and X7 are aspartic acid and X1, X2, X3, X6 are threonine, threonine, serine, and cysteine, respectively.

Also provided herein is a method for increasing the production of malonyl-CoA in a photosynthetic organism. Malonyl-CoA is created by the carboxylation of Acetyl-CoA and is the committed step in fatty acid synthesis. Malonyl-CoA is the central carbon donor in fatty acid synthesis and is thought to be rate limiting. In fatty acid synthesis, the malonyl group is transferred from CoA to a protein co-factor on the acyl carrier protein (ACP). Malonyl-ACP then undergoes a series of condensation reactions with acyl-ACP. The first of these reactions catalyzed by the condensing enzyme 3-ketoacyl ACP synthase III (KASIII) forms a four-carbon product. Another enzyme KASI is involved in producing products of varying lengths. Additional reactions take place to produce either saturated or unsaturated fatty acids. The reactions proceed resulting in an increase of the precursor fatty acid by 2 carbons at a time. The elongation is halted when either the acyl group is removed from the ACP by an acyl-ACP thioesterase or acyltransferases in the chloroplast transfer the fatty acid from ACP to glycerol-3-phosphate or monoacylglycerol-3 phosphate. The final fatty acid chain length is determined by the activities of the enzymes present. Thus, the novel ACCases disclosed herein may be introduced into a host cell or organelle to increase the production of malonyl-CoA, which in turn results in increased fatty acid synthesis.

Acetyl-Coenzyme A Carboxylase (ACCase)

Figure 16:
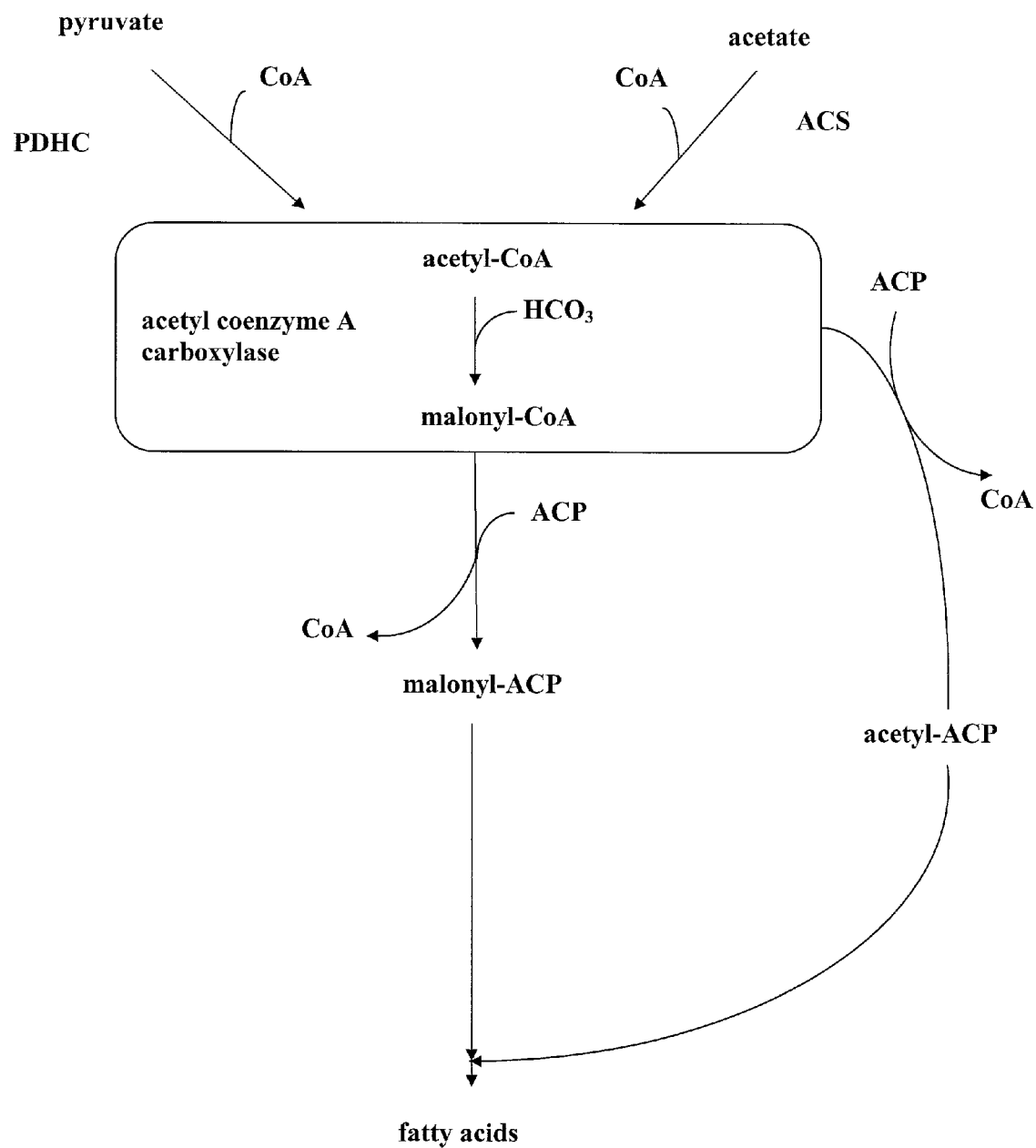
FIG. 16 is a schematic depiction of the fatty acid biosynthesis pathway in plants.

Acetyl-coenzyme A carboxylase (ACCase) has been described, for example, in Roesssler, P. G. and Ohlrogge, J. B., *J. Biol. Chem.* (1993) 268 (26):19254-19259. ACCase is a biotin-containing enzyme that catalyzes the carboxylation of acetyl-CoA to form malonyl-CoA. This reaction is believed to be a key regulatory step in fatty acid biosynthesis in animals, bacteria, yeast, and plants (for example, as described in Kim, K.-H., et al. (1989) *FASEB J.* 3, 2250-2256; Jackowski, S., et al. (1991) *Biochemistry of Lipids, Lipoproteins and Membranes* (Vance, D. E., and Vance, J., eds) pp. 43-85, Elsevier Science Publishers, Amsterdam; Post-Beittenmiller, D., et al. (1991) *J. Biol. Chem.* 266, 1858-1865; and Post-Beittenmiller, D., et al. (1992) *Plant Physiol.* 100, 923-930). Two partial reactions are involved in this process: 1) carboxylation of an enzyme-bound biotin molecule, and 2) transfer of the carboxyl group to acetyl-CoA. FIG. 16 is a schematic depiction of the fatty acid biosynthesis pathway in plants.

ACCase from the bacterium *Escherichia coli* consists of four distinct, separable protein components: 1) biotin carboxyl carrier protein, 2) biotin carboxylase, and 3) α and β subunits of carboxyltransferase.

Figure 17:
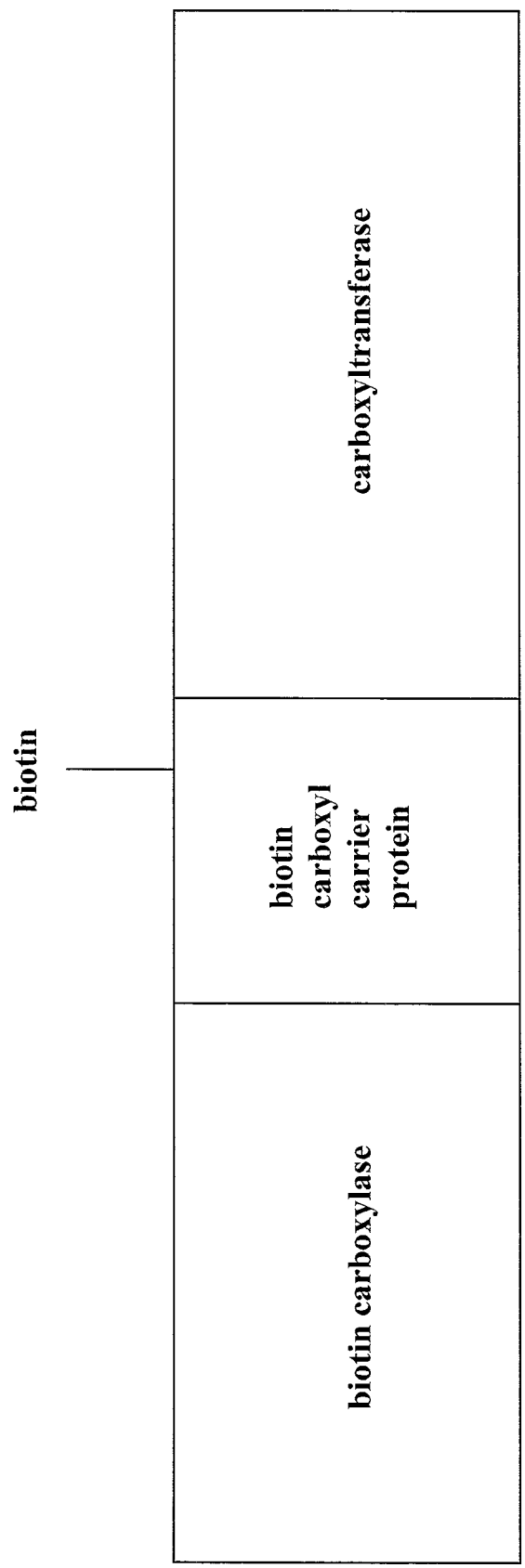
FIG. 17 shows a schematic of the ACCase protein found in eukaryotes, mammals, and yeast. The size of the protein ranges from approximately 2200 to 2500 amino acids.

In eukaryotes, these entities are located on a single, multifunctional polypeptide typically having a molecular mass exceeding 200 kDa (for example, as described in Samols, D. et al. (1988) *J. Biol. Chem.* 263, 6461-6464) and as shown in FIG. 17. The functional ACCase enzyme in eukaryotes is composed of multimers of this large polypeptide. In animals, ACCase has been shown to be a highly regulated enzyme that catalyzes the rate-limiting step in fatty acid biosynthesis (for example, as described in Kim, K.-H., et al. (1989) *FASEB J.* 3, 2250-2256 and Lane, M. D., et al. (1974) *Current Topics in Cellular Recognition* (Horecker, B. L., and Stadtman, E. R., eds) Vol. 8, pp. 139-195, Academic Press, New York).

ACCase has been purified from several higher plants and algae (for example, as described in Roessler, P. G. (1990) *Plant Physiol.* 92, 73-78; Egli, M. A., et al. (1993) *Plant Physiol.* 101, 499-506; Livne, A. and Sukenik, A. (1990) *Plant Physiol.* 31, 851-858; Charles, D. J. and Cherry, J. H. (1986) *Phytochemistry* 25, 1067-1071; Slabas, A. R. and Hellyer, A. (1985) *Plant Sci.* 39, 177-182; Nikolau, B. J. and Hawke, J. C. (1984) *Arch. Biochem. Biophys.* 228, 86-96; Egin-Buhler, B. and Ebel, J. (1983) *Eur. J. Biochem.* 133, 335-339; and Finlayson, S. A. and Dennis, D. T. (1983) *Arch. Biochem. Biophys.* 225, 576-585).

There have only been a few publications describing the isolation of an ACCase-encoding gene from a photosynthetic organism (for example, as described in Roesssler, P. G. and Ohlrogge, J. B., *J. Biol. Chem.* (1993) 268(26):19254-19259).

As discussed in Hu, Q., et al. (The Plant Journal (2008) 54:621-639) ACCases have been purified and kinetically characterized from two unicellular algae, the diatom *Cyclotella cryptic* (Roessler, P. G. (1990) *Plant Physiol.* 92, 73-78) and the prymnesiophyte *Isochrysis galbana* (Livne, A. and Sukenik, A. (1990) *Plant Cell Physiol.* 31, 851-858). Native ACCase isolated from *C. cryptica* has a molecular mass of approximately 740 kDa and appears to be composed of four identical biotin containing subunits. The molecular mass of the native ACCase from *I. galbana* was estimated at 700 kDa. This suggests that ACCases from algae and the majority of ACCases from higher plants are similar in that they are composed of multiple identical subunits, each of which are multifunctional peptides containing domains responsible for both biotin carboxylation and subsequent carboxyl transfer to acetyl CoA (Roessler, P. G. (1990) *Plant Physiol.* 92, 73-78).

The gene that encodes ACCase in *Cyclotella cryptica* has been isolated, cloned, and characterized (Roessler, P. G. and Ohlrogge, J. B. (1993) *J. Biol. Chem.* 268, 19254-19259; and Roessler, P. G., et al., Ann. N.Y. Acad. Sci. (1994) 721:250-256). The gene was shown to encode a polypeptide composed of 2089 amino acids, with a molecular mass of 230 kDa. The deduced amino acid sequence exhibited strong similarity to the sequences of animal and yeast ACCases in the biotin carboxylase and carboxyltransferase domains. Less sequence similarity was observed in the biotin carboxyl carrier protein domain, although the highly conserved Met-Lys-Met sequence of the biotin binding site was present. The N-terminus of the predicted ACCase sequence has characteristics of a signal sequence, indicating that the enzyme may be imported into chloroplasts via the endoplasmic reticulum.

Roessler, P. G., et al. (Applied Biochemistry and Biotechnology (1996) 57/58:223-231) has introduced additional copies of the ACCase gene (acc1) into *C. cryptica* T13L and *N. saprophila* by cotransforming these organisms with pACC1, which contains the genomic ACCase gene, and pACCNpt5.1. Preliminary results showed that for *C. cryptica* introducing additional copies of the ACCase gene may result in the enhanced activity of the enzyme.

ACCase genes have been isolated from three nonphotosynthetic eukaryotes: rat (Lopez-Casillas, et al. (1988) *Proc. Natl. Acad. Sci. U.S.A.* 85, 5784-5788), chicken (Takai, T. et al. (1988) *J. Biol. Chem.* 263, 2651-2657), and yeast (20 Al-Feel, W., et al. (1992) Proc. Natl. Acad. Sci. U.S.A. 89, 4534-4538). In addition, the genes encoding the individual polypeptides comprising the different subunits of ACCase in *E. coli* have been cloned and sequenced (Li, S.-J. and Cronan J. E. Jr., (1992) *J. Biol. Chem.* 267, 855-863; Li, S.-J. and Cronan J. E. Jr., (1992) *J. Biol. Chem.* 267, 16841-16847;

Kondo, H., et al. (1991) *Proc. Natl. Acad. Sci. U.S.A.* 88, 9730-9733; and Alix, J.-H. (1989) DNA (NY) 8, 779-789).

Differences in the rates of fatty acid synthesis in plants may be attributable to changes in ACCase activity (for example, as described in Post-Bcittenmiller, D., et al. (1991) *J. Biol. Chem.* 266, 1858-1865 and Post-Beittenmiller, D., et al. (1992) *Plant Physiol.* 100, 923-930). Increased ACCase activity also appears to play a role in environmentally induced triacylglycerol accumulation in the diatom *Cyclotella cryptica* (for example, as described in Roessler, P. G. (1988) *Arch. Biochem. Biophys.* 267, 521-528). Several allosteric effectors of plant and algal ACCases have been identified that may contribute to the regulation of ACCase activity in vivo (as reviewed in Roessler, P. G. (1990) *Plant Physiol.* 92, 73-78). However, little is known about the regulation of ACCase gene expression in photosynthetic organisms.

The level of ACCase gene expression has clearly been shown to be an important determinant of fatty acid biosynthetic rates in animals (for example, as described in Katsurada, A., et al. (1990) *Eur. J. Biochem.* 190, 435-441 and Pape, M. E., et al. (1988) *Arch. Biochem. Biophys.* 267, 104-109).

Figure 15:
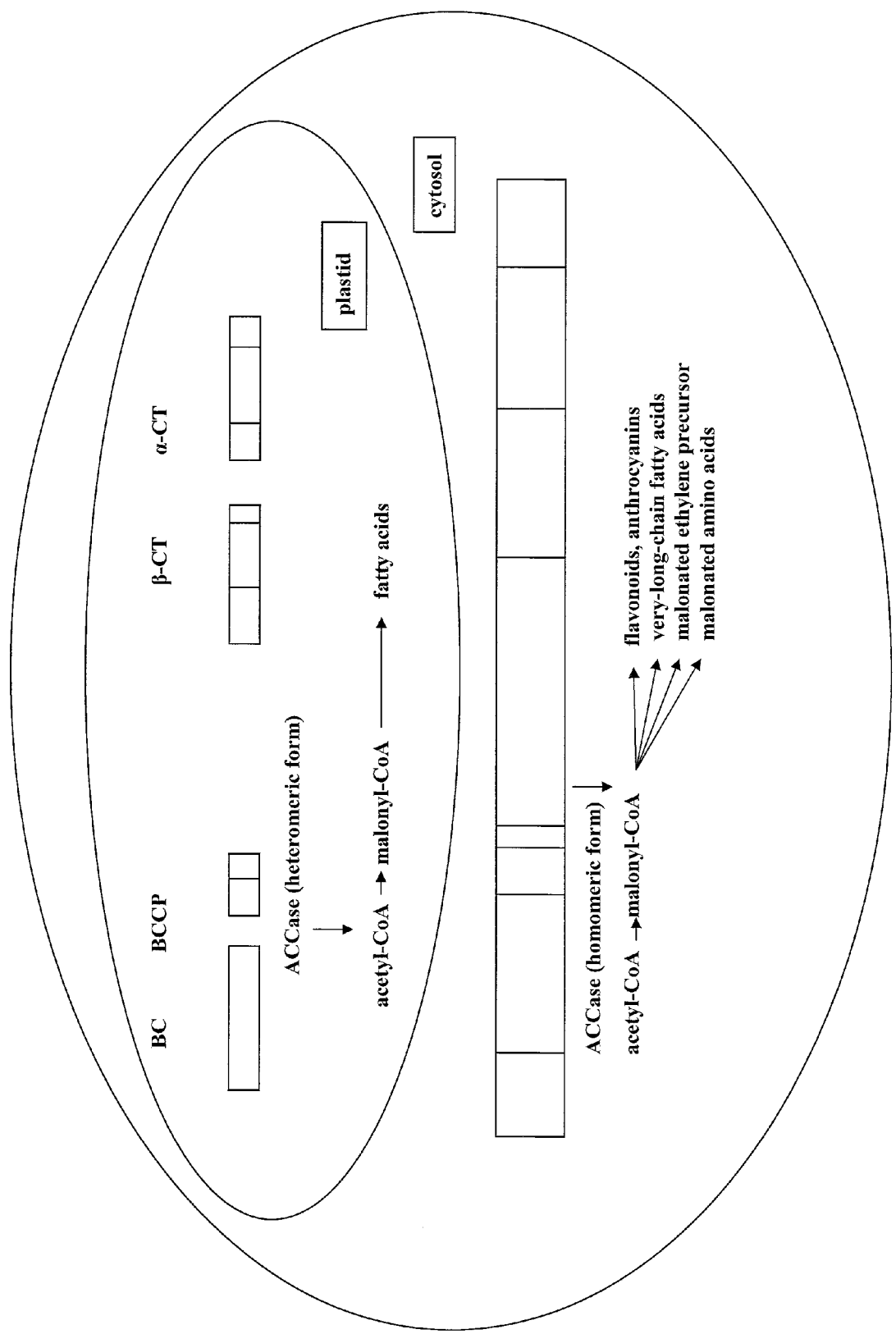
FIG. 15 shows the compartmentation of the two forms of ACCase in plants.

In plants, most ACCase activity is located in plastids of green and non-green plant tissues including leaves and oil seeds. Leaf ACCase activity is primarily located in mesophyll cells, but lesser amounts have been found in C-4 bundle sheath cells and in epidermal cells. The subcellular location of ACCase activity in epidermal cells is unknown, but since synthesis of very long-chain fatty acids (VLCFA) for formation of waxes, cutin, and suberin occurs on the endoplasmic reticulum (ER), malonyl-CoA might also be derived from a cytosolic ACCase. FIG. 15 shows the compartmentation of the two forms of ACCase in plants.

In contrast, rat ACCase is primarily cytosolic or associated with the outer mitochondrial membrane.

De novo fatty acid synthesis in chloroplasts involves successive 2-carbon additions to acetate, using malonate as the 2-C donor. All intermediates are attached to acyl carrier protein (ACP). Synthesis in plastids resembles that in *E. coli* in that the fatty acid synthesis complex can be dissociated into separate enzymes: β-ketoacyl-ACP synthase (KAS), P-ketoacyl-ACP reductase, β-hydroxyl-ACP dehydratase, and enoyl-ACP reductase, acetyl-CoA:ACP transacylase, and malonyl-CoAACP transacylase. A highly active KASIII isozyme catalyzes the condensation of acetyl-CoA and malonyl-ACP. Successive additions of malonyl-CoA to acy-1-ACPs catalyzed by KAS I form C16 acyl-ACP, some of which is converted to C18 acyl-ACP by KAS II and then to C18:1-ACP. Fatty acid metabolism then diverges; de-esterification allows movement to the cytoplasm (eukaryotic path) where fatty acids may be further unsaturated and/or elongated by additions of malonyl-CoA in the ER. Alternatively, fatty acids are linked to glycerol-3-phosphate (prokaryotic path), further unsaturated, and used for synthesis of chloroplast lipids. A portion of cytoplasmic lipids returns to the chloroplast. The relative contributions of these two paths are species-specific but appear to be relatively flexible in mutants blocked in either path. In oil-storing organs such as cotyledons and monocot embryos the triacylglycerides are stored in cytoplasmic oil bodies surrounded by a single unit membrane.

Condensation of malonyl-CoA with phenylpropionyl-CoAs or acetyl-CoA leads to synthesis of flavonoids, anthocyanins, or to polyacetates. Condensation is increased by light, elicitors, or pathogens and may be the rate-limiting step in synthesis of some phytoalexins. In addition to the secondary metabolites derived by de novo synthesis, malonyl conjugates of flavonoid glycosides, formed by malonylCoA: flavonoid glycoside malonyltransferase, D-amino acids and 1-amino-carboxyl-cyclopropane (ethylene precursor) are found in plants. Malonylated compounds accumulate in vacuoles, probably after synthesis in the cytoplasm.

Regulation of plant ACCase by reversible protein phosphorylation has not been studied extensively. Protein phosphorylation is involved in the regulation of many other pathways in plants where complex biochemical controls and light dependence are coordinated (as reviewed in Bennett, J. (1991) *Annu. Rev. Plant Physiol. Plant Mol. Biol.* 42, 281-311 and Huber, S. C., et al. (1994) *Int. Rev. Cytology*, 149, 47-98). In many of these cases, light- and MgATP-dependence, such as that observed for ACCase, are factors involved in the control of the respective protein kinases and protein phosphatases. It has been observed that when fatty acid synthase (FAS) in isolated chloroplasts is inhibited by the addition of photosynthetic inhibitors such as 3-(3,4-dichlorophenyl)-1,1-dimethylurea (DCMU), the inhibition cannot be reversed by supplying the products of photosynthesis, i.e. ATP or NADPH alone (Nakamura, Y. and Yamada, M. (1975) *Plant Cell Physiol.* 1, 163-174 and Roughan, P. G., et al. (1980) *Plant Sci. Lett.* 18, 221-228). Therefore, some intermediary method of control such as protein phosphorylation, instead of a direct dependence on photophosphorylation, has been suggested. Additionally, in yeast and mammals, ACCase is regulated by reversible protein phosphorylation (Kim, K.-H. (1997) *Annu. Rev. Nutr.* 17, 77-99), suggesting the possibility that this method of regulation may also occur in plants.

Plastid fatty acid synthesis is believed to be tightly regulated and under the control of a number of factors including metabolite pools and feedback inhibition (reviewed in Ohlrogge, J. B. and Jaworski, J. (1997) *Annu. Rev. Plant Physiol. Plant Mol. Biol.* 4, 109-136). In all organisms examined so far, ACCase has been found to have a regulatory role over the flux of fatty acid synthesis. Light is one factor long known to regulate the flux of plastid fatty acid synthesis and its effect has largely been attributed to the production of co-factors and alterations of the stromal environment (for example, as described in Hunter, S. C. and Ohlrogge, J. B. (1998) *Arch. Biochem. Biophys.* 359, 170-178). The possibility that some other factor is involved in light activation of FAS in chloroplasts besides photosynthesis and resulting metabolite pools was first proposed by Nakamura, Y. and Yamada, M. (1975) *Plant Cell Physiol.* 1, 163-174, who observed that light-dependent fatty acid synthesis in isolated spinach chloroplasts was not dependent on ATP from photophosphorylation. More recent work has also revealed that ACCase activity from lysates of dark-incubated chloroplasts is low but increases to the levels of light-incubated chloroplast lysates within minutes (Hunter, S. C. and Ohlrogge, J. B. (1998) *Arch. Biochem. Biophys.* 359, 170-178). Since the dark-induced difference could not be attributed to metabolite levels in the diluted extracts, it was therefore speculated that during dark incubation some unknown inhibition or inactivation occurs. Savage, L. J. and Ohlrogge, J. B. (1999) *The Plant Journal*, 18(5), 521-527, set out to determine whether chloroplast ACCase was post-translationally modified by phosphorylation. Based on this work, the β-CT of ACCase is a phosphoprotein. Antibodies to pea β-CT, but not pre-immune serum, immunoprecipitate a protein labeled with [γ-33P]-ATP from pea chloroplasts which co-migrates precisely with endogenous pea β-CT. In addition, *E. coli*-expressed β-CT competes directly for specific antibody binding sites with this labeled protein in immunoprecipitation assays.

Host Cells or Host Organisms

Malonyl-CoA and fatty acid production can be increased by introducing polynucleotides encoding the present novel ACCases in any suitable host cell or organism.

A host cell can contain a polynucleotide encoding a polypeptide of the present disclosure. In some embodiments, a host cell is part of a multicellular organism. In other embodiments, a host cell is cultured as a unicellular organism.

Host organisms can include any suitable host, for example, a microorganism. Microorganisms which are useful for the methods described herein include, for example, photosynthetic bacteria (e.g., cyanobacteria), nonphotosynthetic bacteria (e.g., *E. coli*), yeast (e.g., *Saccharomyces cerevisiae*), and algae (e.g., microalgae such as *Chlamydomonas reinhardtii*).

Examples of host organisms that can be transformed with a polynucleotide of interest include vascular and non-vascular organisms. The organism can be prokaryotic or eukaryotic. The organism can be unicellular or multicellular. A host organism is an organism comprising a host cell. In other embodiments, the host organism is photosynthetic. A photosynthetic organism is one that naturally photosynthesizes (e.g., an alga) or that is genetically engineered or otherwise modified to be photosynthetic. In some instances, a photosynthetic organism may be transformed with a construct or vector of the disclosure which renders all or part of the photosynthetic apparatus inoperable.

By way of example, a non-vascular photosynthetic microalga species (for example, *C. reinhardtii*, *Nannochloropsis oceania*, *N. salina*, *D. salina*, *H. pluvalis*, *S. dimorphus*, *D. viridis*, *Chlorella* sp., and *D. tertiolecta*) can be genetically engineered to produce a polypeptide of interest, for example an ACCase. Production of an ACCase in these microalgae can be achieved by engineering the microalgae to express an ACCase in the algal chloroplast or nucleus.

In other embodiments the host organism is a vascular plant. Non-limiting examples of such plants include various monocots and dicots, including high oil seed plants such as high oil seed *Brassica* (e.g., *Brassica nigra*, *Brassica napus*, *Brassica hirta*, *Brassica rapa*, *Brassica campestris*, *Brassica carinata*, and *Brassica juncea*), soybean (*Glycine max*), castor bean (*Ricinus communis*), cotton, safflower (*Carthamus tinctorius*), sunflower (*Helianthus annus*), flax (*Linum usitatissimum*), corn (*Zea mays*), coconut (*Cocos nucijera*), palm (*Elaeis guineensis*), oil nut trees such as olive (*Olea europaea*), sesame, and peanut (*Arachis hypogaea*), as well as *Arabidopsis*, tobacco, wheat, barley, oats, amaranth, potato, rice, tomato, and legumes (e.g., peas, beans, lentils, alfalfa, etc.).

The host cell can be prokaryotic. Examples of some prokaryotic organisms of the present disclosure include, but are not limited to, cyanobacteria (e.g., *Synechococcus*, *Synechocystis*, *Athrospira*, *Gleocapsa*, *Oscillatoria*, and, *Pseudoanabaena*). Suitable prokaryotic cells include, but are not limited to, any of a variety of laboratory strains of *Escherichia coli*, *Lactobacillus* sp., *Salmonella* sp., and *Shigella* sp. (for example, as described in Carrier et al. (1992) J. Immunol. 148:1176-1181; U.S. Pat. No. 6,447,784; and Sizemore et al. (1995) Science 270:299-302). Examples of *Salmonella* strains which can be employed in the present disclosure include, but are not limited to, *Salmonella typhi* and *S. typhimurium*. Suitable *Shigella* strains include, but are not limited to, *Shigella flexneri*, *Shigella sonnei*, and *Shigella diseriteriae*. Typically, the laboratory strain is one that is non-pathogenic. Non-limiting examples of other suitable bacteria include, but are not limited to, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, and *Rhodococcus* sp.

In some embodiments, the host organism is eukaryotic (e.g. green algae, red algae, brown algae). In some embodiments, the algae is a green algae, for example, a *Chlorophycean*. The algae can be unicellular or multicellular. Suitable eukaryotic host cells include, but are not limited to, yeast cells, insect cells, plant cells, fungal cells, and algal cells. Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, and *Chlamydomonas reinhardtii*. In other embodiments, the host cell is a microalga (e.g., *Chlamydomonas reinhardtii*, *Dunaliella salina*, *Haematococcus pluvialis*, *Nannochloropsis oceania*, *N. salina*, *Scenedesmus dimorphus*, *Chlorella* spp., *D. viridis*, or *D. tertiolecta*).

In some instances the organism is a rhodophyte, chlorophyte, heterokontophyte, tribophyte, glaucophyte, chlorarachniophyte, euglenoid, haptophyte, cryptomonad, dinoflagellum, or phytoplankton.

In some instances a host organism is vascular and photosynthetic. Examples of vascular plants include, but are not limited to, angiosperms, gymnosperms, rhyniophytes, or other tracheophytes.

In some instances a host organism is non-vascular and photosynthetic. As used herein, the term "non-vascular photosynthetic organism," refers to any macroscopic or microscopic organism, including, but not limited to, algae, cyanobacteria and photosynthetic bacteria, which does not have a vascular system such as that found in vascular plants. Examples of non-vascular photosynthetic organisms include bryophtyes, such as marchantiophytes or anthocerotophytes. In some instances the organism is a cyanobacteria. In some instances, the organism is algae (e.g., macroalgae or microalgae). The algae can be unicellular or multicellular algae. For example, the microalgae *Chlamydomonas reinhardtii* may be transformed with a vector, or a linearized portion thereof, encoding one or more proteins of interest (e.g., an ACCase).

Methods for algal transformation are described in U.S. Provisional Patent Application No. 60/142,091. The methods of the present disclosure can be carried out using algae, for example, the microalga, *C. reinhardtii*. The use of microalgae to express a polypeptide or protein complex according to a method of the disclosure provides the advantage that large populations of the microalgae can be grown, including commercially (Cyanotech Corp.; Kailua-Kona Hi.), thus allowing for production and, if desired, isolation of large amounts of a desired product.

The vectors of the present disclosure may be capable of stable or transient transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. Other vectors of the present disclosure are capable of stable or transient transformation of, for example, *C. reinhardtii*, *N. oceania*, *N. sauna*, *D. sauna*, *H. pluvalis*, *S. dimorphus*, *D. viridis*, or *D. tertiolecta*.

Examples of appropriate hosts, include but are not limited to: bacterial cells, such as *E. coli*, *Streptomyces*, *Salmonella typhimurium*; fungal cells, such as yeast; insect cells, such as *Drosophila* S2 and *Spodoptera* Sf9; animal cells, such as CHO, COS or Bowes melanoma; adenoviruses; and plant cells. The selection of an appropriate host is deemed to be within the scope of those skilled in the art.

Polynucleotides selected and isolated as described herein are introduced into a suitable host cell. A suitable host cell is any cell which is capable of promoting recombination and/or reductive reassortment. The selected polynucleotides can be, for example, in a vector which includes appropriate control sequences. The host cell can be, for example, a higher eukaryotic cell, such as a mammalian cell, or a lower eukaryotic cell, such as a yeast cell, or the host cell can be a prokaryotic cell, such as a bacterial cell. Introduction of a construct (vector) into the host cell can be effected by, for example, calcium phosphate transfection, DEAE-Dextran mediated transfection, or electroporation.

Recombinant polypeptides, including protein complexes, can be expressed in plants, allowing for the production of crops of such plants and, therefore, the ability to conveniently produce large amounts of a desired product. Accordingly, the methods of the disclosure can be practiced using any plant, including, for example, microalga and macroalgae. (such as marine algae and seaweeds), as well as plants that grow in soil.

In one embodiment, the host cell is a plant. The term "plant" is used broadly herein to refer to a eukaryotic organism containing plastids, such as chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, and roots. A part of a plant useful for propagation includes, for example, seeds, fruits, cuttings, seedlings, tubers, and rootstocks.

A method of the disclosure can generate a plant containing genomic DNA (for example, a nuclear and/or plastid genomic DNA) that is genetically modified to contain a stably integrated polynucleotide (for example, as described in Hager and Bock, *Appl. Microbiol. Biotechnol.* 54:302-310, 2000). Accordingly, the present disclosure further provides a transgenic plant, e.g. *C. reinhardtii*, which comprises one or more chloroplasts containing a polynucleotide encoding one or more exogenous or endogenous polypeptides, including polypeptides that can allow for secretion of fuel products and/or fuel product precursors (e.g., isoprenoids, fatty acids, lipids, triglycerides). A photosynthetic organism of the present disclosure comprises at least one host cell that is modified to generate, for example, a fuel product or a fuel product precursor.

Some of the host organisms useful in the disclosed embodiments are, for example, are extremophiles, such as hyperthermophiles, psychrophiles, psychrotrophs, halophiles, barophiles and acidophiles. Some of the host organisms which may be used to practice the present disclosure are halophilic (e.g., *Dunaliella saliva*, *D. viridis*, or *D. tertiolecta*). For example, *D. saliva* can grow in ocean water and salt lakes (for example, salinity from 30-300 parts per thousand) and high salinity media (e.g., artificial seawater medium, seawater nutrient agar, brackish water medium, and seawater medium). In some embodiments of the disclosure, a host cell expressing a protein of the present disclosure can be grown in a liquid environment which is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 31., 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, or other salts) may also be present in the liquid environments.

Where a halophilic organism is utilized for the present disclosure, it may be transformed with any of the vectors described herein. For example, *D. salina* may be transformed with a vector which is capable of insertion into the chloroplast or nuclear genome and which contains nucleic acids which encode a protein (e.g., an ACCase). Transformed halophilic organisms may then be grown in high-saline environments (e.g., salt lakes, salt ponds, and high-saline media) to produce the products (e.g., lipids) of interest. Isolation of the products may involve removing a transformed organism from a high-saline environment prior to extracting the product from the organism. In instances where the product is secreted into the surrounding environment, it may be necessary to desalinate the liquid environment prior to any further processing of the product.

The present disclosure further provides compositions comprising a genetically modified host cell. A composition comprises a genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol and dimethylsulfoxide; and nutritional media appropriate to the cell.

For the production of a protein, for example, an isoprenoid or isoprenoid precursor compound, a host cell can be, for example, one that produces, or has been genetically modified to produce, one or more enzymes in a prenyl transferase pathway and/or a mevalonate pathway and/or an isoprenoid biosynthetic pathway. In some embodiments, the host cell is one that produces a substrate of a prenyl transferase, isoprenoid synthase or mevalonate pathway enzyme.

In some embodiments, a genetically modified host cell is a host cell that comprises an endogenous mevalonate pathway and/or isoprenoid biosynthetic pathway and/or prenyl transferase pathway. In other embodiments, a genetically modified host cell is a host cell that does not normally produce mevalonate or IPP via a mevalonate pathway, or FPP, GPP or GGPP via a prenyl transferase pathway, but has been genetically modified with one or more polynucleotides comprising nucleotide sequences encoding one or more mevalonate pathway, isoprenoid synthase pathway or prenyl transferase pathway enzymes (for example, as described in U.S. Patent Publication No. 2004/005678; U.S. Patent Publication No. 2003/0148479; and Martin et al. (2003) Nat. Biotech. 21(7):796-802).

Culturing of Cells or Organisms

An organism may be grown under conditions which permit photosynthesis, however, this is not a requirement (e.g., a host organism may be grown in the absence of light). In some instances, the host organism may be genetically modified in such a way that its photosynthetic capability is diminished or destroyed. In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, and lactose), complex carbohydrates (e.g., starch and glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

Optimal growth of organisms occurs usually at a temperature of about 20° C. to about 25° C., although some organisms can still grow at a temperature of up to about 35° C. Active growth is typically performed in liquid culture. If the organisms are grown in a liquid medium and are shaken or mixed, the density of the cells can be anywhere from about 1 to $5 \times 10^8$ cells/ml at the stationary phase. For example, the density of the cells at the stationary phase for Chlamydomonas sp. can be about 1 to $5 \times 10^7$ cells/ml; the density of the cells at the stationary phase for Nannochloropsis sp. can be about 1 to $5 \times 10^8$ cells/ml; the density of the cells at the stationary phase for Scenedesmus sp. can be about 1 to $5 \times 10^7$ cells/ml; and the density of the cells at the stationary phase for Chlorella sp. can be about 1 to $5 \times 10^8$ cells/ml. Exemplary cell densities at the stationary phase are as follows: Chlamydomonas sp. can be about $1 \times 10^7$ cells/ml; Nannochloropsis sp. can be about $1 \times 10^8$ cells/ml; Scenedesmus sp. can be about $1 \times 10^7$ cells/ml; and Chlorella sp. can be about $1 \times 10^8$ cells/ml. An exemplary growth rate may yield, for example, a two to four fold increase in cells per day, depending on the growth conditions. In addition, doubling times for organisms can be, for example, 5 hours to 30 hours. The organism can also be grown on solid media, for example, media containing about 1.5% agar, in plates or in slants.

One source of energy is fluorescent light that can be placed, for example, at a distance of about 1 inch to about two feet from the organism. Examples of types of fluorescent lights includes, for example, cool white and daylight. Bubbling with air or $CO_2$ improves the growth rate of the organism. Bubbling with CO, can be, for example, at 1% to 5% $CO_2$. If the lights are turned on and off at regular intervals (for example, 12:12 or 14:10 hours of light:dark) the cells of some organisms will become synchronized.

Long term storage of organisms can be achieved by streaking them onto plates, sealing the plates with, for example, Parafilm™, and placing them in dim light at about 10° C. to about 18° C. Alternatively, organisms may be grown as streaks or stabs into agar tubes, capped, and stored at about 10° C. to about 18° C. Both methods allow for the storage of the organisms for several months.

For longer storage, the organisms can be grown in liquid culture to mid to late log phase and then supplemented with a penetrating cryoprotective agent like DMSO or MeOH, and stored at less than −130° C. An exemplary range of DMSO concentrations that can be used is 5 to 8%. An exemplary range of MeOH concentrations that can be used is 3 to 9%.

Organisms can be grown on a defined minimal medium (for example, high salt medium (HSM), modified artificial sea water medium (MASM), or F/2 medium) with light as the sole energy source. In other instances, the organism can be grown in a medium (for example, tris acetate phosphate (TAP) medium), and supplemented with an organic carbon source.

Organisms, such as algae, can grow naturally in fresh water or marine water. Culture media for freshwater algae can be, for example, synthetic media, enriched media, soil water media, and solidified media, such as agar. Various culture media have been developed and used for the isolation and cultivation of fresh water algae and are described in Watanabe, M. W. (2005). Freshwater Culture Media. In R. A. Andersen (Ed.), Algal Culturing Techniques (pp. 13-20). Elsevier Academic Press. Culture media for marine algae can be, for example, artificial seawater media or natural seawater media. Guidelines for the preparation of media are described in Harrison, P. J. and Berges, J. A. (2005). Marine Culture Media. In R. A. Andersen (Ed.), Algal Culturing Techniques (pp. 21-33). Elsevier Academic Press.

Organisms may be grown in outdoor open water, such as ponds, the ocean, seas, rivers, waterbeds, marshes, shallow pools, lakes, aqueducts, and reservoirs. When grown in water, the organism can be contained in a halo-like object comprised of lego-like particles. The halo-like object encircles the organism and allows it to retain nutrients from the water beneath while keeping it in open sunlight.

In some instances, organisms can be grown in containers wherein each container comprises one or two organisms, or a plurality of organisms. The containers can be configured to float on water. For example, a container can be filled by a combination of air and water to make the container and the organism(s) in it buoyant. An organism that is adapted to grow in fresh water can thus be grown in salt water (i.e., the ocean) and vice versa. This mechanism allows for automatic death of the organism if there is any damage to the container.

Culturing techniques for algae are well know to one of skill in the art and are described, for example, in Freshwater Culture Media. In R. A. Andersen (Ed.), Algal Culturing Techniques. Elsevier Academic Press.

Because photosynthetic organisms, for example, algae, require sunlight, $CO_2$ and water for growth, they can be cultivated in, for example, open ponds and lakes. However, these open systems are more vulnerable to contamination than a closed system. One challenge with using an open system is that the organism of interest may not grow as quickly as a potential invader. This becomes a problem when another organism invades the liquid environment in which the organism of interest is growing, and the invading organism has a faster growth rate and takes over the system.

In addition, in open systems there is less control over water temperature, $CO_2$ concentration, and lighting conditions. The growing season of the organism is largely dependent on location and, aside from tropical areas, is limited to the warmer months of the year. In addition, in an open system, the number of different organisms that can be grown is limited to those that are able to survive in the chosen location. An open system, however, is cheaper to set up and/or maintain than a closed system.

Another approach to growing an organism is to use a semi-closed system, such as covering the pond or pool with a structure, for example, a "greenhouse-type" structure. While this can result in a smaller system, it addresses many of the problems associated with an open system. The advantages of a semi-closed system are that it can allow for a greater number of different organisms to be grown, it can allow for an organism to be dominant over an invading organism by allowing the organism of interest to out compete the invading organism for nutrients required for its growth, and it can extend the growing season for the organism. For example, if the system is heated, the organism can grow year round.

A variation of the pond system is an artificial pond, for example, a raceway pond. In these ponds, the organism, water, and nutrients circulate around a "racetrack." Paddlewheels provide constant motion to the liquid in the racetrack, allowing for the organism to be circulated back to the surface of the liquid at a chosen frequency. Paddlewheels also provide a source of agitation and oxygenate the system. These raceway ponds can be enclosed, for example, in a building or a greenhouse, or can be located outdoors.

Raceway ponds are usually kept shallow because the organism needs to be exposed to sunlight, and sunlight can only penetrate the pond water to a limited depth. The depth of a raceway pond can be, for example, about 4 to about 12 inches. In addition, the volume of liquid that can be contained in a raceway pond can be, for example, about 200 liters to about 600,000 liters.

The raceway ponds can be operated in a continuous manner, with, for example, $CO_2$ and nutrients being constantly fed to the ponds, while water containing the organism is removed at the other end.

If the raceway pond is placed outdoors, there are several different ways to address the invasion of an unwanted organism. For example, the pH or salinity of the liquid in which the desired organism is in can be such that the invading organism either slows down its growth or dies.

Also, chemicals can be added to the liquid, such as bleach, or a pesticide can be added to the liquid, such as glyphosate. In addition, the organism of interest can be genetically modified such that it is better suited to survive in the liquid environment. Any one or more of the above strategies can be used to address the invasion of an unwanted organism.

Alternatively, organisms, such as algae, can be grown in closed structures such as photobioreactors, where the environment is under stricter control than in open systems or semi-closed systems. A photobioreactor is a bioreactor which incorporates some type of light source to provide photonic energy input into the reactor. The term photobioreactor can refer to a system closed to the environment and having no direct exchange of gases and contaminants with the environment. A photobioreactor can be described as an enclosed, illuminated culture vessel designed for controlled biomass production of phototrophic liquid cell suspension cultures. Examples of photobioreactors include, for example, glass containers, plastic tubes, tanks, plastic sleeves, and bags. Examples of light sources that can be used to provide the energy required to sustain photosynthesis include, for example, fluorescent bulbs, LEDs, and natural sunlight. Because these systems are closed everything that the organism needs to grow (for example, carbon dioxide, nutrients, water, and light) must be introduced into the bioreactor.

Photobioreactors, despite the costs to set up and maintain them, have several advantages over open systems, they can, for example, prevent or minimize contamination, permit axenic organism cultivation of monocultures (a culture consisting of only one species of organism), offer better control over the culture conditions (for example, pH, light, carbon dioxide, and temperature), prevent water evaporation, lower carbon dioxide losses due to out gassing, and permit higher cell concentrations.

On the other hand, certain requirements of photobioreactors, such as cooling, mixing, control of oxygen accumulation and biofouling, make these systems more expensive to build and operate than open systems or semi-closed systems.

Photobioreactors can be set up to be continually harvested (as is with the majority of the larger volume cultivation systems), or harvested one batch at a time (for example, as with polyethylene bag cultivation). A batch photobioreactor is set up with, for example, nutrients, an organism (for example, algae), and water, and the organism is allowed to grow until the batch is harvested. A continuous photobioreactor can be harvested, for example, either continually, daily, or at fixed time intervals.

High density photobioreactors are described in, for example, Lee, et al., Biotech. Bioengineering 44:1161-1167, 1994. Other types of bioreactors, such as those for sewage and waste water treatments, are described in, Sawayama, et al., Appl. Micro. Biotech., 41:729-731, 1994. Additional examples of photobioreactors are described in, U.S. Appl. Publ. No. 2005/0260553, U.S. Pat. No. 5,958,761, and U.S. Pat. No. 6,083,740. Also, organisms, such as algae may be mass-cultured for the removal of heavy metals (for example, as described in Wilkinson, Biotech. Letters, 11:861-864, 1989), hydrogen (for example, as described in U.S. Patent Application Publication No. 2003/0162273), and pharmaceutical compounds from a water, soil, or other source or sample. Organisms can also be cultured in conventional fermentation bioreactors, which include, but are not limited to, batch, fed-batch, cell recycle, and continuous fermentors. Additional methods of culturing organisms and variations of the methods described herein are known to one of skill in the art.

Organisms can also be grown near ethanol production plants or other facilities or regions (e.g., cities and highways) generating $CO_2$. As such, the methods herein contemplate business methods for selling carbon credits to ethanol plants or other facilities or regions generating $CO_2$ while making fuels or fuel products by growing one or more of the organisms described herein near the ethanol production plant, facility, or region.

The organism of interest, grown in any of the systems described herein, can be, for example, continually harvested, or harvested one batch at a time.

$CO_2$ can be delivered to any of the systems described herein, for example, by bubbling in $CO_2$ from under the surface of the liquid containing the organism. Also, sparges can be used to inject CO, into the liquid. Spargers are, for example, porous disc or tube assemblies that are also referred to as Bubblers, Carbonators, Aerators, Porous Stones and Diffusers.

Nutrients that can be used in the systems described herein include, for example, nitrogen (in the form of $NO_3^-$ or $NH_4^+$), phosphorus, and trace metals (Fe, Mg, K, Ca, Co, Cu, Mn, Mo, Zn, V, and B). The nutrients can come, for example, in a solid form or in a liquid form. If the nutrients are in a solid form they can be mixed with, for example, fresh or salt water prior to being delivered to the liquid containing the organism, or prior to being delivered to a photobioreactor.

Organisms can be grown in cultures, for example large scale cultures, where large scale cultures refers to growth of cultures in volumes of greater than about 6 liters, or greater than about 10 liters, or greater than about 20 liters. Large scale growth can also be growth of cultures in volumes of 50 liters or more, 100 liters or more, or 200 liters or more. Large scale growth can be growth of cultures in, for example, ponds, containers, vessels, or other areas, where the pond, container, vessel, or area that contains the culture is for example, at lease 5 square meters, at least 10 square meters, at least 200 square meters, at least 500 square meters, at least 1,500 square meters, at least 2,500 square meters, in area, or greater.

*Chlamydomonas* sp., *Nannochloropsis* sp., *Scenedesmus* sp., and *Chlorella* sp. are exemplary algae that can be cultured as described herein and can grow under a wide array of conditions.

One organism that can be cultured as described herein is a commonly used laboratory species *C. reinhardtii*. Cells of this species are haploid, and can grow on a simple medium of inorganic salts, using photosynthesis to provide energy. This organism can also grow in total darkness if acetate is provided as a carbon source. *C. reinhardtii* can be readily grown at room temperature under standard fluorescent lights. In addition, the cells can be synchronized by placing them on a light-dark cycle. Other methods of culturing *C. reinhardtii* cells are known to one of skill in the art.

Polynucleotides and Polypeptides

Also provided are isolated polynucleotides encoding a protein, for example, an ACCase described herein. As used herein "isolated polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

The novel ACCases of the present disclosure can be made by any method known in the art. The protein may be synthesized using either solid-phase peptide synthesis or by classical solution peptide synthesis also known as liquid-phase peptide synthesis. Using Val-Pro-Pro, Enalapril and Lisinopril as starting templates, several series of peptide analogs such as X-Pro-Pro, X-Ala-Pro, and X-Lys-Pro, wherein X represents any amino acid residue, may be synthesized using solid-phase or liquid-phase peptide synthesis. Methods for carrying out liquid phase synthesis of libraries of peptides and oligonucleotides coupled to a soluble oligomeric support have also been described. Bayer, Ernst and Mutter, Manfred, Nature 237:512-513 (1972); Bayer, Ernst, et al., J. Am. Chem. Soc. 96:7333-7336 (1974); Bonora, Gian Maria, et al., Nucleic Acids Res. 18:3155-3159 (1990). Liquid phase synthetic methods have the advantage over solid phase synthetic methods in that liquid phase synthesis methods do not require a structure present on a first reactant which is suitable for attaching the reactant to the solid phase. Also, liquid phase synthesis methods do not require avoiding chemical conditions which may cleave the bond between the solid phase and the first reactant (or intermediate product). In addition, reactions in a homogeneous solution may give better yields and more complete reactions than those obtained in heterogeneous solid phase/liquid phase systems such as those present in solid phase synthesis.

In oligomer-supported liquid phase synthesis the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, and eliminates tedious purification steps associated with traditional liquid phase synthesis. Oligomer-supported liquid phase synthesis has also been adapted to automatic liquid phase synthesis of peptides. Bayer, Ernst, et al., Peptides: Chemistry, Structure, Biology, 426.-432.

For solid-phase peptide synthesis, the procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. In a common method, an amino acid is bound to a resin particle, and the peptide generated in a stepwise manner by successive additions of protected amino acids to produce a chain of amino acids. Modifications of the technique described by Merrifield are commonly used. See, e.g., Merrifield, J. Am. Chem. Soc. 96: 2989-93 (1964). In an automated solid-phase method, peptides are synthesized by loading the carboxy-terminal amino acid onto an organic linker (e.g., PAM, 4-oxymethylphenylacetamidomethyl), which is covalently attached to an insoluble polystyrene resin cross-linked with divinyl benzene. The terminal amine may be protected by blocking with t-butyloxycarbonyl. Hydroxyl- and carboxyl-groups are commonly protected by blocking with O-benzyl groups. Synthesis is accomplished in an automated peptide synthesizer, such as that available from Applied Biosystems (Foster City, Calif.). Following synthesis, the product may be removed from the resin. The blocking groups are removed by using hydrofluoric acid or trifluoromethyl sulfonic acid according to established methods. A routine synthesis may produce 0.5 mmole of peptide resin. Following cleavage and purification, a yield of approximately 60 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high pressure liquid chromatography (e.g., using a $C^{18}$ column with 0.1% trifluoroacetic acid and acetonitrile as solvents) if the molecular weight of the peptide is less than 500 daltons. Purified peptide may be lyophilized and stored in a dry state until use. Analysis of the resulting peptides may be accomplished using the common methods of analytical high pressure liquid chromatography (HPLC) and electrospray mass spectrometry (ES-MS).

In other cases, a protein, for example, an ACCase is produced by recombinant methods. For production of any of the proteins described herein, host cells transformed with an expression vector containing the polynucleotide encoding such a protein can be used. The host cell can be a higher eukaryotic cell, such as a mammalian cell, or a lower eukaryotic cell such as a yeast or algal cell, or the host can be a prokaryotic cell such as a bacterial cell. Introduction of the expression vector into the host cell can be accomplished by a variety of methods including calcium phosphate transfection, DEAE-dextran mediated transfection, polybrene, protoplast fusion, liposomes, direct microinjection into the nuclei, scrape loading, biolistic transformation and electroporation. Large scale production of proteins from recombinant organisms is a well established process practiced on a commercial scale and well within the capabilities of one skilled in the art.

In some embodiments, the novel ACCases are provided in a substantially pure or substantially purified form. "Substantially pure" or "substantially purified" means that the substance is free from other contaminating proteins, nucleic acids, and other biologicals derived from the source organism. Purity may be assayed by standard methods, and will ordinarily be at least about 40% pure, at least about 50% pure, at least about 60% pure, at least about 70% pure, least about 75% pure, at least about 80% pure, at least about 85% pure, at least about 90% pure, at least about 95% pure, at least about 98% pure, or at least 99% pure. The analysis may be weight or molar percentages, evaluated, e.g., by gel staining, spectrophotometry, terminus labeling, etc.

It should be recognized that the present disclosure is not limited to transgenic cells, organisms, and plastids containing a protein or proteins as disclosed herein, but also encompasses such cells, organisms, and plastids transformed with additional nucleotide sequences encoding enzymes involved in fatty acid synthesis. Thus, some embodiments involve the introduction of one or more sequences encoding proteins involved in fatty acid synthesis in addition to a protein disclosed herein. For example, several enzymes in a fatty acid production pathway may be linked, either directly or indirectly, such that products produced by one enzyme in the pathway, once produced, are in close proximity to the next enzyme in the pathway. These additional sequences may be contained in a single vector either operatively linked to a single promoter or linked to multiple promoters, e.g. one promoter for each sequence. Alternatively, the additional coding sequences may be contained in a plurality of additional vectors. When a plurality of vectors are used, they can be introduced into the host cell or organism simultaneously or sequentially.

Additional embodiments provide a plastid, and in particular a chloroplast, transformed with a polynucleotide encoding a protein of the present disclosure. The protein may be introduced into the genome of the plastid using any of the methods described herein or otherwise known in the art. The plastid may be contained in the organism in which it naturally occurs. Alternatively, the plastid may be an isolated plastid, that is, a plastid that has been removed from the cell in which it normally occurs. Methods for the isolation of plastids are known in the art and can be found, for example, in Maliga et al. *Methods in Plant Molecular Biology*, Cold Spring Harbor Laboratory Press, 1995; Gupta and Singh, *J. Biosci.*, 21:819 (1996); and Camara et al., *Plant Physiol.*, 73:94 (1983). The isolated plastid transformed with a protein of the present disclosure can be introduced into a host cell. The host cell can be one that naturally contains the plastid or one in which the plastid is not naturally found.

Also within the scope of the present disclosure are artificial plastid genomes, for example chloroplast genomes, that contain nucleotide sequences encoding any one or more of the proteins of the present disclosure. Methods for the assembly of artificial plastid genomes can be found in co-pending U.S. patent application Ser. No. 12/287,230 filed Oct. 6, 2008, published as U.S. Publication No. 2009/0123977 on May 14, 2009, and U.S. patent application Ser. No. 12/384,893 filed Apr. 8, 2009, published as U.S. Publication No. 2009/0269816 on Oct. 29, 2009, each of which is incorporated by reference in its entirety.

Introduction of Polynucleotide into a Host Organism or Cell

To generate a genetically modified host cell, a polynucleotide, or a polynucleotide cloned into a vector, is introduced stably or transiently into a host cell, using established techniques, including, but not limited to, electroporation, calcium phosphate precipitation, DEAE-dextran mediated transfection, and liposome-mediated transfection. For transformation, a polynucleotide of the present disclosure will generally further include a selectable marker, e.g., any of several well-known selectable markers such as neomycin resistance, ampicillin resistance, tetracycline resistance, chloramphenicol resistance, and kanamycin resistance.

A polynucleotide or recombinant nucleic acid molecule described herein, can be introduced into a cell (e.g., alga cell) using any method known in the art. A polynucleotide can be introduced into a cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, *Ann. Rev. Plant. Physiol. Plant Mol. Biol.* 42:205-225, 1991).

As discussed above, microprojectile mediated transformation can be used to introduce a polynucleotide into a cell (for example, as described in Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a cell using a device such as the BIOLISTIC PD-1000 particle gun (BioRad; Hercules Calif.). Methods for the transformation using biolistic methods are well known in the art (for example, as described in Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., *Nature Biotech.* 14:494-498, 1996; and Shimamoto, *Curr. Opin. Biotech.* 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

The basic techniques used for transformation and expression in photosynthetic microorganisms are similar to those commonly used for *E. coli, Saccharomyces cerevisiae* and other species. Transformation methods customized for a photosynthetic microorganisms, e.g., the chloroplast of a strain of algae, are known in the art. These methods have been described in a number of texts for standard molecular biological manipulation (see Packer & Glaser, 1988, "Cyanobacteria", Meth. Enzymol., Vol. 167; Weissbach & Weissbach, 1988, "Methods for plant molecular biology," Academic Press, New York, Sambrook, Fritsch & Maniatis, 1989, "Molecular Cloning: A laboratory manual," 2nd edition Cold Spring Harbor Laboratory Press, Cold Spring Harbor, N.Y.; and Clark M S, 1997, Plant Molecular Biology, Springer, N.Y.). These methods include, for example, biolistic devices (See, for example, Sanford, Trends In Biotech. (1988) δ: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell.

Plastid transformation is a routine and well known method for introducing a polynucleotide into a plant cell chloroplast (see U.S. Pat. Nos. 5,451,513, 5,545,817, and 5,545,818; WO 95/16783; McBride et al., *Proc. Natl. Acad. Sci., USA* 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci., USA* 87:8526-8530, 1990), and can result in stable homoplasmic transformants, at a frequency of approximately one per 100 bombardments of target leaves.

A further refinement in chloroplast transformation/expression technology that facilitates control over the timing and tissue pattern of expression of introduced DNA coding sequences in plant plastid genomes has been described in PCT International Publication WO 95/16783 and U.S. Pat. No. 5,576,198. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase.

When nuclear transformation is utilized, the protein can be modified for plastid targeting by employing plant cell nuclear transformation constructs wherein DNA coding sequences of interest are fused to any of the available transit peptide sequences capable of facilitating transport of the encoded enzymes into plant plastids, and driving expression by employing an appropriate promoter. Targeting of the protein can be achieved by fusing DNA encoding plastid, e.g., chloroplast, leucoplast, amyloplast, etc., transit peptide sequences to the 5' end of DNAs encoding the enzymes. The sequences that encode a transit peptide region can be obtained, for example, from plant nuclear-encoded plastid proteins, such as the small subunit (SSU) of ribulose bisphosphate carboxylase, EPSP synthase, plant fatty acid biosynthesis related genes including fatty acyl-ACP thioesterases, acyl carrier protein (ACP), stearoyl-ACP desaturase, β-ketoacyl-ACP synthase and acyl-ACP thioesterase, or LHCPII genes, etc. Plastid transit peptide sequences can also be obtained from nucleic acid sequences encoding carotenoid biosynthetic enzymes, such as GGPP synthase, phytoene synthase, and phytoene desaturase. Other transit peptide sequences are disclosed in Von Heijne et al. (1991) *Plant Mol. Biol. Rep.* 9: 104; Clark et al. (1989) *J. Biol. Chem.* 264: 17544; della-Cioppa et al. (1987) *Plant Physiol.* 84: 965; Romer et al. (1993) *Biochem. Biophys. Res. Commun.* 196: 1414; and Shah et al. (1986) *Science* 233: 478. Another transit peptide sequence is that of the intact ACCase from *Chlamydomonas* (genbank EDO96563, amino acids 1-33). The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present disclosure are not critical as long as delivery into a plastid is obtained. Proteolytic processing within the plastid then produces the mature enzyme. This technique has proven successful with enzymes involved in polyhydroxyalkanoate biosynthesis (Nawrath et al. (1994) *Proc. Natl. Acad. Sci. USA* 91: 12760), and neomycin phosphotransferase II (NPT-II) and CP4 EPSPS (Padgette et al. (1995) *Crop Sci.* 35: 1451), for example.

Of interest are transit peptide sequences derived from enzymes known to be imported into the leucoplasts of seeds. Examples of enzymes containing useful transit peptides include those related to lipid biosynthesis (e.g., subunits of the plastid-targeted dicot acetyl-CoA carboxylase, biotin carboxylase, biotin carboxyl carrier protein, α-carboxy-transferase, and plastid-targeted monocot multifunctional acetyl-CoA carboxylase (Mw, 220,000); plastidic subunits of the fatty acid synthase complex (e.g., acyl carrier protein (ACP), malonyl-ACP synthase, KASI, KASII, and KASIII); steroyl-ACP desaturase; thioesterases (specific for short, medium, and long chain acyl ACP); plastid-targeted acyl transferases (e.g., glycerol-3-phosphate and acyl transferase); enzymes involved in the biosynthesis of aspartate family amino acids; phytoene synthase; gibberellic acid biosynthesis (e.g., ent-kaurene synthases 1 and 2); and carotenoid biosynthesis (e.g., lycopene synthase).

In some embodiments, an alga is transformed with a nucleic acid which encodes a protein of interest, for example, an ACCase, a prenyl transferase, an isoprenoid synthase, or an enzyme capable of converting a precursor into a fuel product or a precursor of a fuel product (e.g., an isoprenoid or fatty acid).

In one embodiment, a transformation may introduce a nucleic acid into a plastid of the host alga (e.g., chloroplast). In another embodiments a transformation may introduce a nucleic acid into the nuclear genome of the host alga. In still another embodiment, a transformation may introduce nucleic acids into both the nuclear genome and into a plastid.

Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized: Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Transporter and/or product screening may be performed by any method known in the art, for example ATP turnover assay, substrate transport assay, HPLC or gas chromatography.

The expression of the protein or enzyme can be accomplished by inserting a polynucleotide sequence (gene) encoding the protein or enzyme into the chloroplast or nuclear genome of a microalgae. The modified strain of microalgae can be made homoplasmic to ensure that the polynucleotide will be stably maintained in the chloroplast genome of all descendents. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

Vectors

Construct, vector and plasmid are used interchangeably throughout the disclosure. Nucleic acids encoding the novel ACCases can be contained in vectors, including cloning and expression vectors. A cloning vector is a self-replicating DNA molecule that serves to transfer a DNA segment into a host cell. Three common types of cloning vectors are bacterial plasmids, phages, and other viruses. An expression vector is a cloning vector designed so that a coding sequence inserted at a particular site will be transcribed and translated into a protein. Both cloning and expression vectors can contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences.

In some embodiments, a polynucleotide of the present disclosure is cloned or inserted into an expression vector using cloning techniques know to one of skill in the art. The nucleotide sequences may be inserted into a vector by a variety of methods. In the most common method the sequences are inserted into an appropriate restriction endonuclease site(s) using procedures commonly known to those skilled in the art and detailed in, for example, Sambrook et al., Molecular Cloning, A Laboratory Manual, 2nd Ed., Cold Spring Harbor Press, (1989) and Ausubel et al., Short Protocols in Molecular Biology, 2nd Ed., John Wiley & Sons (1992).

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, and herpes simplex virus), PI-based artificial chromosomes, yeast plasmids, yeast artificial chromosomes, and any other vectors specific for specific hosts of interest (such as *E. coli* and yeast). Thus, for example, a polynucleotide encoding an ACCase can be inserted into any one of a variety of expression vectors that are capable of expressing the enzyme. Such vectors can include, for example, chromosomal, nonchromosomal and synthetic DNA sequences.

Suitable expression vectors include chromosomal, non-chromosomal and synthetic DNA sequences, for example, SV 40 derivatives; bacterial plasmids; phage DNA; baculovirus; yeast plasmids: vectors derived from combinations of plasmids and phage DNA; and viral DNA such as vaccinia, adenovirus, fowl pox virus, and pseudorabies. In addition, any other vector that is replicable and viable in the host may be used. For example, vectors such as Ble2A, Arg7/2A, and SEnuc357 can be used for the expression of a protein.

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET21a-d(+) vectors (Novagen), and pSVLSV40 (Pharmacia). However, any other plasmid or other vector may be used so long as it is compatible with the host cell.

The expression vector, or a linearized portion thereof, can encode one or more exogenous or endogenous nucleotide sequences. Examples of exogenous nucleotide sequences that can be transformed into a host include genes from bacteria, fungi, plants, photosynthetic bacteria or other algae. Examples of other types of nucleotide sequences that can be transformed into a host, include, but are not limited to, transporter genes, isoprenoid producing genes, genes which encode for proteins which produce isoprenoids with two phosphates (e.g., GPP synthase and/or FPP synthase), genes which encode for proteins which produce fatty acids, lipids, or triglycerides, for example, ACCases, endogenous promoters, and 5' UTRs from the psbA, atpA, or rbcL genes. In some instances, an exogenous sequence is flanked by two homologous sequences.

Homologous sequences are, for example, those that have at least 50%, at least 60%, at least 70%, at least 80%, at least 90%, at least 95%, at least 98%, or at least at least 99% sequence identity to a reference amino acid sequence or nucleotide sequence, for example, the amino acid sequence or nucleotide sequence that is found naturally in the host cell. The first and second homologous sequences enable recombination of the exogenous or endogenous sequence into the genome of the host organism. The first and second homologous sequences can be at least 100, at least 200, at least 300, at least 400, at least 500, or at least 1500 nucleotides in length.

The polynucleotide sequence may comprise nucleotide sequences that are codon biased for expression in the organism being transformed. The skilled artisan is well aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. In some organisms, codon bias differs between the nuclear genome and organelle genomes, thus, codon optimization or biasing may be performed for the target genome (e.g., nuclear codon biased or chloroplast codon biased). In some embodiments, codon biasing occurs before mutagenesis to generate a polypeptide. In other embodiments, codon biasing occurs after mutagenesis to generate a polynucleotide. In yet other embodiments, codon biasing occurs before mutagenesis as well as after mutagenesis. Codon bias is described in detail herein.

In some embodiments, a vector comprises a polynucleotide operably linked to one or more control elements, such as a promoter and/or a transcription terminator. A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, $2^{nd}$ Ed., Cold Spring Harbor Press, (1989) and Ausubel et al., *Short Protocols in Molecular Biology*, $2^{nd}$ Ed., John Wiley & Sons (1992).

A vector in some embodiments provides for amplification of the copy number of a polynucleotide. A vector can be, for example, an expression vector that provides for expression of an ACCase, a prenyl transferase, an isoprenoid synthase, or a mevalonate synthesis enzyme in a host cell, e.g., a prokaryotic host cell or a eukaryotic host cell.

A polynucleotide or polynucleotides can be contained in a vector or vectors. For example, where a second (or more) nucleic acid molecule is desired, the second nucleic acid molecule can be contained in a vector, which can, but need not be, the same vector as that containing the first nucleic acid molecule. The vector can be any vector useful for introducing a polynucleotide into a genome and can include a nucleotide sequence of genomic DNA (e.g., nuclear or plastid) that is sufficient to undergo homologous recombination with genomic DNA, for example, a nucleotide sequence comprising about 400 to about 1500 or more substantially contiguous nucleotides of genomic DNA.

A regulatory or control element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, and an IRES. A regulatory element can include a promoter and transcriptional and translational stop signals. Elements may be provided with linkers for the purpose of introducing specific restriction sites facilitating ligation of the control sequences with the coding region of a nucleotide sequence encoding a polypeptide. Additionally, a sequence comprising a cell compartmentalization signal (i.e., a sequence that targets a polypeptide to the cytosol, nucleus, chloroplast membrane or cell membrane) can be attached to the polynucleotide encoding a protein of interest. Such signals are well known in the art and have been widely reported (see, e.g., U.S. Pat. No. 5,776,689).

Promoters are untranslated sequences located generally 100 to 1000 base pairs (bp) upstream from the start codon of a structural gene that regulate the transcription and translation of nucleic acid sequences under their control.

Promoters useful for the present disclosure may come from any source (e.g., viral, bacterial, fungal, protist, and animal). The promoters contemplated herein can be specific to photosynthetic organisms, non-vascular photosynthetic organisms, and vascular photosynthetic organisms (e.g., algae, flowering plants). In some instances, the nucleic acids above are inserted into a vector that comprises a promoter of a photosynthetic organism, e.g., algae. The promoter can be a constitutive promoter or an inducible promoter. A promoter typically includes necessary nucleic acid sequences near the start site of transcription, (e.g., a TATA element). Common promoters used in expression vectors include, but are not limited to, LTR or SV40 promoter, the *E. coli* lac or trp promoters, and the phage lambda PL promoter. Other promoters known to control the expression of genes in prokaryotic or eukaryotic cells can be used and are known to those skilled in the art. Expression vectors may also contain a ribosome binding site for translation initiation, and a transcription terminator. The vector may also contain sequences useful for the amplification of gene expression.

A "constitutive" promoter is a promoter that is active under most environmental and developmental conditions. An "inducible" promoter is a promoter that is active under controllable environmental or developmental conditions. Examples of inducible promoters/regulatory elements include, for example, a nitrate-inducible promoter (for example, as described in Bock et al, *Plant Mol. Biol.* 17:9 (1991)), or a light-inducible promoter, (for example, as described in Feinbaum et al, Mol. Gen. Genet. 226:449 (1991); and Lam and Chua, Science 248:471 (1990)), or a heat responsive promoter (for example, as described in Muller et al., Gene 111: 165-73 (1992)).

In many embodiments, a polynucleotide of the present disclosure includes a nucleotide sequence encoding a protein or enzyme of the present disclosure, where the nucleotide sequence encoding the polypeptide is operably linked to an inducible promoter. Inducible promoters are well known in the art. Suitable inducible promoters include, but are not limited to, the pL of bacteriophage λ; Placo; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (for example, as described in Guzman et al. (1995) J. Bacteriol. 177:4121-4130); a xylose-inducible promoter, e.g., Pxy1 (for example, as described in Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; and a heat-inducible promoter, e.g., heat inducible lambda $P_L$ promoter and a promoter controlled by a heat-sensitive repressor (e.g., C1857-repressed lambda-based expression vectors; for example, as described in Hoffmann et al. (1999) FEMS Microbiol Lett. 177(2):327-34).

In many embodiments, a polynucleotide of the present disclosure includes a nucleotide sequence encoding a protein or enzyme of the present disclosure, where the nucleotide sequence encoding the polypeptide is operably linked to a constitutive promoter. Suitable constitutive promoters for use in prokaryotic cells are known in the art and include, but are not limited to, a sigma70 promoter, and a consensus sigma70 promoter.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter; an araBAD promoter; in vivo regulated promoters, such as an ssaG promoter or a related promoter (for example, as described in U.S. Patent Publication No. 20040131637), a pagC promoter (for example, as described in Pulkkinen and Miller, J. Bacteriol., 1991: 173 (1): 86-93; and Alpuche-Aranda et al., PNAS, 1992; 89(21): 10079-83), a nirB promoter (for example, as described in Harborne et al. (1992) Mol. Micro. 6:2805-2813; Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (for example, GenBank Accession Nos. AX798980, AX798961, and AX798183); a stationary phase promoter, e.g., a dps promoter, a spy promoter; a promoter derived from the pathogenicity island SPI-2 (for example, as described in WO96/17951); an actA promoter (for example, as described in Shetron-Rama et al. (2002) Infect. Immun. 70:1087-1096); an rpsM promoter (for example, as described in Valdivia and Falkow (1996). Mol. Microbiol. 22:367-378); a tet promoter (for example, as described in Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); and an SP6 promoter (for example, as described in Melton et al. (1984) Nucl. Acids Res. 12:7035-7056).

In yeast, a number of vectors containing constitutive or inducible promoters may be used. For a review of such vectors see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (for example, as described in Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Non-limiting examples of suitable eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression.

A vector utilized in the practice of the disclosure also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, and sequences that encode a selectable marker. As such, the vector can contain, for example, one or more cloning sites such as a multiple cloning site, which can, but need not be positioned such that a exogenous or endogenous polynucleotide can be inserted into the vector and operatively linked to a desired element.

The vector also can contain a prokaryote origin of replication (ori), for example, an *E. coli* on or a cosmid ori, thus allowing passage of the vector into a prokaryote host cell, as well as into a plant chloroplast. Various bacterial and viral origins of replication are well known to those skilled in the art and include, but are not limited to the pBR322 plasmid origin, the 2u plasmid origin, and the SV40, polyoma, adenovirus, VSV, and BPV viral origins.

A regulatory or control element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IRES. Additionally, an element can be a cell compartmentalization signal (i.e., a sequence that targets a polypeptide to the cytosol, nucleus, chloroplast membrane or cell membrane). In some aspects of the present disclosure, a cell compartmentalization signal (e.g., a cell membrane targeting sequence) may be ligated to a gene and/or transcript, such that translation of the gene occurs in the chloroplast. In other aspects, a cell compartmentalization signal may be ligated to a gene such that, following translation of the gene, the protein is transported to the cell membrane. Cell compartmentalization signals are well known in the art and have been widely reported (see, e.g., U.S. Pat. No. 5,776,689).

A vector, or a linearized portion thereof, may include a nucleotide sequence encoding a reporter polypeptide or other selectable marker. The term "reporter" or "selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (for example, as described in Giacomin, *Plant Sci.* 116:59-72, 1996; Scikantha, *J. Bacteriol.* 178:121, 1996; Gerdes, *FEBS Lett.* 389:44-47, 1996; and Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain, for example, prokaryotic cells, eukaryotic cells, and/or plant cells that express the marker and, therefore, can be useful as a component of a vector of the disclosure. The selection gene or marker can encode for a protein necessary for the survival or growth of the host cell transformed with the vector. One class of selectable markers are native or modified genes which restore a biological or physiological function to a host cell (e.g., restores photosynthetic capability or restores a metabolic pathway). Other examples of selectable markers include, but are not limited to, those that confer antimetabolite resistance, for example, dihydrofolate reductase, which confers resistance to methotrexate (for example, as described in Reiss, *Plant Physiol.* (*Life Sci. Adv.*) 13:143-149, 1994); neomycin phosphotransferase, which confers resistance to the aminoglycosides neomycin, kanamycin and paromycin (for example, as described in Herrera-Estrella, *EMBO J.* 2:987-995, 1983), hygro, which confers resistance to hygromycin (for example, as described in Marsh, *Gene* 32:481-485, 1984), trpB, which allows cells to utilize indole in place of tryptophan; hisD, which allows cells to utilize histinol in place of histidine (for example, as described in Hartman, *Proc. Natl. Acad. Sci., USA* 85:8047, 1988); mannose-6-phosphate isomerase which allows cells to utilize mannose (for example, as described in PCT Publication Application No. WO 94/20627); ornithine decarboxylase, which confers resistance to the ornithine decarboxylase inhibitor, 2-(difluoromethyl)-DL-ornithine (DFMO; for example, as described in McConlogue, 1987, In: Current Communications in Molecular Biology, Cold Spring Harbor Laboratory ed.); and deaminase from *Aspergillus terreus*, which confers resistance to Blasticidin S (for example, as described in Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (for example, as described in White et al., *Nucl. Acids Res.* 18:1062, 1990; and Spencer et al., *Theor. Appl. Genet.* 79:625-631, 1990), a mutant EPSPV-synthase, which confers glyphosate resistance (for example, as described in Hinchee et al., *BioTechnology* 91:915-922, 1998), a mutant acetolactate synthase, which confers imidazolione or sulfonylurea resistance (for example, as described in Lee et al., *EMBO J.* 7:1241-1248, 1988), a mutant psbA, which confers resistance to atrazine (for example, as described in Smeda et al., *Plant Physiol.* 103:911-917, 1993), or a mutant protoporphyrinogen oxidase (for example, as described in U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells; tetramycin or ampicillin resistance for prokaryotes such as *E. coli*; and bleomycin, gentamycin, glyphosate, hygromycin, kanamycin, methotrexate, phleomycin, phosphinotricin, spectinomycin, dtreptomycin, streptomycin, sulfonamide and sulfonylurea resistance in plants (for example, as described in Maliga et al., Methods in Plant Molecular Biology, Cold Spring Harbor Laboratory Press, 1995, page 39). The selection marker can have its own promoter or its expression can be driven by a promoter driving the expression of a polypeptide of interest.

Reporter genes greatly enhance the ability to monitor gene expression in a number of biological organisms. Reporter genes have been successfully used in chloroplasts of higher plants, and high levels of recombinant protein expression have been reported. In addition, reporter genes have been used in the chloroplast of *C. reinhardtii*. In chloroplasts of higher plants, β-glucuronidase (uidA, for example, as described in Staub and Maliga, *EMBO J.* 12:601-606, 1993), neomycin phosphotransferase (nptII, for example, as described in Carrer et al., *Mol. Gen. Genet.* 241:49-56, 1993), adenosyl-3-adenyltransf-erase (aadA, for example, as described in Svab and Maliga, *Proc. Natl. Acad. Sci., USA* 90:913-917, 1993), and the *Aequorea victoria* GFP (for example, as described in Sidorov et al., *Plant J.* 19:209-216, 1999) have been used as reporter genes (for example, as described in Heifetz, *Biochemie* 82:655-666, 2000). Each of these genes has attributes that make them useful reporters of chloroplast gene expression, such as ease of analysis, sensitivity, or the ability to examine expression in situ. Based upon these studies, other exogenous proteins have been expressed in the chloroplasts of higher plants such as *Bacillus thuringiensis* Cry toxins, conferring resistance to insect herbivores (for example, as described in Kota et al., *Proc. Natl. Acad. Sci., USA* 96:1840-1845, 1999), or human somatotropin (for example, as described in Staub et al., *Nat. Biotechnol.* 18:333-338, 2000), a potential biopharmaceutical. Several reporter genes have been expressed in the chloroplast of the eukaryotic green alga, *C. reinhardtii*, including aadA (for example, as described in Goldschmidt-Clermont, *Nucl. Acids Res.* 19:4083-4089 1991; and Zerges and Rochaix, *Mol. Cell. Biol.* 14:5268-5277, 1994), uidA (for example, as described in Sakamoto et al., *Proc. Natl. Acad. Sci., USA* 90:477-501, 1993; and Ishikura et al., *J. Biosci. Bioeng.* 87:307-314 1999), *Renilla* luciferase (for example, as described in Minko et al., *Mol. Gen. Genet.* 262:421-425, 1999) and the amino glycoside phosphotransferase from *Acinetobacter baumanii*, aphA6 (for example, as described in Bateman and Purton, *Mol. Gen. Genet* 263:404-410, 2000). In one embodiment the protein described herein is modified by the addition of an N-terminal strep tag epitope to add in the detection of protein expression. In one embodiment the ACCases described herein are modified by the addition of an N-terminal strep tag epitope to add in detection of ACCase expression.

In some instances, the vectors of the present disclosure will contain elements such as an *E. coli* or *S. cerevisiae* origin of replication. Such features, combined with appropriate selectable markers, allows for the vector to be "shuttled" between the target host cell and a bacterial and/or yeast cell. The ability to passage a shuttle vector of the disclosure in a secondary host may allow for more convenient manipulation of the features of the vector. For example, a reaction mixture containing the vector and inserted polynucleotide(s) of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant cell chloroplasts, wherein a polypeptide of interest can be expressed and, if desired, isolated according to a method of the disclosure.

Knowledge of the chloroplast or nuclear genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, *J. Mol. Biol.* 312:425-438, 2001; Staub and Maliga, *Plant Cell* 4:39-45, 1992; and Kavanagh et al., *Genetics* 152:1111-1122, 1999, each of which is incorporated herein by reference). The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link; J. Maul, J. W. Lilly, and D. B. Stern, unpublished results; revised Jan. 28, 2002; to be published as GenBank Acc. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector (also described in Maul, J. E., et al. (2002) The Plant Cell, Vol. 14 (2659-2679)). For example, the chloroplast vector, p322, is a clone extending from the Eco (Eco RI) site at about position 143.1 kb to the Xho (Xho 1) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

In addition, the entire nuclear-genome of *C. reinhardtii* is described in Merchant, S. S., et al., Science (2007), 318 (5848):245-250, thus facilitating one of skill in the art to select a sequence or sequences useful for constructing a vector.

For expression of the polypeptide in a host, an expression cassette or vector may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous or endogenous proteins. A selectable marker operative in the expression host may be present.

The nucleotide sequences may be inserted into a vector by a variety of methods. In the most common method the sequences are inserted into an appropriate restriction endonuclease site(s) using procedures commonly known to those skilled in the art and detailed in, for example, Sambrook et al., *Molecular Cloning, A Laboratory Manual*, 2nd Ed., Cold Spring Harbor Press, (1989) and Ausubel et al., *Short Protocols in Molecular Biology*, 2nd Ed., John Wiley & Sons (1992).

The description herein provides that host cells may be transformed with vectors. One of skill in the art will recognize that such transformation includes transformation with circular or linearized vectors, or linearized portions of a vector. Thus, a host cell comprising a vector may contain the entire vector in the cell (in either circular or linear form), or may contain a linearized portion of a vector of the present disclosure. In some instances 0.5 to 1.5 kb flanking nucleotide sequences of chloroplast genomic DNA may be used. In some instances 0.5 to 1.5 kb flanking nucleotide sequences of nuclear genomic DNA may be used, or 2.0 to 5.0 kb may be used.

Codon Optimization

As discussed above, one or more codons of an encoding polynucleotide can be "biased" or "optimized" to reflect the codon usage of the host organism. For example, one or more codons of an encoding polynucleotide can be "biased" or "optimized" to reflect chloroplast codon usage (Table A) or nuclear codon usage (Table B). Most amino acids are encoded by two or more different (degenerate) codons, and it is well recognized that various organisms utilize certain codons in preference to others. "Biased" or codon "optimized" can be used interchangeably throughout the specification. Codon bias can be variously skewed in different plants, including, for example, in alga as compared to tobacco. Generally, the codon bias selected reflects codon usage of the plant (or organelle therein) which is being transformed with the nucleic acids of the present disclosure.

A polynucleotide that is biased for a particular codon usage can be synthesized de novo, or can be genetically modified using routine recombinant DNA techniques, for example, by a site directed mutagenesis method, to change one or more codons such that they are biased for chloroplast codon usage.

Such preferential codon usage, which is utilized in chloroplasts, is referred to herein as "chloroplast codon usage." Table A (below) shows the chloroplast codon usage for *C. reinhardtii* (see U.S. Patent Application Publication No.: 2004/0014174, published Jan. 22, 2004).

TABLE A

Chloroplast Codon Usage in *Chlamydomonas reinhardtii*

| | | | |
|---|---|---|---|
| UUU 34.1*(348**) | UCU 19.4(198) | UAU 23.7(242) | UGU 8.5(87) |
| UUC 14.2(145) | UCC 4.9(50) | UAC 10.4(106) | UGC 2.6(27) |
| UUA 72.8(742) | UCA 20.4(208) | UAA 2.7(28) | UGA 0.1(1) |
| UUG 5.6(57) | UCG 5.2(53) | UAG 0.7(7) | UGG 13.7(140) |
| CUU 14.8(151) | CCU 14.9(152) | CAU 11.1(113) | CGU 25.5(260) |
| CUC 1.0(10) | CCC 5.4(55) | CAC 8.4(86) | CGC 5.1(52) |
| CUA 6.8(69) | CCA 19.3(197) | CAA 34.8(355) | CGA 3.8(39) |
| CUG 7.2(73) | CCG 3.0(31) | CAG 5.4(55) | CGG 0.5(5) |
| AUU 44.6(455) | ACU 23.3(237) | AAU 44.0(449) | AGU 16.9(172) |
| AUC 9.7(99) | ACC 7.8(80) | AAC 19.7(201) | AGC 6.7(68) |
| AUA 8.2(84) | ACA 29.3(299) | AAA 61.5(627) | AGA 5.0(51) |
| AUG 23.3(238) | ACG 4.2(43) | AAG 11.0(112) | AGG 1.5(15) |
| GUU 27.5(280) | GCU 30.6(312) | GAU 23.8(243) | GGU 40.0(408) |
| GUC 4.6(47) | GCC 11.1(113) | GAC 11.6(118) | GGC 8.7(89) |
| GUA 26.4(269) | GCA 19.9(203) | GAA 40.3(411) | GGA 9.6(98) |
| GUG 7.1(72) | GCG 4.3(44) | GAG 6.9(70) | GGG 4.3(44) |

*Frequency of codon usage per 1,000 codons.
**Number of times observed in 36 chloroplast coding sequences (10,193 codons).

The chloroplast codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect chloroplast codon usage, or can be the de novo synthesis of polynucleotide sequence such that the change (bias) is introduced as a consequence of the synthesis procedure.

In addition to utilizing chloroplast codon bias as a means to provide efficient translation of a polypeptide, it will be recognized that an alternative means for obtaining efficient translation of a polypeptide in a chloroplast is to re-engineer the chloroplast genome (e.g., a *C. reinhardtii* chloroplast genome) for the expression of tRNAs not otherwise expressed in the chloroplast genome. Such an engineered algae expressing one or more exogenous tRNA molecules provides the advantage that it would obviate a requirement to modify every polynucleotide of interest that is to be introduced into and expressed from a chloroplast genome; instead, algae such as *C. reinhardtii* that comprise a genetically modified chloroplast genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 1996; Duret, Trends Genet. 16:287-289, 2000; Goldman et. al., J. Mol. Biol. 245:467-473, 1995; and Komar et. al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into chloroplasts to complement rare or unused tRNA genes in a chloroplast genome, such as a *C. reinhardtii* chloroplast genome.

Generally, the chloroplast codon bias selected for purposes of the present disclosure, including, for example, in preparing a synthetic polynucleotide as disclosed herein reflects chloroplast codon usage of a plant chloroplast, and includes a codon bias that, with respect to the third position of a codon, is skewed towards A/T, for example, where the third position has greater than about 66% AT bias, or greater than about 70% AT bias. In one embodiment, the chloroplast codon usage is biased to reflect alga chloroplast codon usage, for example, *C. reinhardtii*, which has about 74.6% AT bias in the third codon position. Preferred codon usage in the chloroplasts of algae has been described in US 2004/0014174.

Table B exemplifies codons that are preferentially used in algal nuclear genes. The nuclear codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect nuclear codon usage, or can be the de novo synthesis of polynucleotide sequence such that the change (bias) is introduced as a consequence of the synthesis procedure.

In addition to utilizing nuclear codon bias as a means to provide efficient translation of a polypeptide, it will be recognized that an alternative means for obtaining efficient translation of a polypeptide in a nucleus is to re-engineer the nuclear genome (e.g., a *C. reinhardtii* nuclear genome) for the expression of tRNAs not otherwise expressed in the nuclear genome. Such an engineered algae expressing one or more exogenous tRNA molecules provides the advantage that it would obviate a requirement to modify every polynucleotide of interest that is to be introduced into and expressed from a nuclear genome; instead, algae such as *C. reinhardtii* that comprise a genetically modified nuclear genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 1996; Duret, Trends Genet. 16:287-289, 2000; Goldman et. Al., J. Mol. Biol. 245:467-473, 1995; and Komar et. Al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001.). Utilizing endogenous tRNA genes, site directed mutagenesis can be used to make a synthetic tRNA gene, which can be introduced into the nucleus to complement rare or unused tRNA genes in a nuclear genome, such as a *C. reinhardtii* nuclear genome.

Generally, the nuclear codon bias selected for purposes of the present disclosure, including, for example, in preparing a synthetic polynucleotide as disclosed herein, can reflect nuclear codon usage of an algal nucleus and includes a codon bias that results in the coding sequence containing greater than 60% G/C content.

Table C lists the codon selected at each position for back-translating the protein to a DNA sequence for synthesis. The selected codon is the sequence recognized by the tRNA encoded in the chloroplast genome when present; the stop codon (TAA) is the codon most frequently present in the chloroplast encoded genes. If an undesired restriction site is created, the next best choice according to the regular *Chlamydomonas* chloroplast usage table that eliminates the restriction site is selected.

TABLE C

| Amino acid | Codon utilized |
|---|---|
| F | TTC |
| L | TTA |
| I | ATC |
| V | GTA |
| S | TCA |
| P | CCA |
| T | ACA |
| A | GCA |
| Y | TAC |
| H | CAC |
| Q | CAA |
| N | AAC |
| K | AAA |
| D | GAC |
| E | GAA |
| C | TGC |
| R | CGT |
| G | GGC |
| W | TGG |
| M | ATG |
| STOP | TAA |

Percent Sequence Identity

One example of an algorithm that is suitable for determining percent sequence identity or sequence similarity between nucleic acid or polypeptide sequences is the BLAST algorithm, which is described, e.g., in Altschul et al., *J. Mol. Biol.* 215:403-410 (1990). Software for performing BLAST analysis is publicly available through the National Center for Biotechnology Information. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of

TABLE B

Nuclear Codon Usage in *Chlamydomonas reinhardtii*

| | | | |
|---|---|---|---|
| UUU 5.0 (2110) | UCU 4.7 (1992) | UAU 2.6 (1085) | UGU 1.4 (601) |
| UUC 27.1 (11411) | UCC 16.1 (6782) | UAC 22.8 (9579) | UGC 13.1 (5498) |
| UUA 0.6 (247) | UCA 3.2 (1348) | UAA 1.0 (441) | UGA 0.5 (227) |
| UUG 4.0 (1673) | UCG 16.1 (6763) | UAG 0.4 (183) | UGG 13.2 (5559) |
| CUU 4.4 (1869) | CCU 8.1 (3416) | CAU 2.2 (919) | CGU 4.9 (2071) |
| CUC 13.0 (5480) | CCC 29.5 (12409) | CAC 17.2 (7252) | CGC 34.9 (14676) |
| CUA 2.6 (1086) | CCA 5.1 (2124) | CAA 4.2 (1780) | CGA 2.0 (841) |
| CUG 65.2 (27420) | CCG 20.7 (8684) | CAG 36.3 (15283) | CGG 11.2 (4711) |
| AUU 8.0 (3360) | ACU 5.2 (2171) | AAU 2.8 (1157) | AGU 2.6 (1089) |
| AUC 26.6 (11200) | ACC 27.7 (11663) | AAC 28.5 (11977) | AGC 22.8 (9590) |
| AUA 1.1 (443) | ACA 4.1 (1713) | AAA 2.4 (1028) | AGA 0.7 (287) |
| 0AUG 25.7 (10796) | ACG 15.9 (6684) | AAG 43.3 (18212) | AGG 2.7 (1150) |
| GUU 5.1 (2158) | GCU 16.7 (7030) | GAU 6.7 (2805) | GGU 9.5 (3984) |
| GUC 15.4 (6496) | GCC 54.6 (22960) | GAC 41.7 (17519) | GGC 62.0 (26064) |
| GUA 2.0 (857) | GCA 10.6 (4467) | GAA 2.8 (1172) | GGA 5.0 (2084) |
| GUG 46.5 (19558) | GCG 44.4 (18688) | GAG 53.5 (22486) | GGG 9.7 (4087) | fields: [triplet] [frequency: per thousand] ([number])
Coding GC 66.30% 1$^{st}$ letter GC 64.80% 2$^{nd}$ letter GC 47.90% 3$^{rd}$ letter GC 86.21%

10, and the BLOSUM62 scoring matrix (as described, for example, in Henikoff & Henikoff (1989) *Proc. Natl. Acad. Sci. USA*, 89:10915). In addition to calculating percent sequence identity, the BLAST algorithm also can perform a statistical analysis of the similarity between two sequences (for example, as described in Karlin & Altschul, *Proc. Nat'l. Acad. Sci. USA*, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

Fatty Acids and Glycerol Lipids

The present disclosure describes host cells capable of making polypeptides that contribute to the accumulation and/or secretion of fatty acids, glycerol lipids, or oils, by transforming host cells (e.g., alga cells such as *C. reinhardtii*, *D. salina*, *H. pluvalis*, and cyanobacterial cells) with nucleic acids encoding one or more different enzymes. Examples of such enzymes include acetyl-CoA carboxylase, ketoreductase, thioesterase, malonyltransferase, dehydratase, acyl-CoA ligase, ketoacylsynthase, enoylreductase, and desaturase. The enzymes can be, for example, catabolic or biodegrading enzymes.

In some instances, the host cell will naturally produce the fatty acid, glycerol lipid, triglyceride, or oil of interest. Therefore, transformation of the host cell with a polynucleotide encoding an enzyme, for example an ACCase, will allow for the increased activity of the enzyme and/or increased accumulation and/or secretion of a molecule of interest (e.g., a lipid) in the cell.

A change in the accumulation and/or secretion of a desired product, for example, fatty acids, glycerol lipids, or oils, by a transformed host cell can include, for example, a change in the total lipid content over that normally present in the cell, or a change in the type of lipids that are normally present in the cell.

Increased malonyl CoA production is required for increased fatty acid biosynthesis. Increased fatty acid biosynthesis is required for increased accumulation of fatty acid based lipids. An increase in fatty acid based lipids can be measured by methyl tert-butyl ether (MTBE) extraction.

Some host cells may be transformed with multiple genes encoding one or more enzymes. For example, a single transformed cell may contain exogenous nucleic acids encoding enzymes that make up an entire glycerolipid synthesis pathway. One example of a pathway might include genes encoding an acetyl CoA carboxylase, a malonyltransferase, a ketoacylsynthase, and a thioesterase. Cells transformed with an entire pathway and/or enzymes extracted from those cells, can synthesize, for example, complete fatty acids or intermediates of the fatty acid synthesis pathway. Constructs may contain, for example, multiple copies of the same gene, multiple genes encoding the same enzyme from different organisms, and/or multiple genes with one or more mutations in the coding sequence(s).

The enzyme(s) produced by the modified cells may result in the production of fatty acids, glycerol lipids, triglycerides, or oils that may be collected from the cells and/or the surrounding environment (e.g., bioreactor or growth medium). In some embodiments, the collection of the fatty acids, glycerol lipids, triglycerides, or oils is performed after the product is secreted from the cell via a cell membrane transporter.

Examples of candidate *Chlamydomonas* genes encoding enzymes of glycerolipid metabolism that can be used in the described embodiments are described in The *Chlamydomonas* Sourcebook Second Edition, Organellar and Metabolic Processes, Vol. 2, pp. 41-68, David B. Stern (Ed.), (2009), Elsevier Academic Press.

For example, enzymes involved in plastid, mitochondrial, and cytosolic pathways, along with plastidic and cytosolic isoforms of fatty acid desaturases, and triglyceride synthesis enzymes are described (and their accession numbers provided). An exemplary chart of some of the genes described is provided below:

| | | |
|---|---|---|
| Acyl-ACP thioesterase | FAT1 | EDP08596 |
| Long-chain acyl-CoA synthetase | LCS1 | EDO96800 |
| CDP-DAG: Inositol phosphotransferase | PIS1 | EDP06395 |
| Acyl-CoA: Diacylglycerol acyltransferase | DGA1 | EDO96893 |
| Phospholipid: Diacylglycerol acyltransferase | LRO1(LCA1) | EDP07444 |

Examples of the types of fatty acids and/or glycerol lipids that a host cell or organism can produce, are described below.

Lipids are a broad group of naturally occurring molecules which includes fats, waxes, sterols, fat-soluble vitamins (such as vitamins A, D, E and K), monoglycerides, diglycerides, phospholipids, and others. The main biological functions of lipids include energy storage, as structural components of cell membranes, and as important signaling molecules.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits or "building blocks": ketoacyl and isoprene groups. Lipids may be divided into eight categories: fatty acyls, glycerolipids, glycerophospholipids, sphingolipids, saccharolipids and polyketides (derived from condensation of ketoacyl subunits); and sterol lipids and prenol lipids (derived from condensation of isoprene subunits). For this disclosure, saccharolipids will not be discussed.

Fats are a subgroup of lipids called triglycerides. Lipids also encompass molecules such as fatty acids and their derivatives (including tri-, di-, and monoglycerides and phospholipids), as well as other sterol-containing metabolites such as cholesterol. Humans and other mammals use various biosynthetic pathways to both break down and synthesize lipids.

Fatty Acyls

Fatty acyls, a generic term for describing fatty acids, their conjugates and derivatives, are a diverse group of molecules synthesized by chain-elongation of an acetyl-CoA primer with malonyl-CoA or methylmalonyl-CoA groups in a process called fatty acid synthesis. A fatty acid is any of the aliphatic monocarboxylic acids that can be liberated by hydrolysis from naturally occurring fats and oils. They are made of a hydrocarbon chain that terminates with a carboxylic acid group; this arrangement confers the molecule with a polar, hydrophilic end, and a nonpolar, hydrophobic end that is insoluble in water. The fatty acid structure is one of the most fundamental categories of biological lipids, and is commonly used as a building block of more structurally complex lipids. The carbon chain, typically between four to 24 carbons long, may be saturated or unsaturated, and may be attached to functional groups containing oxygen, halogens, nitrogen and sulfur; branched fatty acids and hydroxyl fatty acids also occur, and very long chain acids of over 30 carbons are found in waxes. Where a double bond exists, there is the possibility of either a cis or trans geometric isomerism, which significantly affects the molecules molecular configuration. Cis-double bonds cause the fatty acid chain to bend, an effect that is more pronounced the more double bonds there are in a chain. This in turn plays an important role in the structure and function of cell membranes. Most naturally occurring fatty acids are of the cis configuration, although the trans form does exist in some natural and partially hydrogenated fats and oils.

Examples of biologically important fatty acids are the eicosanoids, derived primarily from arachidonic acid and eicosapentaenoic acid, which include prostaglandins, leukotrienes, and thromboxanes. Other major lipid classes in the fatty acid category are the fatty esters and fatty amides. Fatty esters include important biochemical intermediates such as wax esters, fatty acid thioester coenzyme A derivatives, fatty acid thioester ACP derivatives and fatty acid carnitines. The fatty amides include N-acyl ethanolamines.

Glycerolipids

Glycerolipids are composed mainly of mono-, di- and tri-substituted glycerols, the most well-known being the fatty acid esters of glycerol (triacylglycerols), also known as triglycerides. In these compounds, the three hydroxyl groups of glycerol are each esterified, usually by different fatty acids. Because they function as a food store, these lipids comprise the bulk of storage fat in animal tissues. The hydrolysis of the ester bonds of triacylglycerols and the release of glycerol and fatty acids from adipose tissue is called fat mobilization.

Additional subclasses of glycerolipids are represented by glycosylglycerols, which are characterized by the presence of one or more sugar residues attached to glycerol via a glycosidic linkage. An example of a structure in this category is the digalactosyldiacylglycerols found in plant membranes.

Exemplary *Chlamydomonas* glycerolipids include: DGDG, digalactosyldiacylglycerol; DGTS, diacylglyceryl-N,N,N-trimethylhomoserine; MGDG, monogalactosyldiacylglycerol; PtdEtn, phosphatidylethanolamine; PidGro, phosphatidylglycerol; PtdIns, phosphatidylinositol; SQDG, sulfoquinovosyldiacylglycerol; and TAG, triacylglycerol.

Glycerophospholipids

Glycerophospholipids are any derivative of glycerophosphoric acid that contains at least one O-acyl, O-alkyl, or O-alkenyl group attached to the glycerol residue. The common glycerophospholipids are named as derivatives of phosphatidic acid (phosphatidyl choline, phosphatidyl serine, and phosphatidyl ethanolamine).

Glycerophospholipids, also referred to as phospholipids, are ubiquitous in nature and are key components of the lipid bilayer of cells, as well as being involved in metabolism and cell signaling. Glycerophospholipids may be subdivided into distinct classes, based on the nature of the polar headgroup at the sn-3 position of the glycerol backbone in eukaryotes and eubacteria, or the sn-1 position in the case of archaebacteria.

Examples of glycerophospholipids found in biological membranes are phosphatidylcholine (also known as PC, GPCho or lecithin), phosphatidylethanolamine (PE or GPEtn) and phosphatidylserine (PS or GPSer). In addition to serving as a primary component of cellular membranes and binding sites for intra- and intercellular proteins, some glycerophospholipids in eukaryotic cells, such as phosphatidylinositols and phosphatidic acids are either precursors of, or are themselves, membrane-derived second messengers. Typically, one or both of these hydroxyl groups are acylated with long-chain fatty acids, but there are also alkyl-linked and 1Z-alkenyl-linked (plasmalogen) glycerophospholipids, as well as dialkylether variants in archaebacteria.

Sphingolipids

Sphingolipids are any of class of lipids containing the long-chain amino diol, sphingosine, or a closely related base (i.e. a sphingoid). A fatty acid is bound in an amide linkage to the amino group and the terminal hydroxyl may be linked to a number of residues such as a phosphate ester or a carbohydrate. The predominant base in animals is sphingosine while in plants it is phytosphingosine.

The main classes are: (1) phosphosphigolipids (also known as sphingophospholipids), of which the main representative is sphingomyelin; and (2) glycosphingolipids, which contain at least one monosaccharide and a sphingoid, and include the cerebrosides and gangliosides. Sphingolipids play an important structural role in cell membranes and may be involved in the regulation of protein kinase C.

As mentioned above, sphingolipids are a complex family of compounds that share a common structural feature, a sphingoid base backbone, and are synthesized de novo from the amino acid serine and a long-chain fatty acyl CoA, that are then converted into ceramides, phosphosphingolipids, glycosphingolipids and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms.

The major phosphosphingolipids of mammals are sphingomyelins (ceramide phosphocholines), whereas insects contain mainly ceramide phosphoethanolamines, and fungi have phytoceramide phosphoinositols and mannose-containing head groups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol Lipids

Sterol lipids, such as cholesterol and its derivatives, are an important component of membrane lipids, along with the glycerophospholipids and sphingomyelins. The steroids, all derived from the same fused four-ring core structure, have different biological roles as hormones and signaling molecules. The eighteen-carbon (C18) steroids include the estrogen family whereas the C19 steroids comprise the androgens such as testosterone and androsterone. The C21 subclass includes the progestogens as well as the glucocorticoids and mineralocorticoids. The secosteroids, comprising various forms of vitamin D, are characterized by cleavage of the B ring of the core structure. Other examples of sterols are the bile acids and their conjugates, which in mammals are oxidized derivatives of cholesterol and are synthesized in the liver. The plant equivalents are the phytosterols, such as O-sitosterol, stigmasterol, and brassicasterol; the latter compound is also used as a biomarker for algal growth. The predominant sterol in fungal cell membranes is ergosterol.

Prenol Lipids

Prenol lipids are synthesized from the 5-carbon precursors isopentenyl diphosphate and dimethylallyl diphosphate that are produced mainly via the mevalonic acid (MVA) pathway. The simple isoprenoids (for example, linear alcohols and diphosphates) are formed by the successive addition of C5 units, and are classified according to the number of these terpene units. Structures containing greater than 40 carbons are known as polyterpenes. Carotenoids are important simple isoprenoids that function as antioxidants and as precursors of vitamin A. Another biologically important class of molecules is exemplified by the quinones and hydroquinones, which contain an isoprenoid tail attached to a quinonoid core of non-isoprenoid origin. Prokaryotes synthesize polyprenols (called bactoprenols) in which the terminal isoprenoid unit attached to oxygen remains unsaturated, whereas in animal polyprenols (dolichols) the terminal isoprenoid is reduced.

Polyketides

Polyketides or sometimes acetogenin are any of a diverse group of natural products synthesized via linear poly-β-ketones, which are themselves formed by repetitive head-to-tail addition of acetyl (or substituted acetyl) units indirectly derived from acetate (or a substituted acetate) by a mechanism similar to that for fatty-acid biosynthesis but without the intermediate reductive steps. In many case, acetyl-CoA functions as the starter unit and malonyl-CoA as the extending unit. Various molecules other than acetyl-CoA may be used as starter, often with methoylmalonyl-CoA as the extending unit. The poly-β-ketones so formed may undergo a variety of further types of reactions, which include alkylation, cyclization, glycosylation, oxidation, and reduction. The classes of product formed—and their corresponding starter substances—comprise inter alia: coniine (of hemlock) and orsellinate (of lichens)—acetyl-CoA; flavanoids and stilbenes—cinnamoyl-CoA; tetracyclines—amide of malonyl-CoA; urushiols (of poison ivy)—palmitoleoyl-CoA; and erythonolides—propionyl-CoA and methyl-malonyl-CoA as extender.

Polyketides comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, and/or other processes. Many commonly used anti-microbial, anti-parasitic, and anti-cancer agents are polyketides or polyketide derivatives, such as erythromycins, tetracyclines, avermectins, and antitumor epothilones

EXAMPLES

The following examples are intended to provide illustrations of the application of the present disclosure. The following examples are not intended to completely define or otherwise limit the scope of the disclosure.

One of skill in the art will appreciate that many other methods known in the art may be substituted in lieu of the ones specifically described or referenced herein.

Example 1

Analyses of the *Chlamydomonas reinhardtii* Plastid β-ACCase Gene

The *Chlamydomonas* plastid β-ACCase gene was examined (SEQ ID NO: 1; genbank EDO096563). All amino acid position numbers refer to SEQ ID NO: 1 unless otherwise noted.

Annotation of this gene describes a chloroplast transit peptide as expected; this gene is present in the nuclear genome but active in the chloroplast. The mature gene sequence was submitted to the Swiss-Model server to produce a homology model based on the crystal structure of the β-subunit of the *Staphylococcus aureus* ACCase (PDB structure 2F9I). From examination of this structure, it was apparent that residue 255 (cysteine 255) would be across the heterotetramer axis from the other β-subunit, and conceivably could form a disulfide bond under oxidizing conditions. Another cysteine residue would be predicted to be buried within the protein, and probably not under redox control. Finally, four cysteine residues were predicted to form a zinc-binding cluster at the n-terminus of the protein. While this could form a locus for redox control, no modification was conceived of that could produce a "constitutively reduced" state for this site. Therefore, the mutation Cys255Ser was hypothesized as a potential constitutively activating mutation.

For prediction of potential phosphorylation sites, a number of methods have been used. The simplest method is by utilization of an artificial neural network trained on known phosphorylation sites in eukaryotic proteins to predict potential sites in a new eukaryotic protein. One publicly available tool is NetPhos 2.0 (as described, for example, in Blom, N., et al. (1999) J. Mol. Biol. 294:1351-1362; and the website of the Center for Biological Sequence Analysis at the Technical University of Denmark). Analysis of the *Chlamydomonas* ACCase sequence with this server predicted 19 potential phosphorylation sites. Table 1 lists the 19 sites.

TABLE 1

| T6D | S36D | S38D | S50D | S62D |
| S64D | S78D | S121D | S122D | T134D |
| T141D | S143D | S151D | S155D | C255S |
| T269D | T302D | Y337D | T365D | |

After examining these residues on the homology model, six residues appeared to be present on the surface of the protein, present in loop structures, and therefore, both accessible to an activating kinase and capable of altering local structure or interactions with other subunits of the complex. These residues were Threonine 134, Threonine 141, Serine 143, Serine 151, Serine 155, and Tyrosine 337.

Example 2

Figure 4:
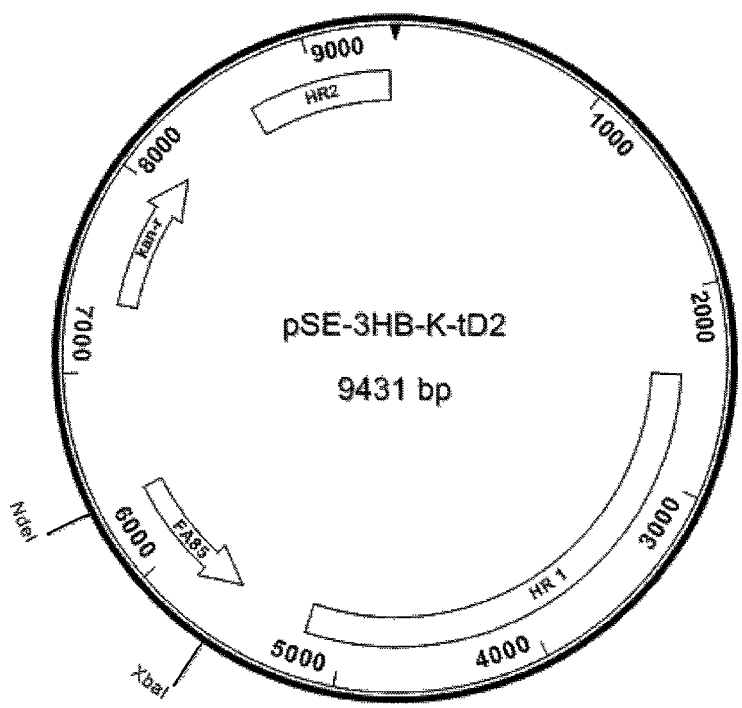
FIG. 4 shows a schematic of an exemplary expression vector pSE-3HB-K-tD2.

Mutagenesis of the Gene Encoding the Wild-Type *Chlamydomonas reinhardtii* ACCase β-Subunit To determine if a mutation of one or more of the above residues to aspartic acid (or serine, if the native amino acid is cysteine) would produce an ACCase β-subunit that would make a constitutively active complex with the endogenous alpha and biotin domain proteins, a gene encoding the wild-type *Chlamydomonas* ACCase β-subunit open reading frame, codon optimized for chloroplast expression and containing an N-terminal Strept tag epitope (ATGGGTTCTGCTTGGTCT-CATCCACAATTTGAAAAACAT; SEQ ID NO: 25), was synthesized and cloned into the pSE-3HB-K-tD2 *Chlamydomonas* plastid expression vector downstream of a D2 promoter (FIG. 4). The vector was then transformed into both 137c and 1690 background *Chlamydomonas*.

In parallel, seven pairs of oligonucleotides (SEQ ID NOs: 40 to 53) encoding the proposed activating mutations were designed (C255S, T134D, T141D, S143D, S151D, S155D, and Y337D) and used to mutagenize the wild-type gene to produce the desired point mutants.

Table 2 shows the seven pairs of oligonucleotides used to create the seven mutants; "F" is the forward primer and "R" is the reverse primer. The nucleotides that encode for the mutated amino acids are underlined and bolded.

TABLE 2

| T134D-F | TTAATTGATGCTGGTGATTGGCGTCCACTTGAT (SEQ ID NO: 40) |
| T134D-R | ATCAAGTGGACGCCAATCACCAGCATCAATTAA (SEQ ID NO: 41) |

TABLE 2-continued

| | |
|---|---|
| T141D-F | CGTCCACTTGATGAAGATCTTTCTCCAGTAGAT<br>(SEQ ID NO: 42) |
| T141D-R | ATCTACTGGAGAAAGATCTTCATCAAGTGGACG<br>(SEQ ID NO: 43) |
| T143D-F | CTTGATGAAACTCTTGATCCAGTAGATCCTTTA<br>(SEQ ID NO: 44) |
| T143D-R | TAAAGGATCTACTGGATCAAGAGTTTCATCAAG<br>(SEQ ID NO: 45) |
| S151D-F | GATCCTTTAGAATTTGATGACTTAAAATCTTAT<br>(SEQ ID NO: 46) |
| S151D-R | ATAAGATTTTAAGTCATCAAATTCTAAAGGATC<br>(SEQ ID NO: 47) |
| S155D-F | TTTTCTGACTTAAAAGATTATACTGATCGTATT<br>(SEQ ID NO: 48) |
| S155D-R | AATACGATCAGTATAATCTTTTAAGTCAGAAAA<br>(SEQ ID NO: 49) |
| C255S-F | CATGTACATCAAACTCAGCTAATCTTTTATAC<br>(SEQ ID NO: 50) |
| C255S-R | GTATAAAGATTAGCTGAGTTTTGATGTACATG<br>(SEQ ID NO: 51) |
| Y337D-F | CTTAAAGGTGCATTAGATGAAATCATTGACTTT<br>(SEQ ID NO: 52) |
| Y337D-R | AAAGTCAATGATTTCATCTAATGCACCTTTAAG<br>(SEQ ID NO: 53) |

Table 3 shows the PCR reaction parameters that were used to create the point mutations.

TABLE 3

| 50 µl QuikChange PCR Master Mix | | | | | |
|---|---|---|---|---|---|
| | | µl | | Cycling Parameters | |
| 1 | Buffer, 10X | 5 | 1 | 95 C. | 2 min |
| 2 | MgSO₄, 25 mM | 3 | 2 | 95 C. | 20 sec |
| 3 | dNTPs 10X | 5 | 3 | 55 C. | 15 sec |
| 4 | Oligo-f (10 µM) | 1.5 | 4 | 70 C. | 2.5 min |
| 5 | Oligo-r (10 µM) | 1.5 | 5 | Go to step 2, 24 cycles | |
| 6 | Polymerase (KOD, 1.0 U/µl) | 1 | 6 | 70 C. | 5 min |
| 7 | DNA | 1 | 7 | 4 C. | Forever |
| 8 | H₂O | 32 | | | |
| | Total volume | 50 | | | |

After the PCR reactions were run, 1 µl of DpnI was added to each of the PCR tubes to digest the template DNA. The DpnI reaction was incubated for 1 hour at 37° C.

50 µl of Top10 competent cells (Invitrogen, U.S.A.) were transformed with 3 µl of DpnI treated reaction mixture and plated onto LB Amp (100 µg/ml) plates. Individual colonies were picked and grown up overnight in LB Amp (100 µg/ml) media. After overnight growth, plasmid DNA was prepared.

Plasmid DNA was sequence verified and DNA containing each of the seven mutations were selected for subcloning into the plastid transformation vector (FIG. 4).

The wild-type gene and each of the seven plasmids containing the desired mutation were digested with both NdeI and XbaI. Each of the NdeI-XbaI inserts, each of which include at the 5' end epitope tag (SEQ ID NO: 25), were subcloned into *Chlamydomonas reinhardtii* chloroplast transformation vector pSE-3HB-K-tD2 (FIG. 4).

Individual plasmids containing either the wild-type gene or the desired mutation were transformed into *Chlamydomonas reinhardtii* (1690 and 137 C) using a microprojectile mediated (biolistic) particle gun (Biorad).

*Chlamydomonas* expression vector pSE-3HB-K-tD2 (FIG. 4) contains a Kanamycin resistance gene driven by the *Chlamydomonas* atpA promoter, and the gene of interest ("FA85") is flanked by two homologous regions to drive integration into the *Chlamydomonas* chloroplast genome 3HB site. The wild type or a mutated ACCase β-subunit is driven by the psbD promoter (a truncated *Chlamydomonas* D2 promoter-accurate). FA85 is the gene encoding wild-type *C. reinhardtii* ACCase β-subunit.

Example 3

Creation of Multiple Mutations in the Gene Encoding the *Chlamydomonas reinhardtii* ACCase β-Subunit In addition to the seven single mutations that were made in the ACCase gene, several combinations of the seven single mutations were also made in the ACCase gene. Specifically, S151D+S155D; S151D+S155D+Y337D; and S151D+S155D+C255S.

The forward and reverse primers that were used to create the S151D+S155D double mutant are listed below. The nucleotides that encode for the mutated amino acids are underlined and bolded.

S151D/S155D-forward
(SEQ ID NO: 54)
ATCCTTTAGAATTTGATGACTTAAAAGATTATACTGATCGTATT S151D/S155D-reverse
(SEQ ID NO: 55)
AATACGATCAGTATAAATCTTTTAAGTCATCAAATTCTAAAGGATC The triple mutant S151D+S 155D+Y337D was made by using the PCR product of the double mutant (S151D+S155D) as template DNA and using the forward and reverse primers listed above (SEQ ID NOs: 52 and 53) that were used for the single mutant Y337D.

The triple mutant S151D+S155D+C255S was made by using the PCR product of the double mutant (S151D+S155D) as template DNA and using the forward and reverse primers listed above (SEQ ID NOs: 50 and 51) that were used for the single mutant C255S.

Table 3 above shows the PCR reaction parameters that were used to create the double mutant and the two triple mutants.

After the PCR reactions were run, 1 µl of DpnI was added to each of the PCR tubes to digest the template DNA. The DpnI reaction was incubated for 1 hour at 37° C.

50 µl of Top10 competent cells (Invitrogen, U.S.A.) were transformed with 3 µl of DpnI treated reaction mixture and plated onto LB Amp (100 µg/ml) plates. Individual colonies were picked and grown up overnight in LB Amp (100 µg/ml) media. After overnight growth, plasmid DNA was prepared.

Plasmid DNA was sequence verified and DNA containing the double and triple mutants were selected for subcloning into the plastid transformation vector (FIG. 4).

The plasmids containing the double or triple mutants were digested with both NdeI and XbaI. Each of the NdeI-XbaI inserts, each of which include at the 5' end an epitope tag (SEQ ID NO: 25), were subcloned into *Chlamydomonas reinhardtii* chloroplast transformation vector pSE-3HB-K-tD2 (FIG. 4).

Individual plasmids containing the desired double or triple mutations were transformed into *Chlamydomonas reinhardtii* (1690 and 137 C) using a microprojectile mediated (biolistic) particle gun (Biorad).

*Chlamydomonas* expression vector pSE-3HB-K-tD2 (FIG. 4) contains a Kanamycin resistance gene driven by the *Chlamydomonas* atpA promoter, and the gene of interest ("FA85") is flanked by two homologous regions to drive integration into the *Chlamydomonas* chloroplast genome 3HB site. The double or triple mutant ACCase β-subunit is driven by the psbD (a truncated *Chlamydomonas* D2 promoter).

Example 4

FA85 Plasmicity Screen by PCR

In order to determine whether all copies of the chloroplast genome were successfully transformed with the target gene a plasmicity screen was conducted by PCR. The PCR reaction conditions are provided below in Table 4.

TABLE 4

| 25 μl multi screen PCR master mix | μl | # rxns 100 | cycling parameters | |
|---|---|---|---|---|
| 1 Buffer, 10x | 2.5 | 275 | 1 95° C. | 2 min |
| 2 2.5 mM dNTPs, 10x | 0.5 | 55 | 2 95° C. | 30 sec |
| 3 MgCl₂ (12.5 mM) | 1 | 110 | 3 55° C. | 30 sec |
| 4 primer 79 (SEQ ID NO: 123) (10 μM) | 1.25 | 137.5 | 4 72° C. | 30 sec |
| 5 primer 80 (SEQ ID NO: 124) (10 μM) | 1.25 | 137.5 | 5 go to step 2 | 39 cycles |
| 6 primer 1995 (SEQ ID NO: 121) (10 μM) | 1.25 | 137.5 | 6 72° C. | 2 min |
| 7 primer 1996 (SEQ ID NO: 122) (10 μM) | 1.25 | 137.5 | 7 4° C. | Forever |
| 8 polymerase (Taq, 5.0 U/μl) | 0.4 | 44 | | |
| DNA | 2 | 220 | | |
| H₂O | 13.6 | 1496 | | |
| total volume | 25 | | | |

The presence of a single PCR band indicates homoplasmicity, and the presence of two PCR bands indicates heteroplasmicity. Primers 1995, 1996, 79, and 80 (SEQ ID NO: 121, SEQ ID NO: 122, SEQ ID NO: 123, and SEQ ID NO:124, respectively), were used in the PCR reaction.

1) Reverse primer, 100216-DM-1995: TGTTTGTTAAG-GCTAGCTGC (SEQ ID NO: 121). 3HB-D2 multi screen primer shows a band of 212 base pairs if no insert is present.

2) Forward primer, 100216-DM-1996: CGCCACTGT-CATCCTTTAAGT (SEQ ID NO: 122). 3HB-D2 multi screen primer shows a band of 212 base pairs if no insert is present.

3) Reverse primer, 100216-DM-79: CCGAACTGAGGT-TGGGTTTA (SEQ ID NO: 123) (tD2-3HB multi-screen primer).

4) Forward primer, 100216-DM-80: GGGGGAGCGAAT-AGGATTAG (SEQ ID NO: 124) (tD2-3HB multi-screen primer).

Primer pair 79 and 80 was used as a control PCR for amplification of the chloroplast genome. The use of primers 79 and 80 in a PCR reaction will result in the amplification of an approximately 513 bp fragment. Use of primers 1995 and 1996 will result in a 212 bp amplicon if the integration cassette, which includes the target gene, is not integrated into the chloroplast genome. If the integration cassette which includes the target gene is integrated into the genome, use of primer pair 1995 and 1996 in theory, should result in a PCR product of about 7 kb. However, an extension time (as described above) of 72° C. for 30 seconds will not allow for a 7 kb fragment to be made, a longer extension time is required.

Figure 5:
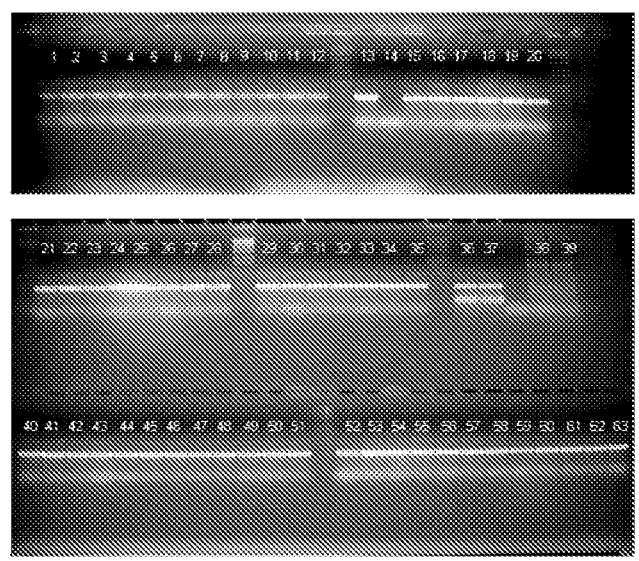
FIG. 5 shows a plasmicity screen using PCR.

A lack of a 212 bp amplicon indicates homoplasmity. FIG. 5 shows that wild-type, single, double, and triple mutants are all homoplasmic for the desired gene. Table 5 below is a key to FIG. 5.

TABLE 5

| Column | Gene Description |
|---|---|
| 1 | FA85-wild type |
| 2-4 | FA85-T134D |
| 5-12 | FA85-T141D |
| 13-20 | FA85-S143D |
| 14 | Blank |
| 21-28 | FA85-S151D |
| 29-31 | FA85-S155D |
| 32-35 | FA85-Y337D |
| 36-37 | Untransformed *Chlamydomonas reinhardtii* (1690) |
| 38-39 | negative control (water) |
| 40-51 | FA85-S151D, S155D |
| 52-58 | FA85-S151D, S155D, C255S |
| 59-63 | FA85-S151D, S155D, Y337D |

Example 5

Gene Specific Screen by PCR

Figure 6:
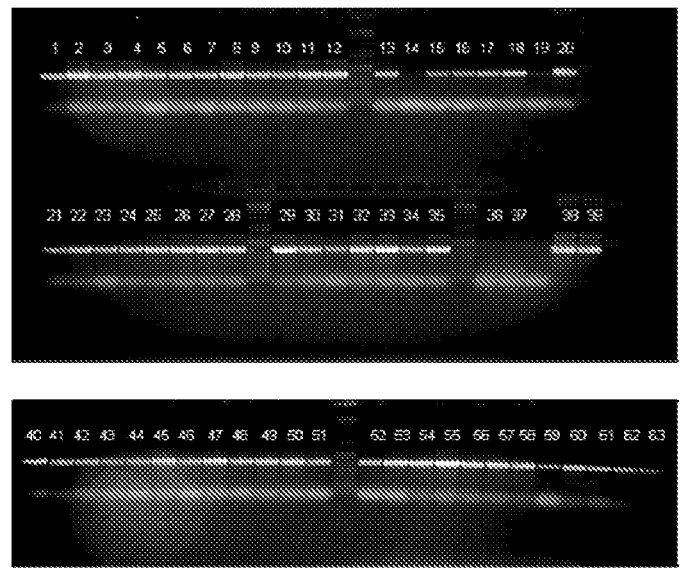
FIG. 6 shows a gene specific screen using PCR.
Figure 7:
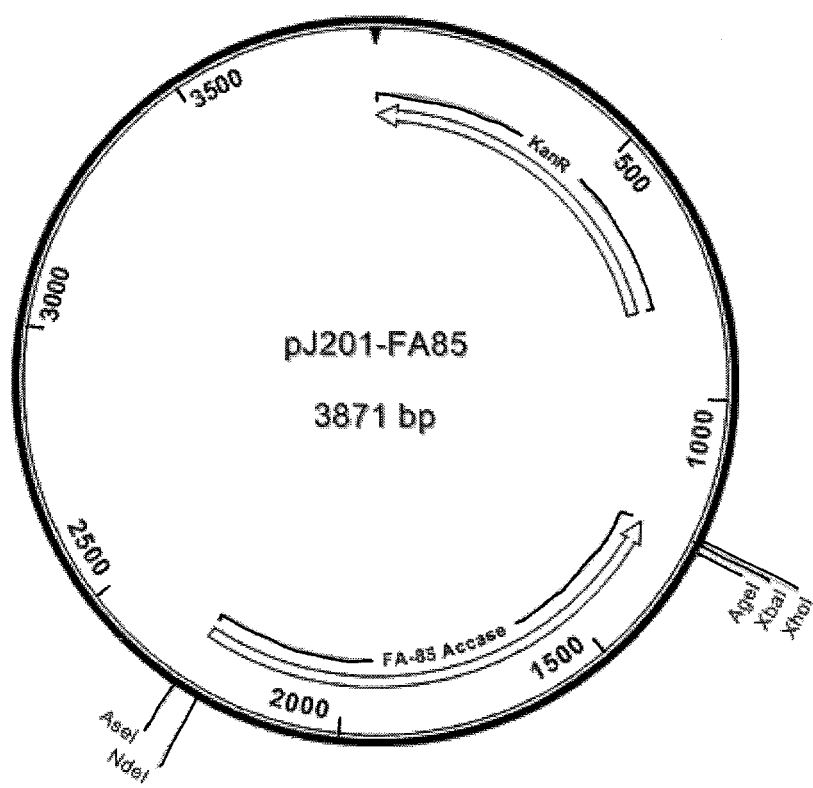
FIG. 7 shows a schematic of an exemplary expression vector pJ201-FA85.

In order to ensure that the desired gene is integrated into the chloroplast genome a PCR gene screen was conducted. A gene specific primer #4764 (SEQ ID NO: 126) was designed to be specific for the codon-optimized gene of interest and will not bind to the endogenous ACCase O-subunit gene sequence. The gene specific primer was used with an integration vector specific primer #270 (SEQ ID NO: 125). The vector specific primer sequence is not homologous to any portion of the *C. reinhardtii* chloroplast genome. The presence of the wild-type, single, double, and triple mutants were confirmed by the PCR gene screen. Table 6 below is a key to FIG. 6.

TABLE 6

| Column | Gene Description |
|---|---|
| 1 | FA85-wild type |
| 2-4 | FA85-T134D |
| 5-12 | FA85-T141D |
| 13-20 | FA85-S143D |
| 14 | Blank |
| 21-28 | FA85-S151D |
| 29-31 | FA85-S155D |
| 32-35 | FA85-Y337D |
| 36-37 | untransformed *C. reinhardtii* (1690) |

TABLE 6-continued

| Column | Gene Description |
|---|---|
| 38-39 | positive control (wild-type FA85 plasmid DNA) |
| 40-51 | FA85-S151D, S155D |
| 52-58 | FA85-S151D, S155D, C255S |
| 59-63 | FA85-S151D, S155D, Y337D |

Example 6

Bodipy Staining of ACCase Mutants by Guava

To determine the initial phenotype of the wild-type and single mutant ACCases, two experiments were conducted. In the first experiment, cells of biological replicate strains containing the various versions of the ACCase gene were grown in liquid culture, stained with one of three lipid dyes (BODIPY, Nile red, and Lipitox green), and analyzed for fluorescence using Guava Easycyte cytometer. Between three and ten biological replicate strains were isolated for each ACCase variant. The fold change in the population median fluorescence signal was plotted against that of the FA85 wild type transgenic population median fluorescence signal. Staining with nile red and lipitox green were inconclusive, but staining with BODIPY showed that several of the mutants have increased staining. In particular, cells containing the S155D transgene has significantly higher fluorescence than those containing the wild-type transgene (FIG. 1). The y-axis of FIG. 1 is relative fluorescence and the x-axis represents the various mutants and the wild type transgene. Error bars at +/−1 standard deviation. S155D is significantly different from wild type (p<0.05).

Example 7

Distribution of Engineered ACCase Genes in the Pre- and Post-Sort Populations

Figure 2:
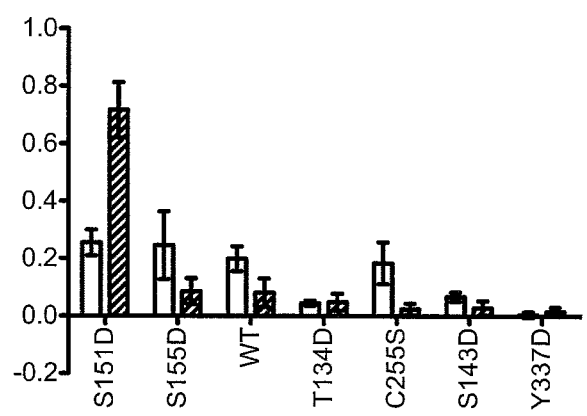
FIG. 2 shows the distribution of algae containing mutated ACCase polynucleotides (S151D, S155D, T134D, C255S, S143D, and Y337D) in pre- and post-sort populations as compared to the wild-type algae (WT).

The second experiment consisted of growing all of the strains carrying the single-mutant ACCase transgene (except for T141D), along with cells overexpressing the wild-type non-mutated gene (WT), and non-transformed genetic background cells in liquid culture. The cultures were mixed to produce a heterogeneous population of cells containing non-transformed cells of *C. reinhardtii* strain 1690 background, cells overexpressing the wild-type non-mutated gene, and the six single-mutant transgenic versions of ACCase. This population was plated to isolate clonal colonies, and 288 colonies were picked from this pre-sorting population. The mixed population of cells were subjected to sequential staining and fluorescence-gated cell sorting with the various lipid dyes to isolate strongly stained cells; thus the population was selected for those showing the strongest fluorescence from the three lipid staining dyes. This post-sort population was plated out, and 864 colonies were selected and grown. Once colonies of the pre- and post-sort populations were obtained, all were analyzed by PCR amplification of the ACCase transgene cassette to determine whether or not the colony carried the engineered ACCase transgene. For those colonies that did carry a transgene (for example, S151D), the PCR amplicon was sequenced to determine which version of the engineered ACCase gene was carried by that colony. The distribution of engineered ACCase genes in the pre- and post-sort populations are shown in FIG. 2. The y-axis represents the fraction of the engineered population and the x-axis represents the clones tested (wild type or mutant). The pre-sort population is shown by an empty bar and the post-sort population is shown by a cross-hatched bar.

Example 8

Change in Proportion of ACCase Genotypes from Pre-Sort to Post-Sort Populations

Figure 3:
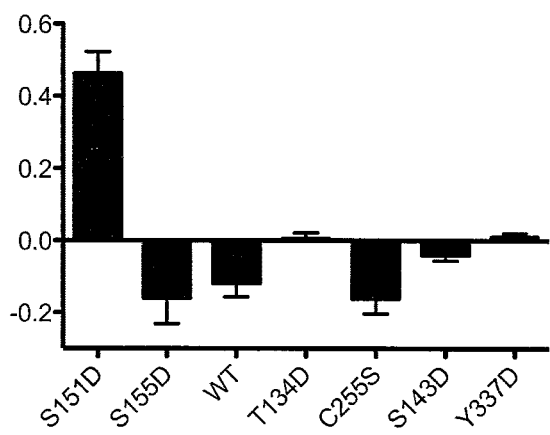
FIG. 3 shows the change in the proportion of ACCase genotypes form pre-sort to post-sort populations.

If the introduced ACCase transgene had no effect on the response to lipid specific staining, or if all of the various single mutants and wild-type transgene had the same impact on response to staining, it would be expected that the distribution of the various versions of the gene after sorting would resemble the distribution present pre-sorting. Instead, a significant change in the distribution of the genotype is observed. FIG. 3 shows the change in the proportion of the observed genotypes from the pre-sort to post-sort populations. As is clear in the figure, the sorting strongly selected for the presence of the S151D mutant ACCase, at the expense of the other genotypes. The y-axis represents the change in fraction of population from pre- to post-sort and the x-axis represents the clones tested (wild type or single mutant).

Example 9

Cloning of Five Novel Transcripts of an ACCase β-Subunit from *Scenedesmus dimorphus* UTEX 1237

29 Acetyl-CoA carboxylase (ACCase) β-subunit protein sequences from diverse organisms (e.g. plant and algae) were aligned and six conserved amino acid regions (motifs) were identified (Table 7). Motif 5 is FAGK(R)RVIEQTL (SEQ ID NO: 174) and is written below as Motifs 5 and 6.

TABLE 7

| Motif 1 | MGGSMGSVVGEK (SEQ ID NO: 56) |
| Motif 2 | SGGARMQEG (SEQ ID NO: 57) |
| Motif 3 | SLMQMAKI (SEQ ID NO: 58) |
| Motif 4 | PTTGGVTASF (SEQ ID NO: 59) |
| Motif 5 | FAGKRVIEQTL (SEQ ID NO: 60) |
| Motif 6 | FAGRRVIEQTL (SEQ ID NO: 61) |

The organisms that were compared are provided below in Table 8 along with their GenBank accession numbers.

TABLE 8

YP 001518184: *Acaryochloris marina*
YP 001687225: *Aneura mirabilis*
YP 001023710: *Angiopteris evecta*
NP 777422: *Anthoceros formosae*
ACS14664: *Camellia oleifera*
YP 001671692: *Carica papaya*
YP 635724: *Chara vulgaris*
XP 001703187: *Chlamydomons reinhartdtii*
NP 045833: *Chlorella vulgaris*
YP 817491: *Coffea arabica*
YP 002370462.1: *Cyanothece* sp. PCC 8801
YP 001312211.1: *Cycas taitungensis*
ABO33321.1: *Dunaliella salina*
ACF33357.1: *Gonystylus bancanus*
YP 209520.1: *Huperzia lucidula*
ACP52212.1: *Larix occidentalis*
YP 001595517.1: *Lemna minor*
YP 001718446.1: *Manihot esculenta*
CA 087376.1: *Microcystis aeruginosa*
YP 358685.1: *Nicotiana sylvestris*
NP 054508.1: *Nicotiana tabacum*
YP 001866275.1: *Nostoc punctiforme*
NP 904193.1: *Physcomitrella patens*

TABLE 8-continued

ACP51846.1: *Pinus canariensis*
ACP51156.1: *Pinus taeda*
NP 053808.1: *Porphyra purpurea*
YP 536879.1: *Porphyra yezoensis*
NP 569638.1: *Psilotum nudum*
ABY85555.1: *Silene sorensensis*
YP 514861.1: *Solanum lycopersicum*
YP 635648.1: *Solanum tuberosum*
YP 636397.1: *Staurastrum punctulatum*
YP 002586927.1: *Syntrichia ruralis*
BAG50119.1: *Takakia lepidozioides*
NP 682433.1: *Thermosynechococcus elongatus*
YP 722346.1: *Trichodesmium erythraeum*
YP 636510.1: *Zygnema circumcarinatum*

Degenerate primers were then designed from the identified motif regions. The degenerate primers and the motifs that they target are provided below in Table 9. The standard Mix-Base definitions are provided in Table 10, also below.

TABLE 9

```
SdACC195-dF  ATGGGNGGNWSNATGGGNWSNGTNGTNGG   Motif #1
             (SEQ ID NO: 62)

SdACC196-dF  GGNWSNATGGGNWSNGTNGTNGGNGARAA   Motif #1
             (SEQ ID NO: 63)

SdACC226-dF  WSNGGNGGNGCNMGNATGCARGARGG      Motif #2
             (SEQ ID NO: 64)

SdACC237-dF  WSNYTNATGCARATGGCNAARAT         Motif #3
             (SEQ ID NO: 65)

ScdCC244-dR  DATYTTNGCCATYTGCATNAR           Motif #3
             (SEQ ID NO: 66)

SdACC275-dR  AANSWNGCNGTNACNCCNCCNGTNGTNGG   Motif #4
             (SEQ ID NO: 67)

SdACC302-dR  GTYTGYTCDATNACNCKNYKNCCNGCRAA   Motif #5
             (SEQ ID NO: 68)
```

TABLE 10

| R is A or G | K is G or T | H is A, C or T | D is A, G or T |
|---|---|---|---|
| Y is C or T | S is C or G | B is C, G or T | N is A, C, G, or T |
| M is A or C | W is A or T | V is A, C or G | |

Total RNA was isolated from *Scenedesmus dimorphus* UTEX 1237. The mRNA was purified from total RNA by using Qiagen mRNA purification kit (QIAGEN, U.S.A.). First strand cDNA, was prepared from mRNA with oligo(dT) primer (ATTCTAGAGGCCGAGGCGGCCGACTAT-GTTTTTTTTTTTTTTTTTT) (SEQ ID NO: 69), following the manufacture's protocol.

The putative conservative ACC β-subunit fragment was PCR amplified by using various degenerate primer combinations. The PCR reaction conditions utilized for each of the four fragments are provided in Table 11 below. Four putative ACC fragments SEQ ID NOs: 70-73) were obtained.

TABLE 11

| Reaction component | Volume (μl) | Cycling Parameters | | |
|---|---|---|---|---|
| 10x EX Taq Buffer | 5 | 95° C. | 1 min | |
| 2.5 mM dNTP mixture | 4 | 95° C. | 30 sec | 35 cycles |
| Forward (F) Primer 10 μM | 2.5 | 55° C. | 30 sec | |
| Reverse (R) Primer 10 μM | 2.5 | 72° C. | 1 min | |
| cDNA | 2 | | | |
| Ex Taq | 0.4 | | | |
| Distilled Water | 33.6 | | | |

Primer combinations were as follows: for dg12 (SEQ ID NO: 70), 196dF (SEQ ID NO: 63)/244dR (SEQ ID NO: 66); for dg15 (SEQ ID NO: 71), 195dF (SEQ ID NO: 62)/244dR (SEQ ID NO: 66); for dg61 (SEQ ID NO:72), 237dF (SEQ ID NO: 65)/275dR (SEQ ID NO: 67); and for dg62 (SEQ ID NO: 73), 196dF (SEQ ID NO: 63)/275dR (SEQ ID NO:67).

dg12 (SEQ ID NO: 70)—targeting motifs 1 and 3

```
ATGGGGTCGGTCGTCGGAGAGAAGCTGACGCGCCTGATTGAGTACGCCACGCAGGAGGGGCTCA
CGCTGCTGGTGGTGTGCACCAGCGGAGGCGCGCGCATGCAGGAGGGCATCATGAGCCTAATGCAGATGG
CCAAGATTAAG
``` dg15 (SEC) ID NO: 71)—targeting motifs 1 and 3

```
ATGGGGTCGGTCGTGGGAGAGAAAATTACGCGCCTTTTTGAGTATGCCAGAGAAGAACGATTAC
CTGTTGTCATTTTCACGGCATCAGGAGGAGCTCGTATGCAAGAAGGTATCATGAGCTTTATGCAAATGGC
CAAAATC
``` dg61 (SEQ ID NO: 72)—targeting motifs 3 and 4

```
AGGTTAATGCAGATGGCCAAAATTTCTGCTGCTGTAAAGCGACATTCTAATGCTGGACTTTTTTAT
CTCACCGTATTGACCGACCCCACAACTGGTGGCGTAACCGCCTGGTTA
``` dg62 (SEQ ID NO: 73)—targeting motifs 3 and 4

```
TTGACTGATGCAAATGGCGAAGATCAGCGGCGCGCTGCACGTGCACCAGAATGAGGCCAACCTG
CTGTACATCTCCATCCTGACCAGCCCTACCACAGGTGGCGTCACCGCCTGGTT
```

Figure 23:
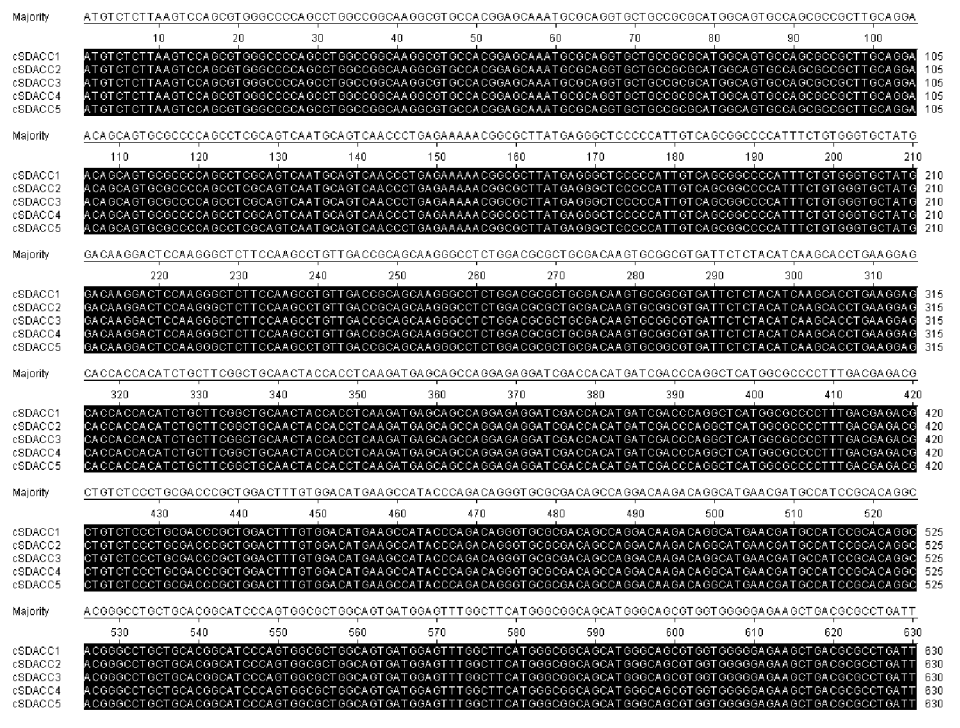
Figure 23:
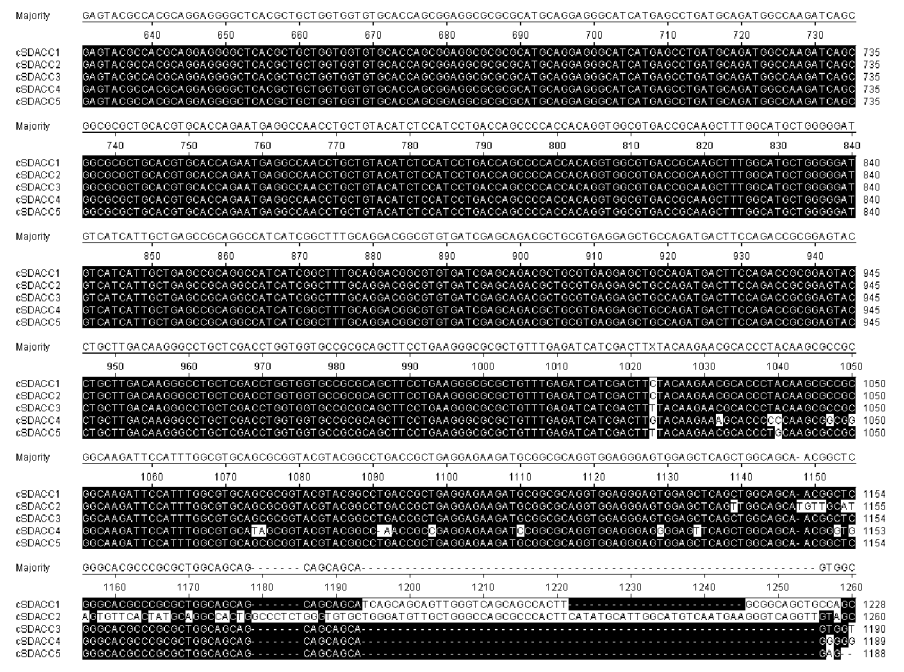
Figure 23:
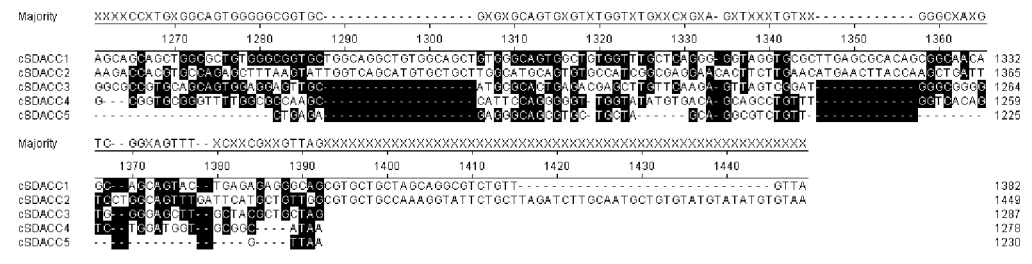
Figure 24:
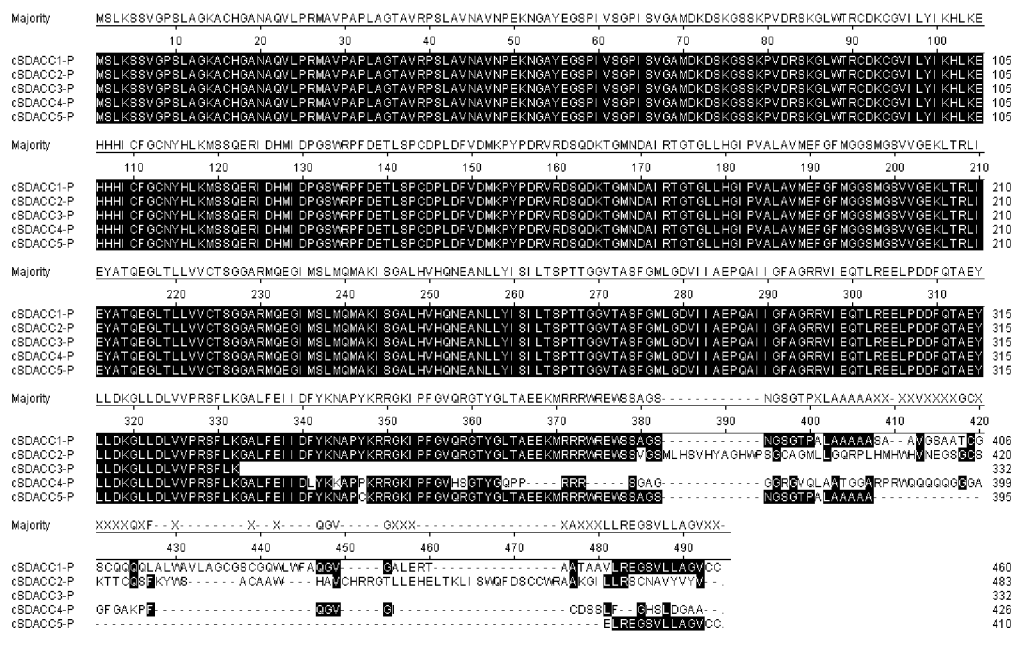

The Rapid Amplification of cDNA Ends (RACE) method (as described for example in Frohman, M. A., et al. (1988) *Proc Natl Acad Sci USA* 85: 8998-9002) was used to extend these four putative ACC fragments. A total of five putative *Scenedesmus dimorphus* ACCase β-subunit (SDACC1-5) transcripts were obtained. The open reading frames of the five sequences are listed as SEQ ID NO: 74 (FIG. 18), SEQ ID NO: 80 (FIG. 19), SEQ ID NO: 84 (FIG. 20), SEQ ID NO: 88 (FIG. 21), and SEQ ID NO: 92 (FIG. 22). All five gene transcripts are conserved at both the nucleic acid level (at the 5' end) and at the protein level (see FIGS. 23 and 24), but have diverse 3' ends and carboxy terminal regions. All five gene transcripts also comprise a 5'-terminal sequence encoding for a putative chloroplast targeting transit peptide (SEQ ID NO: 76). SDACC1 and 2 were the two longest full-length transcripts and were used for further overexpression experiments.

Example 10

Obtaining the Genomic Sequence for SDACC2

The genomic sequence (SEQ ID NO: 96) was obtained for SDACC2 described above (SEQ ID NO: 80). The upstream region was successfully obtained by using Genome Walker Universal Kit (Clontech, U.S.A.) according to manufacturer's instructions. A total of 6986 bp of DNA sequence were obtained. The last 81 nucleotides (of which the sequence of the cDNA has been determined (SEQ ID NO: 80 and SEQ ID NO: 82) were not resolved because of a lack of sequencing information.

Example 11

Codon Optimization of Novel ACCase β-Subunit of *Scenedesmus dimorphus*

A polynucleotide sequence comprising SDACC1 (SEQ ID NO: 75) was codon optimized (SEQ ID NO: 98) for expression in the chloroplast of *Scenedesmus dimorphus* based on the *Chlamydomonas reinhardtii* tRNA codon usage table. A flag tag (SEQ ID NO: 117), that was also codon optimized, was added to the 5' end of SEQ ID NO: 98 after the initial "ATG". The resulting construct is shown in SEQ ID NO: 97.

In addition, a polynucleotide sequence comprising SDACC2 (SEQ ID NO: 82) was codon optimized (SEQ ID NO: 99) for expression in the chloroplast of *Scenedesmus dimorphus* based on the *Chlamydomonas reinhardtii* tRNA codon usage table. A flag tag (SEQ ID NO: 117), that was also codon optimized, was added to the 5' end of SEQ ID NO: 99 after the initial "ATG". The resulting construct is shown in SEQ ID NO: 127.

Since the first 43 amino acids were predicted as a putative chloroplast targeting transit peptide in both SDACC1 (SEQ ID NO: 74) and SDACC2 (SEQ ID NO: 80) by PSORT program prediction (for example, as described in Nakai, K. and Horton, P., *Trends Biochem. Sci*, 24(1)34-35 (1999) and Nakai, K. and Kanehisa, M., *Genomics*, 14, 897-911 (1992)), these regions were eliminated except that a start codon sequence (ATG) was retained for proper protein translation initiation.

Example 12

Mutation of Novel ACCase β-Subunits of *Scenedesmus dimorphus*

The protein sequences of SDACC1 (SEQ ID NO: 78) and SDACC2 (SEQ ID NO: 81) were submitted to the Swiss-Model server to produce a homology model based on the crystal structure of the β-subunit of the *Staphylococcus aureus* ACCase (PDB structure 2F9I).

For prediction of potential phosphorylation sites, a number of methods can been used. One method is by utilization of an artificial neural network trained on known phosphorylation sites in eukaryotic proteins to predict potential sites in a new eukaryotic protein. One publicly available tool is NetPhos 2.0 server (as described, for example, in Blom, N., et a (1999) J. Mol. Biol. 294:1351-1362; and the website of the Center for Biological Sequence Analysis at the Technical University of Denmark). By comparison to the identified *Chlamydomonas reinhardtii* ACCase β-subunit, seven potential phosphorylation sites were identified in both SDACC1 (SEQ ID NO: 78) and SDACC2 (SEQ ID NO: 81).

Table 12 and Table 13, respectively, list the 7 sites that were targeted for mutation in SDACC1 (SEQ ID NO: 78) and SDACC2 (SEQ ID NO: 81). The numbering of the amino acids below relate to the numbering of the amino acids in SEQ ID NO: 78 and SEQ ID NO: 81.

TABLE 12

| SDACC1 |
| --- |
| Ser (S) 133 to Asp (D) |
| Thr (T) 140 to Asp (D) |
| Scr (S) 142 to Asp (D) |
| Val (V) 150 to Asp (D) |
| Pro (P) 154 to Asp (D) |
| Ser (S) 162 to Asp (D) |
| Thr (T) 301 to Asp (D) |

TABLE 13

| SDACC2 |
| --- |
| Ser (S) 133 to Asp (D) |
| Thr (T) 140 to Asp (D) |
| Ser (S) 142 to Asp (D) |
| Val (V) 150 to Asp (D) |
| Pro (P) 154 to Asp (D) |
| Ser (S) 162 to Asp (D) |
| Thr (T) 301 to Asp (D) |

Each of the codon-optimized nucleotide sequences SDACC1 (SEQ ID NO: 97) and SDACC2 (SEQ ID NO: 127) were mutated by mutagenesis to create the seven mutations listed above.

Example 13

Cloning of Mutant and Non-Mutagenized Codon Optimized ACCase β-Subunits of *Scenedesmus dimorphus*

Figure 9:
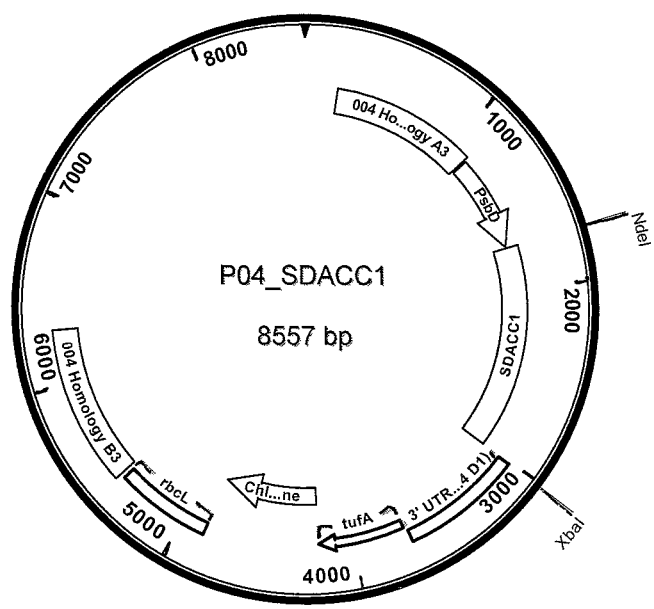
FIG. 9 shows an exemplary expression vector PO4_SDACC1.
Figure 10:
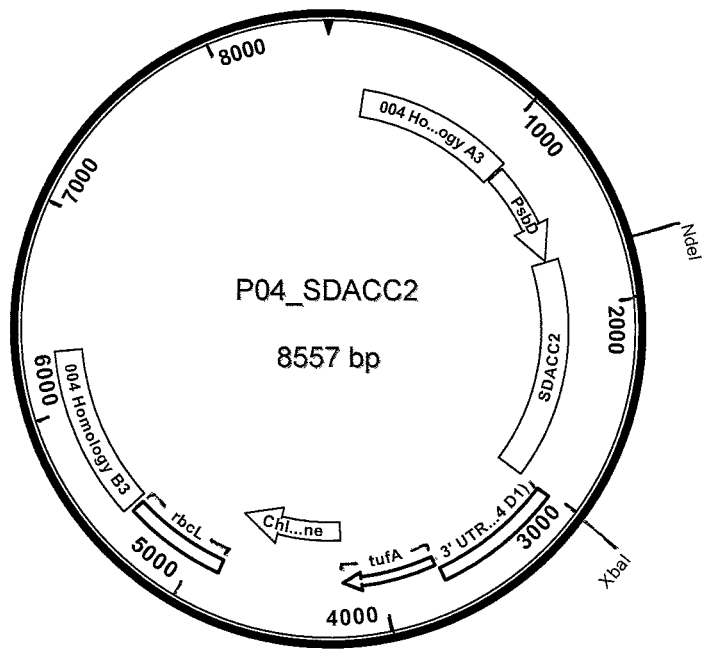
FIG. 10 shows an exemplary expression vector PO4_SDACC2.

The two non-mutagenized codon-optimized SDACC1 (SEQ ID NO: 97) and SDACC2 (SEQ ID NO: 127) sequences were each ligated into P04 vector (FIG. 9 and FIG. 10, respectively) between the NdeI and XbaI sites.

As mentioned above, site-directed mutagenesis was applied to SEQ ID NO: 97 to generate each of the seven mutations. In addition, site-directed mutagenesis was also applied to SEQ ID NO: 127 to generate each of the seven mutations. Nucleotides encoding the 14 mutants (SEQ ID NOs: 128-141) were each ligated into the P04 vector between the NdeI and XbaI sites.

The P04 vector comprises a constitutive PsbD promoter that drives the expression of the target gene. In addition, P04 comprises a sequence encoding for a chloramphenicol resistance gene which was used for selection of desired clones.

The expressed proteins will comprise the amino acid sequence of each of the 14 mutated proteins (SEQ ID NOs: 100 to 113), along with a Flag tag (SEQ ID NO: 118) inserted after the initial Met.

Individual plasmids containing the mutations were transformed into *Scenedesmus dimorphus* using a microprojectile mediated (biolistic) particle gun (Biorad). The range of psi was 500 to 700. Individual clones were picked and grown up in selection media (TAP) comprising a concentration of 34 ng/ul chloramphenicol.

Example 14

Expression of a Eukaryotic Rat ACCase in *Chlamydomonas reinhardtii*

Figure 11:
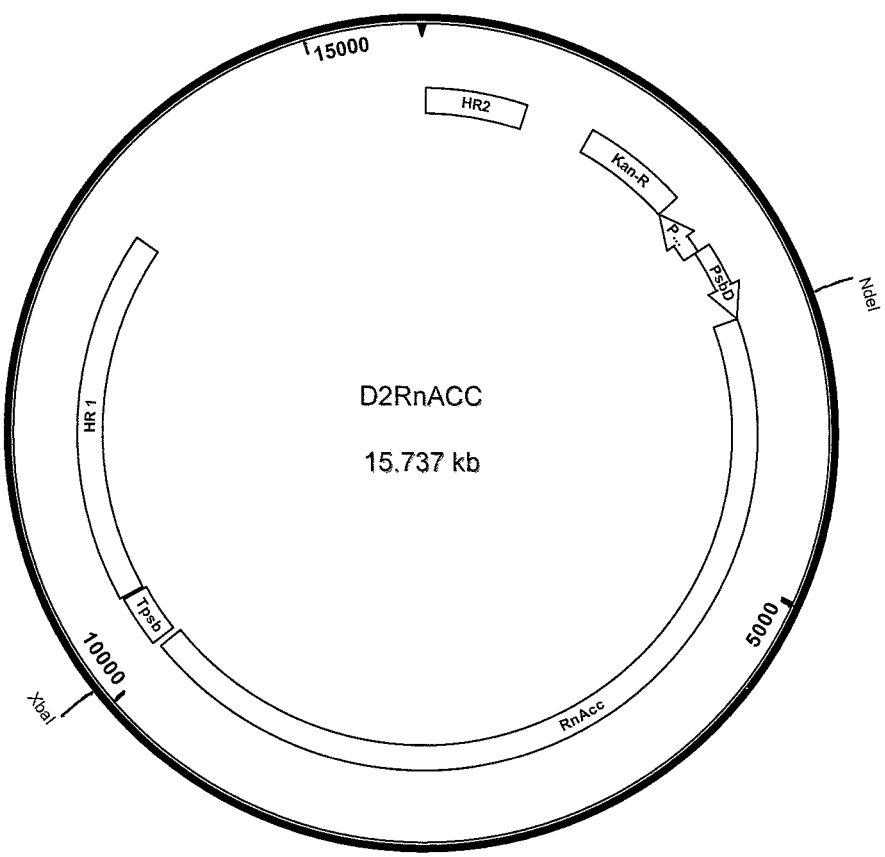
FIG. 11 shows an exemplary expression vector D2RnACC.

The rat ACCase sequence (SEQ ID NO: 115) (NM 022193) was codon-optimized for integration into the chloroplast genome of *Chlamydomonas reinhardtii*. The codon-optimized nucleotide sequence is shown in SEQ ID NO: 114. A Flag tag, also codon-optimized for integration into the chloroplast genome of *Chlamydomonas reinhardtii* (SEQ ID NO: 116), was added to the 3'-end of the codon-optimized gene sequence in front of the stop codon (SEQ ID NO: 156), and cloned into expression vector D2RnACC (FIG. 11) using restriction sites NdeI and XbaI. D2RnACC comprises a PsbD promoter to drive expression of the Rat ACCase protein. SEQ ID NO: 157 is the amino acid sequence of the protein without the carboxy-terminal Flag tag. The expressed protein has the sequence of SEQ ID NO: 157 with the amino acid sequence of the tag (SEQ ID NO: 118) at the carboxy terminus of the protein. Expression of the kanamycin resistance protein is under the control of the PatpA promoter.

The plasmid (D2RnACC) comprising the nucleotide sequence of SEQ ID NO: 156 was transformed into the chloroplast genome of *Chlamydomonas reinhardtii* (1690 and 137 C) using a microprojectile mediated (biolistic) particle gun (Biorad). The transformation product was spread on TAP plates with 100 ng/p. 1 kanamycin.

Figure 8A:
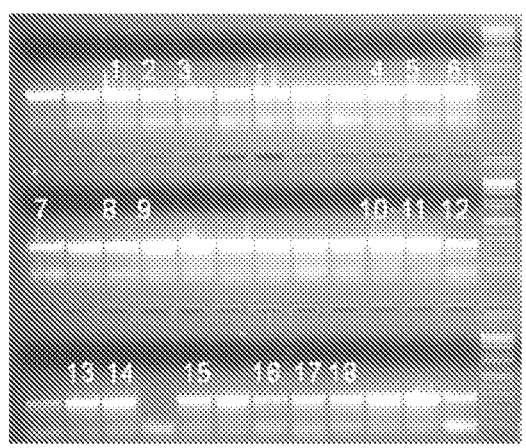
FIGS. 8A and 8B show PCR screening results for D2Rn transgenic cell lines.

FIG. 8A is a screen for the presence of the gene encoding the recombinant Rat ACCase in the chloroplast genome using gene specific primers D2Rv (GGACGTCCTGCCAACTGC-CTATGGTAGC) (SEQ ID NO: 119) and Rn Fw (GT-TGAGGGCACAGTGAAAGCATACGTTTGGG) (SEQ ID NO: 120). Colonies 4, 5, 6, 15, and 16, amongst others, were positive for the presence of the gene.

In order to determine whether all copies of the chloroplast genome were successfully transformed with the target gene a plasmicity screen was conducted by PCR. The PCR reaction conditions are provided below in Table 14.

TABLE 14

25 µl multi screen PCR master mix

| | | µl | | cycling parameters | |
|---|---|---|---|---|---|
| 1 | Ex taq Buffer, 10x | 2.5 | 1 | 95° C. | 2 min |
| 2 | 2.5 mM dNTPs | 2.0 | 2 | 95° C. | 30 sec |
| 3 | | | 3 | 55° C. | 30 sec |
| 4 | primer 79 (SEQ ID NO: 123) (10 µM) | 1.25 | 4 | 72° C. | 30 sec |
| 5 | primer 80 (SEQ ID NO: 124) (10 µM) | 1.25 | 5 | go to step 2 | 39 cycles |
| 6 | primer 1995 (SEQ ID NO: 121) (10 µM) | 1.25 | 6 | 72° C. | 2 min |

TABLE 14-continued

25 µl multi screen PCR master mix

| | | µl | | cycling parameters | |
|---|---|---|---|---|---|
| 7 | primer 1996 (SEQ ID NO: 122) (10 µM) | 1.25 | 7 | 4° C. | Forever |
| 8 | polymerase (Ex Taq, 5.0 U/µl) | 0.4 | | | |
| | DNA | 2 | | | |
| | H₂O | 13.1 | | | |
| | total volume | 25 | | | |

The presence of a single PCR band indicates homoplasmicity, and the presence of two PCR bands indicates heteroplasmicity. All of the primers 1995, 1996, 79, and 80 (SEQ ID NO: 121, SEQ ID NO: 122, SEQ ID NO: 123, and SEQ ID NO:124, respectively), were used in the PCR reaction.

1) Reverse primer, 100216-DM-1995: TGTTTGTTAAG-GCTAGCTGC (SEQ ID NO: 121). 3HB-D2 multi screen primer shows a band of 212 base pairs if no insert is present.

2) Forward primer, 100216-DM-1996: CGCCACTGT-CATCCTTTAAGT (SEQ ID NO: 122). 3HB-D2 multi screen primer shows a band of 212 base pairs if no insert is present.

3) Reverse primer, 100216-DM-79: CCGAACTGAGGT-TGGGTTTA (SEQ ID NO: 123) (tD2-3HB multi-screen primer).

4) Forward primer, 100216-DM-80: GGGGGAGCGAAT-AGGATTAG (SEQ ID NO: 124) (tD2-3HB multi-screen primer).

Primer pair 79 and 80 was used as a control PCR for amplification of the chloroplast genome. The use of primers 79 and 80 in a PCR reaction will result in the amplification of an approximately 513 bp fragment. Use of primers 1995 and 1996 will result in a 212 bp amplicon if the integration cassette, which includes the target gene, is not integrated into the chloroplast genome. If the integration cassette which includes the target gene is integrated into the genome, use of primer pair 1995 and 1996 in theory, should result in a PCR product of about 9750 bp. However, an extension time (as described above) of 72° C. for 30 seconds will not allow for a 9750 bp fragment to be made, a longer extension time is required.

Figure 8B:
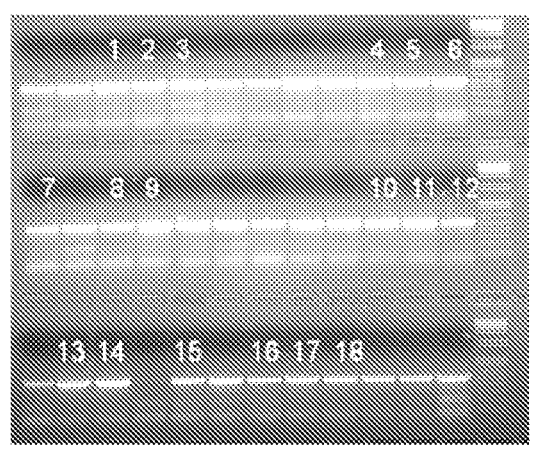

A lack of a 212 bp band indicates homoplasmity. FIG. 8B shows the results of the screen. Colonies 4, 5, 6, 15, and 16, amongst others, were homoplasmic for the gene.

Figure 12:
FIG. 12 shows a Western blot with a clear band of approximately 266 KDa indicating the presence of the RnACC protein in high salt media (HSM) media, and a faint band of approximately 266 KDa indicating the presence of the RnACC protein in TAP media.

The total protein size of RnACC was estimated to be about 266 KDa (as shown in FIG. 12 with a "*"). First, a Western screen with an anti-Flag antibody was conducted; this experiment did not give a clear band. This result is not surprising because of the large size of the protein. It is also possible that the C-terminal fusion Flag tag was contained inside of the protein making it impossible for detection.

Since RnACC is a fully functional anti-biotinylated enzyme, it allows the use of an anti-biotin antibody for screening. First, 50 mls of culture (TAP, and HSM with a $CO_2$ supply) were collected for the crude protein extraction. Then, an anti-biotin resin was subsequently used to partially purify the protein. The partially purified protein was used for the Western screening.

As shown in FIG. 12, a clear band in the expected size was detected in cells grown in HSM (as shown with a "*"), but not in the wild type cells (untransformed *Chlamydomonas reinhardtii*). Transformed cells grown in TAP showed a very faint band.

Example 15

Lipid Accumulation in RnACC Expressing Cell Lines

The RnACC transgenic lines (D2Rn5, D2Rn15, and D2Rn16) along with the wild-type cells were grown in TAP media in an air environment under constant light, until cells reached late log phase. Separately, the same cells were grown in HSM media in a 5% carbon dioxide in an air environment under constant light, until cells reached late log phase. The cells were harvested by centrifugation and analyzed for total gravimetric lipids by methanol/methyl-tert-butyl ether extraction according to a modified Bligh Dyer method (as described in Matyash V., et al. (2008) Journal of Lipid Research 49:1137-1146).

Specifically, biomass was pelleted and excess water removed. After the addition of methanol, samples were vortexed vigorously to lyse cells. MTBE was added and samples were vortexed again for an extended period of time (approximately 1 hr). Addition of water to samples after vortexing gave a ratio of 4:1.2:1; MTBE:MeOH:water respectively. Samples were centrifuged to aid in phase separation. The organic layer was removed and the process repeated a second time. Samples were extracted a third time adding only MTBE; the samples were vortexed, centrifuged, and phase separated as described above. The organic layers were combined, dried with magnesium sulfate, filtered and concentrated into tared vials. The percent extractables was calculated using the ash free dry weight of the sample.

Figure 13:
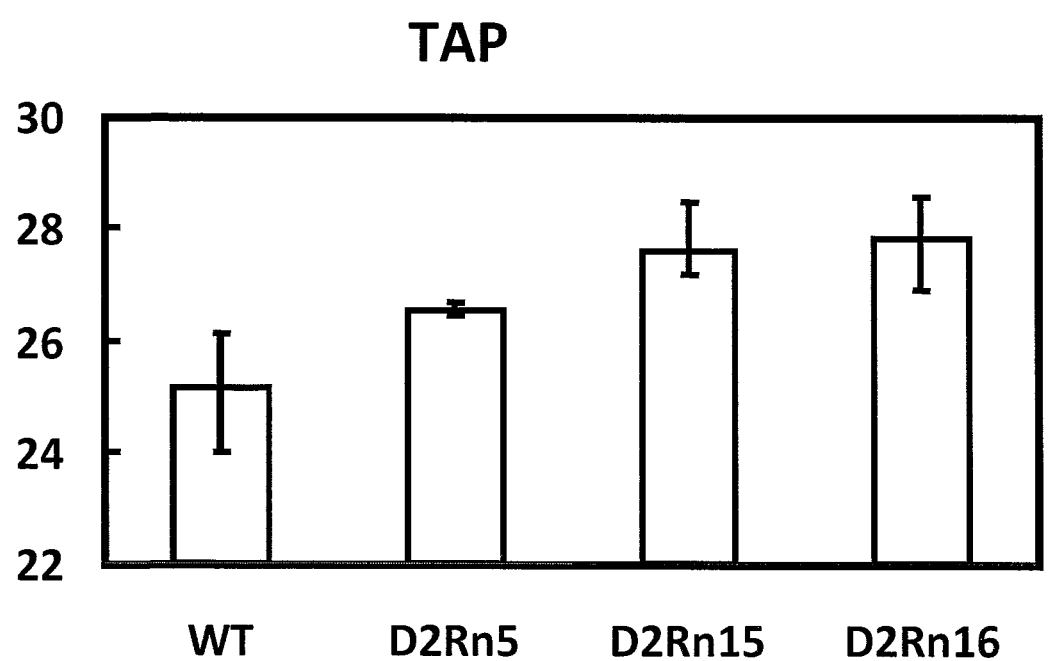
FIG. 13 shows the lipid oil content of three ACCase transgenic *Chlamydomonas reinhardtii* cell lines (D2Rn5, D2Rn15, and D2Rn16) grown in TAP media. The y-axis is lipid content (% MTBE extractable) and the x-axis represents the three clones compared to a wild-type untransformed *Chlamydomonas reinhardtii* cell line.
Figure 14:
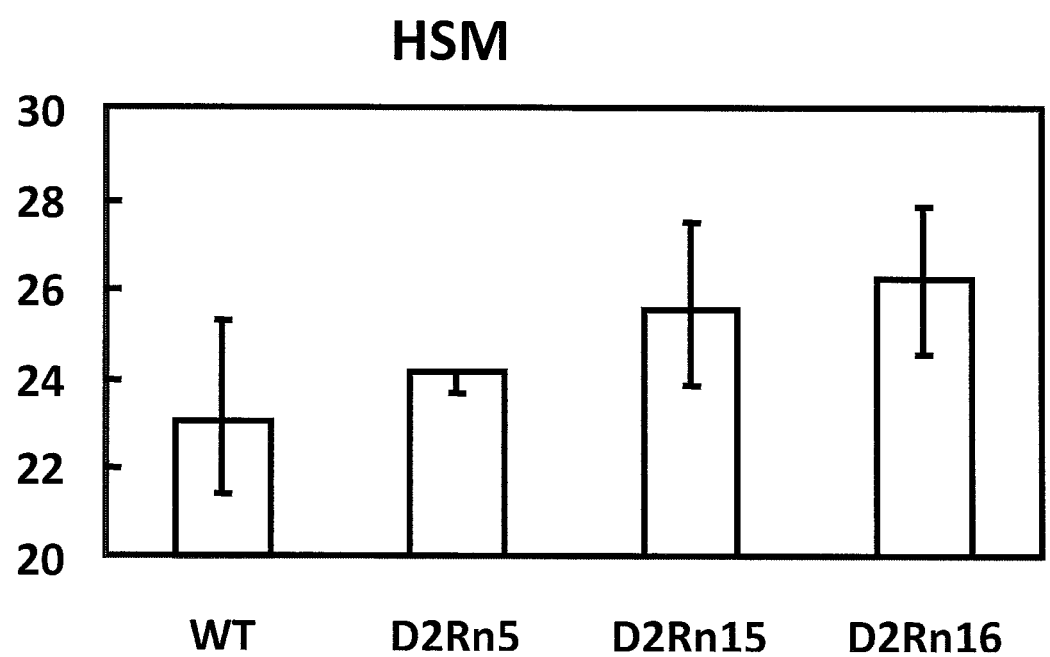
FIG. 14 shows the lipid oil content of three ACCase transgenic *Chlamydomonas reinhardtii* cell lines (D2Rn5, D2Rn15, and D2Rn16) grown in HSM media. The y-axis is lipid content (% MTBE extractable) and the x-axis represents the three clones compared to a wild-type untransformed *Chlamydomonas reinhardtii* cell line.

The measurement of the total gravimetric lipid content in several transgenic cell lines is shown in FIG. 13 and FIG. 14. D2Rn5, D2Rn15, and D2Rn16 are the individual clones shown in FIGS. 8A and 8B. The Y axis shows the lipid content as a percent of the ash-free dry weight of the culture. The X axis shows the strain of algae analyzed. All extractions were conducted in triplicate with error bars showing the standard deviation of the percent extractable.

In TAP growth media, the lipid accumulation in RnACC expressing cell lines can be as high as 27.84% of ash-free dry weight (D2Rn16) compared to 25.12% (WT), an 11% increase (FIG. 13).

In HSM growth media, the lipid accumulation in RnACC overexpressing cell lines can be as high as 26.16% of ash-free dry weight (D2Rn16) compared to 23.08% (WT), a 13.3% increase (FIG. 14).

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A non-vascular photosynthetic organism transformed with a polynucleotide, comprising a nucleic acid sequence that encodes a protein comprising the amino acid sequence of SEQ ID NO: 18, SEQ ID NO: 19, SEQ ID NO: 15, SEQ ID NO: 16, SEQ ID NO: 17, SEQ ID NO: 20, SEQ ID NO: 21, SEQ ID NO: 22, SEQ ID NO: 23, or SEQ ID NO: 24.

2. The non-vascular photosynthetic organism of claim 1, wherein the nucleic acid sequence comprises: the nucleotide sequence of SEQ ID NO: 29, SEQ ID NO: 30, SEQ ID NO: 27, SEQ ID NO: 28, SEQ ID NO: 31, SEQ ID NO: 32, SEQ ID NO: 33, SEQ ID NO: 34, SEQ ID NO: 35, or SEQ ID NO: 36; or a sequence that has at least 80%, at least 90%, at least 95%, at least 98%, or at least at least 99% sequence identity to the nucleotide sequence of SEQ ID NO: 29, SEQ ID NO: 30, SEQ ID NO: 27, SEQ ID NO: 28, SEQ ID NO: 31, SEQ ID NO: 32, SEQ ID NO: 33, SEQ ID NO: 34, SEQ ID NO: 35, or SEQ ID NO: 36.

3. The non-vascular photosynthetic organism of claim 1, wherein the non-vascular photosynthetic organism is an alga.

4. The non-vascular photosynthetic organism of claim 3, wherein the alga is a *Chlorophycean* species.

5. The non-vascular photosynthetic organism of claim 1, wherein the non-vascular photosynthetic organism is a cyanobacterium.

6. A non-vascular photosynthetic organism transformed with a nucleotide sequence comprising SEQ ID NO: 168 or SEQ ID NO: 169; or a nucleotide sequence that has at least 80%, at least 90%, at least 95%, at least 98%, or at least at least 99% sequence identity to the nucleic acid sequence of SEQ ID NO: 168 or SEQ ID NO: 169.

7. The non-vascular photosynthetic organism of claim 6, wherein the non-vascular photosynthetic organism is an alga.

8. The non-vascular photosynthetic organism of claim 7, wherein the alga is a *Chlorophycean* species.

9. The non-vascular photosynthetic organism of claim 6, wherein the non-vascular photosynthetic organism is a cyanobacterium.

10. A non-vascular photosynthetic organism transformed with a polynucleotide, comprising: a nucleic acid sequence that encodes a protein comprising the amino acid sequence of SEQ ID NO: 157; or a sequence that has at least 75%, at least 80%, at least 90%, at least 95%, at least 98%, or at least at least 99% sequence identity to the amino acid sequence of ID NO: 157.

11. The non-vascular photosynthetic organism of claim 10, wherein the nucleic acid sequence comprises: the nucleotide sequence of SEQ ID NO: 114 or SEQ ID NO: 115; or a sequence that has at least 75%, at least 80%, at least 90%, at least 95%, at least 98%, or at least at least 99% sequence identity to the nucleotide sequence of SEQ ID NO: 114 or SEQ ID NO: 115.

12. The non-vascular photosynthetic organism of claim 10, wherein the non-vascular photosynthetic organism is an alga.

13. The non-vascular photosynthetic organism of claim 12, wherein the alga is a *Chlorophycean* species.

14. The non-vascular photosynthetic organism of claim 10, wherein the non-vascular photosynthetic organism is a cyanobacterium.

15. A method for increasing production of malonyl CoA in a non-vascular photosynthetic organism, comprising transforming the non-vascular photosynthetic organism with a polynucleotide encoding a protein comprising the amino acid sequence of: SEQ ID NO: 18, SEQ ID NO: 19, SEQ ID NO: 15, SEQ ID NO: 16, SEQ ID NO: 17, SEQ ID NO: 20, SEQ ID NO: 21, SEQ ID NO: 22, SEQ ID NO: 23, SEQ ID NO: 24, SEQ ID NO: 163, SEQ ID NO: 164, SEQ ID NO: 165, SEQ ID NO: 166, SEQ ID NO: 167, or SEQ ID NO: 157, wherein expression of the protein results in increased production of malonyl CoA in the non-vascular photosynthetic organism.

16. The method of claim 15, wherein the non-vascular photosynthetic organism is an alga.

17. The method of claim 16, wherein the alga is a *Chlorophycean* species.

18. method of claim 15, wherein the non-vascular photosynthetic organism is a cyanobacterium.

* * * * *

SEQUENCE LISTING

<160> NUMBER OF SEQ ID NOS: 174

<210> SEQ ID NO 1
<211> LENGTH: 372
<212> TYPE: PRT
<213> ORGANISM: Chlamydomonas reinhardtii

<400> SEQUENCE: 1

Met Leu Ser Ala Gln Thr Ser Arg Thr Cys Cys Ser Gln Arg Gly Cys
1               5                   10                  15

Asn Gly Val Arg Met Ala Pro Gln Ala Lys Pro Met Val Gly Arg Val
            20                  25                  30

Pro Gly Arg Ser Gly Ser Pro Cys Val Val Ala Ala Gly Glu Ala Asn
        35                  40                  45

Gly Ser Pro Ile Val Thr Gly Pro Ile Ser Val Asn Pro Ser Met Ser
    50                  55                  60

Pro Ala Leu Asp Pro Val Ala Ala Ala Glu Ala Gly Lys Ser Ala Lys
65                  70                  75                  80

Ala Val Asp Arg Ser Lys Gly Leu Trp Thr Arg Cys Asp Lys Cys Gly
                85                  90                  95

Thr Ile Leu Tyr Ile Lys His Leu Lys Glu His His His Ile Cys Phe
            100                 105                 110

Gly Cys Asn Tyr His Leu Lys Met Ser Ser Met Glu Arg Ile Asn His
        115                 120                 125

Leu Ile Asp Ala Gly Thr Trp Arg Pro Leu Asp Glu Thr Leu Ser Pro
    130                 135                 140

Val Asp Pro Leu Glu Phe Ser Asp Leu Lys Ser Tyr Thr Asp Arg Ile
145                 150                 155                 160

Lys Glu Ala Gln Glu Lys Thr Gly Leu Gln Asp Gly Val Arg Thr Gly
                165                 170                 175

-continued

```
Thr Gly Leu Leu His Gly Ile Pro Val Ala Leu Gly Val Met Asp Phe
            180                 185                 190
Thr Tyr Met Gly Gly Ser Met Gly Ser Val Val Gly Glu Lys Leu Thr
        195                 200                 205
Arg Leu Ile Glu Tyr Ala Thr Gln Glu Gly Met Pro Val Ile Ile Val
    210                 215                 220
Cys Thr Ser Gly Gly Ala Arg Met Gln Glu Gly Ile Phe Ser Leu Met
225                 230                 235                 240
Gln Met Ala Lys Ile Ser Ala Ala Leu His Val His Gln Asn Cys Ala
            245                 250                 255
Asn Leu Leu Tyr Ile Ala Ile Leu Thr Ser Pro Thr Thr Gly Gly Val
        260                 265                 270
Thr Ala Ser Phe Gly Met Leu Gly Asp Val Ile Ile Ala Glu Pro Gln
    275                 280                 285
Ala Ile Ile Gly Phe Ala Gly Arg Arg Val Ile Glu Gln Thr Leu Gln
290                 295                 300
Glu Gln Leu Pro Asp Asp Phe Gln Thr Ala Glu Tyr Leu Leu Glu His
305                 310                 315                 320
Gly Leu Leu Asp Leu Val Val Pro Arg Ser Phe Leu Lys Gly Ala Leu
            325                 330                 335
Tyr Glu Ile Ile Asp Phe Tyr Arg Ala Ala Pro Tyr Lys Lys Arg Gly
        340                 345                 350
Met Ile Pro Phe Gly Val Gln His Gly Thr Phe Leu Thr Thr Glu Glu
    355                 360                 365
Lys Val Thr Gly
    370

<210> SEQ ID NO 2
<211> LENGTH: 329
<212> TYPE: PRT
<213> ORGANISM: Artificial Sequence
<220> FEATURE:
<223> OTHER INFORMATION: modified acetyl CoA carboxylase
<220> FEATURE:
<221> NAME/KEY: MISC_FEATURE
<223> OTHER INFORMATION: Combination of Xaa at positions 91, 98, 100,
      108, 112, 212 and 294 cannot be Thr, Thr, Ser, Ser, Ser, Cys, Tyr,
      respectively
<220> FEATURE:
<221> NAME/KEY: MISC_FEATURE
<222> LOCATION: (91)..(91)
<223> OTHER INFORMATION: Xaa can by Thr, Asp, Glu, Asn, His, Gln or Lys
<220> FEATURE:
<221> NAME/KEY: MISC_FEATURE
<222> LOCATION: (98)..(98)
<223> OTHER INFORMATION: Xaa can by any naturally occuring amino acid
<220> FEATURE:
<221> NAME/KEY: MISC_FEATURE
<222> LOCATION: (100)..(100)
<223> OTHER INFORMATION: Xaa can be Ser, Asp, Glu, Asn, His, Gln or Lys
<220> FEATURE:
<221> NAME/KEY: MISC_FEATURE
<222> LOCATION: (108)..(108)
<223> OTHER INFORMATION: Xaa can be Ser, Asp, Glu, Asn, His, Gln or Lys
<220> FEATURE:
<221> NAME/KEY: MISC_FEATURE
<222> LOCATION: (112)..(112)
<223> OTHER INFORMATION: Xaa can be Ser, Asp, Glu, Asn, His, Gln or Lys
<220> FEATURE:
<221> NAME/KEY: MISC_FEATURE
<222> LOCATION: (212)..(212)
<223> OTHER INFORMATION: Xaa can be Cys, Asp, Glu, Asn, His, Gln or Lys
<220> FEATURE:
<221> NAME/KEY: MISC_FEATURE
<222> LOCATION: (294)..(294)
```

<223> OTHER INFORMATION: Xaa can be Tyr, Asp, Glu, Asn, His, Gln or Lys

<400> SEQUENCE: 2

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Xaa Trp Arg Pro Leu Asp
                85                  90                  95

Glu Xaa Leu Xaa Pro Val Asp Pro Leu Glu Phe Xaa Asp Leu Lys Xaa
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Xaa Ala Asn Leu Leu Tyr Ile Ala Ile Leu Thr Ser Pro
            210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Xaa Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
                325
```

<210> SEQ ID NO 3
<211> LENGTH: 343
<212> TYPE: PRT
<213> ORGANISM: Artificial Sequence
<220> FEATURE:
<223> OTHER INFORMATION: modified acetyl CoA carboxylase
<220> FEATURE:
<221> NAME/KEY: MISC_FEATURE
<223> OTHER INFORMATION: Combination of Xaa at positions 105, 112, 114, 122, 126, 226, 308 cannot be Thr, Thr, Ser, Ser, Ser, Cys and Tyr, respectively

```
<220> FEATURE:
<221> NAME/KEY: MISC_FEATURE
<222> LOCATION: (1)..(14)
<223> OTHER INFORMATION: Strep-tag
<220> FEATURE:
<221> NAME/KEY: MISC_FEATURE
<222> LOCATION: (105)..(105)
<223> OTHER INFORMATION: Xaa can be Thr, Asp, Glu, Asn, His, Gln or Lys
<220> FEATURE:
<221> NAME/KEY: MISC_FEATURE
<222> LOCATION: (112)..(112)
<223> OTHER INFORMATION: Xaa can be Thr, Asp, Glu, Asn, His, Gln or Lys
<220> FEATURE:
<221> NAME/KEY: MISC_FEATURE
<222> LOCATION: (114)..(114)
<223> OTHER INFORMATION: Xaa can be Ser, Asp, Glu, Asn, His, Gln or Lys
<220> FEATURE:
<221> NAME/KEY: MISC_FEATURE
<222> LOCATION: (122)..(122)
<223> OTHER INFORMATION: Xaa can be Ser, Asp, Glu, Asn, His, Gln or Lys
<220> FEATURE:
<221> NAME/KEY: MISC_FEATURE
<222> LOCATION: (126)..(126)
<223> OTHER INFORMATION: Xaa can be Ser, Asp, Glu, Asn, His, Gln or Lys
<220> FEATURE:
<221> NAME/KEY: MISC_FEATURE
<222> LOCATION: (226)..(226)
<223> OTHER INFORMATION: Xaa can be Cys, Asp, Glu, Asn, His, Gln or Lys
<220> FEATURE:
<221> NAME/KEY: MISC_FEATURE
<222> LOCATION: (308)..(308)
<223> OTHER INFORMATION: Xaa can be Tyr, Asp, Glu, Asn, His, Gln or Lys

<400> SEQUENCE: 3

Met Gly Ser Ala Trp Ser His Pro Gln Phe Glu Lys His Met Ala Gly
1               5                   10                  15

Glu Ala Asn Gly Ser Pro Ile Val Thr Gly Pro Ile Ser Val Asn Pro
            20                  25                  30

Ser Met Ser Pro Ala Leu Asp Pro Val Ala Ala Glu Ala Gly Lys
        35                  40                  45

Ser Ala Lys Ala Val Asp Arg Ser Lys Gly Leu Trp Thr Arg Cys Asp
    50                  55                  60

Lys Cys Gly Thr Ile Leu Tyr Ile Lys His Leu Lys Glu His His His
65              70                  75                  80

Ile Cys Phe Gly Cys Asn Tyr His Leu Lys Met Ser Ser Met Glu Arg
                85                  90                  95

Ile Asn His Leu Ile Asp Ala Gly Xaa Trp Arg Pro Leu Asp Glu Xaa
            100                 105                 110

Leu Xaa Pro Val Asp Pro Leu Glu Phe Xaa Asp Leu Lys Xaa Tyr Thr
        115                 120                 125

Asp Arg Ile Lys Glu Ala Gln Glu Lys Thr Gly Leu Gln Asp Gly Val
    130                 135                 140

Arg Thr Gly Thr Gly Leu Leu His Gly Ile Pro Val Ala Leu Gly Val
145                 150                 155                 160

Met Asp Phe Thr Tyr Met Gly Gly Ser Met Gly Ser Val Val Gly Glu
                165                 170                 175

Lys Leu Thr Arg Leu Ile Glu Tyr Ala Thr Gln Glu Gly Met Pro Val
            180                 185                 190

Ile Ile Val Cys Thr Ser Gly Gly Ala Arg Met Gln Glu Gly Ile Phe
        195                 200                 205

Ser Leu Met Gln Met Ala Lys Ile Ser Ala Ala Leu His Val His Gln
    210                 215                 220

Asn Xaa Ala Asn Leu Leu Tyr Ile Ala Ile Leu Thr Ser Pro Thr Thr
225                 230                 235                 240
```

```
Gly Gly Val Thr Ala Ser Phe Gly Met Leu Gly Asp Val Ile Ile Ala
            245                 250                 255

Glu Pro Gln Ala Ile Ile Gly Phe Ala Gly Arg Arg Val Ile Glu Gln
        260                 265                 270

Thr Leu Gln Glu Gln Leu Pro Asp Asp Phe Gln Thr Ala Glu Tyr Leu
    275                 280                 285

Leu Glu His Gly Leu Leu Asp Leu Val Val Pro Arg Ser Phe Leu Lys
290                 295                 300

Gly Ala Leu Xaa Glu Ile Ile Asp Phe Tyr Arg Ala Ala Pro Tyr Lys
305                 310                 315                 320

Lys Arg Gly Met Ile Pro Phe Gly Val Gln His Gly Thr Phe Leu Thr
                325                 330                 335

Thr Glu Glu Lys Val Thr Gly
            340

<210> SEQ ID NO 4
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 4

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Asp Trp Arg Pro Leu Asp
                85                  90                  95

Glu Thr Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255
```

```
Glu Gln Thr Leu Gln Glu Gln Leu Pro Asp Asp Phe Gln Thr Ala Glu
                260                 265                 270

Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
                325

<210> SEQ ID NO 5
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 5

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
                20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
        50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Asp Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285
```

```
Leu Lys Gly Ala Leu Tyr Glu Ile Ile Asp Phe Tyr Arg Ala Ala Pro
            290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
                325

<210> SEQ ID NO 6
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 6

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Asp Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
            290                 295                 300

Tyr Lys Lys Arg Gly Met Ile Pro Phe Gly Val Gln His Gly Thr Phe
305                 310                 315                 320
```

```
Leu Thr Thr Glu Glu Lys Val Thr Gly
            325

<210> SEQ ID NO 7
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 7

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30      Ala

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
        50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Asp Asp Leu Lys Ser
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
        210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
        290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
            325

<210> SEQ ID NO 8
```

<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 8

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Asp
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Tyr Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
                325
```

<210> SEQ ID NO 9
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 9

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65              70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Asp Glu Ile Ile Asp Phe Tyr Arg Ala Ala Pro
    290                 295                 300

Tyr Lys Lys Arg Gly Met Ile Pro Phe Gly Val Gln His Gly Thr Phe
305                 310                 315                 320

Leu Thr Thr Glu Glu Lys Val Thr Gly
                325
```

<210> SEQ ID NO 10
<211> LENGTH: 329
<212> TYPE: PRT
<213> ORGANISM: Artificial Sequence
<220> FEATURE:
<223> OTHER INFORMATION: modified acetyl CoA carboxylase

<400> SEQUENCE: 10

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Ala Glu Ala
```

```
                  20                  25                  30
Gly Lys Ser Ala Lys Ala Val Asp Arg Ser Lys Gly Leu Trp Thr Arg
            35                  40                  45
Cys Asp Lys Cys Gly Thr Ile Leu Tyr Ile Lys His Leu Lys Glu His
 50                  55                  60
His His Ile Cys Phe Gly Cys Asn Tyr His Leu Lys Met Ser Ser Met
 65                  70                  75                  80
Glu Arg Ile Asn His Leu Ile Asp Ala Gly Thr Trp Arg Pro Leu Asp
                85                  90                  95
Glu Thr Leu Ser Pro Val Asp Pro Leu Glu Phe Ser Asp Leu Lys Ser
            100                 105                 110
Tyr Thr Asp Arg Ile Lys Glu Ala Gln Glu Lys Thr Gly Leu Gln Asp
        115                 120                 125
Gly Val Arg Thr Gly Thr Gly Leu Leu His Gly Ile Pro Val Ala Leu
    130                 135                 140
Gly Val Met Asp Phe Thr Tyr Met Gly Gly Ser Met Gly Ser Val Val
145                 150                 155                 160
Gly Glu Lys Leu Thr Arg Leu Ile Glu Tyr Ala Thr Gln Glu Gly Met
                165                 170                 175
Pro Val Ile Ile Val Cys Thr Ser Gly Gly Ala Arg Met Gln Glu Gly
            180                 185                 190
Ile Phe Ser Leu Met Gln Met Ala Lys Ile Ser Ala Ala Leu His Val
        195                 200                 205
His Gln Asn Ser Ala Asn Leu Leu Tyr Ile Ala Ile Leu Thr Ser Pro
    210                 215                 220
Thr Thr Gly Gly Val Thr Ala Ser Phe Gly Met Leu Gly Asp Val Ile
225                 230                 235                 240
Ile Ala Glu Pro Gln Ala Ile Ile Gly Phe Ala Gly Arg Arg Val Ile
                245                 250                 255
Glu Gln Thr Leu Gln Glu Gln Leu Pro Asp Asp Phe Gln Thr Ala Glu
            260                 265                 270
Tyr Leu Leu Glu His Gly Leu Leu Asp Leu Val Val Pro Arg Ser Phe
        275                 280                 285
Leu Lys Gly Ala Leu Tyr Glu Ile Ile Asp Phe Tyr Arg Ala Ala Pro
    290                 295                 300
Tyr Lys Lys Arg Gly Met Ile Pro Phe Gly Val Gln His Gly Thr Phe
305                 310                 315                 320
Leu Thr Thr Glu Glu Lys Val Thr Gly
                325

<210> SEQ ID NO 11
<211> LENGTH: 327
<212> TYPE: PRT
<213> ORGANISM: Artificial Sequence
<220> FEATURE:
<223> OTHER INFORMATION: modified acetyl CoA carboxylase
<220> FEATURE:
<221> NAME/KEY: MISC_FEATURE
<223> OTHER INFORMATION: wherein, X at position 92 is not T, and X at
      position 99 is not T, and X at position 101 is not S, and X at
      position 109 is not S, and X at position 113 is not S, and X at
      position 213 is not C, and X at position 295 is not Y
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: MISC_FEATURE
<222> LOCATION: (92)..(92)
```

```
<223> OTHER INFORMATION: X is T, D, E, N, H, Q or K
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (99)..(99)
<223> OTHER INFORMATION: X is T, D, E, N, H, Q or K
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: X is S, D, E, N, H, Q or K
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: MISC_FEATURE
<222> LOCATION: (109)..(109)
<223> OTHER INFORMATION: X is S, D, E, N, H, Q or K
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: MISC_FEATURE
<222> LOCATION: (113)..(113)
<223> OTHER INFORMATION: X is S, D, E, N, H, Q or K
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: MISC_FEATURE
<222> LOCATION: (213)..(213)
<223> OTHER INFORMATION: X is C, D, E, N, H, Q or K
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: MISC_FEATURE
<222> LOCATION: (295)..(295)
<223> OTHER INFORMATION: X is Y, D, E, N, H, Q or K

<400> SEQUENCE: 11

Ala Gly Glu Ala Asn Gly Ser Pro Ile Val Thr Gly Pro Ile Ser Val
 1               5                  10                  15

Asn Pro Ser Met Ser Pro Ala Leu Asp Pro Val Ala Ala Glu Ala
                20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
        50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Xaa Trp Arg Pro Leu Asp
                85                  90                  95

Glu Xaa Leu Xaa Pro Val Asp Pro Leu Glu Phe Xaa Asp Leu Lys Xaa
               100                 105                 110

Tyr Thr Asp Arg Ile Lys Glu Ala Gln Glu Lys Thr Gly Leu Gln Asp
           115                 120                 125

Gly Val Arg Thr Gly Thr Gly Leu Leu His Gly Ile Pro Val Ala Leu
       130                 135                 140
```

```
Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Xaa Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Xaa Glu Ile Ile Asp Phe Tyr Arg Ala Ala Pro
    290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 12
<211> LENGTH: 327
<212> TYPE: PRT
<213> ORGANISM: Chlamydomonas reinhardtii

<400> SEQUENCE: 12

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190
```

```
Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
            290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 13
<211> LENGTH: 370
<212> TYPE: PRT
<213> ORGANISM: Chlamydomonas reinhardtii

<400> SEQUENCE: 13

Met Leu Ser Ala Gln Thr Ser Arg Thr Cys Cys Ser Gln Arg Gly Cys
1               5                   10                  15

Asn Gly Val Arg Met Ala Pro Gln Ala Lys Pro Met Val Gly Arg Val
            20                  25                  30

Pro Gly Arg Ser Gly Ser Pro Cys Val Val Ala Ala Gly Glu Ala Asn
        35                  40                  45

Gly Ser Pro Ile Val Thr Gly Pro Ile Ser Val Asn Pro Ser Met Ser
    50                  55                  60

Pro Ala Leu Asp Pro Val Ala Ala Glu Ala Gly Lys Ser Ala Lys
65                  70                  75                  80

Ala Val Asp Arg Ser Lys Gly Leu Trp Thr Arg Cys Asp Lys Cys Gly
            85                  90                  95

Thr Ile Leu Tyr Ile Lys His Leu Lys Glu His His Ile Cys Phe
            100                 105                 110

Gly Cys Asn Tyr His Leu Lys Met Ser Ser Met Glu Arg Ile Asn His
        115                 120                 125

Leu Ile Asp Ala Gly Thr Trp Arg Pro Leu Asp Glu Thr Leu Ser Pro
    130                 135                 140

Val Asp Pro Leu Glu Phe Ser Asp Leu Lys Ser Tyr Thr Asp Arg Ile
145                 150                 155                 160

Lys Glu Ala Gln Glu Lys Thr Gly Leu Gln Asp Gly Val Arg Thr Gly
            165                 170                 175

Thr Gly Leu Leu His Gly Ile Pro Val Ala Leu Gly Val Met Asp Phe
            180                 185                 190

Thr Tyr Met Gly Gly Ser Met Gly Ser Val Val Gly Glu Lys Leu Thr
        195                 200                 205

Arg Leu Ile Glu Tyr Ala Thr Gln Glu Gly Met Pro Val Ile Ile Val
    210                 215                 220

Cys Thr Ser Gly Gly Ala Arg Met Gln Glu Gly Ile Phe Ser Leu Met
```

```
                 225                 230                 235                 240
        Gln Met Ala Lys Ile Ser Ala Ala Leu His Val His Gln Asn Cys Ala
                        245                 250                 255

Asn Leu Leu Tyr Ile Ala Ile Leu Thr Ser Pro Thr Thr Gly Gly Val
                        260                 265                 270

Thr Ala Ser Phe Gly Met Leu Gly Asp Val Ile Ile Ala Glu Pro Gln
                        275                 280                 285

Ala Ile Ile Gly Phe Ala Gly Arg Arg Val Ile Glu Gln Thr Leu Gln
                        290                 295                 300

Glu Gln Leu Pro Asp Asp Phe Gln Thr Ala Glu Tyr Leu Leu Glu His
        305                 310                 315                 320

Gly Leu Leu Asp Leu Val Pro Arg Ser Phe Leu Lys Gly Ala Leu
                        325                 330                 335

Tyr Glu Ile Ile Asp Phe Tyr Arg Ala Ala Pro Tyr Lys Lys Arg Gly
                        340                 345                 350

Met Ile Pro Phe Gly Val Gln His Gly Thr Phe Leu Thr Thr Glu Glu
                        355                 360                 365

Lys Val
                370

<210> SEQ ID NO 14
<211> LENGTH: 341
<212> TYPE: PRT
<213> ORGANISM: Artificial Sequence
<220> FEATURE:
<223> OTHER INFORMATION: modified acetyl CoA carboxylase

<400> SEQUENCE: 14

Met Gly Ser Ala Trp Ser His Pro Gln Phe Glu Lys His Met Ala Gly
        1               5                   10                  15

Glu Ala Asn Gly Ser Pro Ile Val Thr Gly Pro Ile Ser Val Asn Pro
                        20                  25                  30

Ser Met Ser Pro Ala Leu Asp Pro Val Ala Ala Ala Glu Ala Gly Lys
                        35                  40                  45

Ser Ala Lys Ala Val Asp Arg Ser Lys Gly Leu Trp Thr Arg Cys Asp
         50                 55                  60

Lys Cys Gly Thr Ile Leu Tyr Ile Lys His Leu Lys Glu His His His
         65                 70                  75                  80

Ile Cys Phe Gly Cys Asn Tyr His Leu Lys Met Ser Ser Met Glu Arg
                        85                  90                  95

Ile Asn His Leu Ile Asp Ala Gly Thr Trp Arg Pro Leu Asp Glu Thr
                        100                 105                 110

Leu Ser Pro Val Asp Pro Leu Glu Phe Ser Asp Leu Lys Ser Tyr Thr
                        115                 120                 125

Asp Arg Ile Lys Glu Ala Gln Glu Lys Thr Gly Leu Gln Asp Gly Val
                        130                 135                 140

Arg Thr Gly Thr Gly Leu Leu His Gly Ile Pro Val Ala Leu Gly Val
        145                 150                 155                 160

Met Asp Phe Thr Tyr Met Gly Gly Ser Met Gly Ser Val Val Gly Glu
                        165                 170                 175

Lys Leu Thr Arg Leu Ile Glu Tyr Ala Thr Gln Glu Gly Met Pro Val
                        180                 185                 190

Ile Ile Val Cys Thr Ser Gly Gly Ala Arg Met Gln Glu Gly Ile Phe
                        195                 200                 205

Ser Leu Met Gln Met Ala Lys Ile Ser Ala Ala Leu His Val His Gln
```

Asn Cys Ala Asn Leu Leu Tyr Ile Ala Ile Leu Thr Ser Pro Thr Thr
225                 230                 235                 240

Gly Gly Val Thr Ala Ser Phe Gly Met Leu Gly Asp Val Ile Ile Ala
            245                 250                 255

Glu Pro Gln Ala Ile Ile Gly Phe Ala Gly Arg Arg Val Ile Glu Gln
            260                 265                 270

Thr Leu Gln Glu Gln Leu Pro Asp Asp Phe Gln Thr Ala Glu Tyr Leu
            275                 280                 285

Leu Glu His Gly Leu Leu Asp Leu Val Val Pro Arg Ser Phe Leu Lys
            290                 295                 300

Gly Ala Leu Tyr Glu Ile Ile Asp Phe Tyr Arg Ala Ala Pro Tyr Lys
305                 310                 315                 320

Lys Arg Gly Met Ile Pro Phe Gly Val Gln His Gly Thr Phe Leu Thr
                325                 330                 335

Thr Glu Glu Lys Val
            340

<210> SEQ ID NO 15
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 15

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile Lys His Leu Lys Glu His
            50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Asp Trp Arg Pro Leu Asp
                85                  90                  95

Glu Thr Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
            210                 215                 220

Thr Thr Gly Gly Val Thr Ala Ser Phe Gly Met Leu Gly Asp Val Ile

```
            225                 230                 235                 240
Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
                260                 265                 270

Tyr Leu Leu Glu His Gly Leu Leu Asp Leu Val Val Pro Arg Ser Phe
                275                 280                 285

Leu Lys Gly Ala Leu Tyr Glu Ile Ile Asp Phe Tyr Arg Ala Ala Pro
                290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 16
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 16

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
                20                  25                  30

Gly Lys Ser Ala Lys Ala Val Asp Arg Ser Lys Gly Leu Trp Thr Arg
                35                  40                  45

Cys Asp Lys Cys Gly Thr Ile Leu Tyr Ile Lys His Leu Lys Glu His
            50                  55                  60

His His Ile Cys Phe Gly Cys Asn Tyr His Leu Lys Met Ser Ser Met
65              70                  75                  80

Glu Arg Ile Asn His Leu Ile Asp Ala Gly Thr Trp Arg Pro Leu Asp
                85                  90                  95

Glu Asp Leu Ser Pro Val Asp Pro Leu Glu Phe Ser Asp Leu Lys Ser
                100                 105                 110

Tyr Thr Asp Arg Ile Lys Glu Ala Gln Glu Lys Thr Gly Leu Gln Asp
                115                 120                 125

Gly Val Arg Thr Gly Thr Gly Leu Leu His Gly Ile Pro Val Ala Leu
            130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
                180                 185                 190

Ile Phe Ser Leu Met Gln Met Ala Lys Ile Ser Ala Ala Leu His Val
                195                 200                 205

His Gln Asn Cys Ala Asn Leu Leu Tyr Ile Ala Ile Leu Thr Ser Pro
            210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
```

```
                260                 265                 270
Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
        290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 17
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 17

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Asp Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Tyr Glu Ile Ile Asp Phe Tyr Arg Ala Ala Pro
```

```
                290                 295                 300
Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 18
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 18

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Asp Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Tyr Glu Ile Ile Asp Phe Tyr Arg Ala Ala Pro
    290                 295                 300

Tyr Lys Lys Arg Gly Met Ile Pro Phe Gly Val Gln His Gly Thr Phe
305                 310                 315                 320

Leu Thr Thr Glu Glu Lys Val
```

<210> SEQ ID NO 19
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 19

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Asp
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Cys Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Tyr Glu Ile Ile Asp Phe Tyr Arg Ala Ala Pro
    290                 295                 300

Tyr Lys Lys Arg Gly Met Ile Pro Phe Gly Val Gln His Gly Thr Phe
305                 310                 315                 320

Leu Thr Thr Glu Glu Lys Val
                325
```

<210> SEQ ID NO 20
<211> LENGTH: 327
<212> TYPE: PRT

<213> ORGANISM: Artificial Sequence
<220> FEATURE:
<223> OTHER INFORMATION: modified acetyl CoA carboxylase

<400> SEQUENCE: 20

```
Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
        35                  40                  45

Cys Asp Lys Cys Gly Thr Ile Leu Tyr Ile Lys His Leu Lys Glu His
    50                  55                  60

His His Ile Cys Phe Gly Cys Asn Tyr His Leu Lys Met Ser Ser Met
65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Ser
            100                 105                 110

Tyr Thr Asp Arg Ile Lys Glu Ala Gln Glu Lys Thr Gly Leu Gln Asp
        115                 120                 125

Gly Val Arg Thr Gly Thr Gly Leu Leu His Gly Ile Pro Val Ala Leu
    130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
        195                 200                 205

His Gln Asn Ser Ala Asn Leu Leu Tyr Ile Ala Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
        275                 280                 285

Leu Lys Gly Ala Leu Tyr Glu Ile Ile Asp Phe Tyr Arg Ala Ala Pro
    290                 295                 300

Tyr Lys Lys Arg Gly Met Ile Pro Phe Gly Val Gln His Gly Thr Phe
305                 310                 315                 320

Leu Thr Thr Glu Glu Lys Val
                325
```

<210> SEQ ID NO 21
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 21

```
Ala Gly Glu Ala Asn Gly Ser Pro Ile Val Thr Gly Pro Ile Ser Val
 1               5                  10                  15

Asn Pro Ser Met Ser Pro Ala Leu Asp Pro Val Ala Ala Glu Ala
            20                  25                  30

Gly Lys Ser Ala Lys Ala Val Asp Arg Ser Lys Gly Leu Trp Thr Arg
            35                  40                  45

Cys Asp Lys Cys Gly Thr Ile Leu Tyr Ile His Leu Lys Glu His
 50                  55                  60

His His Ile Cys Phe Gly Cys Asn Tyr His Leu Lys Met Ser Ser Met
 65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Ser Asp Leu Lys Ser
                100                 105                 110

Tyr Thr Asp Arg Ile Lys Glu Ala Gln Glu Lys Thr Gly Leu Gln Asp
                115                 120                 125

Gly Val Arg Thr Gly Thr Gly Leu Leu His Gly Ile Pro Val Ala Leu
            130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
                180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
                260                 265                 270

Tyr Leu Leu Glu His Gly Leu Leu Asp Leu Val Val Pro Arg Ser Phe
            275                 280                 285

Leu Lys Gly Ala Leu Asp Glu Ile Ile Asp Phe Tyr Arg Ala Ala Pro
            290                 295                 300

Tyr Lys Lys Arg Gly Met Ile Pro Phe Gly Val Gln His Gly Thr Phe
305                 310                 315                 320

Leu Thr Thr Glu Glu Lys Val
                325
```

<210> SEQ ID NO 22
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 22

```
Ala Gly Glu Ala Asn Gly Ser Pro Ile Val Thr Gly Pro Ile Ser Val
 1               5                  10                  15

Asn Pro Ser Met Ser Pro Ala Leu Asp Pro Val Ala Ala Glu Ala
            20                  25                  30
```

```
Gly Lys Ser Ala Lys Ala Val Asp Arg Ser Lys Gly Leu Trp Thr Arg
             35                  40                  45

Cys Asp Lys Cys Gly Thr Ile Leu Tyr Ile Lys His Leu Lys Glu His
 50                  55                  60

His His Ile Cys Phe Gly Cys Asn Tyr His Leu Lys Met Ser Ser Met
 65                  70                  75                  80

Glu Arg Ile Asn His Leu Ile Asp Ala Gly Thr Trp Arg Pro Leu Asp
                 85                  90                  95

Glu Thr Leu Ser Pro Val Asp Pro Leu Glu Phe Asp Asp Leu Lys Asp
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Tyr Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val
                325
```

<210> SEQ ID NO 23
<211> LENGTH: 327
<212> TYPE: PRT
<213> ORGANISM: Artificial Sequence
<220> FEATURE:
<223> OTHER INFORMATION: modified acetyl CoA carboxylase
<220> FEATURE:
<221> NAME/KEY: MISC_FEATURE
<223> OTHER INFORMATION: modified acetyl CoA carboxylase

<400> SEQUENCE: 23

```
Ala Gly Glu Ala Asn Gly Ser Pro Ile Val Thr Gly Pro Ile Ser Val
 1               5                  10                  15

Asn Pro Ser Met Ser Pro Ala Leu Asp Pro Val Ala Ala Glu Ala
                20                  25                  30

Gly Lys Ser Ala Lys Ala Val Asp Arg Ser Lys Gly Leu Trp Thr Arg
             35                  40                  45
```

Cys Asp Lys Cys Gly Thr Ile Leu Tyr Ile Lys His Leu Lys Glu His
        50                  55                  60

His His Ile Cys Phe Gly Cys Asn Tyr His Leu Lys Met Ser Ser Met
 65                  70                  75                  80

Glu Arg Ile Asn His Leu Ile Asp Ala Gly Thr Trp Arg Pro Leu Asp
                 85                  90                  95

Glu Thr Leu Ser Pro Val Asp Pro Leu Glu Phe Asp Asp Leu Lys Asp
                100                 105                 110

Tyr Thr Asp Arg Ile Lys Glu Ala Gln Glu Lys Thr Gly Leu Gln Asp
                115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
                180                 185                 190

Ile Phe Ser Leu Met Gln Met Ala Lys Ile Ser Ala Ala Leu His Val
                195                 200                 205

His Gln Asn Ser Ala Asn Leu Leu Tyr Ile Ala Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
                260                 265                 270

Tyr Leu Leu Glu His Gly Leu Leu Asp Leu Val Val Pro Arg Ser Phe
                275                 280                 285

Leu Lys Gly Ala Leu Tyr Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 24
<211> LENGTH: 327
<212> TYPE: PRT
<213> ORGANISM: Artificial Sequence
<220> FEATURE:
<223> OTHER INFORMATION: modified acetyl CoA carboxylase

<400> SEQUENCE: 24

Ala Gly Glu Ala Asn Gly Ser Pro Ile Val Thr Gly Pro Ile Ser Val
1               5                   10                  15

Asn Pro Ser Met Ser Pro Ala Leu Asp Pro Val Ala Ala Glu Ala
                20                  25                  30

Gly Lys Ser Ala Lys Ala Val Asp Arg Ser Lys Gly Leu Trp Thr Arg
                35                  40                  45

Cys Asp Lys Cys Gly Thr Ile Leu Tyr Ile Lys His Leu Lys Glu His
        50                  55                  60

His His Ile Cys Phe Gly Cys Asn Tyr His Leu Lys Met Ser Ser Met
 65                  70                  75                  80

Glu Arg Ile Asn His Leu Ile Asp Ala Gly Thr Trp Arg Pro Leu Asp
                85                  90                  95

Glu Thr Leu Ser Pro Val Asp Pro Leu Glu Phe Asp Asp Leu Lys Asp
            100                 105                 110

Tyr Thr Asp Arg Ile Lys Glu Ala Gln Glu Lys Thr Gly Leu Gln Asp
            115                 120                 125

Gly Val Arg Thr Gly Thr Gly Leu Leu His Gly Ile Pro Val Ala Leu
130                 135                 140

Gly Val Met Asp Phe Thr Tyr Met Gly Gly Ser Met Gly Ser Val Val
145                 150                 155                 160

Gly Glu Lys Leu Thr Arg Leu Ile Glu Tyr Ala Thr Gln Glu Gly Met
                165                 170                 175

Pro Val Ile Ile Val Cys Thr Ser Gly Gly Ala Arg Met Gln Glu Gly
            180                 185                 190

Ile Phe Ser Leu Met Gln Met Ala Lys Ile Ser Ala Ala Leu His Val
            195                 200                 205

His Gln Asn Cys Ala Asn Leu Leu Tyr Ile Ala Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Gln Glu Gln Leu Pro Asp Asp Phe Gln Thr Ala Glu
            260                 265                 270

Tyr Leu Leu Glu His Gly Leu Leu Asp Leu Val Val Pro Arg Ser Phe
            275                 280                 285

Leu Lys Gly Ala Leu Asp Glu Ile Ile Asp Phe Tyr Arg Ala Ala Pro
290                 295                 300

Tyr Lys Lys Arg Gly Met Ile Pro Phe Gly Val Gln His Gly Thr Phe
305                 310                 315                 320

Leu Thr Thr Glu Glu Lys Val
                325

<210> SEQ ID NO 25
<211> LENGTH: 39
<212> TYPE: DNA
<213> ORGANISM: Artificial Sequence
<220> FEATURE:
<223> OTHER INFORMATION: Strep Affinity Tag

<400> SEQUENCE: 25
atgggttctg cttggtctca tccacaattt gaaaaacat                            39

<210> SEQ ID NO 26
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 26
gcaggtgagg caaacggttc tcctattgtt actggtccta tttctgttaa tccatctatg      60
tctccagctc ttgacccagt agctgctgca gaagcaggta atctgcaaa agcagtagac      120 cgttctaaag gtctttggac tcgttgtgac aaatgtggca ctattttata tattaaacac      180 ttaaagaac accatcatat ctgtttcggt tgtaattacc acttaaaaat gtcttctatg      240
gaacgtatta accacttaat tgatgctggt acttggcgtc cacttgatga aactcttttct     300

```
ccagtagatc ctttagaatt ttctgactta aaatcttata ctgatcgtat taaagaggct      360
caagaaaaaa ctggcttaca agatggtgtt cgtactggca ctggtttact tcatggtatt      420
cctgtagcat taggtgtaat ggacttcact tatatgggtg gctctatggg ttctgttgtt      480
ggtgaaaaac ttactcgtct tattgaatac gctactcaag agggtatgcc tgtaattatt      540
gtatgtactt ctggtggtgc tcgtatgcaa gaaggtattt tttctttaat gcaaatggct      600
aaaatttctg ctgctcttca tgtacatcaa aactgcgcta atcttttata cattgctatt      660
ttaacttctc ctactactgg tggcgttact gcttcttttg gtatgttagg tgatgtaatt      720
atcgctgaac tcaagcaat tattggtttt gcaggtcgtc gtgtaattga acaaacttta       780
caagaacaac ttcctgatga cttccaaact gctgaatatt tacttgaaca tggtttatta      840
gatttagtag ttcctcgttc tttccttaaa ggtgcattat atgaaatcat tgactttta      900 cgtgctgcac cttacaaaaa acgtggcatg atcccatttg gtgttcaaca cggtactttt      960
ttaactactg aagagaaagt ta                                               982
```

<210> SEQ ID NO 27
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 27

```
gcaggtgagg caaacggttc tcctattgtt actggtccta tttctgttaa tccatctatg       60
tctccagctc ttgacccagt agctgctgca gaagcaggta atctgcaaa agcagtagac      120 cgttctaaag gtctttggac tcgttgtgac aaatgtggca ctatttata tattaaacac      180 ttaaaagaac accatcatat ctgtttcggt tgtaattacc acttaaaaat gtcttctatg      240
gaacgtatta accacttaat tgatgctggt acttggcgtc cacttgatga aactcttttct      300 ccagtagatc ctttagaatt ttctgactta aaatcttata ctgatcgtat taaagaggct      360
caagaaaaaa ctggcttaca agatggtgtt cgtactggca ctggtttact tcatggtatt      420
cctgtagcat taggtgtaat ggacttcact tatatgggtg gctctatggg ttctgttgtt      480
ggtgaaaaac ttactcgtct tattgaatac gctactcaag agggtatgcc tgtaattatt      540
gtatgtactt ctggtggtgc tcgtatgcaa gaaggtattt tttctttaat gcaaatggct      600
aaaatttctg ctgctcttca tgtacatcaa aactcagcta atcttttata cattgctatt      660
ttaacttctc ctactactgg tggcgttact gcttcttttg gtatgttagg tgatgtaatt      720
atcgctgaac tcaagcaat tattggtttt gcaggtcgtc gtgtaattga acaaacttta       780
caagaacaac ttcctgatga cttccaaact gctgaatatt tacttgaaca tggtttatta      840
gatttagtag ttcctcgttc tttccttaaa ggtgcattat atgaaatcat tgactttta      900 cgtgctgcac cttacaaaaa acgtggcatg atcccatttg gtgttcaaca cggtactttt      960
ttaactactg aagagaaagt ta                                               982
```

<210> SEQ ID NO 28
<211> LENGTH: 989
<212> TYPE: DNA
<213> ORGANISM: Artificial Sequence
<220> FEATURE:
<223> OTHER INFORMATION: modified acetyl CoA carboxylase

<400> SEQUENCE: 28

```
gcaggtgagg caaacggttc tcctattgtt actggtccta tttctgttaa tccatctatg    60
tctccagctc ttgacccagt agctgctgca gaagcaggta aatctgcaaa agcagtagac   120
cgttctaaag gtctttggac tcgttgtgac aaatgtggca ctattttata tattaaacac   180
ttaaaagaac accatcatat ctgtttcggt tgtaattacc acttaaaaat gtcttctatg   240
gaacgtatta accacttaat tgatgctggt acttggcgtc cacttgatga aactcttgat   300
ccagtagatc ctttagaatt ttctgactta aaatctttata ctgatcgtat aaagaggct   360 caagaaaaaa ctggcttaca agatggtgtt cgtactggca ctggtttact tcatggtatt   420
cctgtagcat taggtgtaat ggacttcact tatatgggtg gctctatggg ttctgttgtt   480
ggtgaaaaac ttactcgtct tattgaatac gctactcaag agggtatgcc tgtaattatt   540
gtatgtactt ctggtggtgc tcgtatgcaa gaaggtattt tttctttaat gcaaatggct   600
aaaatttctg ctgctcttca tgtacatcaa aactgcgcta atctttata cattgctatt   660 ttaacttctc ctactactgg tggcgttact gcttcttttg gtatgttagg tgatgtaatt   720
atcgctgaac ctcaagcaat tattggtttt gcaggtcgtc gtgtaattga acaaacttta   780
caagaacaac ttcctgatga cttccaaact gctgaatatt tacttgaaca tggtttatta   840
gatttagtag ttcctcgttc tttccttaaa ggtgcattat atgaaatcat tgacttttat   900
cgtgctgcac cttacaaaaa acgtggcatg atcccatttg gtgttcaaca cggtactttt   960
ttaactactg aagagaaagt taccggtta                                     989

<210> SEQ ID NO 29
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 29
gcaggtgagg caaacggttc tcctattgtt actggtccta tttctgttaa tccatctatg    60
tctccagctc ttgacccagt agctgctgca gaagcaggta aatctgcaaa agcagtagac   120
cgttctaaag gtctttggac tcgttgtgac aaatgtggca ctattttata tattaaacac   180
ttaaaagaac accatcatat ctgtttcggt tgtaattacc acttaaaaat gtcttctatg   240
gaacgtatta accacttaat tgatgctggt acttggcgtc cacttgatga aactctttct   300
ccagtagatc ctttagaatt tgatgactta aaatcttata ctgatcgtat aaagaggct   360 caagaaaaaa ctggcttaca agatggtgtt cgtactggca ctggtttact tcatggtatt   420
cctgtagcat taggtgtaat ggacttcact tatatgggtg gctctatggg ttctgttgtt   480
ggtgaaaaac ttactcgtct tattgaatac gctactcaag agggtatgcc tgtaattatt   540
gtatgtactt ctggtggtgc tcgtatgcaa gaaggtattt tttctttaat gcaaatggct   600
aaaatttctg ctgctcttca tgtacatcaa aactgcgcta atctttata cattgctatt   660 ttaacttctc ctactactgg tggcgttact gcttcttttg gtatgttagg tgatgtaatt   720
atcgctgaac ctcaagcaat tattggtttt gcaggtcgtc gtgtaattga acaaacttta   780
caagaacaac ttcctgatga cttccaaact gctgaatatt tacttgaaca tggtttatta   840
gatttagtag ttcctcgttc tttccttaaa ggtgcattat atgaaatcat tgacttttat   900
cgtgctgcac cttacaaaaa acgtggcatg atcccatttg gtgttcaaca cggtactttt   960
ttaactactg aagagaaagt ta                                            982
```

<210> SEQ ID NO 30
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 30

```
gcaggtgagg caaacggttc tcctattgtt actggtccta tttctgttaa tccatctatg      60
tctccagctc ttgacccagt agctgctgca gaagcaggta atctgcaaa agcagtagac      120
cgttctaaag gtctttggac tcgttgtgac aaatgtggca ctattttata tattaaacac     180
ttaaaagaac accatcatat ctgtttcggt tgtaattacc acttaaaaat gtcttctatg     240
gaacgtatta accacttaat tgatgctggt acttggcgtc cacttgatga aactctttct     300
ccagtagatc ctttagaatt ttctgactta aaagattata ctgatcgtat taaagaggct     360
caagaaaaaa ctggcttaca agatggtgtt cgtactggca ctggtttact tcatggtatt     420
cctgtagcat taggtgtaat ggacttcact tatatgggtg gctctatggg ttctgttgtt     480
ggtgaaaaac ttactcgtct tattgaatac gctactcaag agggtatgcc tgtaattatt     540
gtatgtactt ctggtggtgc tcgtatgcaa gaaggtattt tttctttaat gcaaatggct     600
aaaatttctg ctgctcttca tgtacatcaa aactgcgcta atctttata cattgctatt      660
ttaacttctc ctactactgg tggcgttact gcttcttttg gtatgttagg tgatgtaatt     720
atcgctgaac tcaagcaat tattggttttt gcaggtcgtc gtgtaattga acaaacttta    780
caagaacaac ttcctgatga cttccaaact gctgaatatt tacttgaaca tggtttatta    840
gatttagtag ttcctcgttc tttccttaaa ggtgcattat atgaaatcat tgacttttat    900
cgtgctgcac cttacaaaaa acgtggcatg atcccatttg gtgttcaaca cggtactttt    960
ttaactactg aagagaaagt ta                                             982
```

<210> SEQ ID NO 31
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 31

```
gcaggtgagg caaacggttc tcctattgtt actggtccta tttctgttaa tccatctatg      60
tctccagctc ttgacccagt agctgctgca gaagcaggta atctgcaaa agcagtagac      120
cgttctaaag gtctttggac tcgttgtgac aaatgtggca ctattttata tattaaacac     180
ttaaaagaac accatcatat ctgtttcggt tgtaattacc acttaaaaat gtcttctatg     240
gaacgtatta accacttaat tgatgctggt gattggcgtc cacttgatga aactctttct     300
ccagtagatc ctttagaatt ttctgactta aaatcttata ctgatcgtat taaagaggct     360
caagaaaaaa ctggcttaca agatggtgtt cgtactggca ctggtttact tcatggtatt     420
cctgtagcat taggtgtaat ggacttcact tatatgggtg gctctatggg ttctgttgtt     480
ggtgaaaaac ttactcgtct tattgaatac gctactcaag agggtatgcc tgtaattatt     540
gtatgtactt ctggtggtgc tcgtatgcaa gaaggtattt tttctttaat gcaaatggct     600
aaaatttctg ctgctcttca tgtacatcaa aactgcgcta atctttata cattgctatt      660
ttaacttctc ctactactgg tggcgttact gcttcttttg gtatgttagg tgatgtaatt     720
atcgctgaac tcaagcaat tattggttttt gcaggtcgtc gtgtaattga acaaacttta    780
```

| | |
|---|---|
| caagaacaac ttcctgatga cttccaaact gctgaatatt tacttgaaca tggtttatta | 840 |
| gatttagtag ttcctcgttc tttccttaaa ggtgcattat atgaaatcat tgactttat | 900 |
| cgtgctgcac cttacaaaaa acgtggcatg atcccatttg gtgttcaaca cggtactttt | 960 |
| ttaactactg aagagaaagt ta | 982 |

```
<210> SEQ ID NO 32
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 32
```

| | |
|---|---|
| gcaggtgagg caaacggttc tcctattgtt actggtccta tttctgttaa tccatctatg | 60 |
| tctccagctc ttgacccagt agctgctgca gaagcaggta atctgcaaa agcagtagac | 120 |
| cgttctaaag gtctttggac tcgttgtgac aaatgtggca ctattttata tattaaacac | 180 |
| ttaaaagaac accatcatat ctgtttcggt tgtaattacc acttaaaaat gtcttctatg | 240 |
| gaacgtatta accacttaat tgatgctggt acttggcgtc cacttgatga agatcttcct | 300 |
| ccagtagatc ctttagaatt ttctgactta aaatcttata ctgatcgtat taagaggct | 360 |
| caagaaaaaa ctggcttaca agatggtgtt cgtactggca ctggtttact tcatggtatt | 420 |
| cctgtagcat taggtgtaat ggacttcact tatatgggtg ctctatggg ttctgttgtt | 480 |
| ggtgaaaaac ttactcgtct tattgaatac gctactcaag agggtatgcc tgtaattatt | 540 |
| gtatgtactt ctggtggtgc tcgtatgcaa gaaggtattt ttctcttaat gcaaatggct | 600 |
| aaaatttctg ctgctcttca tgtacatcaa aactgcgcta atcttttata cattgctatt | 660 |
| ttaacttctc ctactactgg tggcgttact gcttctttg gtatgttagg tgatgtaatt | 720 |
| atcgctgaac tcaagcaat tattggtttt gcaggtcgtc gtgtaattga caaactttta | 780 |
| caagaacaac ttcctgatga cttccaaact gctgaatatt tacttgaaca tggtttatta | 840 |
| gatttagtag ttcctcgttc tttccttaaa ggtgcattat atgaaatcat tgactttat | 900 |
| cgtgctgcac cttacaaaaa acgtggcatg atcccatttg gtgttcaaca cggtactttt | 960 |
| ttaactactg aagagaaagt ta | 982 |

```
<210> SEQ ID NO 33
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 33
```

| | |
|---|---|
| gcaggtgagg caaacggttc tcctattgtt actggtccta tttctgttaa tccatctatg | 60 |
| tctccagctc ttgacccagt agctgctgca gaagcaggta atctgcaaa agcagtagac | 120 |
| cgttctaaag gtctttggac tcgttgtgac aaatgtggca ctattttata tattaaacac | 180 |
| ttaaaagaac accatcatat ctgtttcggt tgtaattacc acttaaaaat gtcttctatg | 240 |
| gaacgtatta accacttaat tgatgctggt acttggcgtc cacttgatga aactcttct | 300 |
| ccagtagatc ctttagaatt ttctgactta aaatcttata ctgatcgtat taagaggct | 360 |
| caagaaaaaa ctggcttaca agatggtgtt cgtactggca ctggtttact tcatggtatt | 420 |
| cctgtagcat taggtgtaat ggacttcact tatatgggtg ctctatggg ttctgttgtt | 480 |
| ggtgaaaaac ttactcgtct tattgaatac gctactcaag agggtatgcc tgtaattatt | 540 |

```
gtatgtactt ctggtggtgc tcgtatgcaa gaaggtattt tttctttaat gcaaatggct    600
aaaatttctg ctgctcttca tgtacatcaa aactgcgcta atcttttata cattgctatt    660
ttaacttctc ctactactgg tggcgttact gcttcttttg gtatgttagg tgatgtaatt    720
atcgctgaac ctcaagcaat tattggtttt gcaggtcgtc gtgtaattga acaaacttta    780
caagaacaac ttcctgatga cttccaaact gctgaatatt tacttgaaca tggtttatta    840
gatttagtag ttcctcgttc tttccttaaa ggtgcattag atgaaatcat tgactttat    900 cgtgctgcac cttacaaaaa acgtggcatg atcccatttg tgttcaaca cggtactttt    960 ttaactactg aagagaaagt ta                                             982
```

<210> SEQ ID NO 34
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 34

```
gcaggtgagg caaacggttc tcctattgtt actggtccta tttctgttaa tccatctatg     60
tctccagctc ttgacccagt agctgctgca gaagcaggta atctgcaaa agcagtagac    120 cgttctaaag gtctttggac tcgttgtgac aaatgtggca ctattttata tattaaacac    180
ttaaaagaac accatcatat ctgtttcggt tgtaattacc acttaaaaat gtcttctatg    240
gaacgtatta accacttaat tgatgctggt acttggcgtc cacttgatga aactcttttct    300 ccagtagatc ctttagaatt tgatgactta aaagattata ctgatcgtat taagaggct    360 caagaaaaaa ctggcttaca agatggtgtt cgtactggca ctggtttact tcatggtatt    420
cctgtagcat taggtgtaat ggacttcact tatatgggtg gctctatggg ttctgttgtt    480
ggtgaaaaac ttactcgtct tattgaatac gctactcaag agggtatgcc tgtaattatt    540
gtatgtactt ctggtggtgc tcgtatgcaa gaaggtattt tttctttaat gcaaatggct    600
aaaatttctg ctgctcttca tgtacatcaa aactgcgcta atcttttata cattgctatt    660
ttaacttctc ctactactgg tggcgttact gcttcttttg gtatgttagg tgatgtaatt    720
atcgctgaac ctcaagcaat tattggtttt gcaggtcgtc gtgtaattga acaaacttta    780
caagaacaac ttcctgatga cttccaaact gctgaatatt tacttgaaca tggtttatta    840
gatttagtag ttcctcgttc tttccttaaa ggtgcattat atgaaatcat tgactttat    900 cgtgctgcac cttacaaaaa acgtggcatg atcccatttg tgttcaaca cggtactttt    960 ttaactactg aagagaaagt ta                                             982
```

<210> SEQ ID NO 35
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 35

```
gcaggtgagg caaacggttc tcctattgtt actggtccta tttctgttaa tccatctatg     60
tctccagctc ttgacccagt agctgctgca gaagcaggta atctgcaaa agcagtagac    120 cgttctaaag gtctttggac tcgttgtgac aaatgtggca ctattttata tattaaacac    180
ttaaaagaac accatcatat ctgtttcggt tgtaattacc acttaaaaat gtcttctatg    240
```

| | |
|---|---|
| gaacgtatta accacttaat tgatgctggt acttggcgtc cacttgatga aactctttct | 300 |
| ccagtagatc ctttagaatt tgatgactta aaagattata ctgatcgtat aaagaggct | 360 |
| caagaaaaaa ctggcttaca agatggtgtt cgtactggca ctggtttact tcatggtatt | 420 |
| cctgtagcat taggtgtaat ggacttcact tatatgggtg gctctatggg ttctgttgtt | 480 |
| ggtgaaaaac ttactcgtct tattgaatac gctactcaag agggtatgcc tgtaattatt | 540 |
| gtatgtactt ctggtggtgc tcgtatgcaa gaaggtattt tttctttaat gcaaatggct | 600 |
| aaaatttctg ctgctcttca tgtacatcaa aactgcgcta atctttata cattgctatt | 660 |
| ttaacttctc ctactactgg tggcgttact gcttcttttg gtatgttagg tgatgtaatt | 720 |
| atcgctgaac tcaagcaat tattggtttt gcaggtcgtc gtgtaattga acaaacttta | 780 |
| caagaacaac ttcctgatga cttccaaact gctgaatatt tacttgaaca tggtttatta | 840 |
| gatttagtag ttcctcgttc tttccttaaa ggtgcattag atgaaatcat tgactttat | 900 |
| cgtgctgcac cttacaaaaa acgtggcatg atcccatttg gtgttcaaca cggtactttt | 960 |
| ttaactactg aagagaaagt ta | 982 |

<210> SEQ ID NO 36
<211> LENGTH: 982
<212> TYPE: DNA
<213> ORGANISM: Artificial Sequence
<220> FEATURE:
<223> OTHER INFORMATION: modified acetyl CoA carboxylase

<400> SEQUENCE: 36

| | |
|---|---|
| gcaggtgagg caaacggttc tcctattgtt actggtccta tttctgttaa tccatctatg | 60 |
| tctccagctc ttgacccagt agctgctgca gaagcaggta atctgcaaa agcagtagac | 120 |
| cgttctaaag gtctttggac tcgttgtgac aaatgtggca ctattttata tattaaacac | 180 |
| ttaaaagaac accatcatat ctgtttcggt tgtaattacc acttaaaaat gtcttctatg | 240 |
| gaacgtatta accacttaat tgatgctggt acttggcgtc cacttgatga aactctttct | 300 |
| ccagtagatc ctttagaatt tgatgactta aaagattata ctgatcgtat aaagaggct | 360 |
| caagaaaaaa ctggcttaca agatggtgtt cgtactggca ctggtttact tcatggtatt | 420 |
| cctgtagcat taggtgtaat ggacttcact tatatgggtg gctctatggg ttctgttgtt | 480 |
| ggtgaaaaac ttactcgtct tattgaatac gctactcaag agggtatgcc tgtaattatt | 540 |
| gtatgtactt ctggtggtgc tcgtatgcaa gaaggtattt tttctttaat gcaaatggct | 600 |
| aaaatttctg ctgctcttca tgtacatcaa aactcagcta atctttata cattgctatt | 660 |
| ttaacttctc ctactactgg tggcgttact gcttcttttg gtatgttagg tgatgtaatt | 720 |
| atcgctgaac tcaagcaat tattggtttt gcaggtcgtc gtgtaattga acaaacttta | 780 |
| caagaacaac ttcctgatga cttccaaact gctgaatatt tacttgaaca tggtttatta | 840 |
| gatttagtag ttcctcgttc tttccttaaa ggtgcattat atgaaatcat tgactttat | 900 |
| cgtgctgcac cttacaaaaa acgtggcatg atcccatttg gtgttcaaca cggtactttt | 960 |
| ttaactactg aagagaaagt ta | 982 |

<210> SEQ ID NO 37
<211> LENGTH: 984
<212> TYPE: DNA
<213> ORGANISM: Chlamydomonas reinhardtii

<400> SEQUENCE: 37

| | |
|---|---|
| atggcgggcg aggccaacgg cagccccatc gtgaccggcc ccatctccgt caaccccctcc | 60 |

```
atgtcgcccg ctctggaccc ggtggccgct gctgaggccg gcaagtccgc caaggctgtg    120
gaccgcagca agggcctgtg gacccggtgc gacaagtgcg gcaccatcct gtacatcaag    180
cacctgaagg agcaccacca catctgcttt ggctgcaact accatctcaa gatgagctct    240
atggagcgca tcaaccacct cattgacgcc ggcacctggc gcccgctgga cgagacgctg    300
agccccgtgg acccgctgga gttctccgac ctcaagtctt acaccgaccg catcaaggag    360
gcgcaggaga agacggggct gcaggacggc gtgcgcaccg gcgggcct gctgcacggc      420 atccccgtgg cgctgggcgt catggatttc acctacatgg tggatccat gggcagtgtg     480 gtgggcgaga agctgactcg cctcatcgag tacgccacgc aggagggcat gcccgtcatc    540
attgtgtgca cctcgggcgg cgctcgcatg caggagggca tcttttcgct catgcagatg    600
gccaagatca gcgccgcgct gcacgtgcac cagaactgcg ctaacctgct ctacatcgcc    660
atcctcacct cgcctaccac cggtggtgtg acggcctcgt tcggcatgct gggagacgtc    720
atcatcgccg agccgcaggc catcatcggc ttcgcgggcc gcgtgtgat tgagcagacg     780 ctgcaggagc agctgcccga cgacttccag actgcggagt acctgctgga gcacgggctg    840
ctggacctgg tggtgccgcg ctccttcctc aagggcgcgc tgtacagaga cattgacttc    900
taccgcgccg cccctacaa gaagcgcggc atgatcccct cggcgtgca gcacggcacc       960 ttcctcacca ccgaggagaa ggta                                           984
```

<210> SEQ ID NO 38
<211> LENGTH: 13
<212> TYPE: PRT
<213> ORGANISM: Artificial Sequence
<220> FEATURE:
<223> OTHER INFORMATION: Strep affinity tag

<400> SEQUENCE: 38

Met Gly Ser Ala Trp Ser His Pro Gln Phe Glu Lys His
1               5                   10

<210> SEQ ID NO 39
<211> LENGTH: 43
<212> TYPE: PRT
<213> ORGANISM: Chlamydomonas reinhardtii

<400> SEQUENCE: 39

Met Leu Ser Ala Gln Thr Ser Arg Thr Cys Ser Gln Arg Gly Cys
1               5                   10                  15

Asn Gly Val Arg Met Ala Pro Gln Ala Lys Pro Met Val Gly Arg Val
            20                  25                  30

Pro Gly Arg Ser Gly Ser Pro Cys Val Val Ala
        35                  40

<210> SEQ ID NO 40
<211> LENGTH: 33
<212> TYPE: DNA
<213> ORGANISM: Artificial Sequence
<220> FEATURE:
<223> OTHER INFORMATION: PCR primer

<400> SEQUENCE: 40
ttaattgatg ctggtgattg gcgtccactt gat                                  33

<210> SEQ ID NO 41
<211> LENGTH: 33
<212> TYPE: DNA

<213> ORGANISM: Artificial Sequence
<220> FEATURE:
<223> OTHER INFORMATION: PCR primer

<400> SEQUENCE: 41
atcaagtgga cgccaatcac cagcatcaat taa                33

<210> SEQ ID NO 42
<211> LENGTH: 33
<212> TYPE: DNA
<213> ORGANISM: Artificial Sequence
<220> FEATURE:
<223> OTHER INFORMATION: PCR primer

<400> SEQUENCE: 42
cgtccacttg atgaagatct ttctccagta gat                33

<210> SEQ ID NO 43
<211> LENGTH: 33
<212> TYPE: DNA
<213> ORGANISM: Artificial Sequence
<220> FEATURE:
<223> OTHER INFORMATION: PCR primer

<400> SEQUENCE: 43
atctactgga gaaagatctt catcaagtgg acg                33

<210> SEQ ID NO 44
<211> LENGTH: 33
<212> TYPE: DNA
<213> ORGANISM: Artificial Sequence
<220> FEATURE:
<223> OTHER INFORMATION: PCR primer

<400> SEQUENCE: 44
cttgatgaaa ctcttgatcc agtagatcct tta                33

<210> SEQ ID NO 45
<211> LENGTH: 33
<212> TYPE: DNA
<213> ORGANISM: Artificial Sequence
<220> FEATURE:
<223> OTHER INFORMATION: PCR primer

<400> SEQUENCE: 45
taaaggatct actggatcaa gagtttcatc aag                33

<210> SEQ ID NO 46
<211> LENGTH: 33
<212> TYPE: DNA
<213> ORGANISM: Artificial Sequence
<220> FEATURE:
<223> OTHER INFORMATION: PCR primer

<400> SEQUENCE: 46
gatcctttag aatttgatga cttaaaatct tat                33

<210> SEQ ID NO 47
<211> LENGTH: 33
<212> TYPE: DNA
<213> ORGANISM: Artificial Sequence
<220> FEATURE:
<223> OTHER INFORMATION: PCR primer

<400> SEQUENCE: 47
ataagatttt aagtcatcaa attctaaagg atc                33

<210> SEQ ID NO 48
<211> LENGTH: 33
<212> TYPE: DNA
<213> ORGANISM: Artificial Sequence
<220> FEATURE:
<223> OTHER INFORMATION: PCR primer

<400> SEQUENCE: 48
ttttctgact taaaagatta tactgatcgt att                                    33

<210> SEQ ID NO 49
<211> LENGTH: 33
<212> TYPE: DNA
<213> ORGANISM: Artificial Sequence
<220> FEATURE:
<223> OTHER INFORMATION: PCR primer

<400> SEQUENCE: 49
aatacgatca gtataatctt ttaagtcaga aaa                                    33

<210> SEQ ID NO 50
<211> LENGTH: 33
<212> TYPE: DNA
<213> ORGANISM: Artificial Sequence
<220> FEATURE:
<223> OTHER INFORMATION: PCR primer

<400> SEQUENCE: 50
catgtacatc aaaactcagc taatcttttta tac                                   33

<210> SEQ ID NO 51
<211> LENGTH: 33
<212> TYPE: DNA
<213> ORGANISM: Artificial Sequence
<220> FEATURE:
<223> OTHER INFORMATION: PCR primer

<400> SEQUENCE: 51
gtataaaaga ttagctgagt tttgatgtac atg                                    33

<210> SEQ ID NO 52
<211> LENGTH: 33
<212> TYPE: DNA
<213> ORGANISM: Artificial Sequence
<220> FEATURE:
<223> OTHER INFORMATION: PCR primer

<400> SEQUENCE: 52
cttaaaggtg cattagatga aatcattgac ttt                                    33

<210> SEQ ID NO 53
<211> LENGTH: 33
<212> TYPE: DNA
<213> ORGANISM: Artificial Sequence
<220> FEATURE:
<223> OTHER INFORMATION: PCR primer

<400> SEQUENCE: 53
aaagtcaatg atttcatcta atgcaccttt aag                                    33

<210> SEQ ID NO 54
<211> LENGTH: 44
<212> TYPE: DNA
<213> ORGANISM: Artificial Sequence
<220> FEATURE:

<223> OTHER INFORMATION: PCR primer

<400> SEQUENCE: 54
atcctttaga atttgatgac ttaaaagatt atactgatcg tatt                    44

<210> SEQ ID NO 55
<211> LENGTH: 45
<212> TYPE: DNA
<213> ORGANISM: Artificial Sequence
<220> FEATURE:
<223> OTHER INFORMATION: PCR primer

<400> SEQUENCE: 55
aatacgatca gtataatctt ttaagtcatc aaattctaaa ggatc                   45

<210> SEQ ID NO 56
<211> LENGTH: 12
<212> TYPE: PRT
<213> ORGANISM: Artificial Sequence
<220> FEATURE:
<223> OTHER INFORMATION: conserved motif

<400> SEQUENCE: 56

Met Gly Gly Ser Met Gly Ser Val Val Gly Glu Lys
1               5                   10

<210> SEQ ID NO 57
<211> LENGTH: 9
<212> TYPE: PRT
<213> ORGANISM: Artificial Sequence
<220> FEATURE:
<223> OTHER INFORMATION: conserved motif

<400> SEQUENCE: 57

Ser Gly Gly Ala Arg Met Gln Glu Gly
1               5

<210> SEQ ID NO 58
<211> LENGTH: 8
<212> TYPE: PRT
<213> ORGANISM: Artificial Sequence
<220> FEATURE:
<223> OTHER INFORMATION: conserved motif

<400> SEQUENCE: 58

Ser Leu Met Gln Met Ala Lys Ile
1               5

<210> SEQ ID NO 59
<211> LENGTH: 10
<212> TYPE: PRT
<213> ORGANISM: Artificial Sequence
<220> FEATURE:
<223> OTHER INFORMATION: conserved motif

<400> SEQUENCE: 59

Pro Thr Thr Gly Gly Val Thr Ala Ser Phe
1               5                   10

<210> SEQ ID NO 60
<211> LENGTH: 11
<212> TYPE: PRT
<213> ORGANISM: Artificial Sequence
<220> FEATURE:
<223> OTHER INFORMATION: conserved motif

<400> SEQUENCE: 60

Phe Ala Gly Lys Arg Val Ile Glu Gln Thr Leu
1               5                   10

<210> SEQ ID NO 61
<211> LENGTH: 11
<212> TYPE: PRT
<213> ORGANISM: Artificial Sequence
<220> FEATURE:
<223> OTHER INFORMATION: conserved motif

<400> SEQUENCE: 61

Phe Ala Gly Arg Arg Val Ile Glu Gln Thr Leu
1               5                   10

<210> SEQ ID NO 62
<211> LENGTH: 29
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: N is A, C, G, or T
<220> FEATURE:
<221> NAME/KEY: misc_feature
<222> LOCATION: (9)..(9)
<223> OTHER INFORMATION: N is A, C, G, or T
<220> FEATURE:
<221> NAME/KEY: misc_feature
<222> LOCATION: (10)..(10)
<223> OTHER INFORMATION: W is A or T
<220> FEATURE:
<221> NAME/KEY: misc_feature
<222> LOCATION: (11)..(11)
<223> OTHER INFORMATION: S is C or G
<220> FEATURE:
<221> NAME/KEY: misc_feature
<222> LOCATION: (12)..(12)
<223> OTHER INFORMATION: N is A,C, G or T
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: W is A or T
<220> FEATURE:
<221> NAME/KEY: misc_feature
<222> LOCATION: (20)..(20)
<223> OTHER INFORMATION: S is C or G
<220> FEATURE:
<221> NAME/KEY: misc_feature
<222> LOCATION: (21)..(21)
<223> OTHER INFORMATION: N is A, C, G or T
<220> FEATURE:
<221> NAME/KEY: misc_feature
<222> LOCATION: (24)..(24)
<223> OTHER INFORMATION: N is A, C, G or T
<220> FEATURE:
<221> NAME/KEY: misc_feature
<222> LOCATION: (27)..(27)
<223> OTHER INFORMATION: N is A, C, G or T

<400> SEQUENCE: 62
atgggnggnw snatgggnws ngtngtngg                                29

<210> SEQ ID NO 63
<211> LENGTH: 29
<212> TYPE: DNA
<213> ORGANISM: Artificial Sequence
<220> FEATURE:

```
<223> OTHER INFORMATION: PCR Primer
<220> FEATURE:
<221> NAME/KEY: misc_feature
<222> LOCATION: (3)..(3)
<223> OTHER INFORMATION: N is A, C, G or T
<220> FEATURE:
<221> NAME/KEY: misc_feature
<222> LOCATION: (4)..(4)
<223> OTHER INFORMATION: W is A or T
<220> FEATURE:
<221> NAME/KEY: misc_feature
<222> LOCATION: (5)..(5)
<223> OTHER INFORMATION: S is C or G
<220> FEATURE:
<221> NAME/KEY: misc_feature
<222> LOCATION: (6)..(6)
<223> OTHER INFORMATION: N is A, C, G or T
<220> FEATURE:
<221> NAME/KEY: misc_feature
<222> LOCATION: (12)..(12)
<223> OTHER INFORMATION: N is A, C, G or T
<220> FEATURE:
<221> NAME/KEY: misc_feature
<222> LOCATION: (13)..(13)
<223> OTHER INFORMATION: W is A or T
<220> FEATURE:
<221> NAME/KEY: misc_feature
<222> LOCATION: (14)..(14)
<223> OTHER INFORMATION: S is C or G
<220> FEATURE:
<221> NAME/KEY: misc_feature
<222> LOCATION: (15)..(15)
<223> OTHER INFORMATION: N is A, C, G or T
<220> FEATURE:
<221> NAME/KEY: misc_feature
<222> LOCATION: (18)..(18)
<223> OTHER INFORMATION: N is A, C, G or T
<220> FEATURE:
<221> NAME/KEY: misc_feature
<222> LOCATION: (21)..(21)
<223> OTHER INFORMATION: N is A, C, G or T
<220> FEATURE:
<221> NAME/KEY: misc_feature
<222> LOCATION: (24)..(24)
<223> OTHER INFORMATION: N is A, C, G or T
<220> FEATURE:
<221> NAME/KEY: misc_feature
<222> LOCATION: (27)..(27)
<223> OTHER INFORMATION: R is A or G

<400> SEQUENCE: 63
ggnwsnatgg gnwsngtngt nggngaraa                                             29

<210> SEQ ID NO 64
<211> LENGTH: 26
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (1)..(1)
<223> OTHER INFORMATION: W is A or T
<220> FEATURE:
<221> NAME/KEY: misc_feature
<222> LOCATION: (2)..(2)
<223> OTHER INFORMATION: S is C or G
<220> FEATURE:
<221> NAME/KEY: misc_feature
<222> LOCATION: (3)..(3)
<223> OTHER INFORMATION: N is A, C, G or T
<220> FEATURE:
<221> NAME/KEY: misc_feature
<222> LOCATION: (6)..(6)
<223> OTHER INFORMATION: N is A, C, G or T
<220> FEATURE:
<221> NAME/KEY: misc_feature
```

```
<222> LOCATION: (9)..(9)
<223> OTHER INFORMATION: N is A, C, G or T
<220> FEATURE:
<221> NAME/KEY: misc_feature
<222> LOCATION: (12)..(12)
<223> OTHER INFORMATION: N is A, C, G or T
<220> FEATURE:
<221> NAME/KEY: misc_feature
<222> LOCATION: (13)..(13)
<223> OTHER INFORMATION: M is A or C
<220> FEATURE:
<221> NAME/KEY: misc_feature
<222> LOCATION: (15)..(15)
<223> OTHER INFORMATION: N is A, C, G or T
<220> FEATURE:
<221> NAME/KEY: misc_feature
<222> LOCATION: (21)..(21)
<223> OTHER INFORMATION: R is A or G
<220> FEATURE:
<221> NAME/KEY: misc_feature
<222> LOCATION: (24)..(24)
<223> OTHER INFORMATION: R is A or G

<400> SEQUENCE: 64
wsnggnggng cnmgnatgca rgargg                                        26

<210> SEQ ID NO 65
<211> LENGTH: 23
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (1)..(1)
<223> OTHER INFORMATION: W is A or T
<220> FEATURE:
<221> NAME/KEY: misc_feature
<222> LOCATION: (2)..(2)
<223> OTHER INFORMATION: S is C or G
<220> FEATURE:
<221> NAME/KEY: misc_feature
<222> LOCATION: (3)..(3)
<223> OTHER INFORMATION: N is A, C, G or T
<220> FEATURE:
<221> NAME/KEY: misc_feature
<222> LOCATION: (4)..(4)
<223> OTHER INFORMATION: Y is C or T
<220> FEATURE:
<221> NAME/KEY: misc_feature
<222> LOCATION: (6)..(6)
<223> OTHER INFORMATION: N is A, C, G or T
<220> FEATURE:
<221> NAME/KEY: misc_feature
<222> LOCATION: (12)..(12)
<223> OTHER INFORMATION: R is A or G
<220> FEATURE:
<221> NAME/KEY: misc_feature
<222> LOCATION: (18)..(18)
<223> OTHER INFORMATION: N is A, C, G or T
<220> FEATURE:
<221> NAME/KEY: misc_feature
<222> LOCATION: (21)..(21)
<223> OTHER INFORMATION: R is A or G

<400> SEQUENCE: 65
wsnytnatgc aratggcnaa rat                                           23

<210> SEQ ID NO 66
<211> LENGTH: 21
<212> TYPE: DNA
<213> ORGANISM: Artificial Sequence
<220> FEATURE:
<223> OTHER INFORMATION: PCR Primer
<220> FEATURE:
```

```
<221> NAME/KEY: misc_feature
<222> LOCATION: (1)..(1)
<223> OTHER INFORMATION: D is A, G or T
<220> FEATURE:
<221> NAME/KEY: misc_feature
<222> LOCATION: (4)..(4)
<223> OTHER INFORMATION: Y is C or T
<220> FEATURE:
<221> NAME/KEY: misc_feature
<222> LOCATION: (7)..(7)
<223> OTHER INFORMATION: N is A, C, G or T
<220> FEATURE:
<221> NAME/KEY: misc_feature
<222> LOCATION: (13)..(13)
<223> OTHER INFORMATION: Y is C or T
<220> FEATURE:
<221> NAME/KEY: misc_feature
<222> LOCATION: (19)..(19)
<223> OTHER INFORMATION: N is A, C, G or T
<220> FEATURE:
<221> NAME/KEY: misc_feature
<222> LOCATION: (21)..(21)
<223> OTHER INFORMATION: R is A or G

<400> SEQUENCE: 66
datyttngcc atytgcatna r                                     21

<210> SEQ ID NO 67
<211> LENGTH: 29
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (3)..(3)
<223> OTHER INFORMATION: N is A, C, G or T
<220> FEATURE:
<221> NAME/KEY: misc_feature
<222> LOCATION: (4)..(4)
<223> OTHER INFORMATION: S is C or G
<220> FEATURE:
<221> NAME/KEY: misc_feature
<222> LOCATION: (5)..(5)
<223> OTHER INFORMATION: W is A or T
<220> FEATURE:
<221> NAME/KEY: misc_feature
<222> LOCATION: (6)..(6)
<223> OTHER INFORMATION: N is A, C, G or T
<220> FEATURE:
<221> NAME/KEY: misc_feature
<222> LOCATION: (9)..(9)
<223> OTHER INFORMATION: N is A, C, G or T
<220> FEATURE:
<221> NAME/KEY: misc_feature
<222> LOCATION: (12)..(12)
<223> OTHER INFORMATION: N is A, C, G or T
<220> FEATURE:
<221> NAME/KEY: misc_feature
<222> LOCATION: (15)..(15)
<223> OTHER INFORMATION: N is A, C, G or T
<220> FEATURE:
<221> NAME/KEY: misc_feature
<222> LOCATION: (18)..(18)
<223> OTHER INFORMATION: N is A, C, G or T
<220> FEATURE:
<221> NAME/KEY: misc_feature
<222> LOCATION: (21)..(21)
<223> OTHER INFORMATION: N is A, C, G or T
<220> FEATURE:
<221> NAME/KEY: misc_feature
<222> LOCATION: (24)..(24)
<223> OTHER INFORMATION: N is A, C, G or T
<220> FEATURE:
<221> NAME/KEY: misc_feature
<222> LOCATION: (27)..(27)
<223> OTHER INFORMATION: N is A, C, G or T
```

<400> SEQUENCE: 67
aanswngcng tnacnccncc ngtngtngg                              29

<210> SEQ ID NO 68
<211> LENGTH: 29
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (6)..(6)
<223> OTHER INFORMATION: Y is C or T
<220> FEATURE:
<221> NAME/KEY: misc_feature
<222> LOCATION: (9)..(9)
<223> OTHER INFORMATION: D is A, G or T
<220> FEATURE:
<221> NAME/KEY: misc_feature
<222> LOCATION: (12)..(12)
<223> OTHER INFORMATION: N is A, C, G or T
<220> FEATURE:
<221> NAME/KEY: misc_feature
<222> LOCATION: (15)..(15)
<223> OTHER INFORMATION: N is A, C, G or T
<220> FEATURE:
<221> NAME/KEY: misc_feature
<222> LOCATION: (17)..(17)
<223> OTHER INFORMATION: K is G or T
<220> FEATURE:
<221> NAME/KEY: misc_feature
<222> LOCATION: (18)..(18)
<223> OTHER INFORMATION: N is A, C, G or T
<220> FEATURE:
<221> NAME/KEY: misc_feature
<222> LOCATION: (19)..(19)
<223> OTHER INFORMATION: Y is C or T
<220> FEATURE:
<221> NAME/KEY: misc_feature
<222> LOCATION: (20)..(20)
<223> OTHER INFORMATION: K is G or T
<220> FEATURE:
<221> NAME/KEY: misc_feature
<222> LOCATION: (21)..(21)
<223> OTHER INFORMATION: N is A, C, G or T
<220> FEATURE:
<221> NAME/KEY: misc_feature
<222> LOCATION: (24)..(24)
<223> OTHER INFORMATION: N is A, C, G or T
<220> FEATURE:
<221> NAME/KEY: misc_feature
<222> LOCATION: (27)..(27)
<223> OTHER INFORMATION: R is A or G

<400> SEQUENCE: 68
gtytgytcda tnacncknyk nccngcraa                              29

<210> SEQ ID NO 69
<211> LENGTH: 46
<212> TYPE: DNA
<213> ORGANISM: Artificial Sequence
<220> FEATURE:
<223> OTHER INFORMATION: PCR Primer

<400> SEQUENCE: 69
attctagagg ccgaggcggc cgactatgtt tttttttttt tttttt         46

<210> SEQ ID NO 70

<211> LENGTH: 144
<212> TYPE: DNA
<213> ORGANISM: Scenedesmus dimorphus

<400> SEQUENCE: 70

```
atggggtcgg tcgtcggaga gaagctgacg cgcctgattg agtacgccac gcaggagggg      60
ctcacgctgc tggtggtgtg caccagcgga ggcgcgcgca tgcaggaggg catcatgagc     120
ctaatgcaga tggccaagat taag                                            144
```

<210> SEQ ID NO 71
<211> LENGTH: 141
<212> TYPE: DNA
<213> ORGANISM: Scenedesmus dimorphus

<400> SEQUENCE: 71

```
atggggtcgg tcgtgggaga gaaaattacg cgcctttttg agtatgccag agaagaacga      60
ttacctgttg tcattttcac ggcatcagga ggagctcgta tgcaagaagg tatcatgagc     120
tttatgcaaa tggccaaaat c                                               141
```

<210> SEQ ID NO 72
<211> LENGTH: 114
<212> TYPE: DNA
<213> ORGANISM: Scenedesmus dimorphus

<400> SEQUENCE: 72

```
aggttaatgc agatggccaa aatttctgct gctgtaaagc gacattctaa tgctggactt      60
ttttatctca ccgtattgac cgaccccaca actggtggcg taaccgcctg gtta           114
```

<210> SEQ ID NO 73
<211> LENGTH: 117
<212> TYPE: DNA
<213> ORGANISM: Scenedesmus dimorphus

<400> SEQUENCE: 73

```
ttgactgatg caaatggcga agatcagcgg cgcgctgcac gtgcaccaga atgaggccaa      60
cctgctgtac atctccatcc tgaccagccc taccacaggt ggcgtcaccg cctggtt       117
```

<210> SEQ ID NO 74
<211> LENGTH: 1383
<212> TYPE: DNA
<213> ORGANISM: Scenedesmus dimorphus

<400> SEQUENCE: 74

```
atgtctctta agtccagcgt gggccccagc ctggccggca aggcgtgcca cggagcaaat      60
gcgcaggtgc tgccgcgcat ggcagtgcca gcgccgcttg caggaacagc agtgcgcccc    120
agcctcgcag tcaatgcagt caaccctgag aaaaacggcg cttatgaggg ctcccccatt    180
gtcagcggcc ccatttctgt gggtgctatg acaaggact ccaagggctc ttccaagcct      240
gttgaccgca gcaagggcct ctggacgcgc tgcgacaagt gcggcgtgat tctctacatc    300
aagcacctga aggagcacca ccacatctgc ttcggctgca actaccacct caagatgagc    360
agccaggaga ggatcgacca catgatcgac ccaggctcat ggcgcccctt tgacgagacg    420
ctgtctcccct gcgacccgct ggactttgtg gacatgaagc catacccaga cagggtgcgc    480
gacagccagg acaagacagg catgaacgat gccatccgca caggcacggg cctgctgcac    540
ggcatcccag tggcgctggc agtgatggag tttggcttca tgggcggcag catgggcagc    600
gtggtggggg agaagctgac gcgcctgatt gagtacgcca cgcaggaggg gctcacgctg    660
```

```
ctggtggtgt gcaccagcgg aggcgcgcgc atgcaggagg gcatcatgag cctgatgcag      720
atggccaaga tcagcggcgc gctgcacgtg caccagaatg aggccaacct gctgtacatc      780
tccatcctga ccagccccac acaggtggc gtgaccgcaa gctttggcat gctgggggat       840
gtcatcattg ctgagccgca ggccatcatc ggctttgcag acggcgtgt gatcgagcag       900 acgctgcgtg aggagctgcc agatgacttc cagaccgcgg agtacctgct tgacaagggc      960
ctgctcgacc tggtggtgcc cgcgcagctt ctgaagggcg cgctgtttga gatcatcgac      1020
ttctacaaga acgcacccta caagcgccgc ggcaagattc catttggcgt gcagcgcggt      1080
acgtacggcc tgaccgctga ggagaagatg cggcgcaggt ggagggagtg gagctcagct      1140
ggcagcaacg gctcgggcac gcccgcgctg gcagcagcag cagcatcagc agcagttggg      1200
tcagcagcca cttgcggcag ctgccagcag cagcagctgg cgctgtgggc ggtgctggca      1260
ggctgtggca gctgtgggca gtggctgtgg tttgctcagg gggtaggtgc gcttgagcgc      1320
acagcggcaa cagcagcagt actgagagag ggcagcgtgc tgctagcagg cgtctgttgt      1380
taa                                                                   1383

<210> SEQ ID NO 75
<211> LENGTH: 1257
<212> TYPE: DNA
<213> ORGANISM: Scenedesmus dimorphus

<400> SEQUENCE: 75
atggtcaatg cagtcaaccc tgagaaaaac ggcgcttatg agggctcccc cattgtcagc       60
ggccccattt ctgtgggtgc tatggacaag gactccaagg gctcttccaa gcctgttgac      120
cgcagcaagg gcctctggac gcgctgcgac aagtgcggcg tgattctcta catcaagcac      180
ctgaaggagc accaccacat ctgcttcggc tgcaactacc acctcaagat gagcagccag      240
gagaggatcg accacatgat cgacccaggc tcatggcgcc cctttgacga acgctgtct       300 ccctgcgacc cgctggactt tgtggacatg aagccatacc cagacagggt gcgcgacagc      360
caggacaaga caggcatgaa cgatgccatc cgcacaggca cgggcctgct gcacggcatc      420
ccagtggcgc tggcagtgat ggagtttggc ttcatgggcg gcagcatggg cagcgtggtg      480
ggggagaagc tgacgcgcct gattgagtac gccacgcagg aggggctcac gctgctggtg      540
gtgtgcacca gcgaggcgc gcgcatgcag gagggcatca tgagcctgat gcagatggcc      600
aagatcagcg gcgcgctgca cgtgcaccag aatgaggcca acctgctgta catctccatc      660
ctgaccagcc ccaccacagg tggcgtgacc gcaagctttg gcatgctggg ggatgtcatc      720
attgctgagc cgcaggccat catcggcttt gcaggacggc gtgtgatcga gcagacgctg      780
cgtgaggagc tgccagatga cttccagacc gcggagtacc tgcttgacaa gggcctgctc      840
gacctggtgg tgccgcgcag cttcctgaag gcgcgctgt ttgagatcat cgacttctac       900
aagaacgcac cctacaagcg ccgcggcaag attccatttg gcgtgcagcg cggtacgtac      960
ggcctgaccg ctgaggagaa gatgcggcgc aggtggaggg agtggagctc agctggcagc      1020
aacggctcgg gcacgcccgc gctggcagca gcagcagcat cagcagcagt gggtcagca      1080 gccacttgcg gcagctgcca gcagcagcag ctggcgctgt gggcggtgct ggcaggctgt      1140
ggcagctgtg ggcagtggct gtggtttgct caggggtag gtgcgcttga gcgcacagcg      1200
gcaacagcag cagtactgag agagggcagc gtgctgctag caggcgtctg ttgttaa       1257

<210> SEQ ID NO 76
```

```
<211> LENGTH: 129
<212> TYPE: DNA
<213> ORGANISM: Scenedesmus dimorphus

<400> SEQUENCE: 76
atgtctctta agtccagcgt gggccccagc ctggccggca aggcgtgcca cggagcaaat        60
gcgcaggtgc tgccgcgcat ggcagtgcca gcgccgcttg caggaacagc agtgcgcccc       120
agcctcgca                                                                129

<210> SEQ ID NO 77
<211> LENGTH: 418
<212> TYPE: PRT
<213> ORGANISM: Scenedesmus dimorphus

<400> SEQUENCE: 77
```

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

```
Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala Ala
            340                 345                 350

Ala Ser Ala Ala Val Gly Ser Ala Ala Thr Cys Gly Ser Cys Gln Gln
        355                 360                 365

Gln Gln Leu Ala Leu Trp Ala Val Leu Ala Gly Cys Gly Ser Cys Gly
    370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
                405                 410                 415

Cys Cys

<210> SEQ ID NO 78
<211> LENGTH: 460
<212> TYPE: PRT
<213> ORGANISM: Scenedesmus dimorphus

<400> SEQUENCE: 78

Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His His Ile Cys Phe Gly
            100                 105                 110

Cys Asn Tyr His Leu Lys Met Ser Ser Gln Glu Arg Ile Asp His Met
        115                 120                 125

Ile Asp Pro Gly Ser Trp Arg Pro Phe Asp Glu Thr Leu Ser Pro Cys
    130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
        195                 200                 205

Leu Ile Glu Tyr Ala Thr Gln Glu Gly Leu Thr Leu Val Val Cys
    210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270
```

```
Ala Ser Phe Gly Met Leu Gly Asp Val Ile Ala Glu Pro Gln Ala
        275                 280                 285

Ile Ile Gly Phe Ala Gly Arg Arg Val Ile Glu Gln Thr Leu Arg Glu
    290                 295                 300

Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys Gly Ala Leu Phe
                325                 330                 335

Glu Ile Ile Asp Phe Tyr Lys Asn Ala Pro Tyr Lys Arg Arg Gly Lys
            340                 345                 350

Ile Pro Phe Gly Val Gln Arg Gly Thr Tyr Gly Leu Thr Ala Glu Glu
        355                 360                 365

Lys Met Arg Arg Arg Trp Arg Glu Trp Ser Ser Ala Gly Ser Asn Gly
    370                 375                 380

Ser Gly Thr Pro Ala Leu Ala Ala Ala Ala Ser Ala Ala Val Gly
385                 390                 395                 400

Ser Ala Ala Thr Cys Gly Ser Cys Gln Gln Gln Leu Ala Leu Trp
                405                 410                 415

Ala Val Leu Ala Gly Cys Gly Ser Cys Gly Gln Trp Leu Trp Phe Ala
            420                 425                 430

Gln Gly Val Gly Ala Leu Glu Arg Thr Ala Thr Ala Ala Val Leu
        435                 440                 445

Arg Glu Gly Ser Val Leu Leu Ala Gly Val Cys Cys
    450                 455                 460

<210> SEQ ID NO 79
<211> LENGTH: 43
<212> TYPE: PRT
<213> ORGANISM: Scenedesmus dimorphus

<400> SEQUENCE: 79

Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala
        35                  40

<210> SEQ ID NO 80
<211> LENGTH: 1449
<212> TYPE: DNA
<213> ORGANISM: Scenedesmus dimorphus

<400> SEQUENCE: 80
atgtctctta agtccagcgt gggccccagc ctggccggca aggcgtgcca cggagcaaat      60
gcgcaggtgc tgccgcgcat ggcagtgcca gcgccgcttg caggaacagc agtgcgcccc     120
agcctcgcag tcaatgcagt caaccctgag aaaaacggcg cttatgaggg ctcccccatt     180
gtcagcggcc ccatttctgt gggtgctatg gacaaggact ccaagggctc ttccaagcct     240
gttgaccgca gcaagggcct ctggacgcgc tgcgacaagt gcggcgtgat tctctacatc     300
aagcacctga aggagcacca ccacatctgc ttcggctgca actaccacct caagatgagc     360
agccaggaga ggatcgacca catgatcgac ccaggctcat ggcgcccctt gacgagacg      420 ctgtctccct gcgacccgct ggactttgtg gacatgaagc catacccaga cagggtgcgc     480
gacagccagg acaagacagg catgaacgat gccatccgca caggcacggg cctgctgcac     540
```

```
ggcatcccag tggcgctggc agtgatggag tttggcttca tgggcggcag catgggcagc      600
gtggtggggg agaagctgac gcgcctgatt gagtacgcca cgcaggaggg gctcacgctg      660
ctggtggtgt gcaccagcgg aggcgcgcgc atgcaggagg gcatcatgag cctgatgcag      720
atggccaaga tcagcggcgc gctgcacgtg caccagaatg aggccaacct gctgtacatc      780
tccatcctga ccagccccac cacaggtggc gtgaccgcaa gctttggcat gctgggggat      840
gtcatcattg ctgagccgca ggccatcatc ggctttgcag acggcgtgt gatcgagcag       900 acgctgcgtg aggagctgcc agatgacttc cagaccgcgg agtacctgct tgacaagggc      960
ctgctcgacc tggtggtgcc gcgcagcttc ctgaagggcg cgctgtttga gatcatcgac     1020
ttctacaaga acgcacccta caagcgccgc ggcaagattc catttggcgt gcagcgcggt     1080
acgtacggcc tgaccgctga ggagaagatg cggcgcaggt ggagggagtg gagctcagtt     1140
ggcagcatgt tgcatagtgt tcactatgca ggccactggc cctctgggtg gctgggatg      1200 ttgctgggcc agcgcccact tcatatgcat tggcatgtca atgaagggtc aggttgtagc     1260
aagaccacgt gccagagctt taagtattgg tcagcatgtg ctgcttggca tgcagtgtgc     1320
catcggcgag gaacacttct tgaacatgaa cttaccaagc tgatttcctg gcagtttgat     1380
tcatgctgtt ggcgtgctgc caaaggtatt ctgcttagat cttgcaatgc tgtgtatgta     1440
tatgtgtaa                                                             1449
```

<210> SEQ ID NO 81
<211> LENGTH: 482
<212> TYPE: PRT
<213> ORGANISM: Scenedesmus dimorphus

<400> SEQUENCE: 81

Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His Ile Cys Phe Gly
            100                 105                 110

Cys Asn Tyr His Leu Lys Met Ser Ser Gln Glu Arg Ile Asp His Met
        115                 120                 125

Ile Asp Pro Gly Ser Trp Arg Pro Phe Asp Glu Thr Leu Ser Pro Cys
    130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
        195                 200                 205

```
Leu Ile Glu Tyr Ala Thr Gln Glu Gly Leu Thr Leu Leu Val Val Cys
    210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270

Ala Ser Phe Gly Met Leu Gly Asp Val Ile Ile Ala Glu Pro Gln Ala
        275                 280                 285

Ile Ile Gly Phe Ala Gly Arg Arg Val Ile Glu Gln Thr Leu Arg Glu
    290                 295                 300

Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys Gly Ala Leu Phe
                325                 330                 335

Glu Ile Ile Asp Phe Tyr Lys Asn Ala Pro Tyr Lys Arg Arg Gly Lys
            340                 345                 350

Ile Pro Phe Gly Val Gln Arg Gly Thr Tyr Gly Leu Thr Ala Glu Glu
        355                 360                 365

Lys Met Arg Arg Arg Trp Arg Glu Trp Ser Ser Val Gly Ser Met Leu
    370                 375                 380

His Ser Val His Tyr Ala Gly His Trp Pro Ser Gly Cys Ala Gly Met
385                 390                 395                 400

Leu Leu Gly Gln Arg Pro Leu His Met His Trp His Val Asn Glu Gly
                405                 410                 415

Ser Gly Cys Ser Lys Thr Thr Cys Gln Ser Phe Lys Tyr Trp Ser Ala
            420                 425                 430

Cys Ala Ala Trp His Ala Val Cys His Arg Arg Gly Thr Leu Leu Glu
        435                 440                 445

His Glu Leu Thr Lys Leu Ile Ser Trp Gln Phe Asp Ser Cys Cys Trp
    450                 455                 460

Arg Ala Ala Lys Gly Ile Leu Leu Arg Ser Cys Asn Ala Val Tyr Val
465                 470                 475                 480

Tyr Val

<210> SEQ ID NO 82
<211> LENGTH: 1323
<212> TYPE: DNA
<213> ORGANISM: Scenedesmus dimorphus

<400> SEQUENCE: 82
atggtcaatg cagtcaaccc tgagaaaaac ggcgcttatg agggctcccc cattgtcagc      60
ggccccattt ctgtgggtgc tatggacaag gactccaagg ctcttccaa gcctgttgac     120 cgcagcaagg gcctctggac gcgctgcgac aagtgcggcg tgattctcta catcaagcac     180
ctgaaggagc accaccacat ctgcttcggc tgcaactacc acctcaagat gagcagccag     240
gagaggatcg accacatgat cgacccaggc tcatggcgcc cctttgacga acgctgtct    300 ccctgcgacc cgctggactt tgtggacatg aagccatacc agacagggt gcgcgacagc    360 caggacaaga caggcatgaa cgatgccatc cgcacaggca cgggcctgct gcacggcatc     420
ccagtgcgcg tggcagtgat ggagtttggc ttcatgggcg gcagcatggg cagcgtggtg     480
ggggagaagc tgacgcgcct gattgagtac gccacgcagg agggctcac gctgctggtg     540
```

-continued

```
gtgtgcacca gcggaggcgc gcgcatgcag gagggcatca tgagcctgat gcagatggcc    600
aagatcagcg gcgcgctgca cgtgcaccag aatgaggcca acctgctgta catctccatc    660
ctgaccagcc ccaccacagg tggcgtgacc gcaagctttg gcatgctggg ggatgtcatc    720
attgctgagc gcaggccat catcggcttt gcaggacggc gtgtgatcga gcagacgctg     780
cgtgaggagc tgccagatga cttccagacc gcggagtacc tgcttgacaa gggcctgctc    840
gacctggtgg tgccgcgcag cttcctgaag gcgcgctgt ttgagatcat cgacttctac     900
aagaacgcac cctacaagcg ccgcggcaag attccatttg gcgtgcagcg cggtacgtac    960
ggcctgaccg ctgaggagaa gatgcggcgc aggtggaggg agtggagctc agttggcagc   1020
atgttgcata gtgttcacta tgcaggccac tggccctctg ggtgtgctgg gatgttgctg    1080
ggccagcgcc cacttcatat gcattggcat gtcaatgaag ggtcaggttg tagcaagacc   1140
acgtgccaga gctttaagta ttggtcagca tgtgctgctt ggcatgcagt gtgccatcgg   1200
cgaggaacac ttcttgaaca tgaacttacc aagctgattt cctggcagtt tgattcatgc   1260
tgttggcgtg ctgccaaagg tattctgctt agatcttgca atgctgtgta tgtatatgtg   1320
taa                                                                 1323
```

<210> SEQ ID NO 83
<211> LENGTH: 440
<212> TYPE: PRT
<213> ORGANISM: Scenedesmus dimorphus

<400> SEQUENCE: 83

```
Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220
```

```
Thr Thr Gly Gly Val Thr Ala Ser Phe Gly Met Leu Gly Asp Val Ile
225                 230                 235                 240
Ile Ala Glu Pro Gln Ala Ile Ile Gly Phe Ala Gly Arg Arg Val Ile
            245                 250                 255
Glu Gln Thr Leu Arg Glu Glu Leu Pro Asp Asp Phe Gln Thr Ala Glu
        260                 265                 270
Tyr Leu Leu Asp Lys Gly Leu Leu Asp Leu Val Val Pro Arg Ser Phe
    275                 280                 285
Leu Lys Gly Ala Leu Phe Glu Ile Ile Asp Phe Tyr Lys Asn Ala Pro
290                 295                 300
Tyr Lys Arg Arg Gly Lys Ile Pro Phe Gly Val Gln Arg Gly Thr Tyr
305                 310                 315                 320
Gly Leu Thr Ala Glu Glu Lys Met Arg Arg Trp Arg Glu Trp Ser
                325                 330                 335
Ser Val Gly Ser Met Leu His Ser Val His Tyr Ala Gly His Trp Pro
                340                 345                 350
Ser Gly Cys Ala Gly Met Leu Leu Gly Gln Arg Pro Leu His Met His
            355                 360                 365
Trp His Val Asn Glu Gly Ser Gly Cys Ser Lys Thr Thr Cys Gln Ser
370                 375                 380
Phe Lys Tyr Trp Ser Ala Cys Ala Ala Trp His Ala Val Cys His Arg
385                 390                 395                 400
Arg Gly Thr Leu Leu Glu His Glu Leu Thr Lys Leu Ile Ser Trp Gln
                405                 410                 415
Phe Asp Ser Cys Cys Trp Arg Ala Ala Lys Gly Ile Leu Leu Arg Ser
            420                 425                 430
Cys Asn Ala Val Tyr Val Tyr Val
            435                 440

<210> SEQ ID NO 84
<211> LENGTH: 1287
<212> TYPE: DNA
<213> ORGANISM: Scenedesmus dimorphus

<400> SEQUENCE: 84
atgtctctta agtccagcgt gggccccagc ctggccggca aggcgtgcca cggagcaaat        60
gcgcaggtgc tgccgcgcat ggcagtgcca gcgccgcttg caggaacagc agtgcgcccc       120
agcctcgcag tcaatgcagt caaccctgag aaaaacggcg cttatgaggg ctccccatt        180 gtcagcggcc ccatttctgt gggtgctatg acaaggact ccaagggctc ttccaagcct       240
gttgaccgca gcaagggcct ctggacgcgc tgcgacaagt gcggcgtgat tctctacatc       300
aagcacctga aggagcacca ccacatctgc ttcggctgca actaccacct caagatgagc       360
agccaggaga ggatcgacca catgatcgac ccaggctcat ggcgcccctt tgacgagacg       420
ctgtctccct gcgacccgct ggactttgtg gacatgaagc atacccaga cagggtgcgc       480 gacagccagg acaagacagg catgaacgat gccatccgca caggcacggg cctgctgcac       540
ggcatcccag tggcgctggc agtgatggag tttggcttca tgggcggcag catgggcagc       600 gtggtgggg agaagctgac gcgcctgatt gagtacgcca cgcaggaggg gctcacgctg       660
ctggtggtgt gcaccagcgg aggcgcgcgc atgcaggagg catcatgag cctgatgcag       720 atggccaaga tcagcggcgc gctgcacgtg caccagaatg aggccaacct gctgtacatc       780
tccatcctga ccagccccac cacaggtggc gtgaccgcaa gctttggcat gctgggggat       840
gtcatcattg ctgagccgca ggccatcatc ggctttgcag acggcgtgt gatcgagcag       900
```

-continued

```
acgctgcgtg aggagctgcc agatgacttc cagaccgcgg agtacctgct tgacaagggc    960
ctgctcgacc tggtggtgcc gcgcagcttc ctgaagggcg cgctgtttga gatcatcgac   1020
ttttacaaga acgcacccta caagcgccgc ggcaagattc catttggcgt gcagcgcggt   1080
acgtacggcc tgaccgctga ggagaagatg cggcgcaggt ggagggagtg gagctcagct   1140
ggcagcaacg gctcgggcac gcccgcgctg gcagcagcag cagcagtggt ggcgccgtgc   1200
agcagtggag gagttgcatg cgcactgaga cgagcttgtt caagagttag tcggatgggc   1260
ggggtgggga gcttgctacg ctgctag                                       1287
```

<210> SEQ ID NO 85
<211> LENGTH: 428
<212> TYPE: PRT
<213> ORGANISM: Scenedesmus dimorphus

<400> SEQUENCE: 85

```
Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His Ile Cys Phe Gly
            100                 105                 110

Cys Asn Tyr His Leu Lys Met Ser Ser Gln Glu Arg Ile Asp His Met
        115                 120                 125

Ile Asp Pro Gly Ser Trp Arg Pro Phe Asp Glu Thr Leu Ser Pro Cys
130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
        195                 200                 205

Leu Ile Glu Tyr Ala Thr Gln Glu Gly Leu Thr Leu Val Val Cys
    210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270

Ala Ser Phe Gly Met Leu Gly Asp Val Ile Ala Glu Pro Gln Ala
        275                 280                 285

Ile Ile Gly Phe Ala Gly Arg Arg Val Ile Glu Gln Thr Leu Arg Glu
    290                 295                 300
```

```
Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys Gly Ala Leu Phe
            325                 330                 335

Glu Ile Ile Asp Phe Tyr Lys Asn Ala Pro Tyr Lys Arg Arg Gly Lys
            340                 345                 350

Ile Pro Phe Gly Val Gln Arg Gly Thr Tyr Gly Leu Thr Ala Glu Glu
        355                 360                 365

Lys Met Arg Arg Trp Arg Glu Trp Ser Ser Ala Gly Ser Asn Gly
370                 375                 380

Ser Gly Thr Pro Ala Leu Ala Ala Ala Ala Val Val Ala Pro Cys
385                 390                 395                 400

Ser Ser Gly Gly Val Ala Cys Ala Leu Arg Arg Ala Cys Ser Arg Val
            405                 410                 415

Ser Arg Met Gly Gly Val Gly Ser Leu Leu Arg Cys
            420                 425

<210> SEQ ID NO 86
<211> LENGTH: 1161
<212> TYPE: DNA
<213> ORGANISM: Scenedesmus dimorphus

<400> SEQUENCE: 86
atggtcaatg cagtcaaccc tgagaaaaac ggcgcttatg agggctcccc cattgtcagc      60
ggccccattt ctgtgggtgc tatggacaag gactccaagg gctcttccaa gcctgttgac     120
cgcagcaagg gcctctggac gcgctgcgac aagtgcggcg tgattctcta catcaagcac     180
ctgaaggagc accaccacat ctgcttcggc tgcaactacc acctcaagat gagcagccag     240
gagaggatcg accacatgat cgacccaggc tcatggcgcc ctttgacga cgcgctgtct      300 ccctgcgacc cgctggactt tgtggacatg aagccatacc agacagggt gcgcgacagc      360 caggacaaga caggcatgaa cgatgccatc cgcacaggca cgggcctgct gcacggcatc     420
ccagtggcgc tggcagtgat ggagtttggc ttcatgggcg gcagcatggg cagcgtggtg     480
ggggagaagc tgacgcgcct gattgagtac gccacgcagg aggggctcac gctgctggtg     540
gtgtgcacca gcggaggcgc gcgcatgcag gagggcatca tgagcctgat gcagatggcc     600
aagatcagcg gcgcgctgca cgtgcaccag aatgaggcca actgctgta catctccatc     660 ctgaccagcc ccaccacagg tggcgtgacc gcaagctttg gcatgctggg ggatgtcatc     720
attgctgagc gcaggccat catcggcttt gcaggacggc gtgtgatcga gcagacgctg      780
cgtgaggagc tgccagatga cttccagacc gcggagtacc tgcttgacaa gggcctgctc     840
gacctggtgg tgccgcgcag cttcctgaag ggcgcgctgt ttgagatcat cgactttac    900 aagaacgcac cctacaagcg ccgcggcaag attccatttg gcgtgcagcg cggtacgtac     960
ggcctgaccg ctgaggagaa gatgcggcgc aggtggaggg agtggagctc agctggcagc    1020
aacggctcgg gcacgcccgc gctggcagca gcagcagcag tggtggcgcc gtgcagcagt    1080
ggaggagttg catgcgcact gagacgagct tgttcaagag ttagtcggat gggcggggtg    1140
gggagcttgc tacgctgcta g                                              1161

<210> SEQ ID NO 87
<211> LENGTH: 386
<212> TYPE: PRT
<213> ORGANISM: Scenedesmus dimorphus
```

```
<400> SEQUENCE: 87

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
    290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala
            340                 345                 350

Ala Val Val Ala Pro Cys Ser Ser Gly Gly Val Ala Cys Ala Leu Arg
        355                 360                 365

Arg Ala Cys Ser Arg Val Ser Arg Met Gly Gly Val Gly Ser Leu Leu
    370                 375                 380

Arg Cys
385

<210> SEQ ID NO 88
```

<211> LENGTH: 1278
<212> TYPE: DNA
<213> ORGANISM: Scenedesmus dimorphus

<400> SEQUENCE: 88

```
atgtctctta agtccagcgt gggccccagc ctggccggca aggcgtgcca cggagcaaat    60
gcgcaggtgc tgccgcgcat ggcagtgcca gcgccgcttg caggaacagc agtgcgcccc   120
agcctcgcag tcaatgcagt caaccctgag aaaaacggcg cttatgaggg ctcccccatt   180
gtcagcggcc ccatttctgt gggtgctatg gacaaggact ccaagggctc ttccaagcct   240
gttgaccgca gcaagggcct ctggacgcgc tgcgacaagt gcggcgtgat tctctacatc   300
aagcacctga aggagcacca ccacatctgc ttcggctgca actaccacct caagatgagc   360
agccaggaga ggatcgacca catgatcgac ccaggctcat ggcgcccctt tgacgagacg   420
ctgtctccct gcgacccgct ggactttgtg gacatgaagc catacccaga cagggtgcgc   480
gacagccagg acaagacagg catgaacgat gccatccgca caggcacggg cctgctgcac   540
ggcatcccag tggcgctggc agtgatggag tttggcttca tgggcggcag catgggcagc   600
gtggtggggg agaagctgac gcgcctgatt gagtacgcca cgcaggaggg gctcacgctg   660
ctggtggtgt gcaccagcgg aggcgcgcgc atgcaggagg gcatcatgag cctgatgcag   720
atggccaaga tcagcggcgc gctgcacgtg caccagaatg aggccaacct gctgtacatc   780
tccatcctga ccagccccac acaggtggc gtgaccgcaa gctttggcat gctggggat   840
gtcatcattg ctgagccgca ggccatcatc ggctttgcag acggcgtgt gatcgagcag   900
acgctgcgtg aggagctgcc agatgacttc cagaccgcgg agtacctgct tgacaagggc   960
ctgctcgacc tggtggtgcc gcgcagcttc ctgaagggcg cgctgtttga gatcatcgac  1020
ttgtacaaga aagcaccccc caagcggcgg ggcaagattc catttggcgt gcatagcggt  1080
acgtacggcc aaccgccgag gagaagatcc ggcgcaggtg gagggagggg agttcagctg  1140
gcagcaacgg gtggggcacg cccgcgctgg cagcagcagc agcaggggg cggtgcgggt  1200
tttggcgcca agccattcca gggggttggt atatgtgaca gcagcctgtt tggtcacagt  1260
ctggatggtg cggcataa                                                1278
```

<210> SEQ ID NO 89
<211> LENGTH: 425
<212> TYPE: PRT
<213> ORGANISM: Scenedesmus dimorphus

<400> SEQUENCE: 89

```
Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His His Ile Cys Phe Gly
            100                 105                 110
```

```
            Cys Asn Tyr His Leu Lys Met Ser Gln Glu Arg Ile Asp His Met
                    115                 120                 125
            Ile Asp Pro Gly Ser Trp Arg Pro Phe Asp Glu Thr Leu Ser Pro Cys
            130                 135                 140
            Asp Pro Leu Asp Phe Val Asp Met Lys Pro Tyr Pro Asp Arg Val Arg
            145                 150                 155                 160
            Asp Ser Gln Asp Lys Thr Gly Met Asn Asp Ala Ile Arg Thr Gly Thr
                            165                 170                 175
            Gly Leu Leu His Gly Ile Pro Val Ala Leu Ala Val Met Glu Phe Gly
                        180                 185                 190
            Phe Met Gly Gly Ser Met Gly Ser Val Val Gly Glu Lys Leu Thr Arg
                    195                 200                 205
            Leu Ile Glu Tyr Ala Thr Gln Glu Gly Leu Thr Leu Leu Val Val Cys
                210                 215                 220
            Thr Ser Gly Gly Ala Arg Met Gln Glu Gly Ile Met Ser Leu Met Gln
            225                 230                 235                 240
            Met Ala Lys Ile Ser Gly Ala Leu His Val His Gln Asn Glu Ala Asn
                            245                 250                 255
            Leu Leu Tyr Ile Ser Ile Leu Thr Ser Pro Thr Thr Gly Gly Val Thr
                        260                 265                 270
            Ala Ser Phe Gly Met Leu Gly Asp Val Ile Ile Ala Glu Pro Gln Ala
                    275                 280                 285
            Ile Ile Gly Phe Ala Gly Arg Arg Val Ile Glu Gln Thr Leu Arg Glu
                290                 295                 300
            Glu Leu Pro Asp Asp Phe Gln Thr Ala Glu Tyr Leu Leu Asp Lys Gly
            305                 310                 315                 320
            Leu Leu Asp Leu Val Val Pro Arg Ser Phe Leu Lys Gly Ala Leu Phe
                            325                 330                 335
            Glu Ile Ile Asp Leu Tyr Lys Lys Ala Pro Pro Lys Arg Arg Gly Lys
                        340                 345                 350
            Ile Pro Phe Gly Val His Ser Gly Thr Tyr Gly Gln Pro Pro Arg Arg
                    355                 360                 365
            Arg Ser Gly Ala Gly Gly Arg Gly Val Gln Leu Ala Ala Thr Gly
                370                 375                 380
            Gly Ala Arg Pro Arg Trp Gln Gln Gln Gln Gly Gly Gly Ala Gly
            385                 390                 395                 400
            Phe Gly Ala Lys Pro Phe Gln Gly Val Gly Ile Cys Asp Ser Ser Leu
                            405                 410                 415
            Phe Gly His Ser Leu Asp Gly Ala Ala
                        420                 425

<210> SEQ ID NO 90
<211> LENGTH: 1152
<212> TYPE: DNA
<213> ORGANISM: Scenedesmus dimorphus

<400> SEQUENCE: 90
atggtcaatg cagtcaaccc tgagaaaaac ggcgcttatg agggctcccc cattgtcagc      60 ggcccattt ctgtgggtgc tatggacaag gactccaagg ctcttccaa gcctgttgac      120 cgcagcaagg gcctctggac cgctgcgac aagtgcggcg tgattctcta catcaagcac     180
ctgaaggagc accaccacat ctgcttcggc tgcaactacc acctcaagat gagcagccag     240
gagaggatcg accacatgat cgacccaggc tcatggcgcc ctttgacga acgctgtct      300 ccctgcgacc cgctggactt tgtggacatg aagccatacc cagacagggt gcgcgacagc     360
```

```
caggacaaga caggcatgaa cgatgccatc cgcacaggca cgggcctgct gcacggcatc    420
ccagtggcgc tggcagtgat ggagtttggc ttcatgggcg gcagcatggg cagcgtggtg    480
ggggagaagc tgacgcgcct gattgagtac gccacgcagg aggggctcac gctgctggtg    540
gtgtgcacca gcgaggcgc gcgcatgcag gagggcatca tgagcctgat gcagatggcc    600
aagatcagcg gcgcgctgca cgtgcaccag aatgaggcca acctgctgta catctccatc    660
ctgaccagcc ccaccacagg tggcgtgacc gcaagctttg gcatgctggg ggatgtcatc    720
attgctgagc cgcaggccat catcggcttt gcaggacggc gtgtgatcga gcagacgctg    780
cgtgaggagc tgccagatga cttccagacc gcggagtacc tgcttgacaa gggcctgctc    840
gacctggtgg tgccgcgcag cttcctgaag ggcgcgctgt ttgagatcat cgacttgtac    900
aagaaagcac cccccaagcg gcggggcaag attccatttg gcgtgcatag cggtacgtac    960
ggccaaccgc cgaggagaag atccggcgca ggtggaggga ggggagttca gctggcagca   1020
acgggtgggg cacgcccgcg ctggcagcag cagcagcagg ggggcggtgc gggttttggc   1080
gccaagccat tccaggggt tggtatatgt gacagcagcc tgtttggtca cagtctggat   1140
ggtgcggcat aa                                                      1152
```

<210> SEQ ID NO 91
<211> LENGTH: 383
<212> TYPE: PRT
<213> ORGANISM: Scenedesmus dimorphus

<400> SEQUENCE: 91

```
Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220
```

```
Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Leu Tyr Lys Lys Ala Pro
    290                 295                 300

Pro Lys Arg Arg Gly Lys Ile Pro Phe Gly Val His Ser Gly Thr Tyr
305                 310                 315                 320

Gly Gln Pro Pro Arg Arg Ser Gly Ala Gly Gly Arg Gly Val
                325                 330                 335

Gln Leu Ala Ala Thr Gly Gly Ala Arg Pro Arg Trp Gln Gln Gln Gln
                340                 345                 350

Gln Gly Gly Gly Ala Gly Phe Gly Ala Lys Pro Phe Gln Gly Val Gly
            355                 360                 365

Ile Cys Asp Ser Ser Leu Phe Gly His Ser Leu Asp Gly Ala Ala
        370                 375                 380
```

<210> SEQ ID NO 92
<211> LENGTH: 1230
<212> TYPE: DNA
<213> ORGANISM: Scenedesmus dimorphus

<400> SEQUENCE: 92

```
atgtctctta agtccagcgt gggccccagc ctggccggca aggcgtgcca cggagcaaat    60
gcgcaggtgc tgccgcgcat ggcagtgcca gcgccgcttg caggaacagc agtgcgcccc   120
agcctcgcag tcaatgcagt caaccctgag aaaaacggcg cttatgaggg ctcccccatt   180
gtcagcggcc ccatttctgt gggtgctatg gacaaggact ccaagggctc ttccaagcct   240
gttgaccgca gcaagggcct ctggacgcgc tgcgacaagt gcggcgtgat tctctacatc   300
aagcacctga aggagcacca ccacatctgc ttcggctgca actaccacct caagatgagc   360
agccaggaga ggatcgacca catgatcgac ccaggctcat ggcgccctt tgacgagacg   420
ctgtctccct cgaccccgct ggactttgtg gacatgaagc catacccaga cagggtgcgc   480
gacagccagg acaagacagg catgaacgat gccatccgca caggcacggg cctgctgcac   540
ggcatcccag tggcgctggc agtgatggag tttggcttca tgggcggcag catgggcagc   600
gtggtggggg agaagctgac gcgcctgatt gagtacgcca cgcaggaggg gctcacgctg   660
ctggtggtgt gcaccagcgg aggcgcgcgc atgcaggagg gcatcatgag cctgatgcag   720
atggccaaga tcagcggcgc gctgcacgtg caccagaatg aggccaacct gctgtacatc   780
tccatcctga ccagccccac cacaggtggc gtgaccgcaa gctttggcat gctggggga   840
gtcatcattg ctgagccgca ggccatcatc ggctttgcag acggcgtgt gatcgagcag   900
acgctgcgtg aggagctgcc agatgacttc cagaccgcgg agtacctgct tgacaagggc   960
ctgctcgacc tggtggtgcc gcgcagcttc ctgaagggcg cgctgtttga gatcatcgac  1020
ttttacaaga acgcaccctg caagcgccgc ggcaagattc catttggcgt gcagcgcggt  1080
acgtacggcc tgaccgctga ggagaagatg cggcgcaggt ggagggagtg gagctcagct  1140
ggcagcaacg gctcgggcac gccgcgctg cagcagcag cagcagagct gagagagggc  1200
agcgtgctgc tagcaggcgt ctgttgttaa                                   1230
```

<210> SEQ ID NO 93
<211> LENGTH: 1104
<212> TYPE: DNA
<213> ORGANISM: Scenedesmus dimorphus

<400> SEQUENCE: 93

```
atggtcaatg cagtcaaccc tgagaaaaac ggcgcttatg agggctcccc cattgtcagc      60
ggccccattt ctgtgggtgc tatggacaag gactccaagg gctcttccaa gcctgttgac     120
cgcagcaagg gcctctggac gcgctgcgac aagtgcggcg tgattctcta catcaagcac     180
ctgaaggagc accaccacat ctgcttcggc tgcaactacc acctcaagat gagcagccag     240
gagaggatcg accacatgat cgacccaggc tcatggcgcc cctttgacga cgctgtctc     300
ccctgcgacc cgctggactt tgtggacatg aagccatacc agacagggt gcgcgacagc     360
caggacaaga caggcatgaa cgatgccatc cgcacaggca cgggcctgct gcacggcatc     420
ccagtggcgc tggcagtgat ggagtttggc ttcatgggcg cagcatggg cagcgtggtg     480
ggggagaagc tgacgcgcct gattgagtac gccacgcagg aggggctcac gctgctggtg     540
gtgtgcacca gcgaggcgc gcgcatgcag gagggcatca tgagcctgat gcagatggcc     600
aagatcagcg gcgcgctgca cgtgcaccag aatgaggcca acctgctgta catctccatc     660
ctgaccagcc ccaccacagg tggcgtgacc gcaagctttg catgctggg ggatgtcatc     720
attgctgagc cgcaggccat catcggcttt gcaggacggc gtgtgatcga gcagacgctg     780
cgtgaggagc tgccagatga cttccagacc gcggagtacc tgcttgacaa gggcctgctc     840
gacctggtgg tgccgcgcag cttcctgaag ggcgcgctgt ttgagatcat cgacttttac     900
aagaacgcac cctgcaagcg ccgcggcaag attccatttg gcgtgcagcg cggtacgtac     960
ggcctgaccg ctgaggagaa gatgcggcgc aggtggaggg agtggagctc agctggcagc    1020
aacggctcgg gcacgcccgc gctggcagca gcagcagcag agctgagaga gggcagcgtg    1080
ctgctagcag gcgtctgttg ttaa                                           1104
```

<210> SEQ ID NO 94
<211> LENGTH: 409
<212> TYPE: PRT
<213> ORGANISM: Scenedesmus dimorphus

<400> SEQUENCE: 94

```
Met Ser Leu Lys Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His Ile Cys Phe Gly
            100                 105                 110

Cys Asn Tyr His Leu Lys Met Ser Ser Gln Glu Arg Ile Asp His Met
        115                 120                 125
```

Ile Asp Pro Gly Ser Trp Arg Pro Phe Asp Glu Thr Leu Ser Pro Cys
130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
            195                 200                 205

Leu Ile Glu Tyr Ala Thr Gln Glu Gly Leu Thr Leu Leu Val Val Cys
210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270

Ala Ser Phe Gly Met Leu Gly Asp Val Ile Ile Ala Glu Pro Gln Ala
            275                 280                 285

Ile Ile Gly Phe Ala Gly Arg Arg Val Ile Glu Gln Thr Leu Arg Glu
290                 295                 300

Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys Gly Ala Leu Phe
                325                 330                 335

Glu Ile Ile Asp Phe Tyr Lys Asn Ala Pro Cys Lys Arg Arg Gly Lys
            340                 345                 350

Ile Pro Phe Gly Val Gln Arg Gly Thr Tyr Gly Leu Thr Ala Glu Glu
            355                 360                 365

Lys Met Arg Arg Arg Trp Arg Glu Trp Ser Ser Ala Gly Ser Asn Gly
370                 375                 380

Ser Gly Thr Pro Ala Leu Ala Ala Ala Ala Glu Leu Arg Glu Gly
385                 390                 395                 400

Ser Val Leu Leu Ala Gly Val Cys Cys
                405

<210> SEQ ID NO 95
<211> LENGTH: 367
<212> TYPE: PRT
<213> ORGANISM: Scenedesmus dimorphus

<400> SEQUENCE: 95

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
                20                  25                  30

Lys Gly Ser Ser Lys Pro Val Asp Arg Ser Lys Gly Leu Trp Thr Arg
            35                  40                  45

Cys Asp Lys Cys Gly Val Ile Leu Tyr Ile Lys His Leu Lys Glu His
50                  55                  60

His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

```
Glu Thr Leu Ser Pro Cys Asp Pro Leu Asp Phe Val Asp Met Lys Pro
                100                 105                 110

Tyr Pro Asp Arg Val Arg Asp Ser Gln Asp Lys Thr Gly Met Asn Asp
            115                 120                 125

Ala Ile Arg Thr Gly Thr Gly Leu Leu His Gly Ile Pro Val Ala Leu
        130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
    290                 295                 300

Cys Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala Ala
            340                 345                 350

Ala Glu Leu Arg Glu Gly Ser Val Leu Leu Ala Gly Val Cys Cys
        355                 360                 365

<210> SEQ ID NO 96
<211> LENGTH: 6985
<212> TYPE: DNA
<213> ORGANISM: Scenedesmus dimorphus

<400> SEQUENCE: 96
ggcgtactca atcaggcgcg tcctcacctg tgagcatcgg gttgcgcagg ctgatggcct      60
gcgccagcac caccaggcag gtgctgcctg cagcgccagc cccaggttga gccgctggaa     120
ggtgcccatg tacagctggc cccgcaatgc agcctcctgc agcagcagca gcaacagcag     180
cagcagcagc agcagcagca gcagcagcag cagcaacagc agcagcagca acagcagcac     240
agcttggttg gctgcatgag agtgccttgt gccgttgctg tcgctgctgg tgctccagca     300
ttcaacaaca accagcacac gcattactgc acaccctgag acaacaggca gtcggcttga     360
catgtatcaa gcgcacgtac cttcagggtg tacttgacag tagcactggc tatcagcgtg     420
gctcctgctg cccgtgcaat gctgttcacc actgggtcag tggctgcacc aaccatcagc     480
ccagcaaagt acccaggcag cagtagtgcg gcagctgcag tggccacgcc agcgctgccg     540
agtgtccagt aggccttgga ctgagtggca gggtctgaga ggaagcctgt catggtgcga     600
```

```
gtcactggtg gcagcagcag cagcaacagc agaggagagc agcaggcagc aaagcagtaa      660
gcgtatcagc aatggctgat gacggtgcag tatggcaggc acatgacaag gatgaaggac      720
agcacaaaac actttggtgt tgtggagagg tgtgccaacg catgcattgg ggcaagagct      780
ggtgctcgcc tgctagctcg ccggcaagca gtgacacaac caggcatagt cgtgcaaaca      840
ttcttgccag cagggcagcc ccatgttgca gcctgccaca gctgcgagcg atgtcaccat      900
ggcaacaaac agctgtctgc tgctgctgcc cgtgcacaac tgctgtacaa gagaacgaca      960
gtccaggcgt gtggtggtat caccattgcc cactctccct attccccccc caccccaccc     1020
atctttggcc atggcacatc agatgcaagt ctgtgtagca gcgcttgcct tttgccacat     1080
tcttttccac agccttctcc acgcccttgc tgactggctt gtcattctca cgaaagcaca     1140
caggctgcag catgtaagag gacagcagag gagtgtggtt atgacaaggg tgcctggcag     1200
aactgcaagc tcatgcaccg gcatgaatgc gccgagtgcc agaatgcact ggtcataggc     1260
atgccggaac cgctcgttgc tgctgcttcg acaatgaaag catacccctc agccagctac     1320
tgtcgatgct taccttgaag acaagcttgg tggctctgtt gatgtggcat gcatgtggca     1380
ggtcgcacag cagcatatgc aggagcaggc ctggcacaga ggcactgcca gctgcagcag     1440
tgagcaggga cagatgtcac ccgtcgtcac ttgcgacgtc cgagggacct atacagcctt     1500
tgtgagggag tgcactgttg ttgctgcagc agctactgcc ccaagcctac atcaggactg     1560
gcgctagtgc tagtcagtga gttacgacat gacttacctc gcgcagtggc accgcaacgc     1620
ttgttcagta gcatcatgtg tgtaagaagc gctaaaagaa gaaacacaagg ctgcaacgtc     1680 gcaaacaaac agcgaagatc gaggtgcttg aaacgccttg gtctcttgct cagctggtct     1740
cttgctcagc tggcgcgcgc gcgcgcgcca ctagaaacgg cgtgaccaaa ctcaaatcca     1800
ccgcctgcgt ctatatgaca gccgcaaaac tcttgatttt gacaatacgg tctttttag     1860 gactgaaagt tcacactttc agctgctgtg cgtccaccac tcagtgactg gcacaccacc     1920
agaggtccga ccagacggtc tgcgactgtc tgcagtggtg aacgctgatt tagctggacg     1980
cgtggcaaat ccagagcata cacagggact ttatcaactt actgtctgaa aaacacggca     2040
gcagtgaaca tgacagcagg caggcaggtg taagcacttg agtgaccatg tgtcagcatg     2100
ctccgttcag tttgcctgcc ttgcagtagc ctgcggtgga caacatcaca caacttgagt     2160
tgctgtcaac ctgcttagtt gcgctcagca gcgattgctt cagccttctt cagggccaaa     2220
aacgtcgctt ggactccagc cctgttgatc aagcctcacg tggcagttct cggttcgcaa     2280
gctagaaacg tgcgcaaaca cagcttagta agtggttaga acagtttgag ggctgaatga     2340
cgaggcaagg caaccaaatt tgcttccggt tgtcatgtta ctttccctcg actgtccgca     2400
ttggcgctgc attgatcaaa ttatcgtcca atgtcacgct gtgtaatgtg agtttggtca     2460
aggctgtgtc ttttctgctc atcaaggggt gtaactggac tgcgggcgct tgcttcgtgt     2520
cgaggctgcg taagcttctc attggcttgc gtttagatca gaatcaattg caggatcagc     2580
agcccgggag gttgccaagg gctgctcctc gaacaagatg atgtctctta agtccagcgt     2640 gggcccagc ctggccggca aggcgtgcca cggagcaaat gcgcaggtag gagtctatat      2700
atgccgctca atcccgccag ggttggccct tgtgagcaaa tgcagtctgc tcagtgggcg     2760
ttacataggc agaaagagcc tcaacgcatg tcgctttggg ttatgatcgg gctgaatttg     2820
acttgctatg ccttgataat gcatactagc tgcccatgc atgccaggtg aaccagcagg      2880
cctccagcac gccagcacag caatcatcat cagtgcctgc atcaatccag ccaagcgcac     2940
```

```
tgttgctgct gctgctgctg ccagcattac ttcatgctgc cccgcatgcc cacagaatcc    3000
cacacatgct gcatgcacaa atgcctatca gcatccccac gctccctcgc atccccgtgc    3060
atccccttgc gcaggtgctg ccgcgcatgg cagtgccagc gccgcttgca ggaacagcag    3120
tgcgccccag cctcgcagtc aatgcagtca accctgagaa aaacggcgct tatgagggct    3180
cccccattgt cagcggcccc atttctgtgg gtgctatgga caaggactcc aagggctctt    3240
ccaagcctgt tgaccgcagc aagggcctct ggacgcgctg cgacaagtgc ggcgtgattc    3300
tctacatcaa gcacctgaag gagcaccacc acatctgctt cggctgcaac taccacctca    3360
agatgagcag ccaggagagg atcgaccaca tgatcgaccc aggtgcgcgc ctcaggcatg    3420
gcagcagccg gcgggcatgc atgcgactgt cttgtgcgcg cagcatgttg cagggtggt     3480
agctgtgctt gcaggcatga gctccagggc caaactgctt ggtgctgcst gctgtggctg    3540
cggtgggttg caccactttg tgttgcttcg tgctgtgggt agttagtccc gctgagagta    3600
gcgtgcatgc agcccgtgtc aagttttgaa ggaaccatta tgcagcagca gcgcgcctgc    3660
ccgcctgcac gcaactgcct tccgcatcgc cacctgcgtg ccttgccgtt taccctgtgc    3720
tgagcatgcc cgctgctttc ttcgcaggct catggcgccc ctttgacgag acgctgtctc    3780
cctgcgaccc gctggacttt gtggacatga agccataccc agacagggtg cgcgacagcc    3840
aggacaagac aggtgaggac aatgaagtac tgctgtaacg aaagaatgcc gcagcgaaga    3900
agtgctgtag agtgcgccat ggaagaaggg gcagctcttg gagcacagca gcttgcagtt    3960
acctggcggc acacttgctg acactttgtc ctgtgtacaa cctgtgcatc tctggatagc    4020
gctgcttctg gcaaaggcgc atatgtatct gcttgaccat gtgctgcgct gctgtgctgc    4080
tgcctgctgt gctgctgtcc tgcaggcatg aacgatgcca tccgcacagg cacgggcctg    4140
ctgcacggca tcccagtggc gctggcagtg atggagtttg gcttcatggg cggcagcatg    4200
ggcagcgtgg tgggggagaa gctgacgcgc ctgattgagt acgccacgca ggaggggctc    4260
acgctgctgg tggtgtgcac cagcggaggc gcgcgcatgc aggagggcat catgagcctg    4320
atgcagatgg ccaagatcag cggcgcgctg cacgtgcacc agaatgaggc caacctgctg    4380
tacatctcca tcctgaccag ccccaccaca ggtggcgtga ccgcaagctt tggcatgctg    4440
ggggatgtca tcattgctga gccgcaggcc atcatcggct ttgcaggacg gcgtgtgatc    4500
gagcagacgc tgcgtgagga gctgccagat gacttccagg taggctgggc tggatgatga    4560
tagtaacttt tgtgacagct tagcctgtgt cgtagcattt gcagcagaaa tggcagtatt    4620
gccgctgtgg ctactagact taattgtctg cgctgtgcag gtgcagcaac tatgtgctgc    4680
ttctgcgcgc atgactaacc gtgtacgctg ccatcaacca attgtgtacg ctgctgctgc    4740
tgctgctgct gctgctgctg tgcgtctgcc gtcatcatcg acagaccgcg gagtacctgc    4800
ttgacaaggg cctgctcgac ctggtggtgc cgcgcagctt cctgaagggc gcgctgtttg    4860
agatcatcga cttctacaag gtgggggcaa tcagtagcag caacagcagc gccagcaaca    4920
gcggcagatg gcggactggc agctgtcacg gacgtgcggc cacctaagcg ctgcatgggg    4980
gctgtgtcgg ttcggaggcg ctgcttcagc agacgcctgt cgggtgaagg cttctcgttg    5040
catgccacgc attgctaggg cgagtagcgg cggaggactg tgatgacatg cacaaggcag    5100
ttgcagtggt gcaggctgca acacacttgt aaacgtgtgc cttctcgctg cacggtgttt    5160
tgactggacg cactctgttt gtggtcctat tccttctgtg cagaacgcac cctacaagcg    5220
ccgcggcaag attccatttg gcgtgcagcg cggtacgtac ggcctgaccg ctgaggagaa    5280
gatgcggcgc aggtggaggg agtggagctc agctggcagc aacggctcgg gcacgcccgc    5340
```

```
gctggcagca gcagcagcag agcccagcta ccaggtgcgg cgcggggcag ggtggggtgt    5400
tataagcttg cggatggggt gcctgtgtca gggtcagggt cagcagcagc agcagcgtca    5460
caactgaaat gtttggatgt agtgtgcagc tgctggcatg atggcatgat agcagccaag    5520
accacagtgt gaacaaacac ctggctgcaa tgcacagtcc acaagcacct gtgttgtctt    5580
gccggtgttc acaccacac accattgttg cgtgctgtga gcgctacaca ccaactcaca    5640
ccatctgaca caccctctc cccccccatg gcgccttgcc atactcctat gatctcctgc    5700
aggacctggt ggcgtccttc agcaggtgt gctcctcagc agcagagtcg ctcacgccag    5760
gcgagctgga cgtggcagac ctggtcaagg agcccgcagc actcaacgat gccgtgtcca    5820
ttagccgcga cagcgtgatt gagtggatgg aggcgcagga ggcactgctg ggcaagaagg    5880
agcagcagca gcccgagttt gtgttccggg tgaagccagc aacctactcc ggcagggctg    5940
tgtaagccag cacaggcagc gcagtgcgac acagtgcaga ctggtgttgt gttgtggcaa    6000
gggctgattg aaggggcgct gctggatatg ctgggcaggg gctcagaggt gcagcagcca    6060
ggcaacacag gtgcagctgg cagggcgggg gcgcgctgtt cgaatcagct gccctatatg    6120
ctgcgagcag atgtcacagc agtcggcatg tagctgtggc tgttcggtgg agcaggcacg    6180
cgctggaacc agagcgaaat gggaggcttt cggcactgcc tgcggcacgg ctgctgccca    6240
ggtgcccgcc ttctgactag cagggtgttg aagagcagcg ttgggcataa gcagtggccg    6300
cggcgacggt ttgggacgtt gtttggctgc ctgcaatagc cagacgcgtc tagccaattg    6360
cactgcacag gccttgcagt cctgggcagc agtgcttgga gccctgcgga agttggcgtc    6420
actgatgccc tgcatggcgt agcatgcatg cacgctcata tcagctgtgc atctacactg    6480
aagcagtgca ctgctgcagc attgcatgtt gtatcagctg cagccgtagg gtgtggtgga    6540
gcttgtctcg gggtggtggt ggggtggtcg gggtgggctg ggagggcag ggctggcgtg    6600 gagcaatgta catctgttgg ttgaggttta tgcagccggt gccttggcgc cagtgcaagg    6660
gttgttacaa tggacaggca gtttttgatg cttatgcggc tgcgcagtgg ataatgattt    6720
ggcaccttca ctcagtgagt cacgtgctgc tgctgttggc agcatgttgc atagtgttca    6780
ctatgcaggc cactggccct ctgggtgtgc tgggatgttg ctgggccagc gcccacttca    6840
tatgcattgg catgtcaatg aagggtcagg ttgtagcaag accacgtgcc agagctttaa    6900
gtattggtca gcatgtgctg cttggcatgc agtgtgccat cggcgaggaa cacttcttga    6960
acatgaactt accaagctga tttcc                                          6985
```

<210> SEQ ID NO 97
<211> LENGTH: 1281
<212> TYPE: DNA
<213> ORGANISM: Artificial Sequence
<220> FEATURE:
<223> OTHER INFORMATION: modified acetyl CoA carboxylase

<400> SEQUENCE: 97

```
atggactaca agacgacga cgacaaagta aacgctgtaa acccagaaaa aaacggtgct      60
tacgaaggtt caccaattgt atcaggtcca atttcagtag gtgctatgga caaagactca    120
aaaggttcat caaaaccagt agaccgttca aaaggtttat ggacacgttg tgacaaatgt    180
ggtgtaattt tatacattaa acacttaaaa gaacaccacc acatttgttt cggttgtaac    240
taccacttaa aaatgtcatc acaagaacgt attgaccaca tgattgaccc aggttcatgg    300
cgtccattcg acgaaacatt atcaccatgt gacccattag acttcgtaga catgaaacca    360
```

| | |
|---|---|
| tacccagacc gtgtacgtga ctcacaagac aaaacaggta tgaacgacgc tattcgtaca | 420 |
| ggtacaggtt tattacacgg tattccagta gctttagctg taatggaatt cggtttcatg | 480 |
| ggtggttcaa tgggttcagt agtaggtgaa aaattaacac gtttaattga atacgctaca | 540 |
| caagaaggtt taacattatt agtagtatgt acatcaggtg gtgctcgtat gcaagaaggt | 600 |
| attatgtcat taatgcaaat ggctaaaatt tcaggtgctt acacgtaca ccaaaacgaa | 660 |
| gctaacttat tatacatttc aatttaaca tcaccaacaa caggtggtgt aacagcttca | 720 |
| ttcggtatgt taggtgacgt aattattgct gaaccacaag ctattattgg tttcgctggt | 780 |
| cgtcgtgtaa ttgaacaaac attacgtgaa gaattaccag acgacttcca aacagctgaa | 840 |
| tacttattag acaaaggttt attagactta gtagtaccac gttcattctt aaaaggtgct | 900 |
| ttattcgaaa ttattgactt ctacaaaaac gctccataca aacgtcgtgg taaaattcca | 960 |
| ttcggtgtac aacgtggtac atacggttta acagctgaag aaaaaatgcg tcgtcgttgg | 1020 |
| cgtgaatggt catcagctgg ttcaaacggt tcaggtacac cagctttagc tgctgctgct | 1080 |
| gcttcagctg ctgtaggttc agctgctaca tgtggttcat gtcaacaaca acaattagct | 1140 |
| ttatgggctg tattagctgg ttgtggttca tgtggtcaat ggttatggtt cgctcaaggt | 1200 |
| gtaggtgctt tagaacgtac agctgctaca gctgctgtat tacgtgaagg ttcagtatta | 1260 |
| ttagctggtg tatgttgtta a | 1281 |

<210> SEQ ID NO 98
<211> LENGTH: 1257
<212> TYPE: DNA
<213> ORGANISM: Artificial Sequence
<220> FEATURE:
<223> OTHER INFORMATION: modified acetyl CoA carboxylase

<400> SEQUENCE: 98

| | |
|---|---|
| atggtaaacg ctgtaaaccc agaaaaaaac ggtgcttacg aaggttcacc aattgtatca | 60 |
| ggtccaattt cagtaggtgc tatggacaaa gactcaaaag gttcatcaaa accagtagac | 120 |
| cgttcaaaag gtttatggac acgttgtgac aaatgtggtg taattttata cattaaacac | 180 |
| ttaaaagaac accaccacat tgtttcggt tgtaactacc acttaaaaat gtcatcacaa | 240 |
| gaacgtattg accacatgat tgacccaggt tcatggcgtc cattcgacga acattatca | 300 |
| ccatgtgacc cattagactt cgtagacatg aaaccatacc cagaccgtgt acgtgactca | 360 |
| caagacaaaa caggtatgaa cgacgctatt cgtacaggta caggtttatt acacggtatt | 420 |
| ccagtagctt tagctgtaat ggaattcggt tcatgggtg gttcaatggg ttcagtagta | 480 |
| ggtgaaaaat taacacgttt aattgaatac gctacacaag aaggtttaac attattagta | 540 |
| gtatgtacat caggtggtgc tcgtatgcaa gaaggtatta tgtcattaat gcaaatggct | 600 |
| aaaatttcag gtgctttaca cgtacaccaa aacgaagcta acttattata catttcaatt | 660 |
| ttaacatcac caacaacagg tggtgtaaca gcttcattcg gtatgttagg tgacgtaatt | 720 |
| attgctgaac cacaagctat tattggtttc gctggtcgtc gtgtaattga acaaacatta | 780 |
| cgtgaagaat taccagacga cttccaaaca gctgaatact tattagacaa aggtttatta | 840 |
| gacttagtag taccacgttc attcttaaaa ggtgctttat tcgaaattat tgacttctac | 900 |
| aaaaacgctc catacaaacg tcgtggtaaa attccattcg gtgtacaacg tggtacatac | 960 |
| ggtttaacag ctgaagaaaa aatgcgtcgt cgttggcgtg aatggtcatc agctggttca | 1020 |
| aacggttcag gtacaccagc tttagctgct gctgctgctt cagctgctgt aggttcagct | 1080 |
| gctacatgtg gttcatgtca acaacaacaa ttagctttat gggctgtatt agctggttgt | 1140 |

```
ggttcatgtg gtcaatggtt atggttcgct caaggtgtag gtgctttaga acgtacagct   1200
gctacagctg ctgtattacg tgaaggttca gtattattag ctggtgtatg ttgttaa     1257

<210> SEQ ID NO 99
<211> LENGTH: 1323
<212> TYPE: DNA
<213> ORGANISM: Artificial Sequence
<220> FEATURE:
<223> OTHER INFORMATION: modified acetyl CoA carboxylase

<400> SEQUENCE: 99
atggtaaacg ctgtaaaccc agaaaaaaac ggtgcttacg aaggttcacc aattgtatca     60
ggtccaattt cagtaggtgc tatggacaaa gactcaaaag gttcatcaaa accagtagac    120
cgttcaaaag gttatggaca cgttgtgac aaatgtggtg taattttata cattaaacac     180
ttaaaagaac accaccacat ttgtttcggt tgtaactacc acttaaaaat gtcatcacaa    240
gaacgtattg accacatgat tgacccaggt tcatggcgtc cattcgacga acattatca     300 ccatgtgacc cattagactt cgtagacatg aaaccatacc cagaccgtgt acgtgactca    360
caagacaaaa caggtatgaa cgacgctatt cgtacaggta caggtttatt acacggtatt    420
ccagtagctt tagctgtaat ggaattcggt ttcatgggtg gttcaatggg ttcagtagta    480
ggtgaaaaat taacacgttt aattgaatac gctacacaag aaggtttaac attattagta    540
gtatgtacat caggtggtgc tcgtatgcaa gaaggtatta tgtcattaat gcaaatggct    600
aaaatttcag gtgctttaca cgtacaccaa acgaagcta acttattata catttcaatt    660
ttaacatcac caacaacagg tggtgtaaca gcttcattcg gtatgttagg tgacgtaatt    720
attgctgaac cacaagctat tattggtttc gctggtcgtc gtgtaattga acaaacatta    780
cgtgaagaat taccagacga cttccaaaca gctgaatact tattagacaa aggtttatta    840
gacttagtag taccacgttc attcttaaaa ggtgctttat tcgaaattat tgacttctac    900
aaaaacgctc catacaaacg tcgtggtaaa attccattcg gtgtacaacg tggtacatac    960
ggtttaacag ctgaagaaaa aatgcgtcgt cgttggcgtg aatggtcatc agtaggttca   1020
atgttacact cagtacacta cgctggtcac tggccatcag gttgtgctgg tatgttatta   1080
ggtcaacgtc cattacacat gcactggcac gtaaacgaag gttcaggttg ttcaaaaaca   1140
acatgtcaat cattcaaata ctggtcagct tgtgctgctt ggcacgctgt atgtcaccgt   1200
cgtggtacat tattagaaca cgaattaaca aaattaattt catggcaatt cgactcatgt   1260
tgttggcgtg ctgctaaagg tatttatta cgttcatgta cgctgtata cgtatacgta   1320 taa                                                                 1323

<210> SEQ ID NO 100
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 100

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45
```

Cys Asp Lys Cys Gly Val Ile Leu Tyr Ile Lys His Leu Lys Glu His
 50                  55                  60

His His Ile Cys Phe Gly Cys Asn Tyr His Leu Lys Met Ser Ser Gln
 65                  70                  75                  80

Glu Arg Ile Asp His Met Ile Asp Pro Gly Asp Trp Arg Pro Phe Asp
                 85                  90                  95

Glu Thr Leu Ser Pro Cys Asp Pro Leu Asp Phe Val Asp Met Lys Pro
                100                 105                 110

Tyr Pro Asp Arg Val Arg Asp Ser Gln Asp Lys Thr Gly Met Asn Asp
                115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
                180                 185                 190

Ile Met Ser Leu Met Gln Met Ala Lys Ile Ser Gly Ala Leu His Val
                195                 200                 205

His Gln Asn Glu Ala Asn Leu Leu Tyr Ile Ser Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Gly Phe Ala Gly Arg Arg Val Ile
                245                 250                 255

Glu Gln Thr Leu Arg Glu Glu Leu Pro Asp Asp Phe Gln Thr Ala Glu
                260                 265                 270

Tyr Leu Leu Asp Lys Gly Leu Leu Asp Leu Val Val Pro Arg Ser Phe
                275                 280                 285

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala Ala
                340                 345                 350

Ala Ser Ala Ala Val Gly Ser Ala Ala Thr Cys Gly Ser Cys Gln Gln
                355                 360                 365

Gln Gln Leu Ala Leu Trp Ala Val Leu Ala Gly Cys Gly Ser Cys Gly
                370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
                405                 410                 415

Cys Cys

<210> SEQ ID NO 101
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 101

```
Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Asp Leu Ser Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Pro Arg Ser Phe
        275                 280                 285

Leu Lys Gly Ala Leu Phe Glu Ile Ile Asp Phe Tyr Lys Asn Ala Pro
    290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala Ala
            340                 345                 350

Ala Ser Ala Ala Val Gly Ser Ala Ala Thr Cys Gly Ser Cys Gln Gln
        355                 360                 365

Gln Gln Leu Ala Leu Trp Ala Val Leu Ala Gly Cys Gly Ser Cys Gly
    370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
```

```
                    405                 410                 415

Cys Cys

<210> SEQ ID NO 102
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 102

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
                20                  25                  30

Lys Gly Ser Ser Lys Pro Val Asp Arg Ser Lys Gly Leu Trp Thr Arg
            35                  40                  45

Cys Asp Lys Cys Gly Val Ile Leu Tyr Ile Lys His Leu Lys Glu His
50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Asp Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Trp Arg Glu Trp Ser
                325                 330                 335

Ser Ala Gly Ser Asn Gly Ser Gly Thr Pro Ala Leu Ala Ala Ala Ala
            340                 345                 350
```

```
Ala Ser Ala Ala Val Gly Ser Ala Ala Thr Cys Gly Ser Cys Gln Gln
        355                 360                 365

Gln Gln Leu Ala Leu Trp Ala Val Leu Ala Gly Cys Gly Ser Cys Gly
    370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
            405                 410                 415

Cys Cys

<210> SEQ ID NO 103
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 103

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Asp Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285
```

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Ala Gly Ser Asn Gly Ser Gly Thr Pro Ala Leu Ala Ala Ala Ala
                340                 345                 350

Ala Ser Ala Ala Val Gly Ser Ala Ala Thr Cys Gly Ser Cys Gln Gln
                355                 360                 365

Gln Gln Leu Ala Leu Trp Ala Val Leu Ala Gly Cys Gly Ser Cys Gly
370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
                405                 410                 415

Cys Cys

<210> SEQ ID NO 104
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 104

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
                20                  25                  30

Lys Gly Ser Ser Lys Pro Val Asp Arg Ser Lys Gly Leu Trp Thr Arg
                35                  40                  45

Cys Asp Lys Cys Gly Val Ile Leu Tyr Ile Lys His Leu Lys Glu His
50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Asp
                100                 105                 110

Tyr Pro Asp Arg Val Arg Asp Ser Gln Asp Lys Thr Gly Met Asn Asp
                115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
                180                 185                 190

Ile Met Ser Leu Met Gln Met Ala Lys Ile Ser Gly Ala Leu His Val
                195                 200                 205

His Gln Asn Glu Ala Asn Leu Leu Tyr Ile Ser Ile Leu Thr Ser Pro
                210                 215                 220

Thr Thr Gly Gly Val Thr Ala Ser Phe Gly Met Leu Gly Asp Val Ile

```
            225                 230                 235                 240
Ile Ala Glu Pro Gln Ala Ile Ile Gly Phe Ala Gly Arg Arg Val Ile
                245                 250                 255
Glu Gln Thr Leu Arg Glu Leu Pro Asp Asp Phe Gln Thr Ala Glu
                260                 265                 270
Tyr Leu Leu Asp Lys Gly Leu Asp Leu Val Val Pro Arg Ser Phe
                275                 280                 285
Leu Lys Gly Ala Leu Phe Glu Ile Ile Asp Phe Tyr Lys Asn Ala Pro
290                 295                 300
Tyr Lys Arg Arg Gly Lys Ile Pro Phe Gly Val Gln Arg Gly Thr Tyr
305                 310                 315                 320
Gly Leu Thr Ala Glu Glu Lys Met Arg Arg Trp Arg Glu Trp Ser
                325                 330                 335
Ser Ala Gly Ser Asn Gly Ser Gly Thr Pro Ala Leu Ala Ala Ala
                340                 345                 350
Ala Ser Ala Ala Val Gly Ser Ala Ala Thr Cys Gly Ser Cys Gln Gln
                355                 360                 365
Gln Gln Leu Ala Leu Trp Ala Val Leu Ala Gly Cys Gly Ser Cys Gly
                370                 375                 380
Gln Trp Leu Trp Phe Ala Gln Gly Val Gly Ala Leu Glu Arg Thr Ala
385                 390                 395                 400
Ala Thr Ala Ala Val Leu Arg Glu Gly Ser Val Leu Leu Ala Gly Val
                405                 410                 415
Cys Cys

<210> SEQ ID NO 105
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 105

Met Val Asn Ala Val Asn Pro Glu Lys Asn Gly Ala Tyr Glu Gly Ser
1               5                   10                  15
Pro Ile Val Ser Gly Pro Ile Ser Val Gly Ala Met Asp Lys Asp Ser
                20                  25                  30
Lys Gly Ser Ser Lys Pro Val Asp Arg Ser Lys Gly Leu Trp Thr Arg
            35                  40                  45
Cys Asp Lys Cys Gly Val Ile Leu Tyr Ile Lys His Leu Lys Glu His
        50                  55                  60
His His Ile Cys Phe Gly Cys Asn Tyr His Leu Lys Met Ser Ser Gln
65                  70                  75                  80
Glu Arg Ile Asp His Met Ile Asp Pro Gly Ser Trp Arg Pro Phe Asp
                85                  90                  95
Glu Thr Leu Ser Pro Cys Asp Pro Leu Asp Phe Val Asp Met Lys Pro
            100                 105                 110
Tyr Pro Asp Arg Val Arg Asp Gln Asp Lys Thr Gly Met Asn Asp
            115                 120                 125
Ala Ile Arg Thr Gly Thr Gly Leu Leu His Gly Ile Pro Val Ala Leu
        130                 135                 140
Ala Val Met Glu Phe Gly Phe Met Gly Gly Ser Met Gly Ser Val Val
145                 150                 155                 160
Gly Glu Lys Leu Thr Arg Leu Ile Glu Tyr Ala Thr Gln Glu Gly Leu
                165                 170                 175
```

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
    290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Trp Arg Glu Trp Ser
                325                 330                 335

Ser Ala Gly Ser Asn Gly Ser Gly Thr Pro Ala Leu Ala Ala Ala
            340                 345                 350

Ala Ser Ala Ala Val Gly Ser Ala Ala Thr Cys Gly Ser Cys Gln Gln
        355                 360                 365

Gln Gln Leu Ala Leu Trp Ala Val Leu Ala Gly Cys Gly Ser Cys Gly
    370                 375                 380

Gln Trp Leu Trp Phe Ala Gln Gly Val Gly Ala Leu Glu Arg Thr Ala
385                 390                 395                 400

Ala Thr Ala Ala Val Leu Arg Glu Gly Ser Val Leu Leu Ala Gly Val
                405                 410                 415

Cys Cys

<210> SEQ ID NO 106
<211> LENGTH: 418
<212> TYPE: PRT
<213> ORGANISM: Artificial Sequence
<220> FEATURE:
<223> OTHER INFORMATION: modified acetyl CoA carboxylase

<400> SEQUENCE: 106

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
            100                 105                 110

```
Tyr Pro Asp Arg Val Arg Asp Ser Gln Asp Lys Thr Gly Met Asn Asp
            115                 120                 125
Ala Ile Arg Thr Gly Thr Gly Leu Leu His Gly Ile Pro Val Ala Leu
130                 135                 140
Ala Val Met Glu Phe Gly Phe Met Gly Gly Ser Met Gly Ser Val Val
145                 150                 155                 160
Gly Glu Lys Leu Thr Arg Leu Ile Glu Tyr Ala Thr Gln Glu Gly Leu
                165                 170                 175
Thr Leu Leu Val Val Cys Thr Ser Gly Gly Ala Arg Met Gln Glu Gly
            180                 185                 190
Ile Met Ser Leu Met Gln Met Ala Lys Ile Ser Gly Ala Leu His Val
        195                 200                 205
His Gln Asn Glu Ala Asn Leu Leu Tyr Ile Ser Ile Leu Thr Ser Pro
    210                 215                 220
Thr Thr Gly Gly Val Thr Ala Ser Phe Gly Met Leu Gly Asp Val Ile
225                 230                 235                 240
Ile Ala Glu Pro Gln Ala Ile Ile Gly Phe Ala Gly Arg Arg Val Ile
                245                 250                 255
Glu Gln Asp Leu Arg Glu Glu Leu Pro Asp Asp Phe Gln Thr Ala Glu
            260                 265                 270
Tyr Leu Leu Asp Lys Gly Leu Leu Asp Leu Val Val Pro Arg Ser Phe
        275                 280                 285
Leu Lys Gly Ala Leu Phe Glu Ile Ile Asp Phe Tyr Lys Asn Ala Pro
    290                 295                 300
Tyr Lys Arg Arg Gly Lys Ile Pro Phe Gly Val Gln Arg Gly Thr Tyr
305                 310                 315                 320
Gly Leu Thr Ala Glu Glu Lys Met Arg Arg Arg Trp Arg Glu Trp Ser
                325                 330                 335
Ser Ala Gly Ser Asn Gly Ser Gly Thr Pro Ala Leu Ala Ala Ala Ala
            340                 345                 350
Ala Ser Ala Ala Val Gly Ser Ala Ala Thr Cys Gly Ser Cys Gln Gln
        355                 360                 365
Gln Gln Leu Ala Leu Trp Ala Val Leu Ala Gly Cys Gly Ser Cys Gly
    370                 375                 380
Gln Trp Leu Trp Phe Ala Gln Gly Val Gly Ala Leu Glu Arg Thr Ala
385                 390                 395                 400
Ala Thr Ala Ala Val Leu Arg Glu Gly Ser Val Leu Leu Ala Gly Val
                405                 410                 415
Cys Cys

<210> SEQ ID NO 107
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 107

Met Val Asn Ala Val Asn Pro Glu Lys Asn Gly Ala Tyr Glu Gly Ser
1               5                   10                  15
Pro Ile Val Ser Gly Pro Ile Ser Val Gly Ala Met Asp Lys Asp Ser
            20                  25                  30
Lys Gly Ser Ser Lys Pro Val Asp Arg Ser Lys Gly Leu Trp Thr Arg
        35                  40                  45
Cys Asp Lys Cys Gly Val Ile Leu Tyr Ile Lys His Leu Lys Glu His
```

```
            50                  55                  60
His His Ile Cys Phe Gly Cys Asn Tyr His Leu Lys Met Ser Ser Gln
 65                  70                  75                  80

Glu Arg Ile Asp His Met Ile Asp Pro Gly Asp Trp Arg Pro Phe Asp
                     85                  90                  95

Glu Thr Leu Ser Pro Cys Asp Pro Leu Asp Phe Val Asp Met Lys Pro
                100                 105                 110

Tyr Pro Asp Arg Val Arg Asp Ser Gln Asp Lys Thr Gly Met Asn Asp
            115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
                180                 185                 190

Ile Met Ser Leu Met Gln Met Ala Lys Ile Ser Gly Ala Leu His Val
                195                 200                 205

His Gln Asn Glu Ala Asn Leu Leu Tyr Ile Ser Ile Leu Thr Ser Pro
210                 215                 220

Thr Thr Gly Gly Val Thr Ala Ser Phe Gly Met Leu Gly Asp Val Ile
225                 230                 235                 240

Ile Ala Glu Pro Gln Ala Ile Gly Phe Ala Gly Arg Arg Val Ile
                245                 250                 255

Glu Gln Thr Leu Arg Glu Leu Pro Asp Asp Phe Gln Thr Ala Glu
                260                 265                 270

Tyr Leu Leu Asp Lys Gly Leu Leu Asp Leu Val Val Pro Arg Ser Phe
            275                 280                 285

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Val Gly Ser Met Leu His Ser Val His Tyr Ala Gly His Trp Pro
                340                 345                 350

Ser Gly Cys Ala Gly Met Leu Leu Gly Gln Arg Pro Leu His Met His
                355                 360                 365

Trp His Val Asn Glu Gly Ser Gly Cys Ser Lys Thr Thr Cys Gln Ser
370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
                405                 410                 415

Phe Asp Ser Cys Cys Trp Arg Ala Ala Lys Gly Ile Leu Leu Arg Ser
                420                 425                 430

Cys Asn Ala Val Tyr Val Tyr Val
            435                 440

<210> SEQ ID NO 108
<211> LENGTH: 440
<212> TYPE: PRT
<213> ORGANISM: Artificial Sequence
```

<220> FEATURE:
<223> OTHER INFORMATION: modified acetyl CoA carboxylase

<400> SEQUENCE: 108

```
Met Val Asn Ala Val Asn Pro Glu Lys Asn Gly Ala Tyr Glu Gly Ser
1               5                   10                  15
Pro Ile Val Ser Gly Pro Ile Ser Val Gly Ala Met Asp Lys Asp Ser
            20                  25                  30
Lys Gly Ser Ser Lys Pro Val Asp Arg Ser Lys Gly Leu Trp Thr Arg
        35                  40                  45
Cys Asp Lys Cys Gly Val Ile Leu Tyr Ile Lys His Leu Lys Glu His
    50                  55                  60
His Ile Cys Phe Gly Cys Asn Tyr His Leu Lys Met Ser Ser Gln
65                  70                  75                  80
Glu Arg Ile Asp His Met Ile Asp Pro Gly Ser Trp Arg Pro Phe Asp
                85                  90                  95
Glu Asp Leu Ser Pro Cys Asp Pro Leu Asp Phe Val Asp Met Lys Pro
            100                 105                 110
Tyr Pro Asp Arg Val Arg Asp Ser Gln Asp Lys Thr Gly Met Asn Asp
        115                 120                 125
Ala Ile Arg Thr Gly Thr Gly Leu Leu His Gly Ile Pro Val Ala Leu
    130                 135                 140
Ala Val Met Glu Phe Gly Phe Met Gly Gly Ser Met Gly Ser Val Val
145                 150                 155                 160
Gly Glu Lys Leu Thr Arg Leu Ile Glu Tyr Ala Thr Gln Glu Gly Leu
                165                 170                 175
Thr Leu Leu Val Val Cys Thr Ser Gly Gly Ala Arg Met Gln Glu Gly
            180                 185                 190
Ile Met Ser Leu Met Gln Met Ala Lys Ile Ser Gly Ala Leu His Val
        195                 200                 205
His Gln Asn Glu Ala Asn Leu Leu Tyr Ile Ser Ile Leu Thr Ser Pro
    210                 215                 220
Thr Thr Gly Gly Val Thr Ala Ser Phe Gly Met Leu Gly Asp Val Ile
225                 230                 235                 240
Ile Ala Glu Pro Gln Ala Ile Ile Gly Phe Ala Gly Arg Arg Val Ile
                245                 250                 255
Glu Gln Thr Leu Arg Glu Glu Leu Pro Asp Asp Phe Gln Thr Ala Glu
            260                 265                 270
Tyr Leu Leu Asp Lys Gly Leu Leu Asp Leu Val Val Pro Arg Ser Phe
        275                 280                 285
Leu Lys Gly Ala Leu Phe Glu Ile Ile Asp Phe Tyr Lys Asn Ala Pro
    290                 295                 300
Tyr Lys Arg Arg Gly Lys Ile Pro Phe Gly Val Gln Arg Gly Thr Tyr
305                 310                 315                 320
Gly Leu Thr Ala Glu Glu Lys Met Arg Arg Arg Trp Arg Glu Trp Ser
                325                 330                 335
Ser Val Gly Ser Met Leu His Ser Val His Tyr Ala Gly His Trp Pro
            340                 345                 350
Ser Gly Cys Ala Gly Met Leu Leu Gly Gln Arg Pro Leu His Met His
        355                 360                 365
Trp His Val Asn Glu Gly Ser Gly Cys Ser Lys Thr Thr Cys Gln Ser
    370                 375                 380
Phe Lys Tyr Trp Ser Ala Cys Ala Ala Trp His Ala Val Cys His Arg
385                 390                 395                 400
```

```
Arg Gly Thr Leu Leu Glu His Glu Leu Thr Lys Leu Ile Ser Trp Gln
            405                 410                 415

Phe Asp Ser Cys Cys Trp Arg Ala Ala Lys Gly Ile Leu Leu Arg Ser
            420                 425                 430

Cys Asn Ala Val Tyr Val Tyr Val
            435                 440

<210> SEQ ID NO 109
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 109

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Asp Pro Cys Asp Pro Leu Asp Phe Val Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
        275                 280                 285

Leu Lys Gly Ala Leu Phe Glu Ile Ile Asp Phe Tyr Lys Asn Ala Pro
    290                 295                 300

Tyr Lys Arg Arg Gly Lys Ile Pro Phe Gly Val Gln Arg Gly Thr Tyr
305                 310                 315                 320
```

```
Gly Leu Thr Ala Glu Glu Lys Met Arg Arg Arg Trp Arg Glu Trp Ser
                325                 330                 335

Ser Val Gly Ser Met Leu His Ser Val His Tyr Ala Gly His Trp Pro
            340                 345                 350

Ser Gly Cys Ala Gly Met Leu Leu Gly Gln Arg Pro Leu His Met His
            355                 360                 365

Trp His Val Asn Glu Gly Ser Gly Cys Ser Lys Thr Thr Cys Gln Ser
    370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
                405                 410                 415

Phe Asp Ser Cys Cys Trp Arg Ala Ala Lys Gly Ile Leu Leu Arg Ser
            420                 425                 430

Cys Asn Ala Val Tyr Val Tyr Val
            435                 440

<210> SEQ ID NO 110
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 110

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Asp Asp Met Lys Pro
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Gly Leu
                165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
        195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240
```

```
Ile Ala Glu Pro Gln Ala Ile Gly Phe Ala Gly Arg Arg Val Ile
            245                 250                 255

Glu Gln Thr Leu Arg Glu Leu Pro Asp Asp Phe Gln Thr Ala Glu
            260                 265                 270

Tyr Leu Leu Asp Lys Gly Leu Leu Asp Leu Val Val Pro Arg Ser Phe
            275                 280                 285

Leu Lys Gly Ala Leu Phe Glu Ile Ile Asp Phe Tyr Lys Asn Ala Pro
290                 295                 300

Tyr Lys Arg Arg Gly Lys Ile Pro Phe Gly Val Gln Arg Gly Thr Tyr
305                 310                 315                 320

Gly Leu Thr Ala Glu Lys Met Arg Arg Trp Arg Glu Trp Ser
            325                 330                 335

Ser Val Gly Ser Met Leu His Ser Val His Tyr Ala Gly His Trp Pro
            340                 345                 350

Ser Gly Cys Ala Gly Met Leu Leu Gly Gln Arg Pro Leu His Met His
            355                 360                 365

Trp His Val Asn Glu Gly Ser Gly Cys Ser Lys Thr Thr Cys Gln Ser
            370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
            405                 410                 415

Phe Asp Ser Cys Cys Trp Arg Ala Ala Lys Gly Ile Leu Leu Arg Ser
            420                 425                 430

Cys Asn Ala Val Tyr Val Tyr Val
            435                 440

<210> SEQ ID NO 111
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 111

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Asp
            100                 105                 110

Tyr Pro Asp Arg Val Arg Asp Ser Gln Asp Lys Thr Gly Met Asn Asp
        115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160
```

Gly Glu Lys Leu Thr Arg Leu Ile Glu Tyr Ala Thr Gln Glu Gly Leu
            165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
            195                 200                 205

His Gln Asn Glu Ala Asn Leu Leu Tyr Ile Ser Ile Leu Thr Ser Pro
            210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
            245                 250                 255

Glu Gln Thr Leu Arg Glu Leu Pro Asp Asp Phe Gln Thr Ala Glu
            260                 265                 270

Tyr Leu Leu Asp Lys Gly Leu Leu Asp Leu Val Val Pro Arg Ser Phe
            275                 280                 285

Leu Lys Gly Ala Leu Phe Glu Ile Ile Asp Phe Tyr Lys Asn Ala Pro
            290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Trp Arg Glu Trp Ser
            325                 330                 335

Ser Val Gly Ser Met Leu His Ser Val His Tyr Ala Gly His Trp Pro
            340                 345                 350

Ser Gly Cys Ala Gly Met Leu Gly Gln Arg Pro Leu His Met His
            355                 360                 365

Trp His Val Asn Glu Gly Ser Gly Cys Ser Lys Thr Thr Cys Gln Ser
            370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
            405                 410                 415

Phe Asp Ser Cys Cys Trp Arg Ala Ala Lys Gly Ile Leu Leu Arg Ser
            420                 425                 430

Cys Asn Ala Val Tyr Val Tyr Val
            435                 440

<210> SEQ ID NO 112
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 112

Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
            35                  40                  45

Cys Asp Lys Cys Gly Val Ile Leu Tyr Ile Lys His Leu Lys Glu His
        50                  55                  60

His His Ile Cys Phe Gly Cys Asn Tyr His Leu Lys Met Ser Ser Gln
65                  70                  75                  80

Glu Arg Ile Asp His Met Ile Asp Pro Gly Ser Trp Arg Pro Phe Asp
            85                  90                  95

Glu Thr Leu Ser Pro Cys Asp Pro Leu Asp Phe Val Asp Met Lys Pro
            100                 105                 110

Tyr Pro Asp Arg Val Arg Asp Asp Gln Asp Lys Thr Gly Met Asn Asp
            115                 120                 125

Ala Ile Arg Thr Gly Thr Gly Leu Leu His Gly Ile Pro Val Ala Leu
130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
            165                 170                 175

Thr Leu Leu Val Val Cys Thr Ser Gly Gly Ala Arg Met Gln Glu Gly
            180                 185                 190

Ile Met Ser Leu Met Gln Met Ala Lys Ile Ser Gly Ala Leu His Val
            195                 200                 205

His Gln Asn Glu Ala Asn Leu Leu Tyr Ile Ser Ile Leu Thr Ser Pro
            210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
            245                 250                 255

Glu Gln Thr Leu Arg Glu Glu Leu Pro Asp Asp Phe Gln Thr Ala Glu
            260                 265                 270

Tyr Leu Leu Asp Lys Gly Leu Leu Asp Leu Val Val Pro Arg Ser Phe
            275                 280                 285

Leu Lys Gly Ala Leu Phe Glu Ile Ile Asp Phe Tyr Lys Asn Ala Pro
            290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
            325                 330                 335

Ser Val Gly Ser Met Leu His Ser Val His Tyr Ala Gly His Trp Pro
            340                 345                 350

Ser Gly Cys Ala Gly Met Leu Leu Gly Gln Arg Pro Leu His Met His
            355                 360                 365

Trp His Val Asn Glu Gly Ser Gly Cys Ser Lys Thr Thr Cys Gln Ser
370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
            405                 410                 415

Phe Asp Ser Cys Cys Trp Arg Ala Ala Lys Gly Ile Leu Leu Arg Ser
            420                 425                 430

Cys Asn Ala Val Tyr Val Tyr Val
            435                 440

<210> SEQ ID NO 113
<211> LENGTH: 440
<212> TYPE: PRT
<213> ORGANISM: Artificial Sequence
<220> FEATURE:
<223> OTHER INFORMATION: modified acetyl CoA carboxylase

<400> SEQUENCE: 113

-continued

```
Met Val Asn Ala Val Asn Pro Glu Lys Asn Gly Ala Tyr Glu Gly Ser
1               5                   10                  15

Pro Ile Val Ser Gly Pro Ile Ser Val Gly Ala Met Asp Lys Asp Ser
            20                  25                  30

Lys Gly Ser Ser Lys Pro Val Asp Arg Ser Lys Gly Leu Trp Thr Arg
        35                  40                  45

Cys Asp Lys Cys Gly Val Ile Leu Tyr Ile Lys His Leu Lys Glu His
    50                  55                  60

His His Ile Cys Phe Gly Cys Asn Tyr His Leu Lys Met Ser Ser Gln
65              70                  75                  80

Glu Arg Ile Asp His Met Ile Asp Pro Gly Ser Trp Arg Pro Phe Asp
                85                  90                  95

Glu Thr Leu Ser Pro Cys Asp Pro Leu Asp Phe Val Asp Met Lys Pro
                100                 105                 110

Tyr Pro Asp Arg Val Arg Asp Ser Gln Asp Lys Thr Gly Met Asn Asp
            115                 120                 125

Ala Ile Arg Thr Gly Thr Gly Leu Leu His Gly Ile Pro Val Ala Leu
    130                 135                 140

Ala Val Met Glu Phe Gly Phe Met Gly Gly Ser Met Gly Ser Val Val
145                 150                 155                 160

Gly Glu Lys Leu Thr Arg Leu Ile Glu Tyr Ala Thr Gln Glu Gly Leu
                165                 170                 175

Thr Leu Leu Val Val Cys Thr Ser Gly Gly Ala Arg Met Gln Glu Gly
                180                 185                 190

Ile Met Ser Leu Met Gln Met Ala Lys Ile Ser Gly Ala Leu His Val
                195                 200                 205

His Gln Asn Glu Ala Asn Leu Leu Tyr Ile Ser Ile Leu Thr Ser Pro
    210                 215                 220

Thr Thr Gly Gly Val Thr Ala Ser Phe Gly Met Leu Gly Asp Val Ile
225                 230                 235                 240

Ile Ala Glu Pro Gln Ala Ile Ile Gly Phe Ala Gly Arg Arg Val Ile
                245                 250                 255

Glu Gln Asp Leu Arg Glu Glu Leu Pro Asp Asp Phe Gln Thr Ala Glu
                260                 265                 270

Tyr Leu Leu Asp Lys Gly Leu Leu Asp Leu Val Val Pro Arg Ser Phe
                275                 280                 285

Leu Lys Gly Ala Leu Phe Glu Ile Ile Asp Phe Tyr Lys Asn Ala Pro
    290                 295                 300

Tyr Lys Arg Arg Gly Lys Ile Pro Phe Gly Val Gln Arg Gly Thr Tyr
305                 310                 315                 320

Gly Leu Thr Ala Glu Glu Lys Met Arg Arg Arg Trp Arg Glu Trp Ser
                325                 330                 335

Ser Val Gly Ser Met Leu His Ser Val His Tyr Ala Gly His Trp Pro
                340                 345                 350

Ser Gly Cys Ala Gly Met Leu Leu Gly Gln Arg Pro Leu His Met His
            355                 360                 365

Trp His Val Asn Glu Gly Ser Gly Cys Ser Lys Thr Thr Cys Gln Ser
    370                 375                 380

Phe Lys Tyr Trp Ser Ala Cys Ala Ala Trp His Ala Val Cys His Arg
385                 390                 395                 400

Arg Gly Thr Leu Leu Glu His Glu Leu Thr Lys Leu Ile Ser Trp Gln
                405                 410                 415
```

```
Phe Asp Ser Cys Cys Trp Arg Ala Ala Lys Gly Ile Leu Leu Arg Ser
            420                 425                 430
Cys Asn Ala Val Tyr Val Tyr Val
        435                 440
```

<210> SEQ ID NO 114
<211> LENGTH: 7038
<212> TYPE: DNA
<213> ORGANISM: Artificial Sequence
<220> FEATURE:
<223> OTHER INFORMATION: modified Rat acetyl CoA carboxylase

<400> SEQUENCE: 114

| | | | | | |
|---|---|---|---|---|---|
| atggatgaac | cttcacctttt | agctaagaca | ttagaattaa | atcaacactc | acgtttcatc | 60 |
| attggttcag | tttcagaaga | taattcagaa | gacgaaattt | caaacttagt | taaacttgat | 120 |
| cttgaagaaa | aagaaggatc | attatctcct | gcttcagtat | catcagatac | tttaagtgat | 180 |
| ttaggcatat | cagctttaca | agatggctta | gcatttcaca | tgcgttcttc | tatgtctggt | 240 |
| ttacatttag | taaaacaagg | tcgtgatcgc | aagaaaattg | attcacaaag | agattttacc | 300 |
| gttgcttctc | cagctgaatt | tgttacacgt | ttcggtggta | ataaggttat | tgaaaaagtt | 360 |
| ttaatagcta | acaatggaat | tgcagctgtt | aaatgtatgc | gcagcattcg | tagatggtct | 420 |
| tacgaaatgt | ttcgtaatga | acgtgctatt | cgtttcgttg | ttatggttac | accagaggat | 480 |
| ttaaaagcta | cgccgagta | tattaagatg | gcagatcatt | atgtaccagt | accaggtggt | 540 |
| gccaacaata | taactacgc | aaatgttgag | ttaattcttg | acattgctaa | acgtattcca | 600 |
| gtacaagccg | tttgggctgg | ttggggccat | gcatcagaaa | atccaaaatt | accagaatta | 660 |
| ttacttaaaa | atggaatagc | tttcatgggt | ccaccatcac | aagctatgtg | ggctttaggt | 720 |
| gacaaaatcg | cttctagtat | tgtagcacaa | actgctggta | ttcctacttt | accctggtct | 780 |
| ggtagtggtt | taagagttga | ttggcaggaa | aatgatttta | gtaaacgtat | ccttaatgtt | 840 |
| cctcaagatt | tatatgaaaa | gggttatgtt | aaagatgtag | atgatggttt | aaaagctgct | 900 |
| gaagaagttg | gataccctgt | aatgattaaa | gcaagtgaag | gtggtggtgg | taaaggtata | 960 |
| agaaaggtaa | ataacgcaga | cgattttcct | aaccttttc | gccaggtaca | ggctgaagta | 1020 |
| cccggttcac | ccatttttgt | tatgcgttta | gcaaaacagt | cacgtcactt | agaagtacaa | 1080 |
| attttagctg | atcaatatgg | taatgctatt | tctttattcg | gtcgtgattg | ttcagttcaa | 1140 |
| cgtcgtcatc | agaaaataat | cgaagaagct | cctgctgcaa | ttgctactcc | agccgttttt | 1200 |
| gaacacatgg | aacaatgtgc | tgttaagtta | gctaaaatgg | taggttacgt | ttctgctggt | 1260 |
| actgtagagt | acttatatag | ccaagatggt | agcttttatt | tcttagagtt | aaatccacgc | 1320 |
| ttacaagtag | aacatccttg | cacagaaatg | gtggctgatg | taaatttacc | cgcagctcaa | 1380 |
| ttacaaattg | caatgggtat | tcctttattt | cgtattaaag | atattcgtat | gatgtatgga | 1440 |
| gtaagtccct | ggggcgatgc | tccaattgat | ttcgagaata | gtgctcatgt | accatgtcct | 1500 |
| cgcggacatg | taatagctgc | tcgtatcaca | agtgaaaacc | ctgacgaagg | ttttaaaccc | 1560 |
| tctagtggta | ctgtacaaga | attaaacttt | cgttcaaata | gaacgtttg | gggatatttt | 1620 |
| agtgttgctg | ctgctggcgg | tttacatgaa | tttgctgact | cacaatttgg | tcactgtttt | 1680 |
| tcttggggtg | aaaatcgtga | agaagctata | agtaatatgg | tagtagcttt | aaaagaatta | 1740 |
| tcaattcgtg | gtgattttcg | tacaacagtt | gaatacttaa | tcaaactttt | agagacagaa | 1800 |
| tcttttcaat | aaaatcgcat | tgatacaggt | tggttagatc | gtttaatagc | tgaaaaagtg | 1860 |
| caagctgaac | gtccagatac | tatgttaggt | gtagtttgtg | gtgcattaca | tgttgcagac | 1920 |

```
gttaacttac gcaattctat ttcaaatttc ttacacagct tagaacgtgg tcaagtatta   1980
ccagctcaca ccttattaaa cactgttgac gttgaactta tttatgaagg tatcaaatat   2040
gttttaaaag tgacaagaca atcacctaat agttatgttg taattatgaa tggttcttgc   2100
gttgaagttg atgttcaccg tttatcagac ggtggtcttt tactttctta tgacggttca   2160
agttacacta cctatatgaa agaagaagta gacagatatc gtattactat tggtaataaa   2220
acttgtgtgt ttgaaaaaga aaacgaccca tcagtaatgc gttctccatc agctggtaaa   2280
cttattcaat atattgtaga ggatggtggt catgttttcg caggtcaatg ttatgcagaa   2340
atagaagtaa tgaagatggt tatgacttta acagcagttg aaagtggttg tatccattac   2400
gttaaacgtc caggagcagc tcttgatcca ggttgtgtaa ttgctaaaat gcaattagat   2460
aatccaagta aagtgcaaca agcagaatta catacaggtt ctttaccaca aattcaaagt   2520
acagccttac gtggtgaaaa attacacaga gtatttcact atgttttaga taacttagtg   2580
aatgttatga acggttattg ccttccagat ccattctttt catcaaaagt gaaagattgg   2640
gttgaacgtt taatgaaaac cttacgtgat ccatcattac ctttattaga attacaagac   2700
ataatgacat cagtttctgg tcgcattcca ttaaatgtag aaaaatcaat taagaaagaa   2760
atggcacaat atgcttctaa tattacctct gttttatgtc aattcccatc acaacagatt   2820
gctaacattc ttgattcaca cgctgcaaca ttaaatcgta atcagaacg tgaagtattc   2880
ttcatgaata cacaaagtat tgttcaatta gttcaacgtt atcgcagtgg tattagaggt   2940
cacatgaaag ctgtagttat ggacttatta cgtcaatatt tacgcgtaga aactcaattt   3000
caaaatggtc attatgataa atgtgtattt gctttacgtg aagagaataa atcagacatg   3060
aatactgtac ttaactacat cttttctcat gcccaagtaa ctaagaagaa tttacttgtt   3120
actatgttaa tagatcaatt atgtggtcgc gatccaacat taactgatga attacttaat   3180
atccttacag aacttactca attaagtaaa actacaaatg ctaaagtggc tttacgtgct   3240
cgccaagtgc ttattgcttc tcatttacct tcttatgatg ttagacacaa tcaagttgaa   3300
tcaatctttc tttctgctat tgatatgtat ggacaccaat tctgtattga aaatttacaa   3360
aagttaattc ttagtgaaac atcaattttc gatgttttac caaatttctt ctatcactct   3420
aatcaagtgg ttcgtatggc tgctttagaa gtttatgttc gtcgtgctta tattgcttat   3480
gagttaaatt cagtacaaca tcgtcaatta aaagacaata cctgtgtagt agaatttcaa   3540
ttcatgcttc ctacttcaca tccaaatcgt ggtaatattc caactttaaa ccgtatgtca   3600
ttcgcatcta acttaaatca ctatggcatg actcatgtag catctgtgag tgacgtatta   3660
ttagataacg cttttacacc tccttgtcaa cgtatgggtg gtatggtttc tttccgtaca   3720
tttgaagatt tcgttcgtat ttttgacgaa gttatgggtt gttttgtga tagtccacca   3780
caaagtccaa catttccaga atcaggtcac actagcttat atgatgaaga taaagtacca   3840
cgtgatgaac caattcacat tcttaacgtt gcaattaaaa ctgatggtga tatcgaggat   3900
gaccgtttag ctgcaatgtt tagagagttt acacaacaaa ataaagcaac tttagttgaa   3960
catggtattc gtcgttttaac atttttagta gctcaaaaag atttccgtaa acaagtaaat   4020
tgtgaagtag atcaacgttt tcatcgtgaa tttccaaaat tctttacttt ccgtgctcgt   4080
gataaatttg aagaagatcg tatctatcgt catttagagc cagctttagc attccaatta   4140
gagcttaatc gtatgcgtaa ctttgattta actgcaatcc catgtgctaa tcataaaatg   4200
cacttatact aggcgcagc aaaagttgaa gtaggtacag aagttactga ttatcgtttc   4260
```

```
ttcgttcgtg caattattag acacagcgat ttagtaacaa aggaagcatc tttcgaatac    4320
ttacaaaacg aaggtgaaag acttttactt gaagcaatgg acgaattaga agttgctttc    4380
aataatacta atgttcgtac agattgcaat cacattttct taaactttgt tccaacagta    4440
attatggacc cttctaaaat tgaagaatca gtacgttcaa tggttatgcg ttatggttct    4500
cgcctttgga aattaagagt gttacaagct gaacttaaaa tcaatattcg tcttactaca    4560
actggtaaag caattccaat tcgtttattc cttactaacg aatcaggata ctatcttgat    4620
atttctcttt ataaagaagt aactgatagt cgtactgctc aaattatgtt ccaagcatac    4680
ggtgataaac aaggtccatt acatggaatg ttaatcaaca ctccttatgt tactaaggat    4740
ttattacaaa gtaaacgttt tcaagctcaa tctttaggta caacatacat ctatgacatc    4800
ccagaaatgt ttagacaatc tttaatcaaa ttatgggaat caatgtcaac tcaagcattt    4860
ttaccttcac cacctttacc tagtgacatt ttaacataca cagaattagt attagatgat    4920
caaggacaac ttgttcacat gaatcgttta ccaggcggta atgaaattgg tatggtagct    4980
tggaaaatgt ctcttaaaag cccagaatat ccagatggtc gtgatgttat tgtaatcggc    5040
aatgatatta catatcgcat tggttctttt ggtccacaag aggatctttt attcttacgt    5100
gctagtgagc ttgcacgtgc tgaaggtatt ccccgcattt atgtagctgc aaattcaggc    5160
gcccgtattg gattagctga agaaattcgt cacatgtttc acgtggcatg ggttgattca    5220
gaagatccat acaaaggtta caaatatctt tacttaactc cacaagacta taaacgtgtg    5280
agcgccttaa attctgttca ctgtgaacat gtagaagatg aaggtgaatc acgttacaaa    5340
attacagaca taattggtaa agaagaaggt cttggtgccg aaaatttacg tggaagtggt    5400
atgattgctg gtgaaagttc tttagcttat gatgagatta ttactattag cttagtaact    5460
tgtcgtgcca ttggtattgg tgcatattta gtacgtcttg gtcaacgtac aattcaagta    5520
gaaaatagtc accttatctt aacaggtgca ggcgcactta ataaagtatt aggtcgtgaa    5580
gtatatacaa gtaataacca acttggaggt attcaaataa tgcacaataa cggtgtaaca    5640
cattgtacag tgtgtgatga tttcgaaggt gtatttactg tacttcactg gttatcatat    5700
atgcctaaaa atgtacatag ttcagtacca ttacttaata gtaaagatcc aattgaccgt    5760
ataattgaat ttgtacctac aaaagctcct tatgacccct gttggatgtt agctggtcgt    5820
ccccatccca ctcaaaaagg tcaatggctt agtggatttt tcgattatgg cagctttagt    5880
gaaattatgc aaccctgggc tcaaacagta gtagtaggta gagctcgttt aggtggaatc    5940
cctgtgggta gttgctgt agaaactaga acagtagaac tttcagtacc tgctgatcca    6000
gccaatttag attctgaagc caaatcatt caacaagccg gtcaagtatg gtttcccgat    6060
tctgctttca aaacatatca agcaattaaa gatttcaacc gtgaaggttt acctttaatg    6120
gtattcgcta actggcgtgg tttttctggt ggtatgaaag atatgtatga ccaagttctt    6180
aagttcggtg cctacatcgt ggatggatta cgtgaatgtt ctcaaccagt tatggtatat    6240
attccaccac aagccgaatt acgtggtggc tcttgggttg ttattgatcc aactattaac    6300
ccaagacaca tggaaatgta tgctgatcgt gagtctcgtg gatcagtatt agaaccagaa    6360
ggtactgttg aaataaagtt tcgtaaaaag gatttagtga aaactatgcg tcgtgtagat    6420
cctgtttata ttcgccttgc agaacgttta ggcacccag aattaagtcc aacagaacgt    6480
aaagaattag agtctaagtt aaaagaaaga gaagagttct taattcctat ttaccaccag    6540
gtggcagttc aatttgctga tttacatgat acaccaggtc gtatgcaaga aaaaggtgtt    6600
attaacgaca ttttagattg gaaaacttca cgtacatttt tctactggcg tttacgtcgt    6660
```

-continued

| | |
|---|---|
| cttttacttg aagatttagt gaaaagaaa attcattcag caaatccaga attaacagat | 6720 |
| ggtcaaatac aagctatgct tcgtcgctgg ttcgtagaag ttgagggcac agtgaaagca | 6780 |
| tacgtttggg ataacaataa agacttagtg gaatggttag aaaagcagtt aactgaagaa | 6840 |
| gatggtgtgc gttcagtaat tgaagaaaac atcaaatata tctcacgtga ttatgtatta | 6900 |
| aaacaaattc gttcattagt acaagctaat ccagaagttg ctatggatag cattgttcac | 6960 |
| atgactcaac atattagtcc aacacaacgt gcagaagttg taagaatttt atcaactatg | 7020 |
| gattcaccaa gtacttaa | 7038 |

<210> SEQ ID NO 115
<211> LENGTH: 7038
<212> TYPE: DNA
<213> ORGANISM: Rattus norvegicus

<400> SEQUENCE: 115

| | |
|---|---|
| atggatgaac catctccgtt ggccaaaacc ctggagctga accagcactc ccgattcata | 60 |
| attgggtccg tgtctgaaga caactcagaa gatgagatca gtaacctggt aaagctggac | 120 |
| ctagaggaga aggagggctc cctgtcacca gcctctgtca gctcagatac actttctgat | 180 |
| ttgggaatct ctgccttaca ggatggtttg gcctttcaca tgaggtccag catgtccggc | 240 |
| ttgcacctag taaacaagg tcgagacaga aagaaaatag actctcaacg agatttcact | 300 |
| gtggcttcgc cagcagaatt tgttactcgt tttgggggaa ataaagtgat tgagaaggtt | 360 |
| cttatcgcca acaatggtat tgcagcagtg aaatgcatgc gatctatccg gcggtggtct | 420 |
| tatgaaatgt tccgcaatga acgtgccatc cggtttgttg tcatggttac acccgaagac | 480 |
| cttaaagcca atgcagaata cattaagatg gcggatcact atgttccagt gcctggagga | 540 |
| gcaaacaaca acaattatgc aaatgtggaa ttgattcttg atattgcgaa aaggatacct | 600 |
| gtacaggcag tgtgggctgg ctggggtcat gcctccgaga accccaagct cccggagcta | 660 |
| ctcttaaaaa atggcattgc tttcatgggc cctccgagtc aggccatgtg ggcgttgggg | 720 |
| gataagattg catcgtctat tgtggctcaa actgcaggta tccccactct tccctggagt | 780 |
| ggcagtggtc ttcgagtgga ttggcaagaa aatgattttt cgaaacgcat cttaaatgtt | 840 |
| ccacaggatc tgtatgagaa aggctatgtg aaggatgtgg atgatggact gaaggcagcc | 900 |
| gaggaggttg gctatccagt gatgatcaag gcctcagagg aggaggagg aaggaatc | 960 |
| agaaaagtta caatgcaga tgacttccct aacctcttca gacaggttca agctgaagtc | 1020 |
| cctggatcac ctatatttgt aatgagatta gcaaaacagt ctcgtcatct ggaggtccag | 1080 |
| attctggcgg atcagtatgg caatgcaatt tctttgtttg gtcgtgactg ctctgtacaa | 1140 |
| cgcaggcatc agaagatcat tgaagaagct cctgctgcta ttgctacccc agcagtattt | 1200 |
| gaacacatgg aacagtgtgc tgtaaaactt gccaaaatgg ttggttatgt gagcgctggg | 1260 |
| actgtggaat acttgtacag ccaggacgga agcttctact tcttggaact gaaccctcgg | 1320 |
| ctacaggttg aacatccttg tacagagatg gtggctgatg tcaatcttcc tgcagcacag | 1380 |
| ctccagattg ccatggggat ccctctattt aggatcaagg atattcgtat gatgtatggg | 1440 |
| gtatctcctt ggggtgatgc tcccattgat tttgaaaatt ctgctcatgt tccttgccca | 1500 |
| aggggccatg tgattgctgc tcggatcacc agtgaaaacc cagatgaggg gtttaagccc | 1560 |
| agctctggaa cagttcagga acttaatttt cgcagcaata gaatgtttg gggttatttc | 1620 |
| agtgttgctg ctgctggggg acttcatgaa tttgctgatt ctcagttcgg tcactgcttt | 1680 |

-continued

```
tcctggggag aaaacagaga agaagcaatt tcaaatatgg tggtggcatt gaaggagctg    1740
tctattcggg gtgactttcg aactacagta gaatacctca tcaagctgct ggagacagaa    1800
agctttcagt tgaacagaat cgacactggc tggctggaca gactgattgc agagaaagtg    1860
caggcagagc gtcctgacac catgttggga gttgtgtgtg ggctcttca tgtggcagat     1920
gtgaacctga gaaatagcat ctctaacttc cttcactcct tagagagggg tcaagtcctt    1980
cctgctcaca cacttctgaa cacagtagat gttgaactta tctatgaagg aatcaaatat    2040
gtacttaagg tgactcggca gtctcccaac tcctacgtgg tgataatgaa cggctcgtgt    2100
gtggaagtgg acgtgcaccg gctgagtgat ggtggactgc tcttgtccta cgatggcagc    2160
agttacacca catacatgaa ggaggaggta gacagatacc gaatcacaat tggcaataaa    2220
acctgtgtgt ttgagaagga aaatgacccg tctgtaatgc gctccccgtc tgctgggaag    2280
ttaatccagt atattgtgga agatggaggc catgtgtttg ctggccagtg ctatgcagag    2340
attgaggtaa tgaagatggt aatgactttg acagctgtag aatctggctg catccattat    2400
gtcaagcgac ctggagcagc acttgaccca ggctgtgtga tagccaaaat gcagctggac    2460
aatcccagta aagttcaaca ggctgagctt cacacgggca gtctgcccca gatccagagc    2520
acagctctcc gaggcgaaaa gctccatcga gttttccact atgtcctgga taacctggtc    2580
aatgtgatga atggatactg ccttccagac ccttcttca gcagcaaggt aaaggactgg    2640
gtagaacggt taatgaagac tctgagagac ccctccctgc ctcttctaga attgcaggat    2700
atcatgacca gtgtctctgg ccggatcccc ctcaacgtgg agaagtctat taagaaggaa    2760
atggctcagt atgctagcaa catcacatcg gtcctgtgtc agtttcccag ccagcagatt    2820
gccaacatcc tagatagtca tgcagctaca ctgaaccgga atcggagcg ggaagtcttc    2880
ttcatgaaca cccagagcat tgtccagctg gtgcagaggt accgaagtgg catccgtggc    2940
cacatgaagg ctgtggtgat ggatctgctc cggcagtacc tgcgggtgga gacacagttt    3000
cagaatggcc actacgacaa atgtgtattc gccctcgggg aagagaacaa aagtgacatg    3060
aacaccgtac tgaactacat cttctcccac gcccaggtca ccaagaagaa tctcctggtg    3120
acaatgctta ttgatcagtt gtgtggccgg gaccctacac ttactgatga gctgctaaac    3180
atcctcacag agctaactca gctcagcaaa accaccaacg ccaaagtggc actgcgggct    3240
cgccaggttc ttattgcctc ccatttgcca tcgtacgacg ttcgccataa ccaagtagag    3300
tccatcttct tatcagccat cgacatgtat ggacaccagt tttgcattga aacctgcag    3360
aaactcatcc tatcagaaac atctattttc gatgtcctcc caaacttttt ttaccacagc    3420
aaccaggtgg tgaggatggc ggctctggag gtatatgttc gaagagctta tatcgcctat    3480
gagctcaaca gtgtacagca tcgccagctt aaggacaaca cctgtgtggt agaatttcag    3540
ttcatgctgc ccacatctca tccaaacaga gggaacatcc ccacgctaaa cagaatgtcc    3600
tttgcctcca acctcaacca ctacggcatg actcatgtag ctagtgtcag cgatgttctg    3660
ttggacaacg ccttcacacc accttgtcaa cgcatgggcg ggatggtctc tttccggacc    3720
tttgaagatt tcgtcaggat ctttgatgaa gtaatgggct gcttctgcga ctccccaccc    3780
caaagcccca cattcccaga gtccggtcac acttcactct atgatgagga caaggtcccc    3840
agggacgaac caatacatat tctgaatgtg gctatcaaga ctgatggcga tattgaggat    3900
gacaggcttg cagctatgtt cagagagttc acccaacaga ataaagctac tctggttgag    3960
catgggatcc ggcgacttac gttcctagtt gcacaaaagg atttcagaaa acaagtcaac    4020
tgtgaggtgg atcagagatt tcatagagaa ttccccaaat ttttcacatt ccgagcaagg    4080
```

```
gataagtttg aggaggaccg catttatcga catctggagc ctgctctggc tttccagtta    4140
gagctgaacc ggatgagaaa ttttgacctt actgccattc catgcgctaa tcacaagatg    4200
cacctgtacc ttggggctgc taaggtggaa gtaggcacag aagtgactga ctacaggttc    4260
tttgttcgtg cgatcatcag gcactctgat ctggtcacga aggaagcttc ttttgaatat    4320
ctacaaaatg aaggagagcg actgctcctg gaagccatgg atgaattgga agttgctttc    4380
aataacacaa atgttcgcac agactgtaac catatattcc tcaactttgt gcccacagtc    4440
atcatggacc catcaaagat tgaagaatct gtgcggagca tggtaatgcg ctatggaagc    4500
cggctgtgga aattgcgggt cctccaggca gaactgaaaa tcaacattcg cctgacaaca    4560
actggaaaag cgattcccat ccgcctcttc ctgacaaacg agtctggcta ctacttggac    4620
atcagcctgt ataaggaagt gactgactcc aggacagcac agatcatgtt tcaggcgtat    4680
ggagacaagc agggaccact gcatggaatg ttaatcaata ctccgtatgt gaccaaagac    4740
cttcttcaat caaagaggtt tcaggcacag tccttgggaa caacgtatat atatgatatc    4800
ccagagatgt ttcggcagtc gctcatcaag ctctgggagt ccatgtccac tcaagcattt    4860
cttccttcac ccccttttgcc ttccgacata ctgacgtata ctgaactggt gttggatgat    4920
caaggccagc ttgtccatat gaacagactt ccaggaggaa acgagattgg catggtagcc    4980
tggaaaatga gccttaaaag ccctgaatat ccagatggcc gagatgtcat tgtcatcggc    5040
aatgacatta catatcggat tggctccttt gggcctcagg aagatttgct gtttctcaga    5100
gcttctgaac ttgccagagc agaaggcatc ccacgcatct acgtagcagc caacagtgga    5160
gctagaattg gactggcaga agaaatccgt catatgttcc acgtggcctg ggtagactct    5220
gaggatcctt acaagggata caagtattta tatctgacac cccaggatta taaaagagtg    5280
agtgctctca attctgtcca ctgtgaacat gtggaagatg aaggagaatc caggtacaag    5340
ataacagaca ttatcgggaa agaagaagga cttggagcag agaaccttcg gggttctgga    5400
atgattgctg gggaatcctc attggcttat gatgagatca tcaccatcag cctggttaca    5460
tgccgggcca ttggtattgg ggcttacctt gtccggctgg acaaagaac catccaggtt    5520 gagaactctc acttaattct aacaggagcc ggtgccctca caaagtcct tggtcgggaa    5580 gtatacacct ccaacaatca gcttgggggc atccagataa tgcacaacaa cggagttacc    5640
cattgcactg tttgtgatga ctttgaggga gtgttcacag tcttacactg gctgtcatac    5700
atgcctaaga acgtgcacag ttcagttcct ctcctgaatt ccaaggatcc tatagataga    5760
atcatcgagt ttgttcccac aaaggccccg tatgatcctc ggtggatgct ggcaggccgt    5820
cctcacccaa cccagaaagg ccaatggttg agtggatttt ttgattatgg ctctttctca    5880
gaaatcatgc agccctgggc gcagaccgtg gtagttggca gagccaggtt ggggggaata    5940
cctgtgggag tagttgctgt agaaacccga accgtggagc tcagtgtacc agctgatcct    6000
gcaaacctgg attctgaagc caagataatc cagcaggccg gccaagtttg gtttccagac    6060
tctgcattta agacctatca agctatcaag gactttaacc gtgaagggct acctctaatg    6120
gtctttgcca actggagagg cttctctggt gggatgaaag atatgtatga ccaggtgctc    6180
aagtttggtg cttatattgt ggatggcttg cgggaatgtt cccagcctgt gatggtctac    6240
attcccccac aggctgagct tcggggtggt tcttgggttg tgatcgaccc aaccatcaat    6300
cctcggcaca tggagatgta tgctgaccgg gaaagcaggg gatccgttct ggaaccagaa    6360
gggacagtag aaatcaaatt ccgcaaaaag gatctggtga aaaccatgcg tcgcgtagac    6420
```

```
ccagtctaca tccgcttggc tgagcgactg ggcaccccag agctaagccc cactgagcgg    6480
aaggagctgg agagcaagtt gaaggagcgg gaggagttcc taattcccat ttaccatcag    6540
gtagctgtgc agtttgctga cttgcacgac accccaggcc ggatgcagga gaagggtgtc    6600
attaatgata tcttagattg gaaaacatcc cgcaccttct tctactggcg actgaggcgt    6660
ctcctgctgg aagacctggt caagaagaaa atccacagtg ccaaccctga gctgaccgat    6720
ggccagatcc aggccatgtt gagcgctggt tttgtggaag tggaaggcac agtgaaggct    6780
tacgtctggg acaataataa ggatctggtg aatggctgga gaagcagct gacagaggaa     6840 gatggtgtcc gctctgtgat agaggagaac atcaaataca tcagcaggga ctatgtcctc    6900
aagcagatcc gcagcttggt gcaggccaat ccagaagttc ccatggactc catcgtccac    6960
atgacccagc acatctcccc cactcagcga gcagaggttg taaggatcct ttccactatg    7020 gactccccctt ctacgtag                                                 7038
```

<210> SEQ ID NO 116
<211> LENGTH: 24
<212> TYPE: DNA
<213> ORGANISM: Artificial Sequence
<220> FEATURE:
<223> OTHER INFORMATION: Flag tag

<400> SEQUENCE: 116

```
gattataaag atgatgatga caaa                                             24
```

<210> SEQ ID NO 117
<211> LENGTH: 24
<212> TYPE: DNA
<213> ORGANISM: Artificial Sequence
<220> FEATURE:
<223> OTHER INFORMATION: Flag tag

<400> SEQUENCE: 117

```
gactacaaag acgacgacga caaa                                             24
```

<210> SEQ ID NO 118
<211> LENGTH: 8
<212> TYPE: PRT
<213> ORGANISM: Artificial Sequence
<220> FEATURE:
<223> OTHER INFORMATION: Flag tag

<400> SEQUENCE: 118

```
Asp Tyr Lys Asp Asp Asp Asp Lys
1               5
```

<210> SEQ ID NO 119
<211> LENGTH: 28
<212> TYPE: DNA
<213> ORGANISM: Artificial Sequence
<220> FEATURE:
<223> OTHER INFORMATION: PCR Primer

<400> SEQUENCE: 119

```
ggacgtcctg ccaactgcct atggtagc                                         28
```

<210> SEQ ID NO 120
<211> LENGTH: 31
<212> TYPE: DNA
<213> ORGANISM: Artificial Sequence
<220> FEATURE:
<223> OTHER INFORMATION: PCR Primer

```
<400> SEQUENCE: 120
gttgagggca cagtgaaagc atacgtttgg g                              31

<210> SEQ ID NO 121
<211> LENGTH: 20
<212> TYPE: DNA
<213> ORGANISM: Artificial Sequence
<220> FEATURE:
<223> OTHER INFORMATION: PCR Primer

<400> SEQUENCE: 121
tgtttgttaa ggctagctgc                                           20

<210> SEQ ID NO 122
<211> LENGTH: 21
<212> TYPE: DNA
<213> ORGANISM: Artificial Sequence
<220> FEATURE:
<223> OTHER INFORMATION: PCR Primer

<400> SEQUENCE: 122
cgccactgtc atcctttaag t                                         21

<210> SEQ ID NO 123
<211> LENGTH: 20
<212> TYPE: DNA
<213> ORGANISM: Artificial Sequence
<220> FEATURE:
<223> OTHER INFORMATION: PCR Primer

<400> SEQUENCE: 123
ccgaactgag gttgggttta                                           20

<210> SEQ ID NO 124
<211> LENGTH: 20
<212> TYPE: DNA
<213> ORGANISM: Artificial Sequence
<220> FEATURE:
<223> OTHER INFORMATION: PCR Primer

<400> SEQUENCE: 124
gggggagcga ataggattag                                           20

<210> SEQ ID NO 125
<211> LENGTH: 23
<212> TYPE: DNA
<213> ORGANISM: Artificial Sequence
<220> FEATURE:
<223> OTHER INFORMATION: PCR primer

<400> SEQUENCE: 125
aaatttaacg taacgatgag ttg                                       23

<210> SEQ ID NO 126
<211> LENGTH: 23
<212> TYPE: DNA
<213> ORGANISM: Artificial Sequence
<220> FEATURE:
<223> OTHER INFORMATION: PCR primer

<400> SEQUENCE: 126
cagcagaaat tttagccatt tgc                                       23

<210> SEQ ID NO 127
<211> LENGTH: 1347
```

```
<212> TYPE: DNA
<213> ORGANISM: Artificial Sequence
<220> FEATURE:
<223> OTHER INFORMATION: codon-optimized SDACC2 with Flag tag

<400> SEQUENCE: 127
atggactaca aagacgacga cgacaaagta aacgctgtaa acccagaaaa aaacggtgct      60
tacgaaggtt caccaattgt atcaggtcca atttcagtag gtgctatgga caaagactca     120
aaaggttcat caaaaccagt agaccgttca aaggtttat ggacacgttg tgacaaatgt      180
ggtgtaattt tatacattaa acacttaaaa gaacaccacc acatttgttt cggttgtaac     240
taccacttaa aaatgtcatc acaagaacgt attgaccaca tgattgaccc aggttcatgg     300
cgtccattcg acgaaacatt atcaccatgt gacccattag acttcgtaga catgaaacca     360
tacccagacc gtgtacgtga ctcacaagac aaaacaggta tgaacgacgc tattcgtaca     420
ggtacaggtt tattacacgg tattccagta gctttagctg taatggaatt cggtttcatg     480
ggtggttcaa tgggttcagt agtaggtgaa aaattaacac gtttaattga atacgctaca     540
caagaaggtt taacattatt agtagtatgt acatcaggtg gtgctcgtat gcaagaaggt     600
attatgtcat taatgcaaat ggctaaaatt tcaggtgctt tacacgtaca ccaaaacgaa     660
gctaacttat tatacatttc aattttaaca tcaccaacaa caggtggtgt aacagcttca     720
ttcggtatgt taggtgacgt aattattgct gaaccacaag ctattattgg tttcgctggt     780
cgtcgtgtaa ttgaacaaac attacgtgaa gaattaccag acgacttcca aacagctgaa     840
tacttattag acaaaggttt attagactta gtagtaccac gttcattctt aaaaggtgct     900
ttattcgaaa ttattgactt ctacaaaaac gctccataca acgtcgtgg taaaattcca     960 ttcggtgtac aacgtggtac atacggttta acagctgaag aaaaaatgcg tcgtcgttgg    1020
cgtgaatggt catcagtagg ttcaatgtta cactcagtac actacgctgg tcactggcca    1080
tcaggttgtg ctggtatgtt attaggtcaa cgtccattac acatgcactg gcacgtaaac    1140
gaaggttcag gttgttcaaa acaacatgt caatcattca aatactggtc agcttgtgct    1200
gcttggcacg ctgtatgtca ccgtcgtggt acattattag aacacgaatt aacaaaatta   1260
atttcatggc aattcgactc atgttgttgg cgtgctgcta aggtatttt attacgttca    1320 tgtaacgctg tatacgtata cgtataa                                        1347

<210> SEQ ID NO 128
<211> LENGTH: 1281
<212> TYPE: DNA
<213> ORGANISM: Artificial Sequence
<220> FEATURE:
<223> OTHER INFORMATION: codon-optimized SDACC1 with Flag tag and
      mutation

<400> SEQUENCE: 128
atggactaca aagacgacga cgacaaagta aacgctgtaa acccagaaaa aaacggtgct      60
tacgaaggtt caccaattgt atcaggtcca atttcagtag gtgctatgga caaagactca     120
aaaggttcat caaaaccagt agaccgttca aaggtttat ggacacgttg tgacaaatgt      180
ggtgtaattt tatacattaa acacttaaaa gaacaccacc acatttgttt cggttgtaac     240
taccacttaa aaatgtcatc acaagaacgt attgaccaca tgattgaccc aggtgattgg    300
cgtccattcg acgaaacatt atcaccatgt gacccattag acttcgtaga catgaaacca     360
tacccagacc gtgtacgtga ctcacaagac aaaacaggta tgaacgacgc tattcgtaca     420
ggtacaggtt tattacacgg tattccagta gctttagctg taatggaatt cggtttcatg     480
```

```
ggtggttcaa tgggttcagt agtaggtgaa aaattaacac gtttaattga atacgctaca      540
caagaaggtt taacattatt agtagtatgt acatcaggtg gtgctcgtat gcaagaaggt      600
attatgtcat taatgcaaat ggctaaaatt tcaggtgctt tacacgtaca ccaaaacgaa      660
gctaacttat tatacatttc aattttaaca tcaccaacaa caggtggtgt aacagcttca      720
ttcggtatgt taggtgacgt aattattgct gaaccacaag ctattattgg tttcgctggt      780
cgtcgtgtaa ttgaacaaac attacgtgaa gaattaccag acgacttcca aacagctgaa      840
tacttattag acaaaggttt attagactta gtagtaccac gttcattctt aaaaggtgct      900
ttattcgaaa ttattgactt ctacaaaaac gctccataca aacgtcgtgg taaaattcca      960
ttcggtgtac aacgtggtac atacggttta acagctgaag aaaaaaatgcg tcgtcgttgg     1020 cgtgaatggt catcagctgg ttcaaacggt tcaggtacac cagctttagc tgctgctgct     1080
gcttcagctg ctgtaggttc agctgctaca tgtggttcat gtcaacaaca acaattagct     1140
ttatgggctg tattagctgg ttgtggttca tgtggtcaat ggttatggtt cgctcaaggt     1200
gtaggtgctt tagaacgtac agctgctaca gctgctgtat acgtgaaggg ttcagtatta     1260
ttagctggtg tatgttgtta a                                                1281
```

<210> SEQ ID NO 129
<211> LENGTH: 1281
<212> TYPE: DNA
<213> ORGANISM: Artificial Sequence
<220> FEATURE:
<223> OTHER INFORMATION: codon-optimized SDACC1 with Flag tag and
      mutation

<400> SEQUENCE: 129

```
atggactaca agacgacga cgacaaagta aacgctgtaa acccagaaaa aaacggtgct       60
tacgaaggtt caccaattgt atcaggtcca atttcagtag gtgctatgga caaagactca      120
aaaggttcat caaaaccagt agaccgttca aaaggtttat ggacacgttg tgacaaatgt      180
ggtgtaattt tatacattaa acacttaaaa gaacaccacc acatttgttt cggttgtaac      240
taccacttaa aaatgtcatc acaagaacgt attgaccaca tgattgaccc aggttcatgg      300
cgtccattcg acgaagattt atcaccatgt gacccattag acttcgtaga catgaaacca      360
tacccagacc gtgtacgtga ctcacaagac aaaacaggta tgaacgacgc tattcgtaca      420
ggtacaggtt tattacacgg tattccagta gctttagctg taatggaatt cggtttcatg      480
ggtggttcaa tgggttcagt agtaggtgaa aaattaacac gtttaattga atacgctaca      540
caagaaggtt taacattatt agtagtatgt acatcaggtg gtgctcgtat gcaagaaggt      600
attatgtcat taatgcaaat ggctaaaatt tcaggtgctt tacacgtaca ccaaaacgaa      660
gctaacttat tatacatttc aattttaaca tcaccaacaa caggtggtgt aacagcttca      720
ttcggtatgt taggtgacgt aattattgct gaaccacaag ctattattgg tttcgctggt      780
cgtcgtgtaa ttgaacaaac attacgtgaa gaattaccag acgacttcca aacagctgaa      840
tacttattag acaaaggttt attagactta gtagtaccac gttcattctt aaaaggtgct      900
ttattcgaaa ttattgactt ctacaaaaac gctccataca aacgtcgtgg taaaattcca      960
ttcggtgtac aacgtggtac atacggttta acagctgaag aaaaaaatgcg tcgtcgttgg     1020 cgtgaatggt catcagctgg ttcaaacggt tcaggtacac cagctttagc tgctgctgct     1080
gcttcagctg ctgtaggttc agctgctaca tgtggttcat gtcaacaaca acaattagct     1140
ttatgggctg tattagctgg ttgtggttca tgtggtcaat ggttatggtt cgctcaaggt     1200
```

```
gtaggtgctt tagaacgtac agctgctaca gctgctgtat tacgtgaagg ttcagtatta    1260
ttagctggtg tatgttgtta a                                              1281
```

<210> SEQ ID NO 130
<211> LENGTH: 1281
<212> TYPE: DNA
<213> ORGANISM: Artificial Sequence
<220> FEATURE:
<223> OTHER INFORMATION: codon-optimized SDACC1 with Flag tag and
      mutation

<400> SEQUENCE: 130

```
atggactaca aagacgacga cgacaaagta aacgctgtaa acccagaaaa aaacggtgct     60
tacgaaggtt caccaattgt atcaggtcca atttcagtag gtgctatgga caaagactca    120
aaaggttcat caaaaccagt agaccgttca aaaggtttat ggacacgttg tgacaaatgt    180
ggtgtaattt tatacattaa acacttaaaa gaacaccacc acatttgttt cggttgtaac    240
taccacttaa aaatgtcatc acaagaacgt attgaccaca tgattgaccc aggttcatgg    300
cgtccattcg acgaaacatt agatccatgt gacccattag acttcgtaga catgaaacca    360
tacccagacc gtgtacgtga ctcacaagac aaaacaggta tgaacgacgc tattcgtaca    420
ggtacaggtt tattacacgg tattccagta gctttagctg taatggaatt cggtttcatg    480
ggtggttcaa tgggttcagt agtaggtgaa aaattaacac gtttaattga atacgctaca    540
caagaaggtt taacattatt agtagtatgt acatcaggtg gtgctcgtat gcaagaaggt    600
attatgtcat taatgcaaat ggctaaaatt tcaggtgctt tacacgtaca ccaaaacgaa    660
gctaacttat tatacatttc aattttaaca tcaccaacaa caggtggtgt aacagcttca    720
ttcggtatgt taggtgacgt aattattgct gaaccacaag ctattattgg tttcgctggt    780
cgtcgtgtaa ttgaacaaac attacgtgaa gaattaccag acgacttcca aacagctgaa    840
tacttattag acaaaggttt attagactta gtagtaccac gttcattctt aaaaggtgct    900
ttattcgaaa ttattgactt ctacaaaaac gctccataca acgtcgtgg taaaattcca    960 tcggtgtac aacgtggtac atacggttta acagctgaag aaaaaaatgcg tcgtcgttgg   1020 cgtgaatggt catcagctgg ttcaaacggt tcaggtacac cagctttagc tgctgctgct   1080
gcttcagctg ctgtaggttc agctgctaca tgtggttcat gtcaacaaca acaattagct   1140
ttatgggctg tattagctgg ttgtggttca tgtggtcaat ggttatggtt cgctcaaggt   1200
gtaggtgctt tagaacgtac agctgctaca gctgctgtat tacgtgaagg ttcagtatta   1260
ttagctggtg tatgttgtta a                                             1281
```

<210> SEQ ID NO 131
<211> LENGTH: 1281
<212> TYPE: DNA
<213> ORGANISM: Artificial Sequence
<220> FEATURE:
<223> OTHER INFORMATION: codon-optimized SDACC1 with Flag tag and
      mutation

<400> SEQUENCE: 131

```
atggactaca aagacgacga cgacaaagta aacgctgtaa acccagaaaa aaacggtgct     60
tacgaaggtt caccaattgt atcaggtcca atttcagtag gtgctatgga caaagactca    120
aaaggttcat caaaaccagt agaccgttca aaaggtttat ggacacgttg tgacaaatgt    180
ggtgtaattt tatacattaa acacttaaaa gaacaccacc acatttgttt cggttgtaac    240
```

| | |
|---|---|
| taccacttaa aaatgtcatc acaagaacgt attgaccaca tgattgaccc aggttcatgg | 300 |
| cgtccattcg acgaaacatt atcaccatgt gacccattag acttcgatga catgaaacca | 360 |
| tacccagacc gtgtacgtga ctcacaagac aaaacaggta tgaacgacgc tattcgtaca | 420 |
| ggtacaggtt tattacacgg tattccagta gctttagctg taatggaatt cggtttcatg | 480 |
| ggtggttcaa tgggttcagt agtaggtgaa aaattaacac gtttaattga atacgctaca | 540 |
| caagaaggtt taacattatt agtagtatgt acatcaggtg gtgctcgtat gcaagaaggt | 600 |
| attatgtcat taatgcaaat ggctaaaatt tcaggtgctt tacacgtaca ccaaaacgaa | 660 |
| gctaacttat tatacatttc aattttaaca tcaccaacaa caggtggtgt aacagcttca | 720 |
| ttcggtatgt taggtgacgt aattattgct gaaccacaag ctattattgg tttcgctggt | 780 |
| cgtcgtgtaa ttgaacaaac attacgtgaa gaattaccag acgacttcca acagctgaa | 840 |
| tacttattag acaaaggttt attagactta gtagtaccac gttcattctt aaaaggtgct | 900 |
| ttattcgaaa ttattgactt ctacaaaaac gctccataca acgtcgtgg taaaattcca | 960 |
| ttcggtgtac aacgtggtac atacggttta acagctgaag aaaaaatgcg tcgtcgttgg | 1020 |
| cgtgaatggt catcagctgg ttcaaacggt tcaggtacac cagctttagc tgctgctgct | 1080 |
| gcttcagctg ctgtaggttc agctgctaca tgtggttcat gtcaacaaca acaattagct | 1140 |
| ttatgggctg tattagctgg ttgtggttca tgtggtcaat ggttatggtt cgctcaaggt | 1200 |
| gtaggtgctt tagaacgtac agctgctaca gctgctgtat acgtgaagg ttcagtatta | 1260 |
| ttagctggtg tatgttgtta a | 1281 |

<210> SEQ ID NO 132
<211> LENGTH: 1281
<212> TYPE: DNA
<213> ORGANISM: Artificial Sequence
<220> FEATURE:
<223> OTHER INFORMATION: codon-optimized SDACC1 with Flag tag and mutation

<400> SEQUENCE: 132

| | |
|---|---|
| atggactaca agacgacga cgacaaagta aacgctgtaa acccagaaaa aaacggtgct | 60 |
| tacgaaggtt caccaattgt atcaggtcca atttcagtag gtgctatgga caagactca | 120 |
| aaaggttcat caaaaccagt agaccgttca aaaggtttat ggacacgttg tgacaaatgt | 180 |
| ggtgtaattt tatacattaa acacttaaaa gaacaccacc acatttgttt cggttgtaac | 240 |
| taccacttaa aaatgtcatc acaagaacgt attgaccaca tgattgaccc aggttcatgg | 300 |
| cgtccattcg acgaaacatt atcaccatgt gacccattag acttcgtaga catgaaagat | 360 |
| tacccagacc gtgtacgtga ctcacaagac aaaacaggta tgaacgacgc tattcgtaca | 420 |
| ggtacaggtt tattacacgg tattccagta gctttagctg taatggaatt cggtttcatg | 480 |
| ggtggttcaa tgggttcagt agtaggtgaa aaattaacac gtttaattga atacgctaca | 540 |
| caagaaggtt taacattatt agtagtatgt acatcaggtg gtgctcgtat gcaagaaggt | 600 |
| attatgtcat taatgcaaat ggctaaaatt tcaggtgctt tacacgtaca ccaaaacgaa | 660 |
| gctaacttat tatacatttc aattttaaca tcaccaacaa caggtggtgt aacagcttca | 720 |
| ttcggtatgt taggtgacgt aattattgct gaaccacaag ctattattgg tttcgctggt | 780 |
| cgtcgtgtaa ttgaacaaac attacgtgaa gaattaccag acgacttcca acagctgaa | 840 |
| tacttattag acaaaggttt attagactta gtagtaccac gttcattctt aaaaggtgct | 900 |
| ttattcgaaa ttattgactt ctacaaaaac gctccataca acgtcgtgg taaaattcca | 960 |

```
ttcggtgtac aacgtggtac atacggttta acagctgaag aaaaaatgcg tcgtcgttgg   1020
cgtgaatggt catcagctgg ttcaaacggt tcaggtacac cagctttagc tgctgctgct   1080
gcttcagctg ctgtaggttc agctgctaca tgtggttcat gtcaacaaca acaattagct   1140
ttatgggctg tattagctgg ttgtggttca tgtggtcaat ggttatggtt cgctcaaggt   1200
gtaggtgctt tagaacgtac agctgctaca gctgctgtat tacgtgaagg ttcagtatta   1260
ttagctggtg tatgttgtta a                                             1281
```

<210> SEQ ID NO 133
<211> LENGTH: 1281
<212> TYPE: DNA
<213> ORGANISM: Artificial Sequence
<220> FEATURE:
<223> OTHER INFORMATION: codon-optimized SDACC1 with Flag tag and mutation

<400> SEQUENCE: 133

```
atggactaca aagacgacga cgacaaagta aacgctgtaa acccagaaaa aaacggtgct     60
tacgaaggtt caccaattgt atcaggtcca atttcagtag gtgctatgga caaagactca    120
aaaggttcat caaaaccagt agaccgttca aaaggtttat ggacacgttg tgacaaatgt    180
ggtgtaattt tatacattaa acacttaaaa gaacaccacc acatttgttt cggttgtaac    240
taccacttaa aaatgtcatc acaagaacgt attgaccaca tgattgaccc aggttcatgg    300
cgtccattcg acgaaacatt atcaccatgt gacccattag acttcgtaga catgaaacca    360
tacccagacc gtgtacgtga cgatcaagac aaaacaggta tgaacgacgc tattcgtaca    420
ggtacaggtt tattacacgg tattccagta gctttagctg taatggaatt cggtttcatg    480
ggtggttcaa tgggttcagt agtaggtgaa aaattaacac gtttaattga atacgctaca    540
caagaaggtt taacattatt agtagtatgt acatcaggtg gtgctcgtat gcaagaaggt    600
attatgtcat taatgcaaat ggctaaaatt tcaggtgctt tacacgtaca ccaaaacgaa    660
gctaacttat tatacatttc aatttttaaca tcaccaacaa caggtggtgt aacagcttca    720
ttcggtatgt taggtgacgt aattattgct gaaccacaag ctattattgg tttcgctggt    780
cgtcgtgtaa ttgaacaaac attacgtgaa gaattaccag acgacttcca aacagctgaa    840
tacttattag acaaaggttt attagactta gtagtaccac gttcattctt aaaaggtgct    900
ttattcgaaa ttattgactt ctacaaaaac gctccataca aacgtcgtgg taaaattcca    960
ttcggtgtac aacgtggtac atacggttta acagctgaag aaaaaatgcg tcgtcgttgg   1020
cgtgaatggt catcagctgg ttcaaacggt tcaggtacac cagctttagc tgctgctgct   1080
gcttcagctg ctgtaggttc agctgctaca tgtggttcat gtcaacaaca acaattagct   1140
ttatgggctg tattagctgg ttgtggttca tgtggtcaat ggttatggtt cgctcaaggt   1200
gtaggtgctt tagaacgtac agctgctaca gctgctgtat tacgtgaagg ttcagtatta   1260
ttagctggtg tatgttgtta a                                             1281
```

<210> SEQ ID NO 134
<211> LENGTH: 1281
<212> TYPE: DNA
<213> ORGANISM: Artificial Sequence
<220> FEATURE:
<223> OTHER INFORMATION: codon-optimized SDACC1 with Flag tag and mutation

<400> SEQUENCE: 134

```
atggactaca aagacgacga cgacaaagta aacgctgtaa acccagaaaa aaacggtgct     60
```

```
tacgaaggtt caccaattgt atcaggtcca atttcagtag gtgctatgga caaagactca    120
aaaggttcat caaaaccagt agaccgttca aaggtttat ggacacgttg tgacaaatgt     180
ggtgtaattt tatacattaa acacttaaaa gaacaccacc acatttgttt cggttgtaac    240
taccacttaa aaatgtcatc acaagaacgt attgaccaca tgattgaccc aggttcatgg    300
cgtccattcg acgaaacatt atcaccatgt gacccattag acttcgtaga catgaaacca    360
tacccagacc gtgtacgtga ctcacaagac aaaacaggta tgaacgacgc tattcgtaca    420
ggtacaggtt tattacacgg tattccagta gctttagctg taatggaatt cggtttcatg    480
ggtggttcaa tgggttcagt agtaggtgaa aaattaacac gtttaattga atacgctaca    540
caagaaggtt taacattatt agtagtatgt acatcaggtg gtgctcgtat gcaagaaggt    600
attatgtcat taatgcaaat ggctaaaatt tcaggtgctt tacacgtaca ccaaaacgaa    660
gctaacttat tatacatttc aattttaaca tcaccaacaa caggtggtgt aacagcttca    720
ttcggtatgt taggtgacgt aattattgct gaaccacaag ctattattgg tttcgctggt    780
cgtcgtgtaa ttgaacaaga tttacgtgaa gaattaccag acgacttcca aacagctgaa    840
tacttattag acaaaggttt attagactta gtagtaccac gttcattctt aaaaggtgct    900
ttattcgaaa ttattgactt ctacaaaaac gctccataca acgtcgtgg taaaattcca    960 ttcggtgtac aacgtggtac atacggttta acagctgaag aaaaaatgcg tcgtcgttgg   1020
cgtgaatggt catcagctgg ttcaaacggt tcaggtacac cagctttagc tgctgctgct   1080
gcttcagctg ctgtaggttc agctgctaca tgtggttcat gtcaacaaca acaattagct   1140
ttatgggctg tattagctgg ttgtggttca tgtggtcaat ggttatggtt cgctcaaggt   1200
gtaggtgctt tagaacgtac agctgctaca gctgctgtat acgtgaaggg ttcagtatta   1260
ttagctggtg tatgttgtta a                                            1281
```

<210> SEQ ID NO 135
<211> LENGTH: 1347
<212> TYPE: DNA
<213> ORGANISM: Artificial Sequence
<220> FEATURE:
<223> OTHER INFORMATION: codon-optimized SDACC2 with Flag tag and
      mutation

<400> SEQUENCE: 135

```
atggactaca aagacgacga cgacaaagta aacgctgtaa acccagaaaa aaacggtgct     60
tacgaaggtt caccaattgt atcaggtcca atttcagtag gtgctatgga caaagactca    120
aaaggttcat caaaaccagt agaccgttca aaggtttat ggacacgttg tgacaaatgt     180
ggtgtaattt tatacattaa acacttaaaa gaacaccacc acatttgttt cggttgtaac    240
taccacttaa aaatgtcatc acaagaacgt attgaccaca tgattgaccc aggtgattgg    300
cgtccattcg acgaaacatt atcaccatgt gacccattag acttcgtaga catgaaacca    360
tacccagacc gtgtacgtga ctcacaagac aaaacaggta tgaacgacgc tattcgtaca    420
ggtacaggtt tattacacgg tattccagta gctttagctg taatggaatt cggtttcatg    480
ggtggttcaa tgggttcagt agtaggtgaa aaattaacac gtttaattga atacgctaca    540
caagaaggtt taacattatt agtagtatgt acatcaggtg gtgctcgtat gcaagaaggt    600
attatgtcat taatgcaaat ggctaaaatt tcaggtgctt tacacgtaca ccaaaacgaa    660
gctaacttat tatacatttc aattttaaca tcaccaacaa caggtggtgt aacagcttca    720
ttcggtatgt taggtgacgt aattattgct gaaccacaag ctattattgg tttcgctggt    780
```

```
cgtcgtgtaa ttgaacaaac attacgtgaa gaattaccag acgacttcca aacagctgaa      840
tacttattag acaaaggttt attagactta gtagtaccac gttcattctt aaaaggtgct      900
ttattcgaaa ttattgactt ctacaaaaac gctccataca aacgtcgtgg taaaattcca      960
ttcggtgtac aacgtggtac atacggttta acagctgaag aaaaaatgcg tcgtcgttgg     1020
cgtgaatggt catcagtagg ttcaatgtta cactcagtac actacgctgg tcactggcca     1080
tcaggttgtg ctggtatgtt attaggtcaa cgtccattac acatgcactg gcacgtaaac     1140
gaaggttcag gttgttcaaa acaacatgt caatcattca atactggtc agcttgtgct       1200 gcttggcacg ctgtatgtca ccgtcgtggt acattattag aacacgaatt aacaaaatta     1260
atttcatggc aattcgactc atgttgttgg cgtgctgcta aggtatttt attacgttca      1320 tgtaacgctg tatacgtata cgtataa                                         1347

<210> SEQ ID NO 136
<211> LENGTH: 1347
<212> TYPE: DNA
<213> ORGANISM: Artificial Sequence
<220> FEATURE:
<223> OTHER INFORMATION: codon-optimized SDACC2 with Flag tag and
      mutation

<400> SEQUENCE: 136
atggactaca agacgacga cgacaaagta aacgctgtaa acccagaaaa aaacggtgct       60
tacgaaggtt caccaattgt atcaggtcca atttcagtag gtgctatgga caaagactca     120
aaaggttcat caaaaccagt agaccgttca aaaggtttat ggacacgttg tgacaaatgt     180
ggtgtaattt tatacattaa acacttaaaa gaacaccacc acatttgttt cggttgtaac     240
taccacttaa aaatgtcatc acaagaacgt attgaccaca tgattgaccc aggttcatgg     300
cgtccattcg acgaagattt atcaccatgt gacccattag acttcgtaga catgaaacca     360
tacccagacc gtgtacgtga ctcacaagac aaaacaggta tgaacgacgc tattcgtaca     420
ggtacaggtt tattacacgg tattccagta gctttagctg taatggaatt cggtttcatg     480
ggtggttcaa tgggttcagt agtaggtgaa aaattaacac gtttaattga atacgctaca     540
caagaaggtt taacattatt agtagtatgt acatcaggtg gtgctcgtat gcaagaaggt     600
attatgtcat taatgcaaat ggctaaaatt tcaggtgctt tacacgtaca ccaaaacgaa     660
gctaacttat tatacatttc aattttaaca tcaccaacaa caggtggtgt aacagcttca     720
ttcggtatgt taggtgacgt aattattgct gaaccacaag ctattattgg tttcgctggt     780
cgtcgtgtaa ttgaacaaac attacgtgaa gaattaccag acgacttcca aacagctgaa     840
tacttattag acaaaggttt attagactta gtagtaccac gttcattctt aaaaggtgct     900
ttattcgaaa ttattgactt ctacaaaaac gctccataca aacgtcgtgg taaaattcca     960
ttcggtgtac aacgtggtac atacggttta acagctgaag aaaaaatgcg tcgtcgttgg    1020
cgtgaatggt catcagtagg ttcaatgtta cactcagtac actacgctgg tcactggcca    1080
tcaggttgtg ctggtatgtt attaggtcaa cgtccattac acatgcactg gcacgtaaac    1140
gaaggttcag gttgttcaaa acaacatgt caatcattca atactggtc agcttgtgct      1200 gcttggcacg ctgtatgtca ccgtcgtggt acattattag aacacgaatt aacaaaatta    1260
atttcatggc aattcgactc atgttgttgg cgtgctgcta aggtatttt attacgttca     1320 tgtaacgctg tatacgtata cgtataa                                        1347
```

<210> SEQ ID NO 137
<211> LENGTH: 1347
<212> TYPE: DNA
<213> ORGANISM: Artificial Sequence
<220> FEATURE:
<223> OTHER INFORMATION: codon-optimized SDACC2 with Flag tag and mutation

<400> SEQUENCE: 137

```
atggactaca aagacgacga cgacaaagta aacgctgtaa acccagaaaa aaacggtgct        60
tacgaaggtt caccaattgt atcaggtcca atttcagtag gtgctatgga caaagactca       120
aaaggttcat caaaaccagt agaccgttca aaaggtttat ggacacgttg tgacaaatgt       180
ggtgtaattt tatacattaa acacttaaaa gaacaccacc acatttgttt cggttgtaac       240
taccacttaa aaatgtcatc acaagaacgt attgaccaca tgattgaccc aggttcatgg       300
cgtccattcg acgaaacatt agatccatgt gacccattag acttcgtaga catgaaacca       360
tacccagacc gtacgtgac tcacaagac aaaacaggta tgaacgacgc tattcgtaca       420
ggtacaggtt tattacacgg tattccagta gctttagctg taatggaatt cggtttcatg       480
ggtggttcaa tgggttcagt agtaggtgaa aaattaacac gtttaattga atacgctaca       540
caagaaggtt taacattatt agtagtatgt acatcaggtg tgctcgtat gcaagaaggt       600 attatgtcat taatgcaaat ggctaaaatt tcaggtgctt tacacgtaca ccaaaacgaa       660
gctaacttat tatacatttc aattttaaca tcaccaacaa caggtggtgt aacagcttca       720
ttcggtatgt taggtgacgt aattattgct gaaccacaag ctattattgg tttcgctggt       780
cgtcgtgtaa ttgaacaaac attacgtgaa gaattaccag cgacttcca acagctgaa       840 tacttattag acaaggtttt attagactta gtagtaccac gttcattctt aaaaggtgct       900
ttattcgaaa ttattgactt ctacaaaaac gctccataca acgtcgtgg taaaattcca       960 ttcggtgtac aacgtggtac atacggttta acagctgaag aaaaaatgcg tcgtcgttgg      1020
cgtgaatggt catcagtagg ttcaatgtta cactcagtac actacgctgg tcactggcca      1080
tcaggttgtg ctggtatgtt attaggtcaa cgtccattac acatgcactg gcacgtaaac      1140
gaaggttcag ttgttcaaa acaacatgt caatcattca atactggtc agcttgtgct      1200 gcttggcacg ctgtatgtca ccgtcgtggt acattattag aacacgaatt aacaaaatta      1260
atttcatggc aattcgactc atgttgttgg cgtgctgcta aggtatttt attacgttca      1320 tgtaacgctg tatacgtata cgtataa                                           1347
```

<210> SEQ ID NO 138
<211> LENGTH: 1347
<212> TYPE: DNA
<213> ORGANISM: Artificial Sequence
<220> FEATURE:
<223> OTHER INFORMATION: codon-optimized SDACC2 with Flag tag and mutation

<400> SEQUENCE: 138

```
atggactaca aagacgacga cgacaaagta aacgctgtaa acccagaaaa aaacggtgct        60
tacgaaggtt caccaattgt atcaggtcca atttcagtag gtgctatgga caaagactca       120
aaaggttcat caaaaccagt agaccgttca aaaggtttat ggacacgttg tgacaaatgt       180
ggtgtaattt tatacattaa acacttaaaa gaacaccacc acatttgttt cggttgtaac       240
taccacttaa aaatgtcatc acaagaacgt attgaccaca tgattgaccc aggttcatgg       300
cgtccattcg acgaaacatt atcaccatgt gacccattag acttcgatga catgaaacca       360
```

```
tacccagacc gtgtacgtga ctcacaagac aaaacaggta tgaacgacgc tattcgtaca      420
ggtacaggtt tattacacgg tattccagta gctttagctg taatggaatt cggtttcatg      480
ggtggttcaa tgggttcagt agtaggtgaa aaattaacac gtttaattga atacgctaca      540
caagaaggtt taacattatt agtagtatgt acatcaggtg gtgctcgtat gcaagaaggt      600
attatgtcat taatgcaaat ggctaaaatt tcaggtgctt tacacgtaca ccaaaacgaa      660
gctaacttat tatacatttc aatttaaca tcaccaacaa caggtggtgt aacagcttca       720
ttcggtatgt taggtgacgt aattattgct gaaccacaag ctattattgg tttcgctggt      780
cgtcgtgtaa ttgaacaaac attacgtgaa gaattaccag acgacttcca aacagctgaa      840
tacttattag acaaaggttt attagactta gtagtaccac gttcattctt aaaaggtgct      900
ttattcgaaa ttattgactt ctacaaaaac gctccataca aacgtcgtgg taaaattcca      960
ttcggtgtac aacgtggtac atacggttta acagctgaag aaaaaatgcg tcgtcgttgg     1020
cgtgaatggt catcagtagg ttcaatgtta cactcagtac actacgctgg tcactggcca     1080
tcaggttgtg ctggtatgtt attaggtcaa cgtccattac acatgcactg gcacgtaaac     1140
gaaggttcag gttgttcaaa acaacatgt caatcattca aatactggtc agcttgtgct      1200
gcttggcacg ctgtatgtca ccgtcgtggt acattattag aacacgaatt aacaaaatta     1260
atttcatggc aattcgactc atgttgttgg cgtgctgcta aggtatttt attacgttca      1320 tgtaacgctg tatacgtata cgtataa                                         1347

<210> SEQ ID NO 139
<211> LENGTH: 1347
<212> TYPE: DNA
<213> ORGANISM: Artificial Sequence
<220> FEATURE:
<223> OTHER INFORMATION: codon-optimized SDACC2 with Flag tag and
      mutation

<400> SEQUENCE: 139
atggactaca aagacgacga cgacaaagta aacgctgtaa acccagaaaa aaacggtgct       60
tacgaaggtt caccaattgt atcaggtcca atttcagtag gtgctatgga caaagactca      120
aaaggttcat caaaaccagt agaccgttca aaaggtttat ggacacgttg tgacaaatgt      180
ggtgtaattt tatacattaa acacttaaaa gaacaccacc acatttgttt cggttgtaac      240
taccacttaa aaatgtcatc acaagaacgt attgaccaca tgattgaccc aggttcatgg      300
cgtccattcg acgaaacatt atcaccatgt gacccattag acttcgtaga catgaaagat      360
tacccagacc gtgtacgtga ctcacaagac aaaacaggta tgaacgacgc tattcgtaca      420
ggtacaggtt tattacacgg tattccagta gctttagctg taatggaatt cggtttcatg      480
ggtggttcaa tgggttcagt agtaggtgaa aaattaacac gtttaattga atacgctaca      540
caagaaggtt taacattatt agtagtatgt acatcaggtg gtgctcgtat gcaagaaggt      600
attatgtcat taatgcaaat ggctaaaatt tcaggtgctt tacacgtaca ccaaaacgaa      660
gctaacttat tatacatttc aatttaaca tcaccaacaa caggtggtgt aacagcttca       720
ttcggtatgt taggtgacgt aattattgct gaaccacaag ctattattgg tttcgctggt      780
cgtcgtgtaa ttgaacaaac attacgtgaa gaattaccag acgacttcca aacagctgaa      840
tacttattag acaaaggttt attagactta gtagtaccac gttcattctt aaaaggtgct      900
ttattcgaaa ttattgactt ctacaaaaac gctccataca aacgtcgtgg taaaattcca      960
ttcggtgtac aacgtggtac atacggttta acagctgaag aaaaaatgcg tcgtcgttgg     1020
```

-continued

```
cgtgaatggt catcagtagg ttcaatgtta cactcagtac actacgctgg tcactggcca    1080
tcaggttgtg ctggtatgtt attaggtcaa cgtccattac acatgcactg gcacgtaaac    1140
gaaggttcag gttgttcaaa acaacatgt caatcattca aatactggtc agcttgtgct     1200
gcttggcacg ctgtatgtca ccgtcgtggt acattattag aacacgaatt aacaaaatta    1260
atttcatggc aattcgactc atgttgttgg cgtgctgcta aaggtatttt attacgttca    1320
tgtaacgctg tatacgtata cgtataa                                         1347
```

<210> SEQ ID NO 140
<211> LENGTH: 1347
<212> TYPE: DNA
<213> ORGANISM: Artificial Sequence
<220> FEATURE:
<223> OTHER INFORMATION: codon-optimized SDACC2 with Flag tag and mutation

<400> SEQUENCE: 140

```
atggactaca aagacgacga cgacaaagta aacgctgtaa acccagaaaa aaacggtgct     60
tacgaaggtt caccaattgt atcaggtcca atttcagtag gtgctatgga caaagactca    120
aaaggttcat caaaaccagt agaccgttca aaaggtttat ggacacgttg tgacaaatgt    180
ggtgtaattt tatacattaa acacttaaaa gaacaccacc acatttgttt cggttgtaac    240
taccacttaa aaatgtcatc acaagaacgt attgaccaca tgattgaccc aggttcatgg    300
cgtccattcg acgaaacatt atcaccatgt gacccattag acttcgtaga catgaaacca    360
tacccagacc gtgtacgtga cgatcaagac aaaacaggta tgaacgacgc tattcgtaca    420
ggtacaggtt tattacacgg tattccagta gctttagctg taatggaatt cggtttcatg    480
ggtggttcaa tgggttcagt agtaggtgaa aaattaacac gtttaattga atacgctaca    540
caagaaggtt taacattatt agtagtatgt acatcaggtg gtgctcgtat gcaagaaggt    600
attatgtcat taatgcaaat ggctaaaatt tcaggtgctt tacacgtaca ccaaaacgaa    660
gctaacttat tatacatttc aattttaaca tcaccaacaa caggtggtgt aacagcttca    720
ttcggtatgt taggtgacgt aattattgct gaaccacaag ctattattgg tttcgctggt    780
cgtcgtgtaa ttgaacaaac attacgtgaa gaattaccag acgacttcca aacagctgaa    840
tacttattag acaaaggttt attagactta gtagtaccac gttcattctt aaaaggtgct    900
ttattcgaaa ttattgactt ctacaaaaac gctccataca aacgtcgtgg taaaattcca    960
ttcggtgtac aacgtggtac atacggttta acagctgaag aaaaaatgcg tcgtcgttgg   1020
cgtgaatggt catcagtagg ttcaatgtta cactcagtac actacgctgg tcactggcca   1080
tcaggttgtg ctggtatgtt attaggtcaa cgtccattac acatgcactg gcacgtaaac   1140
gaaggttcag gttgttcaaa acaacatgt caatcattca aatactggtc agcttgtgct    1200
gcttggcacg ctgtatgtca ccgtcgtggt acattattag aacacgaatt aacaaaatta   1260
atttcatggc aattcgactc atgttgttgg cgtgctgcta aaggtatttt attacgttca   1320
tgtaacgctg tatacgtata cgtataa                                        1347
```

<210> SEQ ID NO 141
<211> LENGTH: 1347
<212> TYPE: DNA
<213> ORGANISM: Artificial Sequence
<220> FEATURE:
<223> OTHER INFORMATION: codon-optimized SDACC2 with Flag tag and mutation

<400> SEQUENCE: 141

```
atggactaca aagacgacga cgacaaagta aacgctgtaa acccagaaaa aaacggtgct    60
tacgaaggtt caccaattgt atcaggtcca atttcagtag gtgctatgga caaagactca   120
aaaggttcat caaaaccagt agaccgttca aaaggtttat ggacacgttg tgacaaatgt   180
ggtgtaattt tatacattaa acacttaaaa gaacaccacc acatttgttt cggttgtaac   240
taccacttaa aaatgtcatc acaagaacgt attgaccaca tgattgaccc aggttcatgg   300
cgtccattcg acgaaacatt atcaccatgt gacccattag acttcgtaga catgaaacca   360
tacccagacc gtgtacgtga ctcacaagac aaaacaggta tgaacgacgc tattcgtaca   420
ggtacaggtt tattacacgg tattccagta gctttagctg taatgaattc ggtttcatg    480 ggtggttcaa tgggttcagt agtaggtgaa aaattaacac gtttaattga atacgctaca   540
caagaaggtt taacattatt agtagtatgt acatcaggtg gtgctcgtat gcaagaaggt   600
attatgtcat taatgcaaat ggctaaaatt tcaggtgctt tacacgtaca ccaaaacgaa   660
gctaacttat tatacatttc aatttttaaca tcaccaacaa caggtggtgt aacagcttca   720
ttcggtatgt taggtgacgt aattattgct gaaccacaag ctattattgg tttcgctggt   780
cgtcgtgtaa ttgaacaaga tttacgtgaa gaattaccag acgacttcca aacagctgaa   840
tacttattag acaaaggttt attagactta gtagtaccac gttcattctt aaaaggtgct   900
ttattcgaaa ttattgactt ctacaaaaac gctccataca aacgtcgtgg taaaattcca   960
ttcggtgtac aacgtggtac atacggttta acagctgaag aaaaaatgcg tcgtcgttgg  1020
cgtgaatggt catcagtagg ttcaatgtta cactcagtac actacgctgg tcactggcca  1080
tcaggttgtg ctggtatgtt attaggtcaa cgtccattac acatgcactg gcacgtaaac  1140
gaaggttcag gttgttcaaa aacaacatgt caatcattca aatactggtc agcttgtgct  1200
gcttggcacg ctgtatgtca ccgtcgtggt acattattag aacacgaatt aacaaaatta  1260
atttcatggc aattcgactc atgttgttgg cgtgctgcta aggtattttt attacgttca  1320
tgtaacgctg tatacgtata cgtataa                                      1347
```

<210> SEQ ID NO 142
<211> LENGTH: 52
<212> TYPE: DNA
<213> ORGANISM: Artificial Sequence
<220> FEATURE:
<223> OTHER INFORMATION: PCR primer

<400> SEQUENCE: 142

```
gaccacatga ttgacccagg tgattggcgt ccattcgacg aaacattatc ac          52
```

<210> SEQ ID NO 143
<211> LENGTH: 52
<212> TYPE: DNA
<213> ORGANISM: Artificial Sequence
<220> FEATURE:
<223> OTHER INFORMATION: PCR primer

<400> SEQUENCE: 143

```
gtgataatgt ttcgtcgaat ggacgccaat cacctgggtc aatcatgtgg tc          52
```

<210> SEQ ID NO 144
<211> LENGTH: 51
<212> TYPE: DNA
<213> ORGANISM: Artificial Sequence
<220> FEATURE:
<223> OTHER INFORMATION: PCR primer

<400> SEQUENCE: 144
catggcgtcc attcgacgaa gatttatcac catgtgaccc attagacttc g          51

<210> SEQ ID NO 145
<211> LENGTH: 51
<212> TYPE: DNA
<213> ORGANISM: Artificial Sequence
<220> FEATURE:
<223> OTHER INFORMATION: PCR primer

<400> SEQUENCE: 145
cgaagtctaa tgggtcacat ggtgataaat cttcgtcgaa tggacgccat g          51

<210> SEQ ID NO 146
<211> LENGTH: 51
<212> TYPE: DNA
<213> ORGANISM: Artificial Sequence
<220> FEATURE:
<223> OTHER INFORMATION: PCR primer

<400> SEQUENCE: 146
ggcgtccatt cgacgaaaca ttagatccat gtgacccatt agacttcgta g          51

<210> SEQ ID NO 147
<211> LENGTH: 51
<212> TYPE: DNA
<213> ORGANISM: Artificial Sequence
<220> FEATURE:
<223> OTHER INFORMATION: PCR primer

<400> SEQUENCE: 147
ctacgaagtc taatgggtca catggatcta atgtttcgtc gaatggacgc c          51

<210> SEQ ID NO 148
<211> LENGTH: 47
<212> TYPE: DNA
<213> ORGANISM: Artificial Sequence
<220> FEATURE:
<223> OTHER INFORMATION: PCR primer

<400> SEQUENCE: 148
ccatgtgacc cattagactt cgatgacatg aaaccatacc cagaccg              47

<210> SEQ ID NO 149
<211> LENGTH: 47
<212> TYPE: DNA
<213> ORGANISM: Artificial Sequence
<220> FEATURE:
<223> OTHER INFORMATION: PCR primer

<400> SEQUENCE: 149
cggtctgggt atggtttcat gtcatcgaag tctaatgggt cacatgg              47

<210> SEQ ID NO 150
<211> LENGTH: 50
<212> TYPE: DNA
<213> ORGANISM: Artificial Sequence
<220> FEATURE:
<223> OTHER INFORMATION: PCR primer

<400> SEQUENCE: 150
ccattagact tcgtagacat gaaagattac ccagaccgtg tacgtgactc            50

<210> SEQ ID NO 151
<211> LENGTH: 50

-continued

<212> TYPE: DNA
<213> ORGANISM: Artificial Sequence
<220> FEATURE:
<223> OTHER INFORMATION: PCR primer

<400> SEQUENCE: 151
gagtcacgta cacggtctgg gtaatctttc atgtctacga agtctaatgg         50

<210> SEQ ID NO 152
<211> LENGTH: 52
<212> TYPE: DNA
<213> ORGANISM: Artificial Sequence
<220> FEATURE:
<223> OTHER INFORMATION: PCR primer

<400> SEQUENCE: 152
ccatacccag accgtgtacg tgacgatcaa gacaaaacag gtatgaacga cg       52

<210> SEQ ID NO 153
<211> LENGTH: 52
<212> TYPE: DNA
<213> ORGANISM: Artificial Sequence
<220> FEATURE:
<223> OTHER INFORMATION: PCR primer

<400> SEQUENCE: 153
cgtcgttcat acctgttttg tcttgatcgt cacgtacacg gtctgggtat gg       52

<210> SEQ ID NO 154
<211> LENGTH: 51
<212> TYPE: DNA
<213> ORGANISM: Artificial Sequence
<220> FEATURE:
<223> OTHER INFORMATION: PCR primer

<400> SEQUENCE: 154
ggtcgtcgtg taattgaaca agatttacgt gaagaattac cagacgactt c         51

<210> SEQ ID NO 155
<211> LENGTH: 51
<212> TYPE: DNA
<213> ORGANISM: Artificial Sequence
<220> FEATURE:
<223> OTHER INFORMATION: PCR primer

<400> SEQUENCE: 155
gaagtcgtct ggtaattctt cacgtaaatc ttgttcaatt acacgacgac c         51

<210> SEQ ID NO 156
<211> LENGTH: 7062
<212> TYPE: DNA
<213> ORGANISM: Artificial Sequence
<220> FEATURE:
<223> OTHER INFORMATION: codon optimized rat ACCase with 3' tag

<400> SEQUENCE: 156
atggatgaac cttcaccttt agctaagaca ttagaattaa atcaacactc acgtttcatc    60
attggttcag tttcagaaga taattcgaaa gacgaaattt caaacttagt taaacttgat   120
cttgaagaaa aagaaggatc attatctcct gcttcagtat catcagatac tttaagtgat   180
ttaggcatat cagctttaca agatggctta gcatttcaca tgcgttcttc tatgtctggt   240
ttacatttag taaacaagg tcgtgatcgc aagaaaattg attcacaaag agattttacc   300
gttgcttctc cagctgaatt tgttacacgt ttcggtggta ataaggttat tgaaaaagtt   360

```
ttaatagcta caatggaat tgcagctgtt aaatgtatgc gcagcattcg tagatggtct    420
tacgaaatgt ttcgtaatga acgtgctatt cgtttcgttg ttatggttac accagaggat    480
ttaaaagcta acgccgagta tattaagatg gcagatcatt atgtaccagt accaggtggt    540
gccaacaata taactacgc aaatgttgag ttaattcttg acattgctaa acgtattcca    600
gtacaagccg tttgggctgg ttggggccat gcatcagaaa atccaaaatt accagaatta    660
ttacttaaaa atggaatagc tttcatgggt ccaccatcac aagctatgtg ggctttaggt    720
gacaaaatcg cttctagtat tgtagcacaa actgctggta ttcctacttt accctggtct    780
ggtagtggtt taagagttga ttggcaggaa aatgatttta gtaaacgtat ccttaatgtt    840
cctcaagatt tatatgaaaa gggttatgtt aaagatgtag atgatggttt aaaagctgct    900
gaagaagttg atacccctgt aatgattaaa gcaagtgaag gtggtggtgg taaaggtata    960
agaaaggtaa ataacgcaga cgattttcct aaccttttc gccaggtaca ggctgaagta    1020
cccggttcac ccattttgt tatgcgttta gcaaaacagt cacgtcactt agaagtacaa    1080
attttagctg atcaatatgg taatgctatt tctttattcg gtcgtgattg ttcagttcaa    1140
cgtcgtcatc agaaaataat cgaagaagct cctgctgcaa ttgctactcc agccgttttt    1200
gaacacatgg aacaatgtgc tgttaagtta gctaaaatgg taggttacgt ttctgctggt    1260
actgtagagt acttatatag ccaagatggt agcttttatt tcttagagtt aaatccacgc    1320
ttacaagtag aacatccttg cacagaaatg gtggctgatg taaatttacc cgcagctcaa    1380
ttacaaattg caatgggtat tccttttatt cgtattaaag atattcgtat gatgtatgga    1440
gtaagtccct ggggcgatgc tccaattgat ttcgagaata gtgctcatgt accatgtcct    1500
cgcggacatg taatagctgc tcgtatcaca agtgaaaacc ctgacgaagg ttttaaaccc    1560
tctagtggta ctgtacaaga attaaacttt cgttcaaata agaacgtttg gggatatttt    1620
agtgttgctg ctgctggcgg tttacatgaa tttgctgact cacaatttgg tcactgtttt    1680
tcttggggtg aaaatcgtga agaagctata agtaatatgg tagtagcttt aaagagaatta    1740 tcaattcgtg gtgattttcg tacaacagtt gaatacttaa tcaaacttttt agagacagaa    1800 tcttttcaat taaatcgcat tgatacaggt tggttagatc gtttaatagc tgaaaaagtg    1860
caagctgaac gtccagatac tatgttaggt gtagtttgtg gtgcattaca tgttgcagac    1920
gttaacttac gcaattctat ttcaaatttc ttacacagct tagaacgtgg tcaagtatta    1980
ccagctcaca ccttattaaa cactgttgac gttgaactta tttatgaagg tatcaaatat    2040
gttttaaaag tgacaagaca atcacctaat agttatgttg taattatgaa tggttcttgc    2100
gttgaagttg atgttcaccg tttatcagac ggtggtcttt tactttctta tgacggttca    2160
agttacacta cctatatgaa agaagaagta gacagatatc gtattactat tggtaataaa    2220
acttgtgtgt ttgaaaaaga aaacgaccca tcagtaatgc gttctccatc agctggtaaa    2280
cttattcaat atattgtaga ggatggtggt catgttttcg caggtcaatg ttatgcagaa    2340
atagaagtaa tgaagatggt tatgactta acagcagttg aaagtggttg tatccattac    2400
gttaaacgtc caggagcagc tcttgatcca ggttgtgtaa ttgctaaaat gcaattagat    2460
aatccaagta aagtgcaaca agcagaatta catacaggtt cttaccaca aattcaaagt    2520 acagccttac gtggtgaaaa attacacaga gtatttcact atgttttaga taacttagtg    2580
aatgttatga acggttattg ccttccagat ccattctttt catcaaaagt gaaagattgg    2640
gttgaacgtt taatgaaaac cttacgtgat ccatcattac cttattaga attacaagac    2700 ataatgacat cagtttctgg tcgcattcca ttaaatgtag aaaaatcaat taagaaagaa    2760
```

```
atggcacaat atgcttctaa tattacctct gttttatgtc aattcccatc acaacagatt    2820
gctaacattc ttgattcaca cgctgcaaca ttaaatcgta aatcagaacg tgaagtattc    2880
ttcatgaata cacaaagtat tgttcaatta gttcaacgtt atcgcagtgg tattagaggt    2940
cacatgaaag ctgtagttat ggacttatta cgtcaatatt tacgcgtaga aactcaattt    3000
caaaatggtc attatgataa atgtgtattt gctttacgtg aagagaataa atcagacatg    3060
aatactgtac ttaactacat cttttctcat gcccaagtaa ctaagaagaa tttacttgtt    3120
actatgttaa tagatcaatt atgtggtcgc gatccaacat taactgatga attacttaat    3180
atccttacag aacttactca attaagtaaa actacaaatg ctaaagtggc tttacgtgct    3240
cgccaagtgc ttattgcttc tcatttacct tcttatgatg ttagacacaa tcaagttgaa    3300
tcaatctttc tttctgctat tgatatgtat ggacaccaat tctgtattga aaatttacaa    3360
aagttaattc ttagtgaaac atcaattttc gatgttttac caaatttctt ctatcactct    3420
aatcaagtgg ttcgtatggc tgctttagaa gtttatgttc gtcgtgctta tattgcttat    3480
gagttaaatt cagtacaaca tcgtcaatta aaagacaata cctgtgtagt agaatttcaa    3540
ttcatgcttc ctacttcaca tccaaatcgt ggtaatattc aactttaaa ccgtatgtca    3600 ttcgcatcta acttaaatca ctatggcatg actcatgtag catctgtgag tgacgtatta    3660
ttagataacg cttttacacc tccttgtcaa cgtatgggtg gtatggtttc tttccgtaca    3720
tttgaagatt tcgttcgtat ttttgacgaa gttatgggtt gttttgtga tagtccacca    3780 caaagtccaa catttccaga atcaggtcac actagcttat atgatgaaga taaagtacca    3840
cgtgatgaac caattcacat tcttaacgtt gcaattaaaa ctgatggtga tatcgaggat    3900
gaccgtttag ctgcaatgtt tagagagttt acacaacaaa ataaagcaac tttagttgaa    3960
catggtattc gtcgtttaac attttttagta gctcaaaaag atttccgtaa acaagtaaat    4020
tgtgaagtag atcaacgttt tcatcgtgaa tttccaaaat tctttacttt ccgtgctcgt    4080
gataaatttg aagaagatcg tatctatcgt catttagagc cagctttagc attccaatta    4140
gagcttaatc gtatgcgtaa ctttgattta actgcaatcc catgtgctaa tcataaaatg    4200
cacttatact taggcgcagc aaaagttgaa gtaggtacag aagttactga ttatcgtttc    4260
ttcgttcgtg caattattag acacagcgat ttagtaacaa aggaagcatc tttcgaatac    4320
ttacaaaacg aaggtgaaag acttttactt gaagcaatgg acgaattaga agttgctttc    4380
aataatacta tgttcgtac agattgcaat cacatttct taaactttgt tccaacagta    4440 attatgacc cttctaaaat tgaagaatca gtacgttcaa tggttatgcg ttatggttct    4500
cgcctttgga aattaagagt gttacaagct gaacttaaaa tcaatattcg tcttactaca    4560
actggtaaag caattccaat tcgtttattc cttactaacg aatcaggata ctatcttgat    4620
atttctcttt ataagaagt aactgatagt cgtactgctc aaattatgtt ccaagcatac    4680
ggtgataaac aaggtccatt acatggaatg ttaatcaaca ctccttatgt tactaaggat    4740
ttattacaaa gtaaacgttt tcaagctcaa tctttaggta caacatacat ctatgacatc    4800
ccagaaatgt ttagacaatc tttaatcaaa ttatgggaat caatgtcaac tcaagcatt    4860 ttaccttcac caccttacc tagtgacatt ttaacataca cagaattagt attagatgat    4920
caaggacaac ttgttcacat gaatcgttta ccaggcggta atgaaattgg tatggtagct    4980
tggaaaatgt ctcttaaaag cccagaatat ccagatggtc gtgatgttat tgtaatcggc    5040
aatgatatta catatcgcat tggttctttt ggtccacaag aggatctttt attcttacgt    5100
```

```
gctagtgagc ttgcacgtgc tgaaggtatt ccccgcattt atgtagctgc aaattcaggc    5160
gcccgtattg gattagctga agaaattcgt cacatgtttc acgtggcatg ggttgattca    5220
gaagatccat acaaaggtta caaatatctt tacttaactc cacaagacta taaacgtgtg    5280
agcgccttaa attctgttca ctgtgaacat gtagaagatg aaggtgaatc acgttacaaa    5340
attacagaca taattggtaa agaagaaggt cttggtgccg aaaatttacg tggaagtggt    5400
atgattgctg gtgaaagttc tttagcttat gatgagatta ttactattag cttagtaact    5460
tgtcgtgcca ttggtattgg tgcatatttg gtacgtcttg gtcaacgtac aattcaagta    5520
gaaaatagtc accttatctt aacggtgca ggcgcactta ataaagtatt aggtcgtgaa    5580
gtatatacaa gtaataacca acttggaggt attcaaataa tgcacaataa cggtgtaaca    5640
cattgtacag tgtgtgatga tttcgaaggt gtatttactg tacttcactg gttatcatat    5700
atgcctaaaa atgtacatag ttcagtacca ttacttaata gtaaagatcc aattgaccgt    5760
ataattgaat ttgtacctac aaaagctcct tatgaccctc gttggatgtt agctggtcgt    5820
ccccatccca ctcaaaaagg tcaatggctt agtggatttt tcgattatgg cagctttagt    5880
gaaattatgc aaccctgggc tcaaacagta gtagtaggta gagctcgttt aggtggaatc    5940
cctgtgggtg tagttgctgt agaaactaga acagtagaac tttcagtacc tgctgatcca    6000
gccaatttag attctgaagc caaaatcatt caacaagccg gtcaagtatg gtttcccgat    6060
tctgctttca aaacatatca agcaattaaa gatttcaacc gtgaaggttt acctttaatg    6120
gtattcgcta actggcgtgg tttttctggt ggtatgaaag atatgtatga ccaagttctt    6180
aagttcggtc cctacatcgt ggatggatta cgtgaatgtt ctcaaccagt tatggtatat    6240
attccaccac aagccgaatt acgtggtggc tcttggttg ttattgatcc aactattaac    6300
ccaagacaca tggaaatgta tgctgatcgt gagtctcgtg gatcagtatt agaaccagaa    6360
ggtactgttg aaataaagtt tcgtaaaaag gatttagtga aaactatgcg tcgtgtagat    6420
cctgttata ttcgccttgc agaacgttta ggcaccccag aattaagtcc aacagaacgt    6480
aaagaattag agtctaagtt aaaagaaaga gaagagttct taattcctat ttaccaccag    6540
gtggcagttc aatttgctga tttacatgat acaccaggtc gtatgcaaga aaaaggtgtt    6600
attaacgaca ttttagattg gaaaacttca cgtacatttt tctactggcg tttacgtcgt    6660
cttttacttg aagatttagt gaaaagaaa attcattcag caaatccaga attaacagat    6720
ggtcaaatac aagctatgct tcgtcgctgg ttcgtagaag ttgagggcac agtgaaagca    6780
tacgtttggg ataacaataa agacttagtg gaatggttag aaaagcagtt aactgaagaa    6840
gatggtgtgc gttcagtaat tgaagaaaac atcaaatata tctcacgtga ttatgtatta    6900
aaacaaattc gttcattagt acaagctaat ccagaagttg ctatggatag cattgttcac    6960
atgactcaac atattagtcc aacacaacgt gcagaagttg taagaatttt atcaactatg    7020
gattcaccaa gtactgatta taagatgat gatgacaaat aa                        7062
```

<210> SEQ ID NO 157
<211> LENGTH: 2345
<212> TYPE: PRT
<213> ORGANISM: Rattus norvegicus

<400> SEQUENCE: 157

Met Asp Glu Pro Ser Pro Leu Ala Lys Thr Leu Glu Leu Asn Gln His
1               5                   10                  15

Ser Arg Phe Ile Ile Gly Ser Val Ser Glu Asp Asn Ser Glu Asp Glu
            20                  25                  30

```
Ile Ser Asn Leu Val Lys Leu Asp Leu Glu Glu Lys Glu Gly Ser Leu
            35                  40                  45

Ser Pro Ala Ser Val Ser Ser Asp Thr Leu Ser Asp Leu Gly Ile Ser
    50                  55                  60

Ala Leu Gln Asp Gly Leu Ala Phe His Met Arg Ser Ser Met Ser Gly
65                  70                  75                  80

Leu His Leu Val Lys Gln Gly Arg Asp Arg Lys Lys Ile Asp Ser Gln
                85                  90                  95

Arg Asp Phe Thr Val Ala Ser Pro Ala Glu Phe Val Thr Arg Phe Gly
            100                 105                 110

Gly Asn Lys Val Ile Glu Lys Val Leu Ile Ala Asn Asn Gly Ile Ala
            115                 120                 125

Ala Val Lys Cys Met Arg Ser Ile Arg Arg Trp Ser Tyr Glu Met Phe
            130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys Met Ala Asp His Tyr Val Pro
                165                 170                 175

Val Pro Gly Gly Ala Asn Asn Asn Asn Tyr Ala Asn Val Glu Leu Ile
            180                 185                 190

Leu Asp Ile Ala Lys Arg Ile Pro Val Gln Ala Val Trp Ala Gly Trp
            195                 200                 205

Gly His Ala Ser Glu Asn Pro Lys Leu Pro Glu Leu Leu Leu Lys Asn
            210                 215                 220

Gly Ile Ala Phe Met Gly Pro Pro Ser Gln Ala Met Trp Ala Leu Gly
225                 230                 235                 240

Asp Lys Ile Ala Ser Ser Ile Val Ala Gln Thr Ala Gly Ile Pro Thr
                245                 250                 255

Leu Pro Trp Ser Gly Ser Gly Leu Arg Val Asp Trp Gln Glu Asn Asp
            260                 265                 270

Phe Ser Lys Arg Ile Leu Asn Val Pro Gln Asp Leu Tyr Glu Lys Gly
            275                 280                 285

Tyr Val Lys Asp Val Asp Asp Gly Leu Lys Ala Ala Glu Glu Val Gly
            290                 295                 300

Tyr Pro Val Met Ile Lys Ala Ser Glu Gly Gly Gly Lys Gly Ile
305                 310                 315                 320

Arg Lys Val Asn Asn Ala Asp Asp Phe Pro Asn Leu Phe Arg Gln Val
                325                 330                 335

Gln Ala Glu Val Pro Gly Ser Pro Ile Phe Val Met Arg Leu Ala Lys
            340                 345                 350

Gln Ser Arg His Leu Glu Val Gln Ile Leu Ala Asp Gln Tyr Gly Asn
            355                 360                 365

Ala Ile Ser Leu Phe Gly Arg Asp Cys Ser Val Gln Arg Arg His Gln
            370                 375                 380

Lys Ile Ile Glu Glu Ala Pro Ala Ala Ile Ala Thr Pro Ala Val Phe
385                 390                 395                 400

Glu His Met Glu Gln Cys Ala Val Lys Leu Ala Lys Met Val Gly Tyr
                405                 410                 415

Val Ser Ala Gly Thr Val Glu Tyr Leu Tyr Ser Gln Asp Gly Ser Phe
            420                 425                 430

Tyr Phe Leu Glu Leu Asn Pro Arg Leu Gln Val Glu His Pro Cys Thr
            435                 440                 445
```

```
Glu Met Val Ala Asp Val Asn Leu Pro Ala Ala Gln Leu Gln Ile Ala
450                 455                 460

Met Gly Ile Pro Leu Phe Arg Ile Lys Asp Ile Arg Met Met Tyr Gly
465                 470                 475                 480

Val Ser Pro Trp Gly Asp Ala Pro Ile Asp Phe Glu Asn Ser Ala His
                485                 490                 495

Val Pro Cys Pro Arg Gly His Val Ile Ala Ala Arg Ile Thr Ser Glu
            500                 505                 510

Asn Pro Asp Glu Gly Phe Lys Pro Ser Ser Gly Thr Val Gln Glu Leu
        515                 520                 525

Asn Phe Arg Ser Asn Lys Asn Val Trp Gly Tyr Phe Ser Val Ala Ala
530                 535                 540

Ala Gly Gly Leu His Glu Phe Ala Asp Ser Gln Phe Gly His Cys Phe
545                 550                 555                 560

Ser Trp Gly Glu Asn Arg Glu Glu Ala Ile Ser Asn Met Val Val Ala
                565                 570                 575

Leu Lys Glu Leu Ser Ile Arg Gly Asp Phe Arg Thr Thr Val Glu Tyr
            580                 585                 590

Leu Ile Lys Leu Leu Glu Thr Glu Ser Phe Gln Leu Asn Arg Ile Asp
        595                 600                 605

Thr Gly Trp Leu Asp Arg Leu Ile Ala Glu Lys Val Gln Ala Glu Arg
610                 615                 620

Pro Asp Thr Met Leu Gly Val Val Cys Gly Ala Leu His Val Ala Asp
625                 630                 635                 640

Val Asn Leu Arg Asn Ser Ile Ser Asn Phe Leu His Ser Leu Glu Arg
                645                 650                 655

Gly Gln Val Leu Pro Ala His Thr Leu Leu Asn Thr Val Asp Val Glu
            660                 665                 670

Leu Ile Tyr Glu Gly Ile Lys Tyr Val Leu Lys Val Thr Arg Gln Ser
        675                 680                 685

Pro Asn Ser Tyr Val Val Ile Met Asn Gly Ser Cys Val Glu Val Asp
690                 695                 700

Val His Arg Leu Ser Asp Gly Gly Leu Leu Leu Ser Tyr Asp Gly Ser
705                 710                 715                 720

Ser Tyr Thr Thr Tyr Met Lys Glu Glu Val Asp Arg Tyr Arg Ile Thr
                725                 730                 735

Ile Gly Asn Lys Thr Cys Val Phe Glu Lys Glu Asn Asp Pro Ser Val
            740                 745                 750

Met Arg Ser Pro Ser Ala Gly Lys Leu Ile Gln Tyr Ile Val Glu Asp
        755                 760                 765

Gly Gly His Val Phe Ala Gly Gln Cys Tyr Ala Glu Ile Glu Val Met
770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
            820                 825                 830

Gly Ser Leu Pro Gln Ile Gln Ser Thr Ala Leu Arg Gly Glu Lys Leu
        835                 840                 845

His Arg Val Phe His Tyr Val Leu Asp Asn Leu Val Asn Val Met Asn
850                 855                 860

Gly Tyr Cys Leu Pro Asp Pro Phe Phe Ser Ser Lys Val Lys Asp Trp
```

-continued

```
865                 870                 875                 880
Val Glu Arg Leu Met Lys Thr Leu Arg Asp Pro Ser Leu Pro Leu Leu
                885                 890                 895
Glu Leu Gln Asp Ile Met Thr Ser Val Ser Gly Arg Ile Pro Leu Asn
                900                 905                 910
Val Glu Lys Ser Ile Lys Lys Glu Met Ala Gln Tyr Ala Ser Asn Ile
                915                 920                 925
Thr Ser Val Leu Cys Gln Phe Pro Ser Gln Ile Ala Asn Ile Leu
    930                 935                 940
Asp Ser His Ala Ala Thr Leu Asn Arg Lys Ser Glu Arg Glu Val Phe
945                 950                 955                 960
Phe Met Asn Thr Gln Ser Ile Val Gln Leu Val Gln Arg Tyr Arg Ser
                965                 970                 975
Gly Ile Arg Gly His Met Lys Ala Val Val Met Asp Leu Leu Arg Gln
                980                 985                 990
Tyr Leu Arg Val Glu Thr Gln Phe  Gln Asn Gly His Tyr  Asp Lys Cys
                995                 1000                1005
Val Phe  Ala Leu Arg Glu Glu  Asn Lys Ser Asp Met  Asn Thr Val
    1010                1015                1020
Leu Asn  Tyr Ile Phe Ser His  Ala Gln Val Thr Lys  Lys Asn Leu
    1025                1030                1035
Leu Val  Thr Met Leu Ile Asp  Gln Leu Cys Gly Arg  Asp Pro Thr
    1040                1045                1050
Leu Thr  Asp Glu Leu Leu Asn  Ile Leu Thr Glu Leu  Thr Gln Leu
    1055                1060                1065
Ser Lys  Thr Thr Asn Ala Lys  Val Ala Leu Arg Ala  Arg Gln Val
    1070                1075                1080
Leu Ile  Ala Ser His Leu Pro  Ser Tyr Asp Val Arg  His Asn Gln
    1085                1090                1095
Val Glu  Ser Ile Phe Leu Ser  Ala Ile Asp Met Tyr  Gly His Gln
    1100                1105                1110
Phe Cys  Ile Glu Asn Leu Gln  Lys Leu Ile Leu Ser  Glu Thr Ser
    1115                1120                1125
Ile Phe  Asp Val Leu Pro Asn  Phe Phe Tyr His Ser  Asn Gln Val
    1130                1135                1140
Val Arg  Met Ala Ala Leu Glu  Val Tyr Val Arg Arg  Ala Tyr Ile
    1145                1150                1155
Ala Tyr  Glu Leu Asn Ser Val  Gln His Arg Gln Leu  Lys Asp Asn
    1160                1165                1170
Thr Cys  Val Val Glu Phe Gln  Phe Met Leu Pro Thr  Ser His Pro
    1175                1180                1185
Asn Arg  Gly Asn Ile Pro Thr  Leu Asn Arg Met Ser  Phe Ala Ser
    1190                1195                1200
Asn Leu  Asn His Tyr Gly Met  Thr His Val Ala Ser  Val Ser Asp
    1205                1210                1215
Val Leu  Leu Asp Asn Ala Phe  Thr Pro Pro Cys Gln  Arg Met Gly
    1220                1225                1230
Gly Met  Val Ser Phe Arg Thr  Phe Glu Asp Phe Val  Arg Ile Phe
    1235                1240                1245
Asp Glu  Val Met Gly Cys Phe  Cys Asp Ser Pro Pro  Gln Ser Pro
    1250                1255                1260
Thr Phe  Pro Glu Ser Gly His  Thr Ser Leu Tyr Asp  Glu Asp Lys
    1265                1270                1275
```

-continued

```
Val Pro Arg Asp Glu Pro Ile His Ile Leu Asn Val Ala Ile Lys
    1280                1285                1290

Thr Asp Gly Asp Ile Glu Asp Asp Arg Leu Ala Ala Met Phe Arg
    1295                1300                1305

Glu Phe Thr Gln Gln Asn Lys Ala Thr Leu Val Glu His Gly Ile
    1310                1315                1320

Arg Arg Leu Thr Phe Leu Val Ala Gln Lys Asp Phe Arg Lys Gln
    1325                1330                1335

Val Asn Cys Glu Val Asp Gln Arg Phe His Arg Glu Phe Pro Lys
    1340                1345                1350

Phe Phe Thr Phe Arg Ala Arg Asp Lys Phe Glu Glu Asp Arg Ile
    1355                1360                1365

Tyr Arg His Leu Glu Pro Ala Leu Ala Phe Gln Leu Glu Leu Asn
    1370                1375                1380

Arg Met Arg Asn Phe Asp Leu Thr Ala Ile Pro Cys Ala Asn His
    1385                1390                1395

Lys Met His Leu Tyr Leu Gly Ala Ala Lys Val Glu Val Gly Thr
    1400                1405                1410

Glu Val Thr Asp Tyr Arg Phe Phe Val Arg Ala Ile Ile Arg His
    1415                1420                1425

Ser Asp Leu Val Thr Lys Glu Ala Ser Phe Glu Tyr Leu Gln Asn
    1430                1435                1440

Glu Gly Glu Arg Leu Leu Leu Glu Ala Met Asp Glu Leu Glu Val
    1445                1450                1455

Ala Phe Asn Asn Thr Asn Val Arg Thr Asp Cys Asn His Ile Phe
    1460                1465                1470

Leu Asn Phe Val Pro Thr Val Ile Met Asp Pro Ser Lys Ile Glu
    1475                1480                1485

Glu Ser Val Arg Ser Met Val Met Arg Tyr Gly Ser Arg Leu Trp
    1490                1495                1500

Lys Leu Arg Val Leu Gln Ala Glu Leu Lys Ile Asn Ile Arg Leu
    1505                1510                1515

Thr Thr Thr Gly Lys Ala Ile Pro Ile Arg Leu Phe Leu Thr Asn
    1520                1525                1530

Glu Ser Gly Tyr Tyr Leu Asp Ile Ser Leu Tyr Lys Glu Val Thr
    1535                1540                1545

Asp Ser Arg Thr Ala Gln Ile Met Phe Gln Ala Tyr Gly Asp Lys
    1550                1555                1560

Gln Gly Pro Leu His Gly Met Leu Ile Asn Thr Pro Tyr Val Thr
    1565                1570                1575

Lys Asp Leu Leu Gln Ser Lys Arg Phe Gln Ala Gln Ser Leu Gly
    1580                1585                1590

Thr Thr Tyr Ile Tyr Asp Ile Pro Glu Met Phe Arg Gln Ser Leu
    1595                1600                1605

Ile Lys Leu Trp Glu Ser Met Ser Thr Gln Ala Phe Leu Pro Ser
    1610                1615                1620

Pro Pro Leu Pro Ser Asp Ile Leu Thr Tyr Thr Glu Leu Val Leu
    1625                1630                1635

Asp Asp Gln Gly Gln Leu Val His Met Asn Arg Leu Pro Gly Gly
    1640                1645                1650

Asn Glu Ile Gly Met Val Ala Trp Lys Met Ser Leu Lys Ser Pro
    1655                1660                1665
```

```
Glu Tyr Pro Asp Gly Arg Asp Val Ile Val Ile Gly Asn Asp Ile
1670                1675                1680

Thr Tyr Arg Ile Gly Ser Phe Gly Pro Gln Glu Asp Leu Leu Phe
1685                1690                1695

Leu Arg Ala Ser Glu Leu Ala Arg Ala Glu Gly Ile Pro Arg Ile
1700                1705                1710

Tyr Val Ala Ala Asn Ser Ala Arg Ile Gly Leu Ala Glu Glu
1715                1720                1725

Ile Arg His Met Phe His Val Ala Trp Val Asp Ser Glu Asp Pro
1730                1735                1740

Tyr Lys Gly Tyr Lys Tyr Leu Tyr Leu Thr Pro Gln Asp Tyr Lys
1745                1750                1755

Arg Val Ser Ala Leu Asn Ser Val His Cys Glu His Val Glu Asp
1760                1765                1770

Glu Gly Glu Ser Arg Tyr Lys Ile Thr Asp Ile Ile Gly Lys Glu
1775                1780                1785

Glu Gly Leu Gly Ala Glu Asn Leu Arg Gly Ser Gly Met Ile Ala
1790                1795                1800

Gly Glu Ser Ser Leu Ala Tyr Asp Glu Ile Ile Thr Ile Ser Leu
1805                1810                1815

Val Thr Cys Arg Ala Ile Gly Ile Gly Ala Tyr Leu Val Arg Leu
1820                1825                1830

Gly Gln Arg Thr Ile Gln Val Glu Asn Ser His Leu Ile Leu Thr
1835                1840                1845

Gly Ala Gly Ala Leu Asn Lys Val Leu Gly Arg Glu Val Tyr Thr
1850                1855                1860

Ser Asn Asn Gln Leu Gly Gly Ile Gln Ile Met His Asn Asn Gly
1865                1870                1875

Val Thr His Cys Thr Val Cys Asp Asp Phe Glu Gly Val Phe Thr
1880                1885                1890

Val Leu His Trp Leu Ser Tyr Met Pro Lys Asn Val His Ser Ser
1895                1900                1905

Val Pro Leu Leu Asn Ser Lys Asp Pro Ile Asp Arg Ile Ile Glu
1910                1915                1920

Phe Val Pro Thr Lys Ala Pro Tyr Asp Pro Arg Trp Met Leu Ala
1925                1930                1935

Gly Arg Pro His Pro Thr Gln Lys Gly Gln Trp Leu Ser Gly Phe
1940                1945                1950

Phe Asp Tyr Gly Ser Phe Ser Glu Ile Met Gln Pro Trp Ala Gln
1955                1960                1965

Thr Val Val Gly Arg Ala Arg Leu Gly Gly Ile Pro Val Gly
1970                1975                1980

Val Val Ala Val Glu Thr Arg Thr Val Glu Leu Ser Val Pro Ala
1985                1990                1995

Asp Pro Ala Asn Leu Asp Ser Glu Ala Lys Ile Ile Gln Gln Ala
2000                2005                2010

Gly Gln Val Trp Phe Pro Asp Ser Ala Phe Lys Thr Tyr Gln Ala
2015                2020                2025

Ile Lys Asp Phe Asn Arg Glu Gly Leu Pro Leu Met Val Phe Ala
2030                2035                2040

Asn Trp Arg Gly Phe Ser Gly Gly Met Lys Asp Met Tyr Asp Gln
2045                2050                2055

Val Leu Lys Phe Gly Ala Tyr Ile Val Asp Gly Leu Arg Glu Cys
```

```
                2060                2065                2070
Ser Gln Pro Val Met Val Tyr Ile Pro Pro Gln Ala Glu Leu Arg
    2075                2080                2085
Gly Gly Ser Trp Val Val Ile Asp Pro Thr Ile Asn Pro Arg His
    2090                2095                2100
Met Glu Met Tyr Ala Asp Arg Glu Ser Arg Gly Ser Val Leu Glu
    2105                2110                2115
Pro Glu Gly Thr Val Glu Ile Lys Phe Arg Lys Lys Asp Leu Val
    2120                2125                2130
Lys Thr Met Arg Arg Val Asp Pro Val Tyr Ile Arg Leu Ala Glu
    2135                2140                2145
Arg Leu Gly Thr Pro Glu Leu Ser Pro Thr Glu Arg Lys Glu Leu
    2150                2155                2160
Glu Ser Lys Leu Lys Glu Arg Glu Glu Phe Leu Ile Pro Ile Tyr
    2165                2170                2175
His Gln Val Ala Val Gln Phe Ala Asp Leu His Asp Thr Pro Gly
    2180                2185                2190
Arg Met Gln Glu Lys Gly Val Ile Asn Asp Ile Leu Asp Trp Lys
    2195                2200                2205
Thr Ser Arg Thr Phe Phe Tyr Trp Arg Leu Arg Arg Leu Leu Leu
    2210                2215                2220
Glu Asp Leu Val Lys Lys Lys Ile His Ser Ala Asn Pro Glu Leu
    2225                2230                2235
Thr Asp Gly Gln Ile Gln Ala Met Leu Arg Arg Trp Phe Val Glu
    2240                2245                2250
Val Glu Gly Thr Val Lys Ala Tyr Val Trp Asp Asn Asn Lys Asp
    2255                2260                2265
Leu Val Glu Trp Leu Glu Lys Gln Leu Thr Glu Glu Asp Gly Val
    2270                2275                2280
Arg Ser Val Ile Glu Glu Asn Ile Lys Tyr Ile Ser Arg Asp Tyr
    2285                2290                2295
Val Leu Lys Gln Ile Arg Ser Leu Val Gln Ala Asn Pro Glu Val
    2300                2305                2310
Ala Met Asp Ser Ile Val His Met Thr Gln His Ile Ser Pro Thr
    2315                2320                2325
Gln Arg Ala Glu Val Val Arg Ile Leu Ser Thr Met Asp Ser Pro
    2330                2335                2340
Ser Thr
    2345

<210> SEQ ID NO 158
<211> LENGTH: 1254
<212> TYPE: DNA
<213> ORGANISM: Scenedesmus dimorphus

<400> SEQUENCE: 158
gtcaatgcag tcaaccctga gaaaaacggc gcttatgagg gctcccccat tgtcagcggc      60
cccatttctg tgggtgctat ggacaaggac tccaagggct cttccaagcc tgttgaccgc     120
agcaagggcc tctggacgcg ctgcgacaag tgcggcgtga ttctctacat caagcacctg     180
aaggagcacc accacatctg cttcggctgc aactaccacc tcaagatgag cagccaggag     240
aggatcgacc acatgatcga cccaggctca tggcgcccct tgacgagac gctgtctccc      300 tgcgacccgc tggactttgt ggacatgaag ccatacccag acagggtgcg cgacagccag     360
```

| | |
|---|---|
| gacaagacag gcatgaacga tgccatccgc acaggcacgg gcctgctgca cggcatccca | 420 |
| gtggcgctgg cagtgatgga gtttggcttc atgggcggca gcatgggcag cgtggtgggg | 480 |
| gagaagctga cgcgcctgat tgagtacgcc acgcaggagg ggctcacgct gctggtggtg | 540 |
| tgcaccagcg gaggcgcgcg catgcaggag ggcatcatga gcctgatgca gatggccaag | 600 |
| atcagcggcg cgctgcacgt gcaccagaat gaggccaacc tgctgtacat ctccatcctg | 660 |
| accagcccca ccacaggtgg cgtgaccgca agctttggca tgctggggga tgtcatcatt | 720 |
| gctgagccgc aggccatcat cggctttgca ggacggcgtg tgatcgagca gacgctgcgt | 780 |
| gaggagctgc cagatgactt ccagaccgcg gagtacctgc ttgacaaggg cctgctcgac | 840 |
| ctggtggtgc cgcgcagctt cctgaagggc gcgctgtttg agatcatcga cttctacaag | 900 |
| aacgcaccct acaagcgccg cggcaagatt ccatttggcg tgcagcgcgg tacgtacggc | 960 |
| ctgaccgctg aggagaagat gcggcgcagg tggagggagt ggagctcagc tggcagcaac | 1020 |
| ggctcgggca cgcccgcgct ggcagcagca gcagcatcag cagcagttgg gtcagcagcc | 1080 |
| acttgcggca gctgccagca gcagcagctg gcgctgtggg cggtgctggc aggctgtggc | 1140 |
| agctgtgggc agtggctgtg gtttgctcag ggggtaggtg cgcttgagcg cacagcggca | 1200 |
| acagcagcag tactgagaga gggcagcgtg ctgctagcag gcgtctgttg ttaa | 1254 |

<210> SEQ ID NO 159
<211> LENGTH: 1320
<212> TYPE: DNA
<213> ORGANISM: Scenedesmus dimorphus

<400> SEQUENCE: 159

| | |
|---|---|
| gtcaatgcag tcaaccctga gaaaaacggc gcttatgagg gctcccccat tgtcagcggc | 60 |
| cccatttctg tgggtgctat ggacaaggac tccaagggct cttccaagcc tgttgaccgc | 120 |
| agcaagggcc tctggacgcg ctgcgacaag tgcggcgtga ttctctacat caagcacctg | 180 |
| aaggagcacc accacatctg cttcggctgc aactaccacc tcaagatgag cagccaggag | 240 |
| aggatcgacc acatgatcga cccaggctca tggcgcccct ttgacgagac gctgtctccc | 300 |
| tgcgacccgc tggactttgt ggacatgaag ccatacccag acagggtgcg cgacagccag | 360 |
| gacaagacag gcatgaacga tgccatccgc acaggcacgg gcctgctgca cggcatccca | 420 |
| gtggcgctgg cagtgatgga gtttggcttc atgggcggca gcatgggcag cgtggtgggg | 480 |
| gagaagctga cgcgcctgat tgagtacgcc acgcaggagg ggctcacgct gctggtggtg | 540 |
| tgcaccagcg gaggcgcgcg catgcaggag ggcatcatga gcctgatgca gatggccaag | 600 |
| atcagcggcg cgctgcacgt gcaccagaat gaggccaacc tgctgtacat ctccatcctg | 660 |
| accagcccca ccacaggtgg cgtgaccgca agctttggca tgctggggga tgtcatcatt | 720 |
| gctgagccgc aggccatcat cggctttgca ggacggcgtg tgatcgagca gacgctgcgt | 780 |
| gaggagctgc cagatgactt ccagaccgcg gagtacctgc ttgacaaggg cctgctcgac | 840 |
| ctggtggtgc cgcgcagctt cctgaagggc gcgctgtttg agatcatcga cttctacaag | 900 |
| aacgcaccct acaagcgccg cggcaagatt ccatttggcg tgcagcgcgg tacgtacggc | 960 |
| ctgaccgctg aggagaagat gcggcgcagg tggagggagt ggagctcagt tggcagcatg | 1020 |
| ttgcatagtg ttcactatgc aggccactgg ccctctgggt gtgctgggat gttgctgggc | 1080 |
| cagcgcccac ttcatatgca ttggcatgtc aatgaagggt caggttgtag caagaccacg | 1140 |
| tgccagagct ttaagtattg gtcagcatgt gctgcttggc atgcagtgtg ccatcggcga | 1200 |
| ggaacacttc ttgaacatga acttaccaag ctgatttcct ggcagtttga ttcatgctgt | 1260 |

```
tggcgtgctg ccaaaggtat tctgcttaga tcttgcaatg ctgtgtatgt atatgtgtaa    1320
```

<210> SEQ ID NO 160
<211> LENGTH: 1158
<212> TYPE: DNA
<213> ORGANISM: Scenedesmus dimorphus

<400> SEQUENCE: 160

```
gtcaatgcag tcaaccctga gaaaaacggc gcttatgagg gctcccccat tgtcagcggc      60
cccatttctg tgggtgctat ggacaaggac tccaagggct cttccaagcc tgttgaccgc     120
agcaagggcc tctggacgcg ctgcgacaag tgcggcgtga ttctctacat caagcacctg     180
aaggagcacc accacatctg cttcggctgc aactaccacc tcaagatgag cagccaggag     240
aggatcgacc acatgatcga cccaggctca tggcgcccct tgacgagac gctgtctccc      300
tgcgacccgc tggactttgt ggacatgaag ccatacccag acagggtgcg cgacagccag     360
gacaagacag gcatgaacga tgccatccgc acaggcacgg cctgctgca cggcatccca      420
gtggcgctgg cagtgatgga gtttggcttc atgggcggca gcatgggcag cgtggtgggg     480
gagaagctga cgcgcctgat tgagtacgcc acgcaggagg gctcacgct gctggtggtg      540
tgcaccagcg gaggcgcgcg catgcaggag ggcatcatga gcctgatgca gatggccaag     600
atcagcggcg cgctgcacgt gcaccagaat gaggccaacc tgctgtacat ctccatcctg     660
accagcccca ccacaggtgg cgtgaccgca agctttggca tgctgggga tgtcatcatt      720
gctgagccgc aggccatcat cggctttgca ggacggcgtg tgatcgagca gacgctgcgt     780
gaggagctgc cagatgactt ccagaccgcg gagtacctgc ttgacaaggg cctgctcgac     840
ctggtggtgc cgcgcagctt cctgaagggc gcgctgtttg agatcatcga cttttacaag     900
aacgcaccct acaagcgccg cggcaagatt ccatttggcg tgcagcgcgg tacgtacggc     960
ctgaccgctg aggagaagat gcggcgcagg tggagggagt ggagctcagc tggcagcaac    1020
ggctcgggca cgcccgcgct ggcagcagca gcagcagtgg tggcgccgtg cagcagtgga    1080
ggagttgcat gcgcactgag acgagcttgt tcaagagtta gtcggatggg cggggtgggg    1140
agcttgctac gctgctag                                                  1158
```

<210> SEQ ID NO 161
<211> LENGTH: 1149
<212> TYPE: DNA
<213> ORGANISM: Scenedesmus dimorphus

<400> SEQUENCE: 161

```
gtcaatgcag tcaaccctga gaaaaacggc gcttatgagg gctcccccat tgtcagcggc      60
cccatttctg tgggtgctat ggacaaggac tccaagggct cttccaagcc tgttgaccgc     120
agcaagggcc tctggacgcg ctgcgacaag tgcggcgtga ttctctacat caagcacctg     180
aaggagcacc accacatctg cttcggctgc aactaccacc tcaagatgag cagccaggag     240
aggatcgacc acatgatcga cccaggctca tggcgcccct tgacgagac gctgtctccc      300
tgcgacccgc tggactttgt ggacatgaag ccatacccag acagggtgcg cgacagccag     360
gacaagacag gcatgaacga tgccatccgc acaggcacgg cctgctgca cggcatccca      420
gtggcgctgg cagtgatgga gtttggcttc atgggcggca gcatgggcag cgtggtgggg     480
gagaagctga cgcgcctgat tgagtacgcc acgcaggagg gctcacgct gctggtggtg      540
tgcaccagcg gaggcgcgcg catgcaggag ggcatcatga gcctgatgca gatggccaag     600
```

```
atcagcggcg cgctgcacgt gcaccagaat gaggccaacc tgctgtacat ctccatcctg      660
accagcccca ccacaggtgg cgtgaccgca agctttggca tgctggggga tgtcatcatt      720
gctgagccgc aggccatcat cggctttgca ggacggcgtg tgatcgagca gacgctgcgt      780
gaggagctgc cagatgactt ccagaccgcg gagtacctgc ttgacaaggg cctgctcgac      840
ctggtggtgc cgcgcagctt cctgaagggc gcgctgtttg agatcatcga cttgtacaag      900
aaagcacccc ccaagcggcg gggcaagatt ccatttggcg tgcatagcgg tacgtacggc      960
caaccgccga ggagaagatc cggcgcaggt ggagggaggg gagttcagct ggcagcaacg     1020
ggtggggcac gcccgcgctg gcagcagcag cagcaggggg cggtgcgggg ttttggcgcc     1080
aagccattcc aggggggttgg tatatgtgac agcagcctgt ttggtcacag tctggatggt    1140
gcggcataa                                                             1149
```

<210> SEQ ID NO 162
<211> LENGTH: 1101
<212> TYPE: DNA
<213> ORGANISM: Scenedesmus dimorphus

<400> SEQUENCE: 162

```
gtcaatgcag tcaaccctga gaaaaacggc gcttatgagg gctcccccat tgtcagcggc       60
cccatttctg tgggtgctat ggacaaggac tccaagggct cttccaagcc tgttgaccgc      120 agcaaggggcc tctggacgcg ctgcgacaag tgcggcgtga ttctctacat caagcacctg     180
aaggagcacc accacatctg cttcggctgc aactaccacc tcaagatgag cagccaggag      240
aggatcgacc acatgatcga cccaggctca tggcgcccct tgacgagac gctgtctccc      300 tgcgacccgc tggactttgt ggacatgaag ccatacccag acagggtgcg cgacagccag      360
gacaagacag gcatgaacga tgccatccgc acaggcacgg gcctgctgca cggcatccca     420
gtggcgctgg cagtgatgga gtttggcttc atgggcggca gcatgggcag cgtggtgggg     480
gagaagctga cgcgcctgat tgagtacgcc acgcaggagg ggctcacgct gctggtggtg     540
tgcaccagcg gaggcgcgcg catgcaggag ggcatcatga gcctgatgca gatggccaag     600
atcagcggcg cgctgcacgt gcaccagaat gaggccaacc tgctgtacat ctccatcctg     660
accagcccca ccacaggtgg cgtgaccgca agctttggca tgctggggga tgtcatcatt     720
gctgagccgc aggccatcat cggctttgca ggacggcgtg tgatcgagca gacgctgcgt     780
gaggagctgc cagatgactt ccagaccgcg gagtacctgc ttgacaaggg cctgctcgac     840
ctggtggtgc cgcgcagctt cctgaagggc gcgctgtttg agatcatcga cttttacaag     900
aacgcaccct gcaagcgccg cggcaagatt ccatttggcg tgcagcgcgg tacgtacggc     960
ctgaccgctg aggagaagat gcggcgcagg tggagggagt ggagctcagc tggcagcaac    1020
ggctcgggca cgcccgcgct ggcagcagca gcagcagagc tgagagaggg cagcgtgctg    1080
ctagcaggcg tctgttgtta a                                              1101
```

<210> SEQ ID NO 163
<211> LENGTH: 417
<212> TYPE: PRT
<213> ORGANISM: Scenedesmus dimorphus

<400> SEQUENCE: 163

```
Val Asn Ala Val Asn Pro Glu Lys Asn Gly Ala Tyr Glu Gly Ser Pro
1               5                   10                  15

Ile Val Ser Gly Pro Ile Ser Val Gly Ala Met Asp Lys Asp Ser Lys
            20                  25                  30
```

```
Gly Ser Ser Lys Pro Val Asp Arg Ser Lys Gly Leu Trp Thr Arg Cys
         35                  40                  45

Asp Lys Cys Gly Val Ile Leu Tyr Ile Lys His Leu Lys Glu His His
 50                  55                  60

His Ile Cys Phe Gly Cys Asn Tyr His Leu Lys Met Ser Ser Gln Glu
 65                  70                  75                  80

Arg Ile Asp His Met Ile Asp Pro Gly Ser Trp Arg Pro Phe Asp Glu
                 85                  90                  95

Thr Leu Ser Pro Cys Asp Pro Leu Asp Phe Val Asp Met Lys Pro Tyr
                100                 105                 110

Pro Asp Arg Val Arg Asp Ser Gln Asp Lys Thr Gly Met Asn Asp Ala
                115                 120                 125

Ile Arg Thr Gly Thr Gly Leu Leu His Gly Ile Pro Val Ala Leu Ala
                130                 135                 140

Val Met Glu Phe Gly Phe Met Gly Gly Ser Met Gly Ser Val Val Gly
145                 150                 155                 160

Glu Lys Leu Thr Arg Leu Ile Glu Tyr Ala Thr Gln Glu Gly Leu Thr
                165                 170                 175

Leu Leu Val Cys Thr Ser Gly Ala Arg Met Gln Glu Gly Ile
                180                 185                 190

Met Ser Leu Met Gln Met Ala Lys Ile Ser Gly Ala Leu His Val His
                195                 200                 205

Gln Asn Glu Ala Asn Leu Leu Tyr Ile Ser Ile Leu Thr Ser Pro Thr
                210                 215                 220

Thr Gly Gly Val Thr Ala Ser Phe Gly Met Leu Gly Asp Val Ile Ile
225                 230                 235                 240

Ala Glu Pro Gln Ala Ile Ile Gly Phe Ala Gly Arg Arg Val Ile Glu
                245                 250                 255

Gln Thr Leu Arg Glu Glu Leu Pro Asp Asp Phe Gln Thr Ala Glu Tyr
                260                 265                 270

Leu Leu Asp Lys Gly Leu Leu Asp Leu Val Val Pro Arg Ser Phe Leu
                275                 280                 285

Lys Gly Ala Leu Phe Glu Ile Ile Asp Phe Tyr Lys Asn Ala Pro Tyr
                290                 295                 300

Lys Arg Arg Gly Lys Ile Pro Phe Gly Val Gln Arg Gly Thr Tyr Gly
305                 310                 315                 320

Leu Thr Ala Glu Glu Lys Met Arg Arg Trp Arg Glu Trp Ser Ser
                325                 330                 335

Ala Gly Ser Asn Gly Ser Gly Thr Pro Ala Leu Ala Ala Ala Ala
                340                 345                 350

Ser Ala Ala Val Gly Ser Ala Ala Thr Cys Gly Ser Cys Gln Gln Gln
                355                 360                 365

Gln Leu Ala Leu Trp Ala Val Leu Ala Gly Cys Gly Ser Cys Gly Gln
                370                 375                 380

Trp Leu Trp Phe Ala Gln Gly Val Gly Ala Leu Glu Arg Thr Ala Ala
385                 390                 395                 400

Thr Ala Ala Val Leu Arg Glu Gly Ser Val Leu Leu Ala Gly Val Cys
                405                 410                 415

Cys

<210> SEQ ID NO 164
<211> LENGTH: 439
<212> TYPE: PRT
```

<213> ORGANISM: Scenedesmus dimorphus

<400> SEQUENCE: 164

```
Val Asn Ala Val Asn Pro Glu Lys Asn Gly Ala Tyr Glu Gly Ser Pro
1               5                   10                  15

Ile Val Ser Gly Pro Ile Ser Val Gly Ala Met Asp Lys Asp Ser Lys
            20                  25                  30

Gly Ser Ser Lys Pro Val Asp Arg Ser Lys Gly Leu Trp Thr Arg Cys
        35                  40                  45

Asp Lys Cys Gly Val Ile Leu Tyr Ile Lys His Leu Lys Glu His His
    50                  55                  60

His Ile Cys Phe Gly Cys Asn Tyr His Leu Lys Met Ser Ser Gln Glu
65                  70                  75                  80

Arg Ile Asp His Met Ile Asp Pro Gly Ser Trp Arg Pro Phe Asp Glu
                85                  90                  95

Thr Leu Ser Pro Cys Asp Pro Leu Asp Phe Val Asp Met Lys Pro Tyr
            100                 105                 110

Pro Asp Arg Val Arg Asp Ser Gln Asp Lys Thr Gly Met Asn Asp Ala
        115                 120                 125

Ile Arg Thr Gly Thr Gly Leu Leu His Gly Ile Pro Val Ala Leu Ala
    130                 135                 140

Val Met Glu Phe Gly Phe Met Gly Ser Met Gly Ser Val Val Gly
145                 150                 155                 160

Glu Lys Leu Thr Arg Leu Ile Glu Tyr Ala Thr Gln Glu Gly Leu Thr
                165                 170                 175

Leu Leu Val Val Cys Thr Ser Gly Gly Ala Arg Met Gln Glu Gly Ile
            180                 185                 190

Met Ser Leu Met Gln Met Ala Lys Ile Ser Gly Ala Leu His Val His
        195                 200                 205

Gln Asn Glu Ala Asn Leu Leu Tyr Ile Ser Ile Leu Thr Ser Pro Thr
    210                 215                 220

Thr Gly Gly Val Thr Ala Ser Phe Gly Met Leu Gly Asp Val Ile Ile
225                 230                 235                 240

Ala Glu Pro Gln Ala Ile Ile Gly Phe Ala Gly Arg Arg Val Ile Glu
                245                 250                 255

Gln Thr Leu Arg Glu Glu Leu Pro Asp Asp Phe Gln Thr Ala Glu Tyr
            260                 265                 270

Leu Leu Asp Lys Gly Leu Leu Asp Leu Val Val Pro Arg Ser Phe Leu
        275                 280                 285

Lys Gly Ala Leu Phe Glu Ile Ile Asp Phe Tyr Lys Asn Ala Pro Tyr
    290                 295                 300

Lys Arg Arg Gly Lys Ile Pro Phe Gly Val Gln Arg Gly Thr Tyr Gly
305                 310                 315                 320

Leu Thr Ala Glu Glu Lys Met Arg Arg Trp Arg Glu Trp Ser Ser
                325                 330                 335

Val Gly Ser Met Leu His Ser Val His Tyr Ala Gly His Trp Pro Ser
            340                 345                 350

Gly Cys Ala Gly Met Leu Leu Gly Gln Arg Pro Leu His Met His Trp
        355                 360                 365

His Val Asn Glu Gly Ser Gly Cys Ser Lys Thr Thr Cys Gln Ser Phe
    370                 375                 380

Lys Tyr Trp Ser Ala Cys Ala Ala Trp His Ala Val Cys His Arg Arg
385                 390                 395                 400
```

```
Gly Thr Leu Leu Glu His Glu Leu Thr Lys Leu Ile Ser Trp Gln Phe
                405                 410                 415

Asp Ser Cys Cys Trp Arg Ala Ala Lys Gly Ile Leu Leu Arg Ser Cys
            420                 425                 430

Asn Ala Val Tyr Val Tyr Val
        435

<210> SEQ ID NO 165
<211> LENGTH: 385
<212> TYPE: PRT
<213> ORGANISM: Scenedesmus dimorphus

<400> SEQUENCE: 165

Val Asn Ala Val Asn Pro Glu Lys Asn Gly Ala Tyr Glu Gly Ser Pro
1               5                   10                  15

Ile Val Ser Gly Pro Ile Ser Val Gly Ala Met Asp Lys Asp Ser Lys
            20                  25                  30

Gly Ser Ser Lys Pro Val Asp Arg Ser Lys Gly Leu Trp Thr Arg Cys
        35                  40                  45

Asp Lys Cys Gly Val Ile Leu Tyr Ile Lys His Leu Lys Glu His His
    50                  55                  60

His Ile Cys Phe Gly Cys Asn Tyr His Leu Lys Met Ser Ser Gln Glu
65                  70                  75                  80

Arg Ile Asp His Met Ile Asp Pro Gly Ser Trp Arg Pro Phe Asp Glu
                85                  90                  95

Thr Leu Ser Pro Cys Asp Pro Leu Asp Phe Val Asp Met Lys Pro Tyr
            100                 105                 110

Pro Asp Arg Val Arg Asp Ser Gln Asp Lys Thr Gly Met Asn Asp Ala
        115                 120                 125

Ile Arg Thr Gly Thr Gly Leu Leu His Gly Ile Pro Val Ala Leu Ala
    130                 135                 140

Val Met Glu Phe Gly Phe Met Gly Gly Ser Met Gly Ser Val Val Gly
145                 150                 155                 160

Glu Lys Leu Thr Arg Leu Ile Glu Tyr Ala Thr Gln Glu Gly Leu Thr
                165                 170                 175

Leu Leu Val Val Cys Thr Ser Gly Gly Ala Arg Met Gln Glu Gly Ile
            180                 185                 190

Met Ser Leu Met Gln Met Ala Lys Ile Ser Gly Ala Leu His Val His
        195                 200                 205

Gln Asn Glu Ala Asn Leu Leu Tyr Ile Ser Ile Leu Thr Ser Pro Thr
    210                 215                 220

Thr Gly Gly Val Thr Ala Ser Phe Gly Met Leu Gly Asp Val Ile Ile
225                 230                 235                 240

Ala Glu Pro Gln Ala Ile Ile Gly Phe Ala Gly Arg Arg Val Ile Glu
                245                 250                 255

Gln Thr Leu Arg Glu Glu Leu Pro Asp Asp Phe Gln Thr Ala Glu Tyr
            260                 265                 270

Leu Leu Asp Lys Gly Leu Leu Asp Leu Val Val Pro Arg Ser Phe Leu
        275                 280                 285

Lys Gly Ala Leu Phe Glu Ile Ile Asp Phe Tyr Lys Asn Ala Pro Tyr
    290                 295                 300

Lys Arg Arg Gly Lys Ile Pro Phe Gly Val Gln Arg Gly Thr Tyr Gly
305                 310                 315                 320

Leu Thr Ala Glu Glu Lys Met Arg Arg Arg Trp Arg Glu Trp Ser Ser
                325                 330                 335
```

```
Ala Gly Ser Asn Gly Ser Gly Thr Pro Ala Leu Ala Ala Ala Ala
            340                 345                 350
Val Val Ala Pro Cys Ser Ser Gly Val Ala Cys Ala Leu Arg Arg
            355                 360                 365
Ala Cys Ser Arg Val Ser Arg Met Gly Val Gly Ser Leu Leu Arg
370                 375                 380
Cys
385

<210> SEQ ID NO 166
<211> LENGTH: 382
<212> TYPE: PRT
<213> ORGANISM: Scenedesmus dimorphus

<400> SEQUENCE: 166

Val Asn Ala Val Asn Pro Glu Lys Asn Gly Ala Tyr Glu Gly Ser Pro
1               5                   10                  15
Ile Val Ser Gly Pro Ile Ser Val Gly Ala Met Asp Lys Asp Ser Lys
            20                  25                  30
Gly Ser Ser Lys Pro Val Asp Arg Ser Lys Gly Leu Trp Thr Arg Cys
            35                  40                  45
Asp Lys Cys Gly Val Ile Leu Tyr Ile Lys His Leu Lys Glu His His
        50                  55                  60
His Ile Cys Phe Gly Cys Asn Tyr His Leu Lys Met Ser Ser Gln Glu
65                  70                  75                  80
Arg Ile Asp His Met Ile Asp Pro Gly Ser Trp Arg Pro Phe Asp Glu
                85                  90                  95
Thr Leu Ser Pro Cys Asp Pro Leu Asp Phe Val Asp Met Lys Pro Tyr
            100                 105                 110
Pro Asp Arg Val Arg Asp Ser Gln Asp Lys Thr Gly Met Asn Asp Ala
            115                 120                 125
Ile Arg Thr Gly Thr Gly Leu Leu His Gly Ile Pro Val Ala Leu Ala
        130                 135                 140
Val Met Glu Phe Gly Phe Met Gly Gly Ser Met Gly Ser Val Val Gly
145                 150                 155                 160
Glu Lys Leu Thr Arg Leu Ile Glu Tyr Ala Thr Gln Glu Gly Leu Thr
                165                 170                 175
Leu Leu Val Val Cys Thr Ser Gly Gly Ala Arg Met Gln Glu Gly Ile
            180                 185                 190
Met Ser Leu Met Gln Met Ala Lys Ile Ser Gly Ala Leu His Val His
        195                 200                 205
Gln Asn Glu Ala Asn Leu Leu Tyr Ile Ser Ile Leu Thr Ser Pro Thr
    210                 215                 220
Thr Gly Gly Val Thr Ala Ser Phe Gly Met Leu Gly Asp Val Ile Ile
225                 230                 235                 240
Ala Glu Pro Gln Ala Ile Ile Gly Phe Ala Gly Arg Arg Val Ile Glu
                245                 250                 255
Gln Thr Leu Arg Glu Glu Leu Pro Asp Asp Phe Gln Thr Ala Glu Tyr
            260                 265                 270
Leu Leu Asp Lys Gly Leu Leu Asp Leu Val Pro Arg Ser Phe Leu
            275                 280                 285
Lys Gly Ala Leu Phe Glu Ile Ile Asp Leu Tyr Lys Lys Ala Pro Pro
        290                 295                 300
Lys Arg Arg Gly Lys Ile Pro Phe Gly Val His Ser Gly Thr Tyr Gly
```

```
                305                 310                 315                 320
        Gln Pro Pro Arg Arg Ser Gly Ala Gly Gly Arg Gly Val Gln
                        325                 330                 335

Leu Ala Ala Thr Gly Gly Ala Arg Pro Arg Trp Gln Gln Gln Gln
                        340                 345                 350

Gly Gly Gly Ala Gly Phe Gly Ala Lys Pro Phe Gln Gly Val Gly Ile
                        355                 360                 365

Cys Asp Ser Ser Leu Phe Gly His Ser Leu Asp Gly Ala Ala
                370                 375                 380

<210> SEQ ID NO 167
<211> LENGTH: 366
<212> TYPE: PRT
<213> ORGANISM: Scenedesmus dimorphus

<400> SEQUENCE: 167

Val Asn Ala Val Asn Pro Glu Lys Asn Gly Ala Tyr Glu Gly Ser Pro
1               5                   10                  15

Ile Val Ser Gly Pro Ile Ser Val Gly Ala Met Asp Lys Asp Ser Lys
                20                  25                  30

Gly Ser Ser Lys Pro Val Asp Arg Ser Lys Gly Leu Trp Thr Arg Cys
            35                  40                  45

Asp Lys Cys Gly Val Ile Leu Tyr Ile Lys His Leu Lys Glu His His
        50                  55                  60

His Ile Cys Phe Gly Cys Asn Tyr His Leu Lys Met Ser Ser Gln Glu
65                  70                  75                  80

Arg Ile Asp His Met Ile Asp Pro Gly Ser Trp Arg Pro Phe Asp Glu
                85                  90                  95

Thr Leu Ser Pro Cys Asp Pro Leu Asp Phe Val Asp Met Lys Pro Tyr
            100                 105                 110

Pro Asp Arg Val Arg Asp Ser Gln Asp Lys Thr Gly Met Asn Asp Ala
        115                 120                 125

Ile Arg Thr Gly Thr Gly Leu Leu His Gly Ile Pro Val Ala Leu Ala
    130                 135                 140

Val Met Glu Phe Gly Phe Met Gly Gly Ser Met Gly Ser Val Val Gly
145                 150                 155                 160

Glu Lys Leu Thr Arg Leu Ile Glu Tyr Ala Thr Gln Glu Gly Leu Thr
                165                 170                 175

Leu Leu Val Val Cys Thr Ser Gly Gly Ala Arg Met Gln Glu Gly Ile
            180                 185                 190

Met Ser Leu Met Gln Met Ala Lys Ile Ser Gly Ala Leu His Val His
        195                 200                 205

Gln Asn Glu Ala Asn Leu Leu Tyr Ile Ser Ile Leu Thr Ser Pro Thr
    210                 215                 220

Thr Gly Gly Val Thr Ala Ser Phe Gly Met Leu Gly Asp Val Ile Ile
225                 230                 235                 240

Ala Glu Pro Gln Ala Ile Ile Gly Phe Ala Gly Arg Arg Val Ile Glu
                245                 250                 255

Gln Thr Leu Arg Glu Glu Leu Pro Asp Asp Phe Gln Thr Ala Glu Tyr
            260                 265                 270

Leu Leu Asp Lys Gly Leu Leu Asp Leu Val Val Pro Arg Ser Phe Leu
        275                 280                 285

Lys Gly Ala Leu Phe Glu Ile Ile Asp Phe Tyr Lys Asn Ala Pro Cys
    290                 295                 300
```

Lys Arg Arg Gly Lys Ile Pro Phe Gly Val Gln Gly Thr Tyr Gly
305                 310                 315                 320

Leu Thr Ala Glu Glu Lys Met Arg Arg Arg Trp Arg Glu Trp Ser Ser
                325                 330                 335

Ala Gly Ser Asn Gly Ser Gly Thr Pro Ala Leu Ala Ala Ala Ala
                340                 345                 350

Glu Leu Arg Glu Gly Ser Val Leu Leu Ala Gly Val Cys Cys
                355                 360                 365

```
<210> SEQ ID NO 168
<211> LENGTH: 1254
<212> TYPE: DNA
<213> ORGANISM: Artificial Sequence
<220> FEATURE:
<223> OTHER INFORMATION: modified acetyl CoA carboxylase

<400> SEQUENCE: 168
gtaaacgctg taaacccaga aaaaacggt gcttacgaag gttcaccaat tgtatcaggt      60
ccaatttcag taggtgctat ggacaaagac tcaaaaggtt catcaaaacc agtagaccgt    120
tcaaaaggtt tatggacacg ttgtgacaaa tgtggtgtaa ttttatacat taaacactta    180
aaagaacacc accacatttg tttcggttgt aactaccact aaaaatgtc atcacaagaa     240 cgtattgacc acatgattga cccaggttca tggcgtccat tcgacgaaac attatcacca    300
tgtgacccat tagcttcgt agacatgaaa ccatacccag accgtgtacg tgactcacaa     360
gacaaaacag gtatgaacga cgctattcgt acaggtacag gtttattaca cggtattcca    420
gtagctttag ctgtaatgga attcggtttc atgggtggtt caatgggttc agtagtaggt    480
gaaaaattaa cacgtttaat tgaatacgct acacaagaag gtttaacatt attagtagta    540
tgtacatcag gtggtgctcg tatgcaagaa ggtattatgt cattaatgca aatggctaaa    600
atttcaggtg ctttacacgt acaccaaaac gaagctaact tattatacat ttcaattta    660 acatcaccaa caacaggtgg tgtaacagct tcattcggta tgttaggtga cgtaattatt    720
gctgaaccac aagctattat tggtttcgct ggtcgtcgtg taattgaaca acattacgt     780 gaagaattac cagacgactt ccaaacagct gaatacttat tagacaaagg tttattagac    840
ttagtagtac cacgttcatt cttaaaaggt gctttattcg aaattattga cttctacaaa    900
aacgctccat acaaacgtcg tggtaaaatt ccattcggtg tacaacgtgg tacatacggt    960
ttaacagctg aagaaaaaat gcgtcgtcgt tggcgtgaat ggtcatcagc tggttcaaac    1020
ggttcaggta caccagcttt agctgctgct gctgcttcag ctgctgtagg ttcagctgct    1080
acatgtggtt catgtcaaca acaacaatta gctttatggg ctgtattagc tggttgtggt    1140
tcatgtggtc aatggttatg gttcgctcaa ggtgtaggtg ctttagaacg tacagctgct    1200
acagctgctg tattacgtga aggttcagta ttattagctg gtgtatgttg ttaa         1254

<210> SEQ ID NO 169
<211> LENGTH: 1320
<212> TYPE: DNA
<213> ORGANISM: Artificial Sequence
<220> FEATURE:
<223> OTHER INFORMATION: modified acetyl CoA carboxylase

<400> SEQUENCE: 169
gtaaacgctg taaacccaga aaaaacggt gcttacgaag gttcaccaat tgtatcaggt      60
ccaatttcag taggtgctat ggacaaagac tcaaaaggtt catcaaaacc agtagaccgt    120
tcaaaaggtt tatggacacg ttgtgacaaa tgtggtgtaa ttttatacat taaacactta    180
```

```
aaagaacacc accacatttg tttcggttgt aactaccact taaaaatgtc atcacaagaa      240
cgtattgacc acatgattga cccaggttca tggcgtccat cgacgaaac attatcacca       300 tgtgacccat tagacttcgt agacatgaaa ccatacccag accgtgtacg tgactcacaa     360
gacaaaacag gtatgaacga cgctattcgt acaggtacag gtttattaca cggtattcca    420
gtagctttag ctgtaatgga attcggtttc atgggtggtt caatgggttc agtagtaggt   480
gaaaaattaa cacgtttaat tgaatacgct acacaagaag gtttaacatt attagtagta   540
tgtacatcag gtggtgctcg tatgcaagaa ggtattatgt cattaatgca aatggctaaa   600
atttcaggtg ctttacacgt acaccaaaac gaagctaact tattatacat ttcaattta    660 acatcaccaa caacaggtgg tgtaacagct tcattcggta tgttaggtga cgtaattatt   720
gctgaaccac aagctattat tggtttcgct ggtcgtcgtg taattgaaca aacattacgt   780
gaagaattac cagacgactt ccaaacagct gaatacttat tagacaaagg tttattagac   840
ttagtagtac cacgttcatt cttaaaaggt gctttattcg aaattattga cttctacaaa   900
aacgctccat acaaacgtcg tggtaaaatt ccattcggtg tacaacgtgg tacatacggt   960
ttaacagctg aagaaaaaat gcgtcgtcgt tggcgtgaat ggtcatcagt aggttcaatg  1020
ttacactcag tacactacgc tggtcactgg ccatcaggtt gtgctggtat gttattaggt  1080
caacgtccat tacacatgca ctggcacgta aacgaaggtt caggttgttc aaaaacaaca  1140
tgtcaatcat tcaaatactg gtcagcttgt gctgcttggc acgctgtatg tcaccgtcgt  1200
ggtacattat tagaacacga attaacaaaa ttaatttcat ggcaattcga ctcatgttgt  1260
tggcgtgctg ctaaaggtat tttattacgt tcatgtaacg ctgtatacgt atacgtataa  1320
```

<210> SEQ ID NO 170
<211> LENGTH: 1382
<212> TYPE: DNA
<213> ORGANISM: Scenedesmus dimorphus

<400> SEQUENCE: 170

```
atgtctctta agtccagcgt gggccccagc ctggccggca aggcgtgcca cggagcaaat      60
gcgcaggtgc tgccgcgcat ggcagtgcca gcgccgcttg caggaacagc agtgcgcccc     120
agcctcgcag tcaatgcagt caaccctgag aaaaacggcg cttatgaggg ctcccccatt     180
gtcagcggcc ccatttctgt gggtgctatg acaaggact ccaagggctc ttccaagcct     240
gttgaccgca gcaagggcct ctggacgcgc tgcgacaagt gcggcgtgat tctctacatc    300
aagcacctga aggagcacca ccacatctgc ttcggctgca actaccacct caagatgagc    360
agccaggaga ggatcgacca catgatcgac ccaggctcat ggcgcccctt tgacgagacg    420
ctgtctccct gcgacccgct ggactttgtg gacatgaagc cataccagca gggtgcgc     480 gacagccagg acaagacagg catgaacgat gccatccgca caggcacggg cctgctgcac    540
ggcatcccag tggcgctggc agtgatggag tttggcttca tgggcggcag catgggcagc    600 gtggtgggg agaagctgac gcgcctgatt gagtacgcca cgcaggaggg gctcacgctg     660
ctggtggtgt gcaccagcgg aggcgcgcgc atgcaggagg gcatcatgag cctgatgcag    720
atggccaaga tcagcggcgc gctgcacgtg caccagaatg aggccaacct gctgtacatc    780
tccatcctga ccagccccac cacaggtggc gtgaccgcaa gctttggcat gctgggggat    840
gtcatcattg ctgagccgca ggccatcatc ggctttgcag acggcgtgt gatcgagcag    900 acgctgcgtg aggagctgcc agatgacttc cagaccgcgg agtacctgct tgacaagggc    960
```

-continued

| | |
|---|---|
| ctgctcgacc tggtggtgcc gcgcagcttc ctgaagggcg cgctgtttga gatcatcgac | 1020 |
| ttctacaaga acgcacccta caagcgccgc ggcaagattc catttggcgt gcagcgcggt | 1080 |
| acgtacggcc tgaccgctga ggagaagatg cggcgcaggt ggagggagtg gagctcagct | 1140 |
| ggcagcaacg gctcgggcac gcccgcgctg gcagcagcag cagcatcagc agcagttggg | 1200 |
| tcagcagcca cttgcggcag ctgccagcag cagcagctgg cgctgtgggc ggtgctggca | 1260 |
| ggctgtggca gctgtgggca gtggctgtgg tttgctcagg gggtaggtgc gcttgagcgc | 1320 |
| acagcggcaa cagcagcagt actgagagag ggcagcgtgc tgctagcagg cgtctgttgt | 1380 |
| ta | 1382 |

```
<210> SEQ ID NO 171
<211> LENGTH: 1344
<212> TYPE: DNA
<213> ORGANISM: artificial sequence
<220> FEATURE:
<223> OTHER INFORMATION: synthesized
<220> FEATURE:
<221> NAME/KEY: misc_feature
<222> LOCATION: (1023)..(1023)
<223> OTHER INFORMATION: n=a, g, c, or t
<220> FEATURE:
<221> NAME/KEY: misc_feature
<222> LOCATION: (1191)..(1194)
<223> OTHER INFORMATION: n=a, g, c, or t
<220> FEATURE:
<221> NAME/KEY: misc_feature
<222> LOCATION: (1197)..(1197)
<223> OTHER INFORMATION: n=a, g, c, or t
<220> FEATURE:
<221> NAME/KEY: misc_feature
<222> LOCATION: (1200)..(1200)
<223> OTHER INFORMATION: n=a, g, c, or t
<220> FEATURE:
<221> NAME/KEY: misc_feature
<222> LOCATION: (1219)..(1219)
<223> OTHER INFORMATION: n=a, g, c, or t
<220> FEATURE:
<221> NAME/KEY: misc_feature
<222> LOCATION: (1221)..(1221)
<223> OTHER INFORMATION: n=a, g, c, or t
<220> FEATURE:
<221> NAME/KEY: misc_feature
<222> LOCATION: (1228)..(1228)
<223> OTHER INFORMATION: n=a, g, c, or t
<220> FEATURE:
<221> NAME/KEY: misc_feature
<222> LOCATION: (1231)..(1231)
<223> OTHER INFORMATION: n=a, g, c, or t
<220> FEATURE:
<221> NAME/KEY: misc_feature
<222> LOCATION: (1236)..(1236)
<223> OTHER INFORMATION: n=a, g, c, or t
<220> FEATURE:
<221> NAME/KEY: misc_feature
<222> LOCATION: (1239)..(1240)
<223> OTHER INFORMATION: n=a, g, c, or t
<220> FEATURE:
<221> NAME/KEY: misc_feature
<222> LOCATION: (1242)..(1242)
<223> OTHER INFORMATION: n=a, g, c, or t
<220> FEATURE:
<221> NAME/KEY: misc_feature
<222> LOCATION: (1244)..(1244)
<223> OTHER INFORMATION: n=a, g, c, or t
<220> FEATURE:
<221> NAME/KEY: misc_feature
<222> LOCATION: (1247)..(1247)
<223> OTHER INFORMATION: n=a, g, c, or t
<220> FEATURE:
<221> NAME/KEY: misc_feature
<222> LOCATION: (1249)..(1251)
<223> OTHER INFORMATION: n=a, g, c, or t
```

```
<220> FEATURE:
<221> NAME/KEY: misc_feature
<222> LOCATION: (1255)..(1256)
<223> OTHER INFORMATION: n=a, g, c, or t
<220> FEATURE:
<221> NAME/KEY: misc_feature
<222> LOCATION: (1261)..(1261)
<223> OTHER INFORMATION: n=a, g, c, or t
<220> FEATURE:
<221> NAME/KEY: misc_feature
<222> LOCATION: (1263)..(1263)
<223> OTHER INFORMATION: n=a, g, c, or t
<220> FEATURE:
<221> NAME/KEY: misc_feature
<222> LOCATION: (1269)..(1269)
<223> OTHER INFORMATION: n=a, g, c, or t
<220> FEATURE:
<221> NAME/KEY: misc_feature
<222> LOCATION: (1275)..(1275)
<223> OTHER INFORMATION: n=a, g, c, or t
<220> FEATURE:
<221> NAME/KEY: misc_feature
<222> LOCATION: (1277)..(1278)
<223> OTHER INFORMATION: n=a, g, c, or t
<220> FEATURE:
<221> NAME/KEY: misc_feature
<222> LOCATION: (1281)..(1282)
<223> OTHER INFORMATION: n=a, g, c, or t
<220> FEATURE:
<221> NAME/KEY: misc_feature
<222> LOCATION: (1288)..(1344)
<223> OTHER INFORMATION: n=a, g, c, or t

<400> SEQUENCE: 171
```

| | | | | | |
|---|---|---|---|---|---|
| atgtctctta | agtccagcgt | gggccccagc | ctggccggca | aggcgtgcca | cggagcaaat | 60 |
| gcgcaggtgc | tgccgcgcat | ggcagtgcca | gcgccgcttg | caggaacagc | agtgcgcccc | 120 |
| agcctcgcag | tcaatgcagt | caaccctgag | aaaaacggcg | cttatgaggg | ctcccccatt | 180 |
| gtcagcggcc | ccatttctgt | gggtgctatg | gacaaggact | ccaagggctc | ttccaagcct | 240 |
| gttgaccgca | gcaagggcct | ctggacgcgc | tgcgacaagt | gcggcgtgat | tctctacatc | 300 |
| aagcacctga | aggagcacca | ccacatctgc | ttcggctgca | actaccacct | caagatgagc | 360 |
| agccaggaga | ggatcgacca | catgatcgac | ccaggctcat | ggcgccccct | tgacgagacg | 420 |
| ctgtctccct | gcgacccgct | ggactttgtg | gacatgaagc | catacccaga | cagggtgcgc | 480 |
| gacagccagg | acaagacagg | catgaacgat | gccatccgca | caggcacggg | cctgctgcac | 540 |
| ggcatcccag | tggcgctggc | agtgatggag | tttggcttca | tgggcggcag | catgggcagc | 600 |
| gtggtggggg | agaagctgac | gcgcctgatt | gagtacgcca | cgcaggaggg | gctcacgctg | 660 |
| ctggtggtgt | gcaccagcgg | aggcgcgcgc | atgcaggagg | gcatcatgag | cctgatgcag | 720 |
| atggccaaga | tcagcggcgc | gctgcacgtg | caccagaatg | aggccaacct | gctgtacatc | 780 |
| tccatcctga | ccagcccccac | cacaggtggc | gtgaccgcaa | gctttggcat | gctgggggat | 840 |
| gtcatcattg | ctgagccgca | ggccatcatc | ggctttgcag | gacggcgtgt | gatcgagcag | 900 |
| acgctgcgtg | aggagctgcc | agatgacttc | cagaccgcgg | agtacctgct | tgacaagggc | 960 |
| ctgctcgacc | tggtggtgcc | gcgcagcttc | ctgaagggcg | cgctgtttga | gatcatcgac | 1020 |
| ttntacaaga | acgcacccta | caagcgccgc | ggcaagattc | catttggcgt | gcagcgcggt | 1080 |
| acgtacggcc | tgaccgctga | ggagaagatg | cggcgcaggt | ggagggagtg | gagctcagct | 1140 |
| ggcagcaacg | gctcgggcac | gcccgcgctg | gcagcagcag | cagcagtggc | nnnccntgn | 1200 |
| ggcagtgggg | gcggtgcgng | ngcagtgngt | ntggtntgnn | cngnagntnn | ntgtnngggc | 1260 |
| nangtcggna | gtttncnncg | nngttagnnn | nnnnnnnnnn | nnnnnnnnnn | nnnnnnnnnn | 1320 | nnnnnnnnn nnnnnnnnn nnnn                                             1344

<210> SEQ ID NO 172
<211> LENGTH: 443
<212> TYPE: PRT
<213> ORGANISM: artificial sequence
<220> FEATURE:
<223> OTHER INFORMATION: synthesized
<220> FEATURE:
<221> NAME/KEY: MISC_FEATURE
<222> LOCATION: (389)..(389)
<223> OTHER INFORMATION: Xaa is Ala or Leu
<220> FEATURE:
<221> NAME/KEY: MISC_FEATURE
<222> LOCATION: (396)..(396)
<223> OTHER INFORMATION: Xaa is Ser or His or Arg
<220> FEATURE:
<221> NAME/KEY: MISC_FEATURE
<222> LOCATION: (397)..(397)
<223> OTHER INFORMATION: Xaa is Ala or Met or Pro
<220> FEATURE:
<221> NAME/KEY: MISC_FEATURE
<222> LOCATION: (399)..(399)
<223> OTHER INFORMATION: Xaa is Ala or His or Gln
<220> FEATURE:
<221> NAME/KEY: MISC_FEATURE
<222> LOCATION: (401)..(401)
<223> OTHER INFORMATION: Xaa is Gly or Asn or Gln
<220> FEATURE:
<221> NAME/KEY: MISC_FEATURE
<222> LOCATION: (402)..(402)
<223> OTHER INFORMATION: Xaa is Ser or Glu or Gln
<220> FEATURE:
<221> NAME/KEY: MISC_FEATURE
<222> LOCATION: (403)..(403)
<223> OTHER INFORMATION: Xaa is Ala or Gly or Gln
<220> FEATURE:
<221> NAME/KEY: MISC_FEATURE
<222> LOCATION: (404)..(404)
<223> OTHER INFORMATION: Xaa is Ala or Ser or Gly
<220> FEATURE:
<221> NAME/KEY: MISC_FEATURE
<222> LOCATION: (407)..(407)
<223> OTHER INFORMATION: Xaa is Ala or Ser or Gly
<220> FEATURE:
<221> NAME/KEY: MISC_FEATURE
<222> LOCATION: (408)..(408)
<223> OTHER INFORMATION: Xaa is Ser or Lys or Gly
<220> FEATURE:
<221> NAME/KEY: MISC_FEATURE
<222> LOCATION: (409)..(409)
<223> OTHER INFORMATION: Xaa is Cys or Thr or Phe
<220> FEATURE:
<221> NAME/KEY: MISC_FEATURE
<222> LOCATION: (410)..(410)
<223> OTHER INFORMATION: Xaa is Gln or Thr or Gly
<220> FEATURE:
<221> NAME/KEY: MISC_FEATURE
<222> LOCATION: (411)..(411)
<223> OTHER INFORMATION: Xaa is Gln or Cys or Ala
<220> FEATURE:
<221> NAME/KEY: MISC_FEATURE
<222> LOCATION: (413)..(413)
<223> OTHER INFORMATION: Xaa is Gln or Ser or Pro
<220> FEATURE:
<221> NAME/KEY: MISC_FEATURE
<222> LOCATION: (422)..(422)
<223> OTHER INFORMATION: Xaa is Ala or Leu or Ile
<220> FEATURE:
<221> NAME/KEY: MISC_FEATURE
<222> LOCATION: (427)..(427)
<223> OTHER INFORMATION: Xaa is Thr or Lys or Asp
<220> FEATURE:
<221> NAME/KEY: MISC_FEATURE
<222> LOCATION: (428)..(428)
<223> OTHER INFORMATION: Xaa is Ala or Gly or Ser
<220> FEATURE:
<221> NAME/KEY: MISC_FEATURE
<222> LOCATION: (429)..(429)
<223> OTHER INFORMATION: Xaa is Ala or Ile or Ser

<400> SEQUENCE: 172

```
Met Ser Leu Lys Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
            35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His Ile Cys Phe Gly
            100                 105                 110

Cys Asn Tyr His Leu Lys Met Ser Ser Gln Glu Arg Ile Asp His Met
            115                 120                 125

Ile Asp Pro Gly Ser Trp Arg Pro Phe Asp Glu Thr Leu Ser Pro Cys
130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
            195                 200                 205

Leu Ile Glu Tyr Ala Thr Gln Glu Gly Leu Thr Leu Leu Val Val Cys
210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270

Ala Ser Phe Gly Met Leu Gly Asp Val Ile Ile Ala Glu Pro Gln Ala
            275                 280                 285

Ile Ile Gly Phe Ala Gly Arg Arg Val Ile Glu Gln Thr Leu Arg Glu
290                 295                 300

Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys Gly Ala Leu Phe
                325                 330                 335

Glu Ile Ile Asp Phe Tyr Lys Asn Ala Pro Tyr Lys Arg Arg Gly Lys
            340                 345                 350

Ile Pro Phe Gly Val Gln Arg Gly Thr Tyr Gly Leu Thr Ala Glu Glu
            355                 360                 365

Lys Met Arg Arg Arg Trp Arg Glu Trp Ser Ser Ala Gly Ser Asn Gly
370                 375                 380

Ser Gly Thr Pro Xaa Leu Ala Ala Ala Ala Xaa Xaa Trp Xaa Val
385                 390                 395                 400
```

Xaa Xaa Xaa Xaa Gly Cys Xaa Xaa Xaa Xaa Gln Xaa Phe Trp Cys
                405             410             415

Trp Gln Gly Val Gly Xaa Leu Glu Ala Ala Xaa Xaa Xaa Leu Leu Arg
            420             425             430

Glu Gly Ser Val Leu Leu Ala Gly Val Cys Cys
            435             440

<210> SEQ ID NO 173
<211> LENGTH: 332
<212> TYPE: PRT
<213> ORGANISM: Scenedesmus dimorphus

<400> SEQUENCE: 173

Met Ser Leu Lys Ser Ser Val Gly Pro Ser Leu Ala Gly Lys Ala Cys
1               5                   10                  15

His Gly Ala Asn Ala Gln Val Leu Pro Arg Met Ala Val Pro Ala Pro
            20                  25                  30

Leu Ala Gly Thr Ala Val Arg Pro Ser Leu Ala Val Asn Ala Val Asn
        35                  40                  45

Pro Glu Lys Asn Gly Ala Tyr Glu Gly Ser Pro Ile Val Ser Gly Pro
    50                  55                  60

Ile Ser Val Gly Ala Met Asp Lys Asp Ser Lys Gly Ser Ser Lys Pro
65                  70                  75                  80

Val Asp Arg Ser Lys Gly Leu Trp Thr Arg Cys Asp Lys Cys Gly Val
                85                  90                  95

Ile Leu Tyr Ile Lys His Leu Lys Glu His His Ile Cys Phe Gly
            100                 105                 110

Cys Asn Tyr His Leu Lys Met Ser Ser Gln Glu Arg Ile Asp His Met
        115                 120                 125

Ile Asp Pro Gly Ser Trp Arg Pro Phe Asp Glu Thr Leu Ser Pro Cys
    130                 135                 140

Asp Pro Leu Asp Phe Val Asp Met Lys Pro Tyr Pro Asp Arg Val Arg
145                 150                 155                 160

Asp Ser Gln Asp Lys Thr Gly Met Asn Asp Ala Ile Arg Thr Gly Thr
                165                 170                 175

Gly Leu Leu His Gly Ile Pro Val Ala Leu Ala Val Met Glu Phe Gly
            180                 185                 190

Phe Met Gly Gly Ser Met Gly Ser Val Val Gly Glu Lys Leu Thr Arg
        195                 200                 205

Leu Ile Glu Tyr Ala Thr Gln Glu Gly Leu Thr Leu Leu Val Val Cys
    210                 215                 220

Thr Ser Gly Gly Ala Arg Met Gln Glu Gly Ile Met Ser Leu Met Gln
225                 230                 235                 240

Met Ala Lys Ile Ser Gly Ala Leu His Val His Gln Asn Glu Ala Asn
                245                 250                 255

Leu Leu Tyr Ile Ser Ile Leu Thr Ser Pro Thr Thr Gly Gly Val Thr
            260                 265                 270

Ala Ser Phe Gly Met Leu Gly Asp Val Ile Ala Glu Pro Gln Ala
        275                 280                 285

Ile Ile Gly Phe Ala Gly Arg Arg Val Ile Glu Gln Thr Leu Arg Glu
    290                 295                 300

Glu Leu Pro Asp Asp Phe Gln Thr Ala Glu Tyr Leu Leu Asp Lys Gly
305                 310                 315                 320

Leu Leu Asp Leu Val Val Pro Arg Ser Phe Leu Lys

```
<210> SEQ ID NO 174
<211> LENGTH: 12
<212> TYPE: PRT
<213> ORGANISM: artificial sequence
<220> FEATURE:
<223> OTHER INFORMATION: synthesized

<400> SEQUENCE: 174

Phe Ala Gly Lys Arg Arg Val Ile Glu Gln Thr Leu
1               5                   10
```